United States Patent
Chafeev

(10) Patent No.: US 11,358,956 B2
(45) Date of Patent: Jun. 14, 2022

(54) COMPOUNDS CONTAINING POLYSUBSTITUTED BENZO[D][1,3]OXATHIOLE, BENZO[D][1,3]OXATHIOLE 3-OXIDE OR BENZO[D][1,3]OXATHIOLE 3,3-DIOXIDE AND METHODS/USES THEREOF AS AGONISTS OF G PROTEIN-COUPLED RECEPTOR 119

(71) Applicant: PRAMANA PHARMACEUTICALS INC., Vancouver (CA)

(72) Inventor: Mikhail Chafeev, Kiev (UA)

(73) Assignee: PRAMANA PHARMACEUTICALS INC., Vancouver (CA)

( * ) Notice: Subject to any disclaimer, the term of this patent is extended or adjusted under 35 U.S.C. 154(b) by 66 days.

(21) Appl. No.: 16/768,293

(22) PCT Filed: Nov. 6, 2018

(86) PCT No.: PCT/CA2018/051403
§ 371 (c)(1),
(2) Date: May 29, 2020

(87) PCT Pub. No.: WO2019/104418
PCT Pub. Date: Jun. 6, 2019

(65) Prior Publication Data
US 2021/0188825 A1 Jun. 24, 2021

Related U.S. Application Data

(60) Provisional application No. 62/593,015, filed on Nov. 30, 2017.

(51) Int. Cl.
*C07D 411/14* (2006.01)
*A61K 45/06* (2006.01)

(52) U.S. Cl.
CPC ............ *C07D 411/14* (2013.01); *A61K 45/06* (2013.01)

(58) Field of Classification Search
CPC ............................. C07D 411/14; A61K 45/06
See application file for complete search history.

(56) References Cited

U.S. PATENT DOCUMENTS

| 2008/0103141 A1 | 5/2008 | Brandt et al. |
| 2014/0274701 A1 | 9/2014 | Eckelbarger et al. |

FOREIGN PATENT DOCUMENTS

| CA | 1117944 | 2/1982 |
| EP | 0157603 | 10/1985 |
| KR | 10-2014-0127991 | 11/2014 |
| RU | 2576037 | 2/2016 |
| WO | 2005121121 | 12/2005 |
| WO | 2009050522 | 4/2009 |
| WO | 2012069917 | 5/2012 |
| WO | 2013187646 | 12/2013 |
| WO | 2017210794 | 12/2017 |

OTHER PUBLICATIONS

Chu, Z.L. et al. "A Role for B-Cell-Expressed G Protein-Coupled Receptor 119 in Glycemic Control by Enhancing Glucose-Dependent Insulin Release" Endocrin. 2007, 148, pp. 2601-2609.
Chu, Z.L. et al. "A Role for Intestinal Endocrine Cell-Expressed G Protein-Coupled Receptor 119 in Glycemic Control by Enhancing Glucagon-Like Peptide-1 and Glucose-Dependent Insulinotropic Peptide Release" Endocrin. 2008, 149, pp. 2038-2047.
Davey, J. "A Role for Intestinal Endocrine Cell-Expressed G Protein-Coupled Receptor 119 in Glycemic Control by Enhancing Glucagon-Like Peptide-1 and Glucose-Dependent Insulinotropic Peptide Release" Exp. Opin. Ther. Targ. 2004, 8, pp. 165-170.
DeFronzo, R.A. et al. "Novel Agents for the Treatment of Type 2 Diabetes" Diabetes Spectrum 2014, 27, pp. 100-112.
Jones, R.M. et al. "GPR119 agonists for the treatment of type 2 diabetes" Expert Opin. Ther. Pat. 2009, 19, pp. 1339-1359.
Kim, S. et al. "HD047703, a New Promising Anti-Diabetic Drug Candidate:In Vivo Preclinical Studies" Biomol. Ther. 2014, 22, pp. 400-405.
Oshima, H. et al. "Novel GPR119 agonist AS1669058 potentiates insulin secretion from rat islets and has potent anti-diabetic effects in ICR and diabetic db/db mice" Life Sci. 2013, 92, pp. 167-173.

(Continued)

*Primary Examiner* — Alicia L Otton
(74) *Attorney, Agent, or Firm* — Snell & Wilmer L.L.P.

(57) ABSTRACT

There are provided compounds having formula (I), in which: $X^1$ and $X^2$ are selected from certain combinations of O, S, SO and $SO_2$; $X^3$ is selected from CH, CF and N; $X^4$ is selected from CH and N; $X^6$, $X^{6'}$ and $X^{6''}$ are selected from H, halogen, and certain alkyl, haloalkyl, alkoxy, hydroxyalkyl, and amide groups; $X^7$ and $X^{7'}$ are selected from H, halogen, and certain alkyl, haloalkyl, alkoxy, hydroxyalkyl, aminoalkyl and amide groups, or both $X^7$ and $X^{7'}$ together form a cycloalkyl or heterocycle; and A is selected from certain optionally substituted, alkoxy, piperazinyl and pyrrolidinyl groups. Also provided are compositions comprising these compounds, as well as uses/methods related thereto, including treatment of diseases and conditions associated with GPR119 dysregulation, Type 2 diabetes mellitus, and related metabolic disorders. (I)

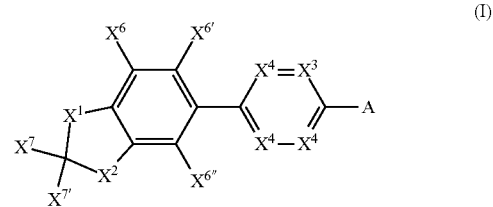

20 Claims, No Drawings

(56) References Cited

OTHER PUBLICATIONS

Ritter, K. et al. "G Protein-Coupled Receptor 119 (GPR119) Agonists for the Treatment of Diabetes: Recent Progress and Prevailing Challenges" J. Med. Chem. 2016, 59, pp. 3579-3592 (47 pages).
Semple, G. et al. "Discovery of a second generation agonist of the orphan G-protein coupled receptor GPR119 with an improved profile" Bioorg Med. Chem. Lett. 2012, 22, pp. 1750-1755.
Shah, U. et al. "GPR119 Agonists for the Potential Treatment of Type 2 Diabetes and Related Metabolic Disorders" Vitam. Horm., 2010, 84, pp. 415-448.
Vangaveti, V. et al. "Free fatty acid receptors: emerging targets for treatment of diabetes and its complications" Ther. Adv. Endocrin. Metabol. 2010, 1, pp. 165-175.
Wacker, D.A. et al. "Discovery of 5-Chloro-4-((1-(5-chloropyrimidin-2-yl)piperidin-4-yl)oxy)-1-(2-fluoro-4-(methylsulfonyl)phenyl)pyridin-2(1H)-one (BMS-903452), an Antidiabetic Clinical Candidate Targeting GPR119" J. Med. Chem. 2014, 57, pp. 7499-7508.
Yoshida, S. et al. "The role of small molecule GPR119 agonist, AS1535907, in glucose-stimulated insulin secretion and pancreatic β-cell function" Diabetes, Obesity Metabol. 2011, 13, pp. 34-41.
Zhu et al. "The first pharmacophore model for potent G protein-coupled receptor 119 agonist" Eur. J. Med. Chem. 2011, 46, pp. 2901-2907.
International Search Report and Written Opinion dated Sep. 7, 2017 for PCT International Application No. PCT/CA2017/050703.
International Search Report and Written Opinion dated Feb. 6, 2019 for PCT International Application No. PCT/CA2018/051403.

COMPOUNDS CONTAINING POLYSUBSTITUTED BENZO[D][1,3]OXATHIOLE, BENZO[D][1,3]OXATHIOLE 3-OXIDE OR BENZO[D][1,3]OXATHIOLE 3,3-DIOXIDE AND METHODS/USES THEREOF AS AGONISTS OF G PROTEIN-COUPLED RECEPTOR 119

CROSS-REFERENCE TO RELATED APPLICATIONS

This application is a U.S. national phase filing under 35 U.S.C. § 371 of PCT/CA2018/051403 filed on Nov. 6, 2018 entitled "COMPOUNDS CONTAINING POLYSUBSTITUTED BENZO[D][1,3]OXATHIOLE, BENZO[D][1,3] OXATHIOLE 3-OXIDE OR BENZO[D][1,3]OXATHIOLE 3,3-DIOXIDE AND METHODS/USES THEREOF AS AGONISTS OF G PROTEIN-COUPLED RECEPTOR 119," which claims priority to U.S. Provisional Patent Application No. 62/593,015 filed on Nov. 30, 2017, the disclosures of which are incorporated herein by reference.

FIELD OF INVENTION

The present invention relates to polysubstituted benzo[d] [1,3]oxathioles, benzo[d][1,3]oxathiole 3-oxides, benzo[d] [1,3]oxathiole 3,3-dioxides, and related compounds and pharmaceutical compositions comprising the compounds, as well as uses and methods related thereto.

BACKGROUND OF THE INVENTION

Insulin is a hormone that regulates blood sugar produced by the pancreas. Diabetes is a chronic disease that occurs either when the pancreas does not produce enough insulin or when the body cannot effectively use the insulin it produces. Hyperglycemia, or raised blood sugar, is a common effect of uncontrolled diabetes and over time leads to serious damage to many of the body's systems, especially the nerves and blood vessels. The global prevalence of diabetes is estimated to be over 9% of adults aged 18+ years, corresponding to about 2-fold increase in the last ten years. There are three types of diabetes: Type 1 also known as insulin-dependent or juvenile requires daily administration of insulin. Type 2 diabetes (T2DM) also known as non-insulin dependent diabetes mellitus results from the body's ineffective use or ability to regulate insulin. Gestational diabetes is a condition where the blood glucose values are above normal but below those characteristic of diabetes occurring during pregnancy. Diabetes increases the risk of heart failure, stroke, neuropathy in the feet, retinopathy which is an important cause of blindness and kidney failure.

Several therapies for T2DM have been used in patients and include: 1) glucose-lowering effectors, such as metformin which reduces glucose production from the liver; 2) insulin or insulin secretagogues, such as sulphonylureas, which increase insulin production from pancreatic β-cells; 3) activators of the peroxisome proliferator-activated receptor-γ (PPAR-γ), such as the thiazolidinediones, which enhance insulin action; 4) α-glucosidase inhibitors which interfere with gut glucose production; 5) Glucagon-like peptide 1 (GLP-1) analogs, 6) sodium glucose transporter 2 inhibitors (SGLT2) and 7) dipeptidyl peptidase 4 (DPP-IV) inhibitors (DeFronzo, R. A. et al. *Diabetes Spectrum* 2014, 27, 100-112). Other potential therapeutics under investigation include glucagon receptor antagonists, glucokinase activators, fructose-1,6-bisphosphatase inhibitors, acetyl-CoA carboxylase inhibitors, bile acids sequestrates, activators of bile acid farnesoid X receptor and AMPK activators (Vangaveti, V. et al. *Ther. Adv. Endocrin. Metabol.* 2010, 1, 165-175), G-protein coupled receptors 139 and 142 and somatostatin receptor 3 antagonists. There are, however, deficiencies associated with currently available treatments, including edema, weight gain, hypoglycemic episodes, and a relatively high frequency of gastrointestinal side effects Small molecule DPP-4 inhibitors enhance glucose-dependent insulin release by inhibiting the degradation of endogenous GLP-1.

The G protein-coupled receptor 119 (GPR119) is a class A (rhodopsin-type) orphan GPCR without close primary sequence relative in the human genome (Shah, U. et al. *Vitam. Horm.*, 2010, 84, 415-448). It is expressed on L- and K-cells in intestine and on β cells in the pancreas and foetal liver. GPR119 homologs have been identified in several vertebrate species, including rodents (rat, mice, and hamster), chimpanzee, rhesus monkey, cattle and dog (Davey, J. Exp. Opin. Ther. Targ. 2004, 8, 165-170). High-level expression of GPR119 in cells led to an increase in intracellular cAMP levels via activation of adenylate cyclase (Chu, Z. L. et al. *Endocrin.* 2007, 148, 2601-2609), indicating that this receptor couples efficiently to $G\alpha_s$. GPR119 stimulates the release of several key molecules: 1) GIP, a major insulinotropic hormone of the gut, produced primarily in the duodenal K cells, 2) GLP-1 and 3) at least one other L-cell peptide, peptide YY (3-36) (PYY) (Chu, Z. L. et al. *Endocrin.* 2008, 149, 2038-2047).

These findings validate GPR119 receptor as a biological target for agonist development that can be potentially used as therapeutics in T2DM, obesity and metabolic syndrome treatment. Many agents have been disclosed as potent agonists (Ritter, K. et al. *J. Med. Chem.* 2016, 59, 3579-3592), with activity in rodents including APD668, APD597 (WO05121121) (Semple, G. et al. *Bioorg. Med. Chem. Lett.* 2012, 22, 1750-1755), PSN-821 (Fyfe, M. WO2009050522), HD047703 (Kim, S. et al. *Biomol. Ther.* 2014, 22, 400-405), AS1669058 (Oshima, H. et al. *Life Sci.* 2013, 92, 167-173), AS1535907 (Yoshida, S. et al. *Diabetes, Obesity Metabol.* 2011, 13, 34-41).

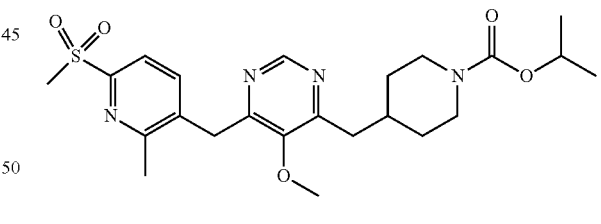

APD597

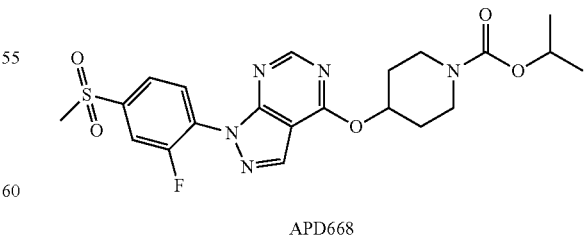

APD668

Sulphone containing agonists include GSK-1292263 (Zhu et al. *Eur. J. Med. Chem.* 2011, 46, 2901-2907) and BMS-903452 (Wacker, D. A. et al. *J. Med. Chem.* 2014, 57, 7499-7508),

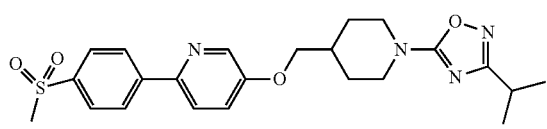

GSK1292263

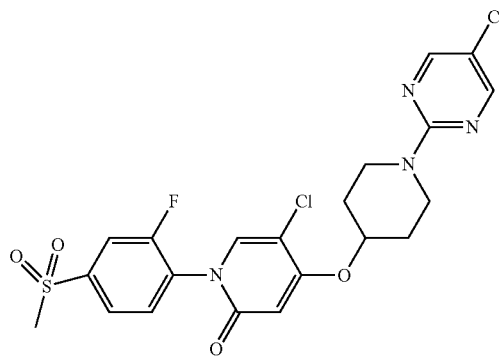

BMS-903452

MBX-2982 is a a tetrazole containing GPR agonist lacking the sulphone functional group (Jones, R. M. et al. *Expert Opin. Ther. Pat.* 2009, 19, 1339-1359).

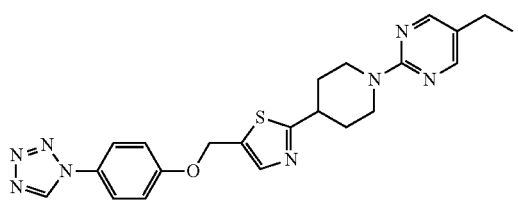

MBX-2982

Russian patent application RU2576037C1 discloses substituted 1,3-benzoxathioles as GPR119 receptor agonists where R is H, $C_1$-$C_5$ alkyl, halogen-substituted $C_1$-$C_5$ alkyl, acyl selected from the group $C_1$-$C_5$ alkyl(C=O) and phenyl (C=O), substituted heteroaryl representing an aromatic monocyclic group with two nitrogen atoms which is substituted by a halogen atom or ($C_1$-$C_5$) alkyl, ($C_1$-$C_3$) alkylsulphonyl, phenylsulphonyl; $R^1$, $R^2$, $R^3$, $R^4$ represent hydrogen or one or two substitutents simultaneously selected from a halogen, ($C_1$-$C_3$)alkyl, halogen-substituted ($C_1$-$C_3$)alkylsulphonyl and a cyano group.

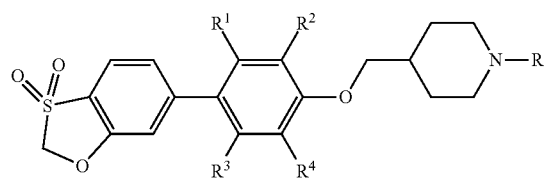

To date, disease and conditions associated with dysregulation of GPR119 such as T2DM, diabetes-mediated diseases and conditions, and metabolic disorders remain a major health concern. There is a clear and present need to identify additional compounds capable of modulating GPR119 activity as well as compounds that are therapeutically useful for the treatment of disease and conditions associated with dysregulation of GPR119 such as T2DM, diabetes-mediated diseases and conditions, and metabolic disorders.

BRIEF SUMMARY OF THE INVENTION

Various embodiments of the present invention relate to a compound having formula (I):

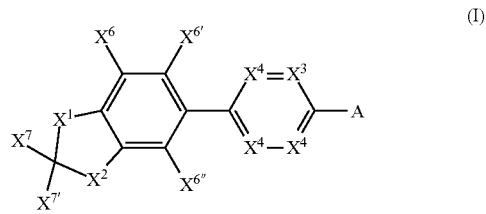

(I)

or an enantiomer, diastereomer, hydrate, solvate, or pharmaceutically acceptable salt of formula (I), or a prodrug or complex thereof, wherein:

$X^1$ is O and $X^2$ is S, SO or $SO_2$; or $X^2$ is O and $X^1$ is S, SO or $SO_2$;

$X^3$ is CH, CF and N;

each $X^4$ is independently CH and N;

A is

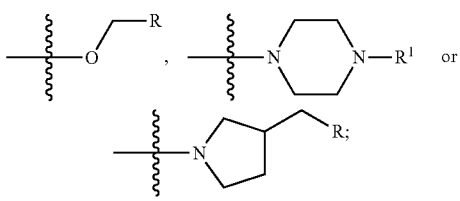

R is

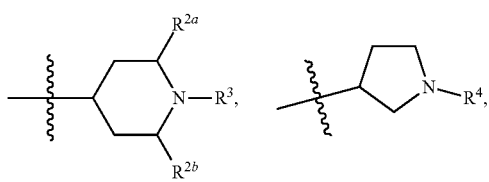

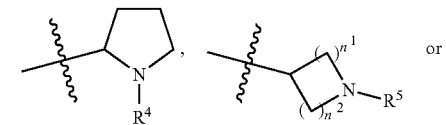

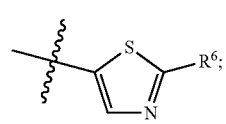

$R^1$ is hydrogen, C(O)O-tert-butyl or

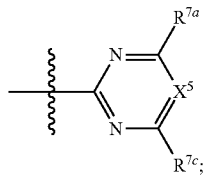

$R^{2a}$ is hydrogen or $C_{1-6}$ alkyl;
$R^{2b}$ is hydrogen or $C_{1-6}$ alkyl;
$R^3$ is hydrogen, $C_{1-6}$ alkyl, $C_{1-6}$ haloalkyl, C(O)$R^9$, C(O)O$R^{10}$, C(O)N$R^{10a}R^{10b}$, CH$_2$C(O)O$R^{10a}$,

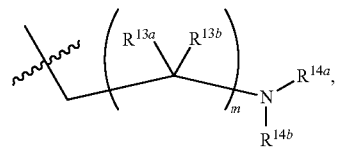

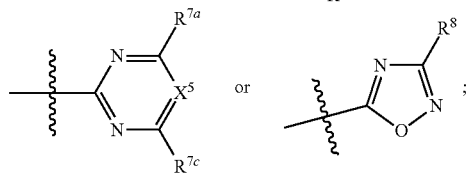

$R^4$ is hydrogen, $C_{1-6}$ alkyl, $C_{1-6}$ haloalkyl, C(O)$R^9$, C(O)O$R^{10}$, C(O)N$R^{10a}R^{10b}$,

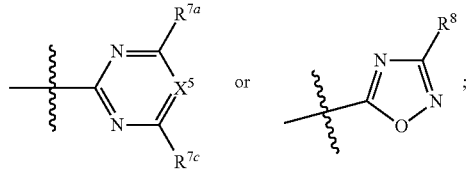

$R^5$ is hydrogen, $C_{1-6}$ alkyl, $C_{1-6}$ haloalkyl, C(O)$R^9$, C(O)O$R^{10}$, C(O)N$R^{10a}R^{10b}$,

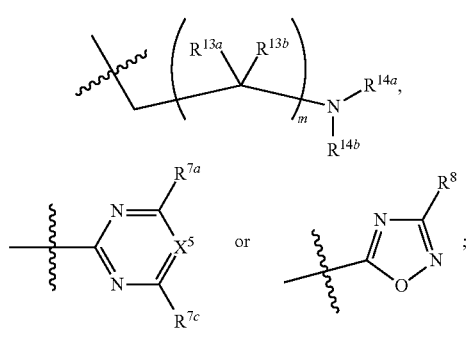

$R^6$ is

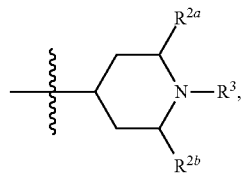

NH$R^{11}$ or CH$_2$NH$R^{12}$;
$R^{7a}$ is hydrogen, halogen, $C_{1-6}$ alkyl, $C_{3-7}$ branched alkyl, $C_{1-6}$ haloalkyl or $C_{1-6}$ alkoxy;
$R^{7b}$ is hydrogen, halogen, $C_{1-6}$ alkyl, $C_{3-7}$ branched alkyl, $C_{1-6}$ haloalkyl or $C_{1-6}$ alkoxy;
$R^{7c}$ is hydrogen, halogen, $C_{1-6}$ alkyl, $C_{3-7}$ branched alkyl, $C_{1-6}$ haloalkyl or $C_{1-6}$ alkoxy;
$R^8$ is hydrogen, halogen, $C_{1-6}$ alkyl, $C_{3-7}$ branched alkyl or $C_{3-7}$ cycloalkyl;
$R^9$ is $C_{1-6}$ alkyl, $C_{3-7}$ branched alkyl or

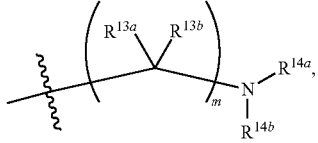

$R^{10}$ is $C_{1-6}$ alkyl or $C_{3-7}$ branched alkyl;
$R^{10a}$ is hydrogen, $C_{1-6}$ alkyl or $C_{3-7}$ branched alkyl;
$R^{10b}$ is hydrogen, $C_{1-6}$ alkyl or $C_{3-7}$ branched alkyl;
$R^{11}$ is

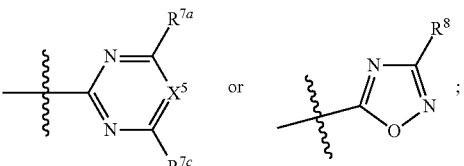

$R^{12}$ is

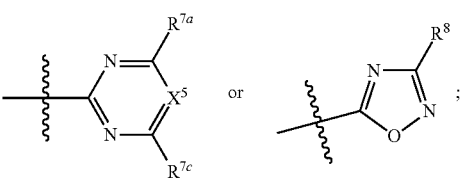

each $R^{13a}$ is independently hydrogen, $C_{1-6}$ alkyl or $C_{3-7}$ branched alkyl;
each $R^{13b}$ is independently hydrogen, $C_{1-6}$ alkyl or $C_{3-7}$ branched alkyl;
each $R^{14a}$ is independently hydrogen, $C_{1-6}$ alkyl, $C_{3-7}$ branched alkyl or C(O)O-tert-butyl;
each $R^{14b}$ is independently hydrogen, $C_{1-6}$ alkyl or $C_{3-7}$ branched alkyl;
$X^5$ is N or C$R^{7b}$;
$n^1$ is 1 or 2;
$n^2$ is 1 or 2;
and m is 1, 2, 3, 4, 5, 6 or 7;

each of $X^6$, $X^{6'}$ and $X^{6''}$ is independently H, halogen, $C_{1-3}$ alkyl, $C_{1-3}$ haloalkyl, $C_{1-3}$ alkoxy, $C_{1-3}$ hydroxyalkyl, or $C_{1-3}(O)NR^{15a}R^{15b}$;

each of $X^7$ and $X^{7'}$ is independently hydrogen, halogen, $C_{1-3}$ alkyl, $C_{1-3}$ haloalkyl, $C_{1-3}$ alkoxy, $C_{1-3}$ hydroxyalkyl, $C_{1-3}$ aminoalkyl or $C_{1-3}(O)NR^{15a}R^{15b}$, or both $X^7$ and $X^{7'}$ together form $C_{3-6}$ cycloalkyl or a heterocycle ring having 3-6 carbons and 0 or 1 oxygen, sulphur or nitrogen atom in the ring, wherein each carbon ring atom of the $C_{3-6}$ cycloalkyl or the heterocycle is independently substituted with hydrogen, $C_{1-3}$ alkyl, hydroxyl, halogen, amino, $C_{1-3}$ haloalkyl, $C_{1-3}$ alkoxy, $C_{1-3}$ hydroxyalkyl or $C_{1-3}(O)NR^{15a}R^{15b}$;

when each of $X^6$, $X^{6'}$ and $X^{6''}$ is hydrogen, at least $X^7$ or $X^{7'}$ is not hydrogen;

when both $X^7$ and $X^{7'}$ are hydrogen, at least one of $X^6$, $X^{6'}$ and $X^{6''}$ is not hydrogen; and each of $R^{15a}$ and $R^{15b}$ is independently hydrogen, $C_{1-3}$ alkyl or $C_3$ branched alkyl.

In some embodiments, the compound excludes any compound having formula (Ia)

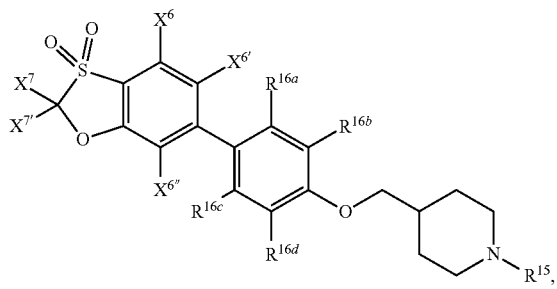

(Ia)

wherein:

$X^6$, $X^{6'}$, $X^{6''}$, $X^7$ and $X^{7'}$ are as defined for any embodiments defined herein;

$R^{15}$ is: hydrogen; $C_1$-$C_5$ alkyl; halogen-substituted $C_1$-$C_5$ alkyl; acyl selected from the group $C_1$-$C_5$ alkyl(C=O) and phenyl(C=O); substituted heteroaryl representing a monocyclic aromatic group with two nitrogen atoms which is substituted by a halogen or $(C_1$-$C_5)$ alkyl; $(C_1$-$C_3)$ alkylsulphonyl; or phenylsulphonyl; and $R^{16a}$, $R^{16b}$, $R^{16c}$ and $R^{16d}$ are hydrogen or one or two substitutents simultaneously selected from the group consisting of halogen, $(C_1$-$C_3)$ alkyl, halogen-substituted $(C_1$-$C_3)$alkyl, $(C_1$-$C_3)$alkylsulphonyl or cyano.

In some embodiments, $R^3$ is not $C(O)OR^{10}$.

In some embodiments, one, two or three of $X^6$, $X^{6'}$ and $X^{6''}$ are fluorine. In some embodiments, $X^6$, $X^{6'}$ and $X^{6''}$ are: F, H and H, respectively; H, F and H, respectively; or H, H and F, respectively. In some embodiments, $X^6$, $X^{6'}$ and $X^{6''}$ are each H.

In some embodiments, both of $X^7$ and $X^{7'}$ are hydrogen. In some embodiments, both of $X^7$ and $X^{7'}$ are $CH_3$. In some embodiments, at least one of $X^7$ and $X^{7'}$ is halogen.

In some embodiments, the compound has formula (II) or an enantiomer, diastereomer, hydrate, solvate, or pharmaceutically acceptable salt of formula (II), or a complex thereof:

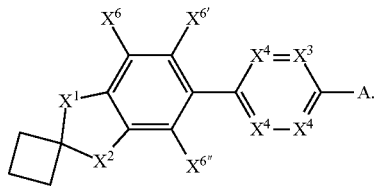

(II)

In some embodiments, the compound has formula (III) or an enantiomer, diastereomer, hydrate, solvate, or pharmaceutically acceptable salt of formula (III), or a complex thereof:

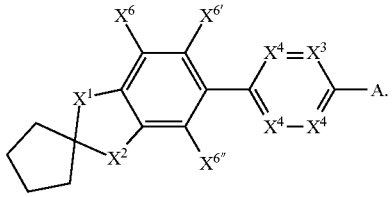

(III)

In some embodiments, the compound has formula (IV) or an enantiomer, diastereomer, hydrate, solvate, or pharmaceutically acceptable salt of formula (IV), or a complex thereof:

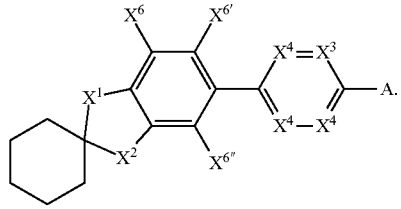

(IV)

In some embodiments, the compound has formula (V) or an enantiomer, diastereomer, hydrate, solvate, or pharmaceutically acceptable salt of formula (V), or a complex thereof:

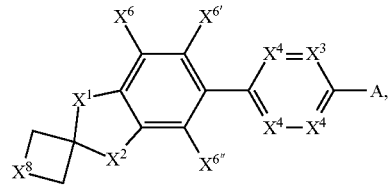

(V)

wherein $X^8$ is NH or O.

In some embodiments, the compound has formula (VI) or an enantiomer, diastereomer, hydrate, solvate, or pharmaceutically acceptable salt of formula (VI), or a complex thereof:

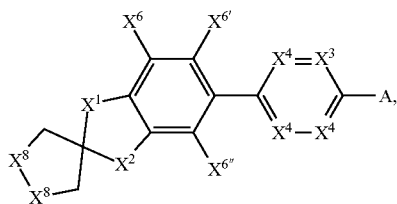

(VI)

wherein: one $X^8$ is NH or O; and one $X^8$ is $CH_2$.

In some embodiments, the compound has formula (VII) or an enantiomer, diastereomer, hydrate, solvate, or pharmaceutically acceptable salt of formula (VII), or a complex thereof:

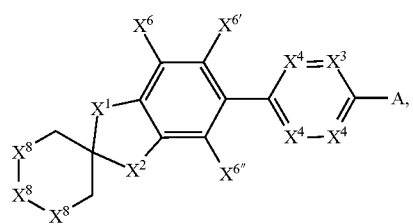

(VII)

wherein: one $X^8$ is NH or O; and each of two $X^8$ is $CH_2$.

In some embodiments: $X^1$ is O and $X^2$ is $SO_2$; or $X^1$ is $SO_2$ and $X^2$ is O. In some embodiments: $X^1$ is O and $X^2$ is SO; or $X^1$ is SO and $X^2$ is O. In some embodiments: $X^1$ is O and $X^2$ is S; or $X^1$ is S and $X^2$ is O. In some embodiments $X^1$ is O. In some embodiments $X^2$ is O.

In some embodiments, the compound has formula (VIII) or an enantiomer, diastereomer, hydrate, solvate, or pharmaceutically acceptable salt of formula (VIII), or a complex thereof:

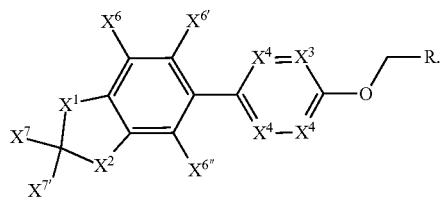

(VIII)

In some embodiments, the compound has formula (IX) or an enantiomer, diastereomer, hydrate, solvate, or pharmaceutically acceptable salt of formula (IX), or a complex thereof:

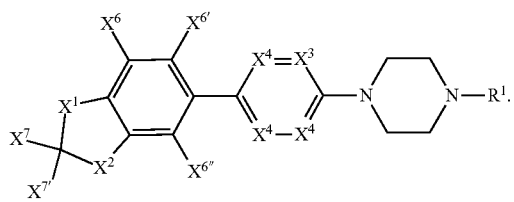

(IX)

In some embodiments, the compound has formula (X) or an enantiomer, diastereomer, hydrate, solvate, or pharmaceutically acceptable salt of formula (X), or a complex thereof:

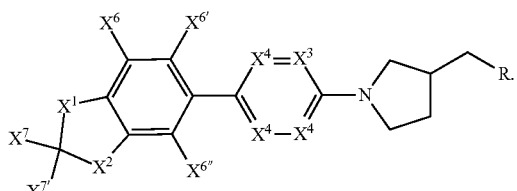

(X)

In some embodiments, the compound has formula (XI) or an enantiomer, diastereomer, hydrate, solvate, or pharmaceutically acceptable salt of formula (XI), or a complex thereof:

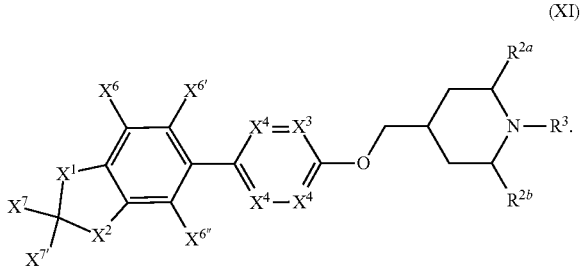

(XI)

In some embodiments, the compound has formula (XII) or an enantiomer, diastereomer, hydrate, solvate, or pharmaceutically acceptable salt of formula (XII), or a complex thereof:

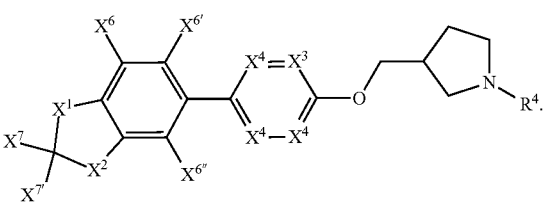

(XII)

In some embodiments, the compound has formula (XIII) or an enantiomer, diastereomer, hydrate, solvate, or pharmaceutically acceptable salt of formula (XIII), or a complex thereof:

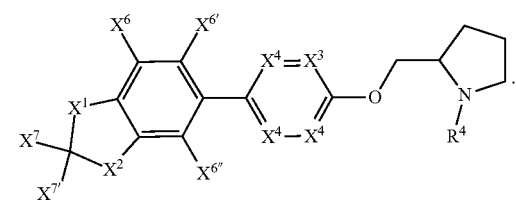

(XIII)

In some embodiments, the compound has formula (XIV) or an enantiomer, diastereomer, hydrate, solvate, or pharmaceutically acceptable salt of formula (XIV), or a complex thereof:

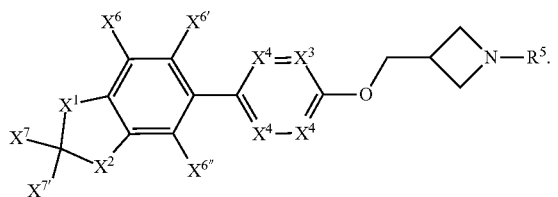

(XIV)

In some embodiments, the compound has formula (XV) or an enantiomer, diastereomer, hydrate, solvate, or pharmaceutically acceptable salt of formula (XV), or a complex thereof:

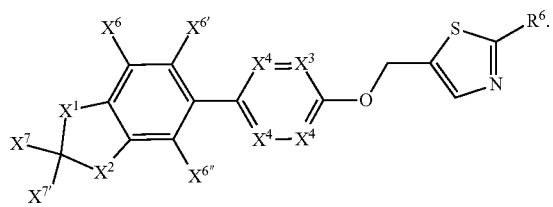

(XV)

In some embodiments, the compound has formula (XVI) or an enantiomer, diastereomer, hydrate, solvate, or pharmaceutically acceptable salt of formula (XVI), or a complex thereof:

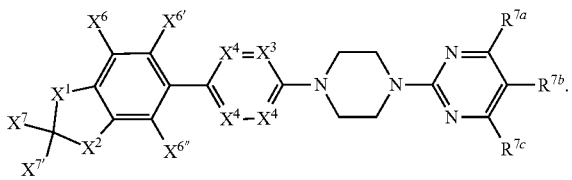

(XVI)

In some embodiments, the compound has formula (XVII) or an enantiomer, diastereomer, hydrate, solvate, or pharmaceutically acceptable salt of formula (XVII), or a complex thereof

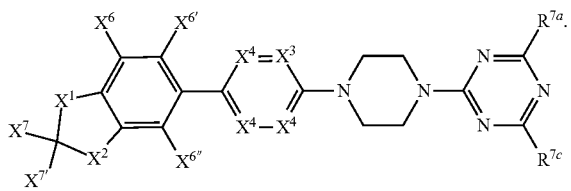

(XVII)

In some embodiments, the compound has formula (XVIII) or an enantiomer, diastereomer, hydrate, solvate, or pharmaceutically acceptable salt of formula (XVIII), or a complex thereof:

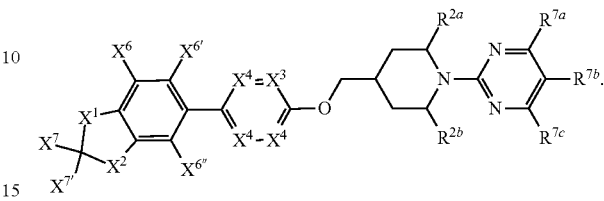

(XVIII)

In some embodiments, the compound has formula (XIX) or an enantiomer, diastereomer, hydrate, solvate, or pharmaceutically acceptable salt of formula (XIX), or a complex thereof:

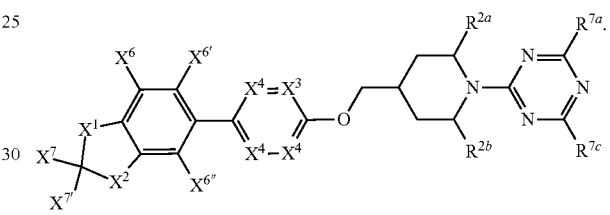

(XIX)

In some embodiments, the compound has formula (XX) or an enantiomer, diastereomer, hydrate, solvate, or pharmaceutically acceptable salt of formula (XX), or a complex thereof:

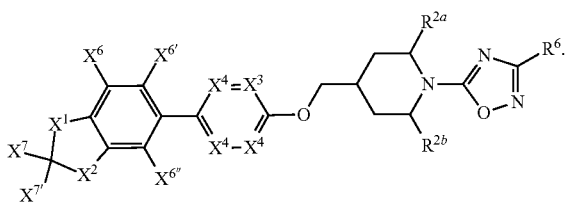

(XX)

In some embodiments, the compound has formula (XXI) or an enantiomer, diastereomer, hydrate, solvate, or pharmaceutically acceptable salt of formula (XXI), or a complex thereof:

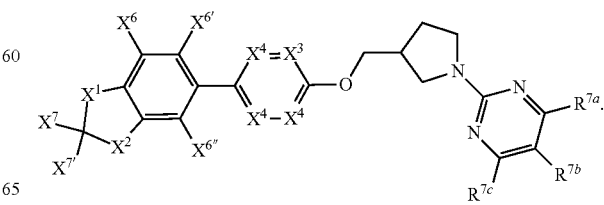

(XXI)

In some embodiments, the compound has formula (XXII) or an enantiomer, diastereomer, hydrate, solvate, or pharmaceutically acceptable salt of formula (XXII), or a complex thereof:

(XXII)

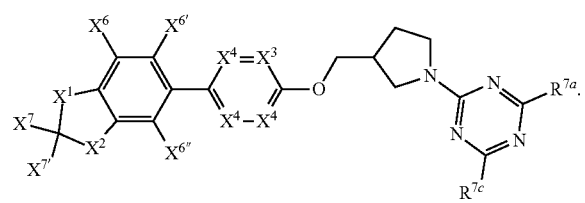

In some embodiments, the compound has formula (XXIII) or an enantiomer, diastereomer, hydrate, solvate, or pharmaceutically acceptable salt of formula (XXIII), or a complex thereof:

(XXIII)

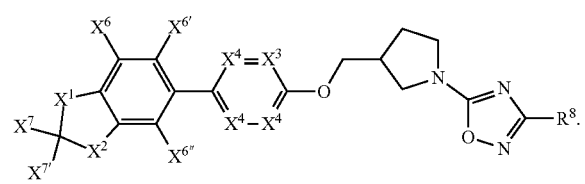

In some embodiments, the compound has formula (XXIV) or an enantiomer, diastereomer, hydrate, solvate, or pharmaceutically acceptable salt of formula (XXIV), or a complex thereof:

(XXIV)

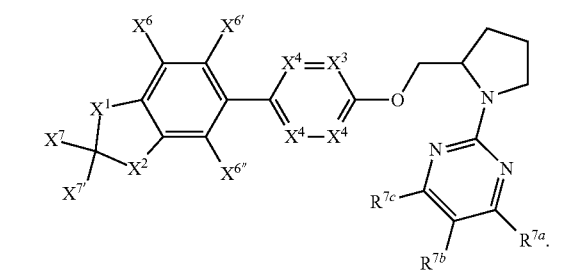

In some embodiments, the compound has formula (XXV) or an enantiomer, diastereomer, hydrate, solvate, or pharmaceutically acceptable salt of formula (XXV), or a complex thereof:

(XXV)

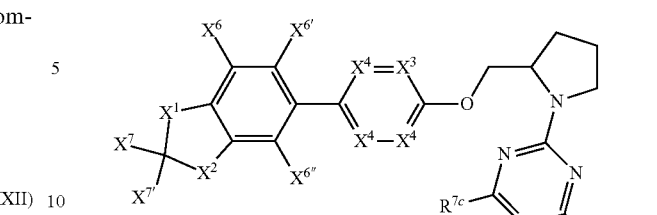

In some embodiments, the compound has formula (XXVI) or an enantiomer, diastereomer, hydrate, solvate, or pharmaceutically acceptable salt of formula (XXVI), or a complex thereof:

(XXVI)

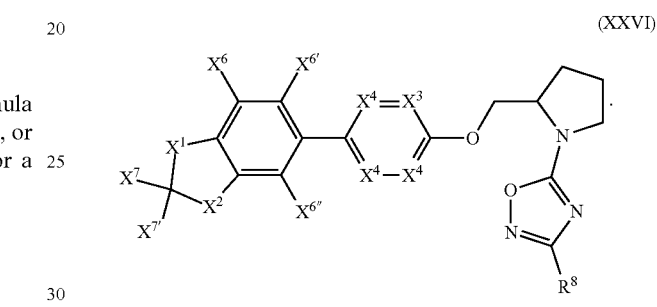

In some embodiments, the compound has formula (XXVII) or an enantiomer, diastereomer, hydrate, solvate, or pharmaceutically acceptable salt of formula (XXVII), or a complex thereof:

(XXVII)

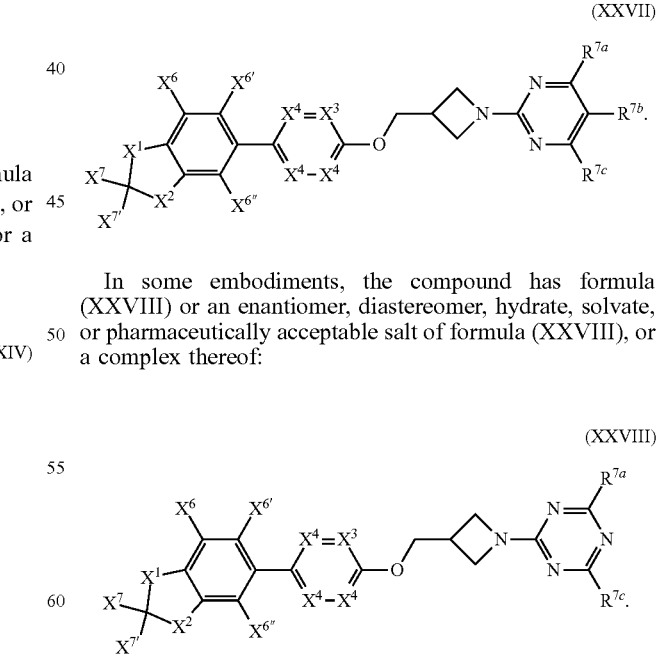

In some embodiments, the compound has formula (XXVIII) or an enantiomer, diastereomer, hydrate, solvate, or pharmaceutically acceptable salt of formula (XXVIII), or a complex thereof:

(XXVIII)

In some embodiments, the compound has formula (XXIX) or an enantiomer, diastereomer, hydrate, solvate, or pharmaceutically acceptable salt of formula (XXIX), or a complex thereof:

(XXIX)

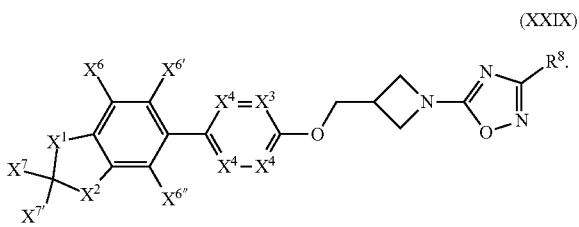

In some embodiments, the compound has formula (XXX) or an enantiomer, diastereomer, hydrate, solvate, or pharmaceutically acceptable salt of formula (XXIX), or a complex thereof:

(XXX)

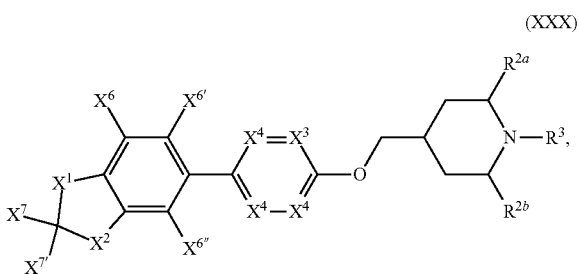

wherein, in alternative embodiments, $X^1$, $X^2$, $X^3$, $X^4$, $R^{2a}$, $R^{2b}$ and $R^3$ are as defined for each entry in Table 1A and for each of the 80 entries in Table 1A, $X^6$, $X^{6'}$, $X^{6''}$, $X^7$, $X^{7'}$ are as defined for each entry in Table 1B.

In some embodiments, $X^3$ is CF or N.

Various embodiments of the present invention relate to a compound, which is: 5-chloro-2-(4-{[4-(2,2-dimethyl-3,3-dioxido-1,3-benzoxathiol-6-yl)-2-fluorophenoxy]methyl}piperidin-1-yl)pyrimidine; 5-chloro-2-(4-{[4-(3,3-dioxidospiro[1,3-benzoxathiole-2,1'-cyclopentan]-6-yl)-2-fluorophenoxy]methyl}piperidin-1-yl)pyrimidine; 5-chloro-2-(4-{[4-(3,3-dioxidospiro[1,3-benzoxathiole-2,1'-cyclohexan]-6-yl)-2-fluorophenoxy]methyl}piperidin-1-yl)pyrimidine; or 5-chloro-2-(4-{[4-(3,3-dioxidospiro[1,3-benzoxathiole-2,1'-cyclobutan]-6-yl)-2-fluorophenoxy]methyl}piperidin-1-yl)pyrimidine.

Various embodiments of the present invention relate to a composition (e.g. a pharmaceutical composition) comprising one or more compounds defined herein and an excipient (e.g. a pharmaceutically acceptable excipient). The composition may further comprise an anti-diabetic agent. Various embodiments relate to a composition (e.g. a pharmaceutical composition) comprising one or more compounds defined herein and an anti-diabetic agent.

Various embodiments of the present invention relate to an effective amount of one or more compounds defined herein and a treatment for a tyrosine kinases-mediated disease or condition.

Various embodiments of the present invention relate to an effective amount of one or more compounds defined herein, a treatment for a tyrosine kinases-mediated disease or condition, and an excipient.

Various embodiments of the present invention relate to a method for treating or preventing diabetes-mediated diseases or conditions, such as Type 2 diabetes mellitus as well as other diseases and related metabolic disorders and conditions associated with GPR119 dysregulation, said method comprising administering to a subject an effective amount of certain compound(s) or composition(s) defined herein. Various embodiments of the present invention relate to use of certain compound(s) defined herein for treating, or for manufacturing a medicament for treating, a disease or condition associated with GPR119 dysregulation. The disease or condition may be Type 2 diabetes mellitus.

Various embodiments of the present invention relate to use of certain compound(s) defined herein in in vitro assays for modulating GPR119 receptor activity (e.g. as an agonist, whether as a full agonist or as a partial agonist). Various embodiments of the present invention relate to use of certain compound(s) defined herein in vivo assays for modulating GPR119 receptor activity (e.g. as an agonist, whether as a full agonist or as a partial agonist).

DETAILED DESCRIPTION OF THE INVENTION

Certain novel benzo[d][1,3]oxathioles, benzo[d][1,3]oxathiole 3-oxides, benzo[d][1,3]oxathiole 3,3-dioxides and related compounds of the present disclosure are agonists of the GPR119 receptor (whether as full or partial agonists). Accordingly, certain of these compounds are capable of treating and/or preventing diseases associated with GPR119 dysregulation, for example Type 2 diabetes mellitus as well as other diseases and related metabolic disorders and conditions associated with GPR119 dysregulation. Certain GPR119 activity modulators (partial or full agonists) of the present invention are capable of treating and preventing diseases associated with dysregulation of GPR119 activity, for example Type 2 diabetes mellitus, diabetes-mediated diseases or conditions, and metabolic disorders. In addition, without wishing to be limited by theory, it is believed that certain compounds of the disclosure can ameliorate, abate, otherwise cause to be controlled, diseases or conditions caused by GPR119 dysregulation.

I. Definitions

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a compound, method, product, use, composition, etcetera.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $—CF_3$, $—CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydroquinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1-C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1-C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposes of the present disclosure fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

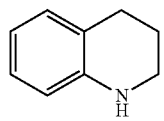

is, for the purposes of the present disclosure, considered a heterocyclic unit. 6,7-Dihydro-5H-cyclopentapyrimidine having the formula:

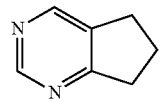

is, for the purposes of the present disclosure, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

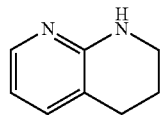

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the disclosure. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present disclosure to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (A-I)), —CN, —$NO_2$, oxo (=O), —$OR^{15}$, —$SR^{15}$, —$N(R^{15})_2$, —$NR^{15}C(O)R^{15}$, —$SO_2R^{15}$, —$SO_2OR^{15}$, —$SO_2N(R^{15})_2$, —$C(O)R^{15}$, —$C(O)OR^{15}$, —$C(O)N(R^{15})_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and $R^{15}$; wherein $R^{15}$, at each occurrence, independently is hydrogen, —OR$^{16}$, —SR$^{16}$, —C(O)R$^{16}$, —C(O)OR$^{16}$, —C(O)N(R$^{16}$)$_2$, —SO$_2$R$^{16}$, —S(O)$_2$OR$^{16}$, —N(R$^{16}$)$_2$, —NRC(O)R$^{16}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{15}$ units taken together with the atom(s) to which they are bound form an optionally substituted carbocycle or heterocycle wherein said carbocycle or heterocycle has 3 to 7 ring atoms; wherein $R^{16}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{16}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{17}$; for example, —OH, —OCH$_3$, —OCH$_2$CH$_3$, —OCH$_2$CH$_2$CH$_3$;
ii) —C(O)R$^{17}$; for example, —COCH$_3$, —COCH$_2$CH$_3$, —COCH$_2$CH$_2$CH$_3$;
iii) —C(O)OR$^{17}$; for example, —CO$_2$CH$_3$, —CO$_2$CH$_2$CH$_3$, —CO$_2$CH$_2$CH$_2$CH$_3$;
iv) —C(O)N(R$^{17}$)$_2$; for example, —CONH$_2$, —CONHCH$_3$, —CON(CH$_3$)$_2$;
v) —N(R$^{17}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{17}$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^{17}$)C(O)R$^{17}$;
xiii) Oxo (=O);
xiv) Heterocycle; and
xv) Heteroaryl;
wherein each $R^{17}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^{17}$ units can be taken together to form a ring comprising 3-7 ring atoms. In certain embodiments, each $R^{17}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present disclosure, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present disclosure the terms "compound," "analog," and "composition of matter" stand equally well for the compounds of the disclosure described herein, including all enantiomeric forms, diastereomeric forms, salts, and the like, and the terms "compound," "analog," and "composition of matter" are used interchangeably throughout the present disclosure.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R$^{16}$)$_2$, each $R^{16}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

II. Compounds of the Invention

There are disclosed compounds having formula (I):

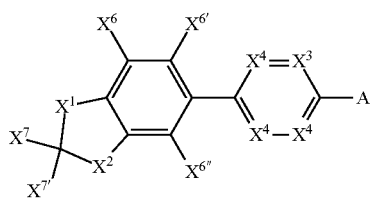

or an enantiomer, diastereomer, hydrate, solvate, or pharmaceutically acceptable salt of formula (I), or a prodrug or complex thereof, wherein:
$X^1$ is O and $X^2$ is S, SO or $SO_2$; or $X^2$ is O and $X^1$ is S, SO or $SO_2$;
$X^3$ is CH, CF and N;
each $X^4$ is independently CH and N;
A is

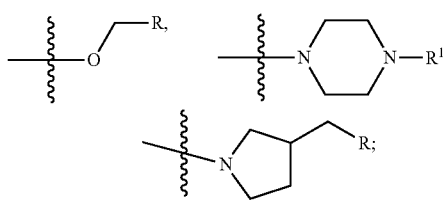

R is

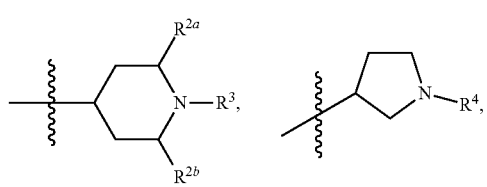

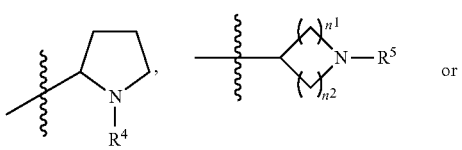

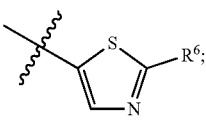

$R^1$ is hydrogen, C(O)O-tert-butyl or

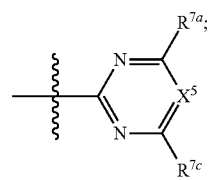

$R^{2a}$ is hydrogen or $C_{1-6}$ alkyl;
$R^{2b}$ is hydrogen or $C_{1-6}$ alkyl;
$R^3$ is hydrogen, $C_{1-6}$ alkyl, $C_{1-6}$ haloalkyl, $C(O)R^9$, $C(O)OR^{10}$, $C(O)NR^{10a}R^{10b}$, $CH_2C(O)OR^{10a}$,

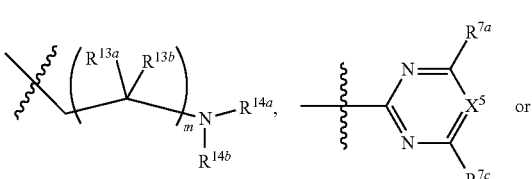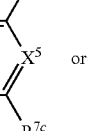

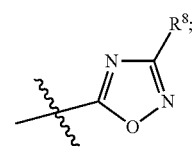

$R^4$ is hydrogen, $C_{1-6}$ alkyl, $C_{1-6}$ haloalkyl, $C(O)R^9$, $C(O)OR^{10}$, $C(O)NR^{10a}R^{10b}$,

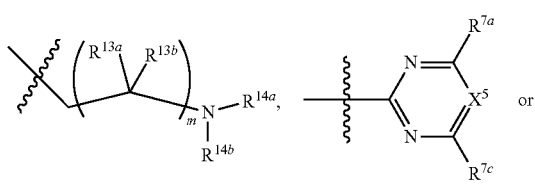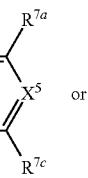

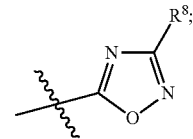

$R^5$ is hydrogen, $C_{1-6}$ alkyl, $C_{1-6}$ haloalkyl, $C(O)R^9$, $C(O)OR^{10}$, $C(O)NR^{10a}R^{10b}$,

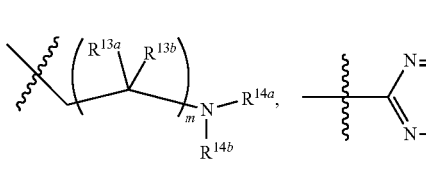

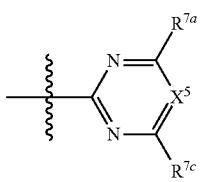

$R^{12}$ is

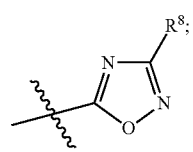

$R^6$ is

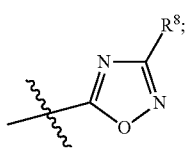

$NHR^{11}$ or $CH_2NHR^{12}$;

$R^{7a}$ is hydrogen, halogen, $C_{1-6}$ alkyl, $C_{3-7}$ branched alkyl, $C_{1-6}$ haloalkyl or $C_{1-6}$ alkoxy;

$R^{7b}$ is hydrogen, halogen, $C_{1-6}$ alkyl, $C_{3-7}$ branched alkyl, $C_{1-6}$ haloalkyl or $C_{1-6}$ alkoxy;

$R^{7c}$ is hydrogen, halogen, $C_{1-6}$ alkyl, $C_{3-7}$ branched alkyl, $C_{1-6}$ haloalkyl or $C_{1-6}$ alkoxy;

$R^8$ is hydrogen, halogen, $C_{1-6}$ alkyl, $C_{3-7}$ branched alkyl or $C_{3-7}$ cycloalkyl;

$R^9$ is $C_{1-6}$ alkyl, $C_{3-7}$ branched alkyl or

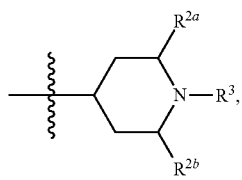

$R^{10}$ is $C_{1-6}$ alkyl or $C_{3-7}$ branched alkyl;

$R^{10a}$ is hydrogen, $C_{1-6}$ alkyl or $C_{3-7}$ branched alkyl;

$R^{10b}$ is hydrogen, $C_{1-6}$ alkyl or $C_{3-7}$ branched alkyl;

$R^{11}$ is

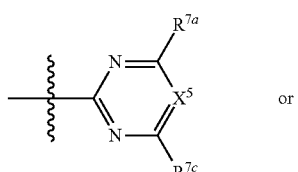

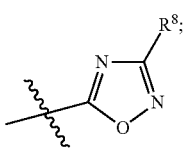

each $R^{13a}$ is independently hydrogen, $C_{1-6}$ alkyl or $C_{3-7}$ branched alkyl;

each $R^{13b}$ is independently hydrogen, $C_{1-6}$ alkyl or $C_{3-7}$ branched alkyl;

each $R^{14a}$ is independently hydrogen, $C_{1-6}$ alkyl, $C_{3-7}$ branched alkyl or C(O)O-tert-butyl;

each $R^{14b}$ is independently hydrogen, $C_{1-6}$ alkyl or $C_{3-7}$ branched alkyl;

$X^5$ is N or $CR^{7b}$;

$n^1$ is 1 or 2;

$n^2$ is 1 or 2;

and m is 1, 2, 3, 4, 5, 6 or 7;

each of $X^6$, $X^{6'}$ and $X^{6''}$ is independently H, halogen, $C_{1-3}$ alkyl, $C_{1-3}$ haloalkyl, $C_{1-3}$ alkoxy, $C_{1-3}$ hydroxyalkyl, or $C_{1-3}(O)NR^{15a}R^{15b}$;

each of $X^7$ and $X^{7'}$ is independently hydrogen, halogen, $C_{1-3}$ alkyl, $C_{1-3}$ haloalkyl, $C_{1-3}$ alkoxy, $C_{1-3}$ hydroxyalkyl, $C_{1-3}$ aminoalkyl or $C_{1-3}(O)NR^{15a}R^{15b}$, or both $X^7$ and $X^{7'}$ together form $C_{3-6}$ cycloalkyl or a heterocycle ring having 3-6 carbons and 0 or 1 oxygen, sulphur or nitrogen atoms in the ring, wherein each carbon ring atom of the $C_{3-6}$ cycloalkyl or the heterocycle is optionally substituted with hydrogen, $C_{1-3}$ alkyl, hydroxyl, halogen, amino, $C_{1-3}$ haloalkyl, $C_{1-3}$ alkoxy, $C_{1-3}$ hydroxyalkyl or $C_{1-3}(O)NR^{15a}R^{15b}$; when each of $X^6$, $X^{6'}$ and $X^{6''}$ is hydrogen, at least $X^7$ or $X^{7'}$ is not hydrogen;

when both $X^7$ and $X^{7'}$ are hydrogen, at least one of $X^6$, $X^{6'}$ and $X^{6''}$ is not hydrogen;

each of $R^{15a}$ and $R^{15b}$ is independently hydrogen, $C_{1-3}$ alkyl or $C_3$ branched alkyl.

In some embodiments, the compounds have formula (II) or an enantiomer, diastereomer, hydrate, solvate, or pharmaceutically acceptable salt of formula (II), or a complex thereof:

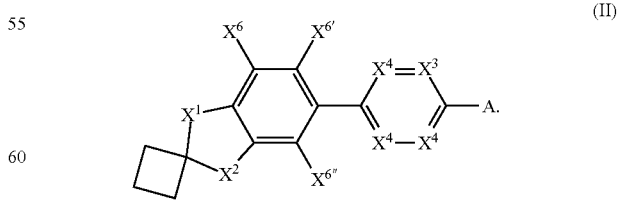

(II)

In some embodiments, the compounds have formula (III) or an enantiomer, diastereomer, hydrate, solvate, or pharmaceutically acceptable salt of formula (III), or a complex thereof:

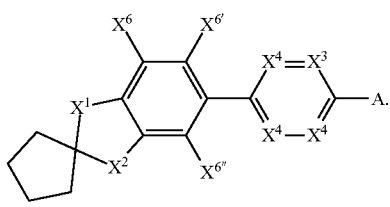

(III)

In some embodiments, the compounds have formula (IV) or an enantiomer, diastereomer, hydrate, solvate, or pharmaceutically acceptable salt of formula (IV), or a complex thereof:

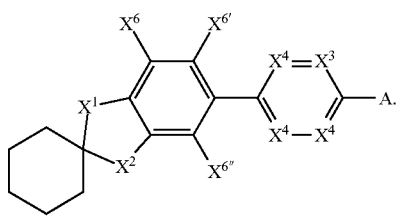

(IV)

In some embodiments, the compounds have formula (V) or an enantiomer, diastereomer, hydrate, solvate, or pharmaceutically acceptable salt of formula (V), or a complex thereof:

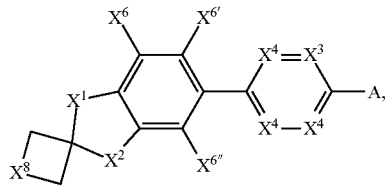

(V)

wherein $X^8$ is NH or O.

In some embodiments, the compounds have formula (VI) or an enantiomer, diastereomer, hydrate, solvate, or pharmaceutically acceptable salt of formula (VI), or a complex thereof:

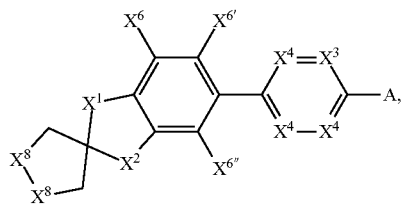

(VI)

wherein: one $X^8$ is NH or O; and one $X^8$ is $CH_2$.

In some embodiments, the compounds have formula (VII) or an enantiomer, diastereomer, hydrate, solvate, or pharmaceutically acceptable salt of formula (VII), or a complex thereof:

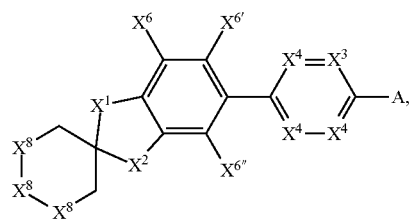

(VII)

wherein: one $X^8$ is NH or O; and each of two $X^8$ is $CH_2$.

In some embodiments, the compounds have formula (VIII) or an enantiomer, diastereomer, hydrate, solvate, or pharmaceutically acceptable salt of formula (VIII), or a complex thereof:

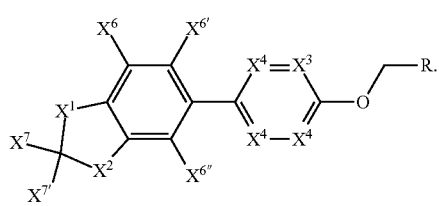

(VIII)

In some embodiments, the compounds have formula (IX) or an enantiomer, diastereomer, hydrate, solvate, or pharmaceutically acceptable salt of formula (IX), or a complex thereof:

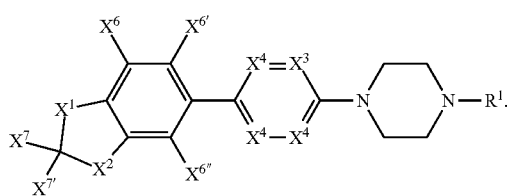

(IX)

In some embodiments, the compounds have formula (X) or an enantiomer, diastereomer, hydrate, solvate, or pharmaceutically acceptable salt of formula (X), or a complex thereof:

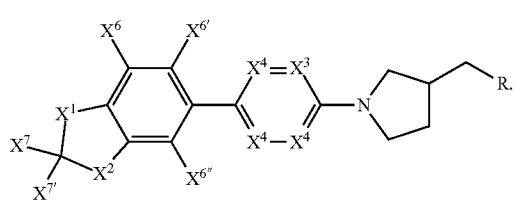

(X)

In some embodiments, the compounds have formula (XI) or an enantiomer, diastereomer, hydrate, solvate, or pharmaceutically acceptable salt of formula (XI), or a complex thereof:

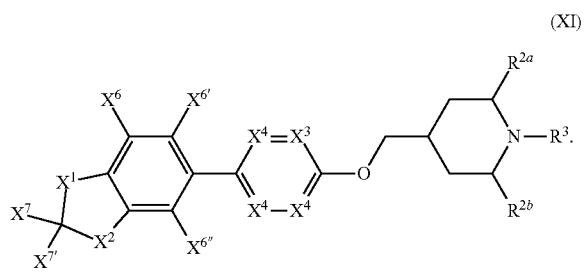

(XI)

In some embodiments, the compounds have formula (XII) or an enantiomer, diastereomer, hydrate, solvate, or pharmaceutically acceptable salt of formula (XII), or a complex thereof:

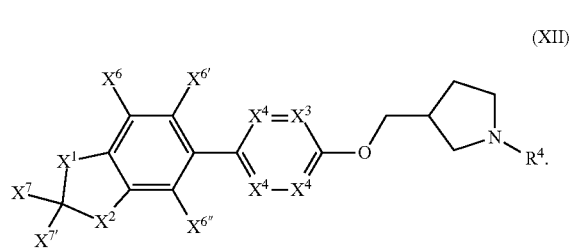

(XII)

In some embodiments, the compounds have formula (XIII) or an enantiomer, diastereomer, hydrate, solvate, or pharmaceutically acceptable salt of formula (XIII), or a complex thereof:

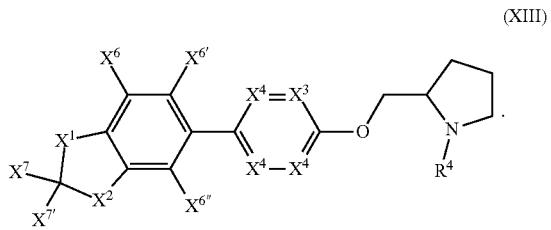

(XIII)

In some embodiments, the compounds have formula (XIV) or an enantiomer, diastereomer, hydrate, solvate, or pharmaceutically acceptable salt of formula (XIV), or a complex thereof:

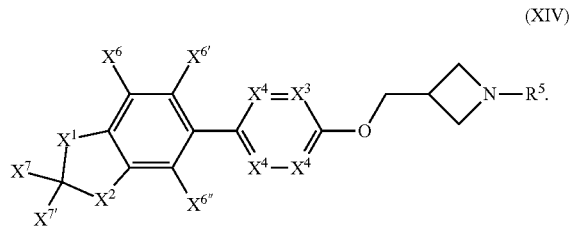

(XIV)

In some embodiments, the compounds have formula (XV) or an enantiomer, diastereomer, hydrate, solvate, or pharmaceutically acceptable salt of formula (XV), or a complex thereof:

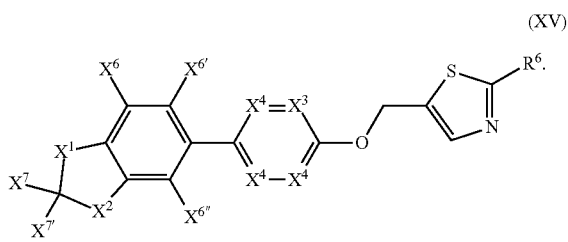

(XV)

In some embodiments, the compounds have formula (XVI) or an enantiomer, diastereomer, hydrate, solvate, or pharmaceutically acceptable salt of formula (XVI), or a complex thereof:

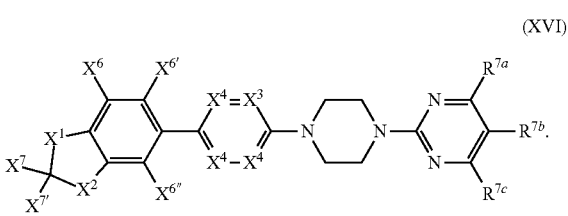

(XVI)

The compounds of the present invention include compounds having formula (XVII) or an enantiomer, diastereomer, hydrate, solvate, or pharmaceutically acceptable salt of formula (XVII), or a complex thereof

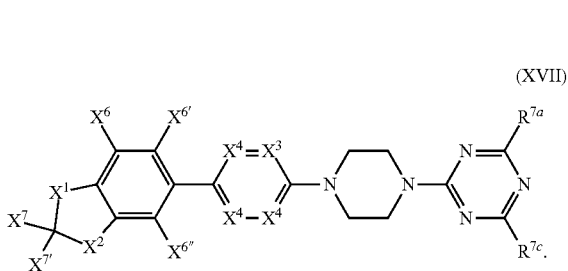

(XVII)

In some embodiments, the compounds have formula (XVIII) or an enantiomer, diastereomer, hydrate, solvate, or pharmaceutically acceptable salt of formula (XVIII), or a complex thereof:

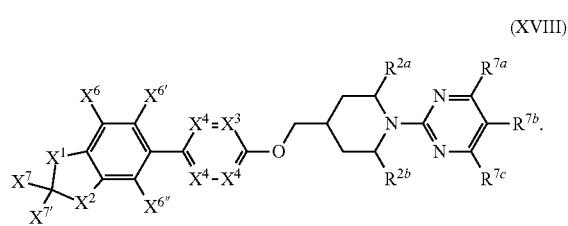

(XVIII)

In some embodiments, the compounds have formula (XIX) or an enantiomer, diastereomer, hydrate, solvate, or pharmaceutically acceptable salt of formula (XIX), or a complex thereof:

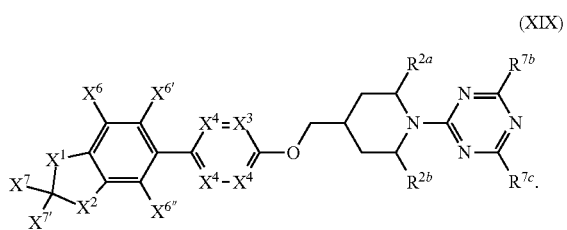

(XIX)

In some embodiments, the compounds have formula (XX) or an enantiomer, diastereomer, hydrate, solvate, or pharmaceutically acceptable salt of formula (XX), or a complex thereof:

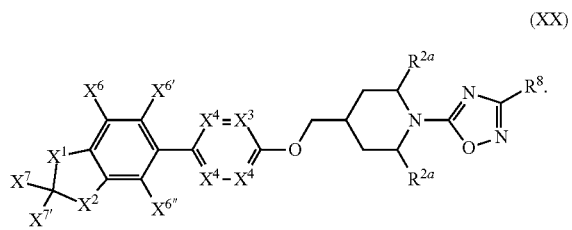

(XX)

In some embodiments, the compounds have formula (XXI) or an enantiomer, diastereomer, hydrate, solvate, or pharmaceutically acceptable salt of formula (XXI), or a complex thereof:

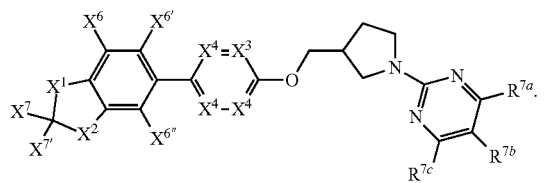

(XXI)

The compounds of the present invention include compounds having formula (XXII) or an enantiomer, diastereomer, hydrate, solvate, or pharmaceutically acceptable salt of formula (XXII), or a complex thereof:

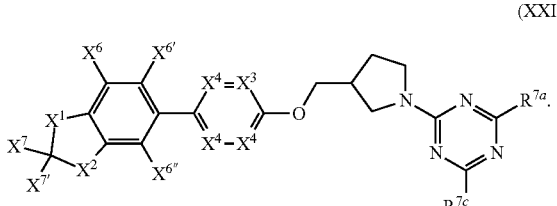

(XXII)

In some embodiments, the compounds have formula (XXIII) or an enantiomer, diastereomer, hydrate, solvate, or pharmaceutically acceptable salt of formula (XXIII), or a complex thereof:

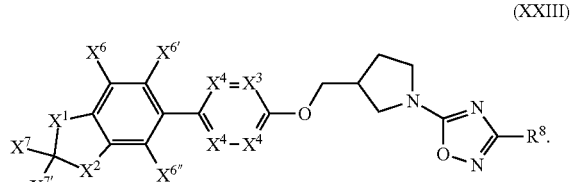

(XXIII)

In some embodiments, the compounds have formula (XXIV) or an enantiomer, diastereomer, hydrate, solvate, or pharmaceutically acceptable salt of formula (XXIV), or a complex thereof:

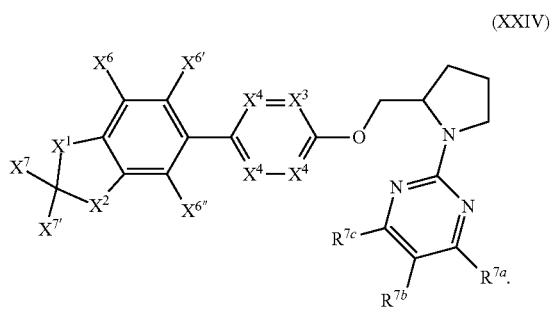

(XXIV)

In some embodiments, the compounds have formula (XXV) or an enantiomer, diastereomer, hydrate, solvate, or pharmaceutically acceptable salt of formula (XXV), or a complex thereof:

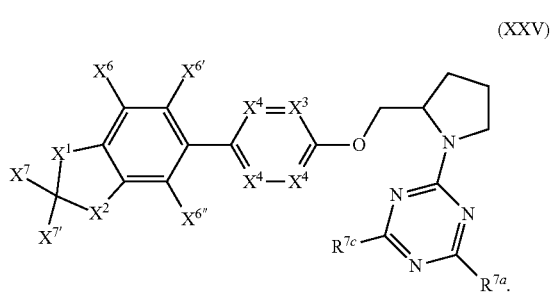

(XXV)

In some embodiments, the compounds have formula (XXVI) or an enantiomer, diastereomer, hydrate, solvate, or pharmaceutically acceptable salt of formula (XXVI), or a complex thereof:

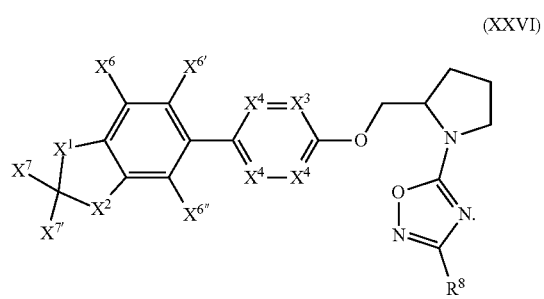

(XXVI)

In some embodiments, the compounds have formula (XXVII) or an enantiomer, diastereomer, hydrate, solvate, or pharmaceutically acceptable salt of formula (XXVII), or a complex thereof:

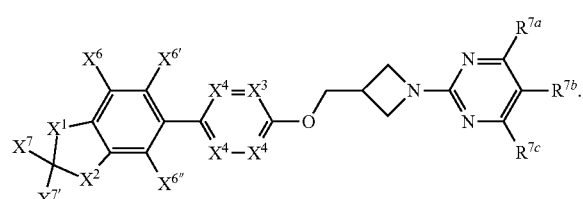
(XXVII)

In some embodiments, the compounds have formula (XXVIII) or an enantiomer, diastereomer, hydrate, solvate, or pharmaceutically acceptable salt of formula (XXVIII), or a complex thereof:

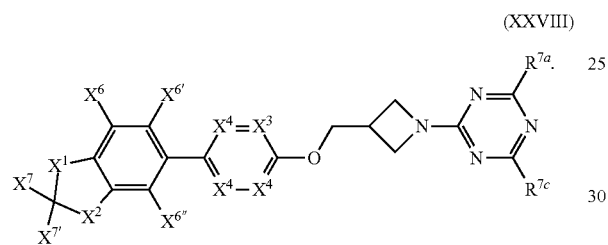
(XXVIII)

In some embodiments, the compounds have formula (XXIX) or an enantiomer, diastereomer, hydrate, solvate, or pharmaceutically acceptable salt of formula (XXIX), or a complex thereof:

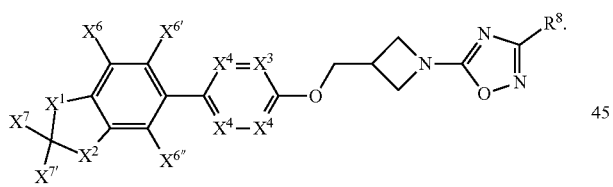
(XXIX)

In some embodiments $X^1$ is O.
In some embodiments $X^1$ is S.
In some embodiments $X^1$ is SO.
In some embodiments $X^1$ is $SO_2$.
In some embodiments $X^2$ is O.
In some embodiments $X^2$ is S.
In some embodiments $X^2$ is SO.
In some embodiments $X^2$ is $SO_2$.
In some embodiments $X^3$ is CH.
In some embodiments $X^3$ is CF or N.
In some embodiments $X^3$ is CF.
In some embodiments $X^3$ is N.
In some embodiments $X^4$ is CH.
In some embodiments $X^4$ is N. In some embodiments only one $X^4$ is N. In some embodiments, two $X^4$ is N. In some embodiments at least one $X^4$ is N and $X^3$ is not N.

In some embodiments A is

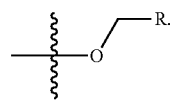

In some embodiments A is

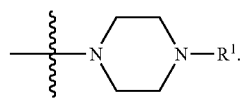

In some embodiments A is

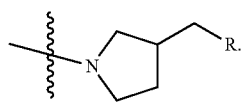

In some embodiments R

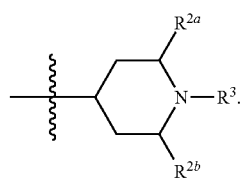

In some embodiments R is

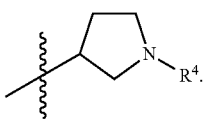

In some embodiments R

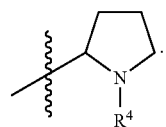

In some embodiments R is

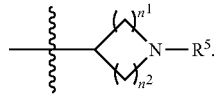

In some embodiments R is

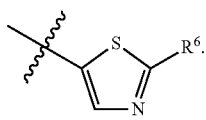

In some embodiments $R^1$ is

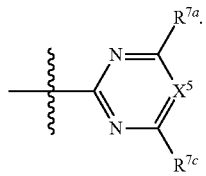

In some embodiments $R^1$ is hydrogen.
In some embodiments $R^1$ is C(O)O-tert-butyl.
In some embodiments $R^{2a}$ is hydrogen.
In some embodiments $R^{2a}$ is $C_{1-6}$ alkyl.
In some embodiments $R^{2b}$ is hydrogen.
In some embodiments $R^{2b}$ is $C_{1-6}$ alkyl.
In some embodiments $R^3$ is hydrogen.
In some embodiments $R^3$ is $C_{1-6}$ alkyl.
In some embodiments $R^3$ is $C_{1-6}$ haloalkyl.
In some embodiments $R^3$ is $C(O)R^9$.
In some embodiments $R^3$ is $C(O)OR^{10}$.
In some embodiments $R^3$ is not $C(O)OR^{10}$.
In some embodiments $R^3$ is $C(O)NR^{10a}R^{10b}$.
In some embodiments $R^3$ is $CH_2C(O)OR^{10a}$.
In some embodiments $R^3$ is

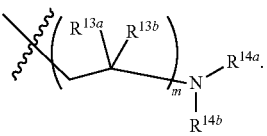

In some embodiments $R^3$ is

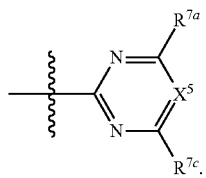

In some embodiments $R^3$ is

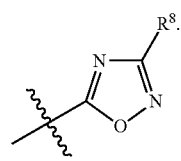

In some embodiments $R^4$ is hydrogen.
In some embodiments $R^4$ is $C_{1-6}$ alkyl.
In some embodiments $R^4$ is $C_{1-6}$ haloalkyl.
In some embodiments $R^4$ is $C(O)R^9$.
In some embodiments $R^4$ is $C(O)OR^{10}$.
In some embodiments $R^4$ is $C(O)NR^{10a}R^{10b}$.
In some embodiments $R^4$ is

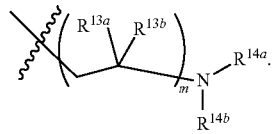

In some embodiments $R^4$ is

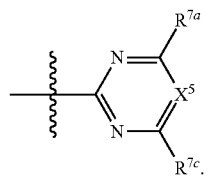

In some embodiments $R^4$ is

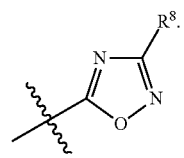

In some embodiments $R^5$ is hydrogen.
In some embodiments $R^5$ is $C_{1-6}$ alkyl.
In some embodiments $R^5$ is $C_{1-6}$ haloalkyl.
In some embodiments $R^5$ is $C(O)R^9$.
In some embodiments $R^5$ is $C(O)OR^{10}$.
In some embodiments $R^5$ is $C(O)NR^{10a}R^{10b}$.
In some embodiments $R^5$ is

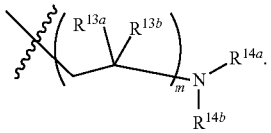

In some embodiments $R^5$ is

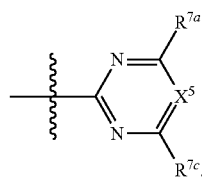

In some embodiments $R^5$ is

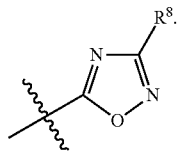

In some embodiments $R^6$ is

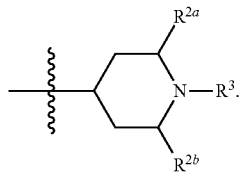

In some embodiments $R^6$ is $NHR^{11}$.
In some embodiments $R^6$ is $CH_2NHR^{12}$.
In some embodiments $R^{7a}$ is hydrogen.
In some embodiments $R^{7a}$ is halogen. In some embodiments $R^{7a}$ is fluorine.
In some embodiments $R^{7a}$ is $C_{1-6}$ alkyl.
In some embodiments $R^{7a}$ is $C_{3-7}$ branched alkyl.
In some embodiments $R^{7a}$ is $C_{1-6}$ haloalkyl.
In some embodiments $R^{7a}$ is $C_{1-6}$ alkoxy.
In some embodiments $R^{7b}$ is hydrogen.
In some embodiments $R^{7b}$ is halogen. In some embodiments $R^{7b}$ is fluorine.
In some embodiments $R^{7b}$ is $C_{1-6}$ alkyl.
In some embodiments $R^{7b}$ is $C_{3-7}$ branched alkyl.
In some embodiments $R^{7b}$ is $C_{1-6}$ haloalkyl.
In some embodiments $R^{7b}$ is $C_{1-6}$ alkoxy.
In some embodiments $R^{7c}$ is hydrogen.
In some embodiments $R^{7c}$ is halogen. In some embodiments $R^{7c}$ is fluorine.
In some embodiments $R^{7c}$ is $C_{1-6}$ alkyl.
In some embodiments $R^{7c}$ is $C_{3-7}$ branched alkyl.
In some embodiments $R^{7c}$ is $C_{1-6}$ haloalkyl.
In some embodiments $R^{7c}$ is $C_{1-6}$ alkoxy.
In some embodiments $R^8$ is hydrogen.
In some embodiments $R^8$ is halogen. In some embodiments $R^8$ is fluorine.
In some embodiments $R^8$ is $C_{1-6}$ alkyl.
In some embodiments $R^8$ is $C_{3-7}$ branched alkyl
In some embodiments $R^8$ is $C_{3-7}$ cycloalkyl.
In some embodiments $R^9$ is $C_{1-6}$ alkyl.
In some embodiments $R^9$ is $C_{3-7}$ branched alkyl.
In some embodiments $R^9$ is

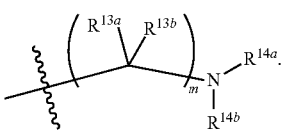

In some embodiments $R^{10}$ is $C_{1-6}$ alkyl.
In some embodiments $R^{10}$ is $C_{3-7}$ branched alkyl.
In some embodiments $R^{10a}$ is hydrogen.
In some embodiments $R^{10a}$ is $C_{1-6}$ alkyl.
In some embodiments $R^{10a}$ is $C_{3-7}$ branched alkyl.
In some embodiments $R^{10b}$ is hydrogen.
In some embodiments $R^{10b}$ is $C_{1-6}$ alkyl.
In some embodiments $R^{10b}$ is $C_{3-7}$ branched alkyl.
In some embodiments $R^{11}$ is

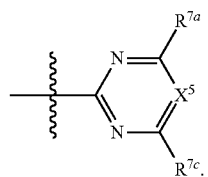

In some embodiments $R^{11}$ is

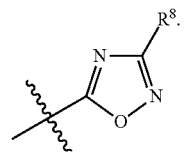

In some embodiments $R^{12}$ is

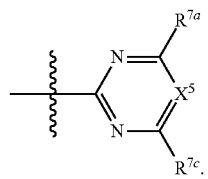

In some embodiments $R^{12}$ is

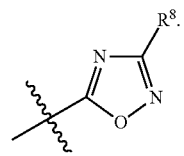

In some embodiments $R^{13a}$ is hydrogen.
In some embodiments $R^{13a}$ is $C_{1-6}$ alkyl.
In some embodiments $R^{13a}$ is $C_{3-7}$ branched alkyl.
In some embodiments $R^{13b}$ is hydrogen.
In some embodiments $R^{13b}$ is $C_{1-6}$ alkyl.
In some embodiments $R^{13b}$ is $C_{3-7}$ branched alkyl.
In some embodiments $R^{14a}$ is hydrogen.
In some embodiments $R^{14a}$ is $C_{1-6}$ alkyl.
In some embodiments $R^{14a}$ is $C_{3-7}$ branched alkyl.
In some embodiments $R^{14a}$ is C(O)O-tert-butyl.
In some embodiments $R^{14b}$ is hydrogen.
In some embodiments $R^{14b}$ is $C_{1-6}$ alkyl.
In some embodiments $R^{14b}$ is $C_{3-7}$ branched alkyl.
In some embodiments $X^5$ is N.
In some embodiments $X^5$ is and $CR^{7b}$.
In some embodiments $n^1$ is 1.
In some embodiments $n^1$ is 2.
In some embodiments $n^2$ is 1.
In some embodiments $n^2$ is 2.
In some embodiments m is 1.
In some embodiments m is 2.
In some embodiments m is 3.
In some embodiments m is 4.

In some embodiments m is 5.
In some embodiments m is 6.
In some embodiments m is 7.
In some embodiments $X^6$ is halogen. The halogen may be chlorine. The halogen may be bromine. The halogen may be iodine. In some embodiments $X^6$ is fluorine.
In some embodiments $X^{6'}$ is halogen. The halogen may be chlorine. The halogen may be bromine. The halogen may be iodine. In some embodiments $X^{6'}$ is fluorine.
In some embodiments $X^{6''}$ is halogen. The halogen may be chlorine. The halogen may be bromine. The halogen may be iodine. In some embodiments $X^{6''}$ is fluorine.
In some embodiments $X^6$ and $X^{6'}$ are halogen. Each halogen may independently be chlorine, bromine, iodine or fluorine. In some embodiments $X^6$ and $X^{6'}$ are both fluorine.
In some embodiments $X^{6'}$ and $X^{6''}$ are halogen. Each halogen may independently be chlorine, bromine, iodine or fluorine. In some embodiments $X^{6'}$ and $X^{6''}$ are both fluorine.
In some embodiments $X^6$ and $X^{6''}$ are halogen. Each halogen may independently be chlorine, bromine, iodine or fluorine. In some embodiments $X^6$ and $X^{6''}$ are both fluorine.
In some embodiments $X^6$, $X^{6'}$ and $X^{6''}$ are halogen. Each halogen may independently be chlorine, bromine, iodine or fluorine. In some embodiments each of $X^6$, $X^{6'}$ and $X^{6''}$ is fluorine.
In some embodiments $X^6$, $X^{6'}$ and $X^{6''}$ are halogen, H and H, respectively. In some embodiments $X^6$, $X^{6'}$ and $X^{6''}$ are H, halogen and H, respectively. In some embodiments $X^6$, $X^{6'}$ and $X^{6''}$ are H, H and halogen, respectively. The halogen may be chlorine. The halogen may be bromine. The halogen may be iodine. In some embodiments $X^6$, $X^{6'}$ and $X^{6''}$ are F, H and H, respectively. In some embodiments $X^6$, $X^{6'}$ and $X^{6''}$ are H, F and H, respectively. In some embodiments $X^6$, $X^{6'}$ and $X^{6''}$ are H, H and F, respectively.

In some embodiments $X^6$, $X^{6'}$ and $X^{6''}$ are each H.
In some embodiments $X^6$ is $C_{1-3}$ alkyl. In some embodiments, $X^6$ is methyl.
In some embodiments $X^6$ is $C_{1-3}$ haloalkyl.
In some embodiments $X^6$ is $C_{1-3}$ alkoxy.
In some embodiments $X^6$ is $C_{1-3}$ hydroxyalkyl.
In some embodiments $X^6$ is $C_{1-3}(O)NR^{15a}R^{15b}$.
In some embodiments $X^{6'}$ is $C_{1-3}$ alkyl. In some embodiments, $X^{6'}$ is methyl.
In some embodiments $X^{6'}$ is $C_{1-3}$ haloalkyl.
In some embodiments $X^{6'}$ is $C_{1-3}$ alkoxy.
In some embodiments $X^{6'}$ is $C_{1-3}$ hydroxyalkyl.
In some embodiments $X^{6'}$ is $C_{1-3}(O)NR^{15a}R^{15b}$.
In some embodiments $X^{6''}$ is $C_{1-3}$ alkyl. In some embodiments, $X^{6''}$ is methyl.
In some embodiments $X^{6''}$ is $C_{1-3}$ haloalkyl.
In some embodiments $X^{6''}$ is $C_{1-3}$ alkoxy.
In some embodiments $X^{6''}$ is $C_{1-3}$ hydroxyalkyl.
In some embodiments $X^{6''}$ is $C_{1-3}(O)NR^{15a}R^{15b}$.
In some embodiments $X^7$ is hydrogen.
In some embodiments $X^7$ is halogen. The halogen may be chlorine. The halogen may be bromine. The halogen may be iodine. In some embodiments $X^7$ is fluorine.
In some embodiments $X^7$ is $C_{1-3}$ alkyl. In some embodiments $X^7$ is methyl. In some embodiments $X^7$ is ethyl.
In some embodiments $X^7$ is $C_{1-3}$ haloalkyl. In some embodiments, $X^7$ is $CH_2CF_3$.
In some embodiments $X^7$ is $C_{1-3}$ alkoxy.
In some embodiments $X^7$ is $C_{1-3}$ hydroxyalkyl.
In some embodiments $X^7$ is $C_{1-3}$ aminoalkyl.
In some embodiments $X^7$ is $C_{1-3}(O)NR^{15a}R^{15b}$.
In some embodiments $X^{7'}$ is hydrogen.

In some embodiments $X^{7'}$ is halogen. The halogen may be chlorine. The halogen may be bromine. The halogen may be iodine. In some embodiments $X^{7'}$ is fluorine.
In some embodiments $X^{7'}$ is $C_{1-3}$ alkyl. In some embodiments $X^{7'}$ is methyl. In some embodiments $X^{7'}$ is ethyl.
In some embodiments $X^{7'}$ is $C_{1-3}$ haloalkyl. In some embodiments, $X^{7'}$ is $CH_2CF_3$.
In some embodiments $X^{7'}$ is $C_{1-3}$ alkoxy.
In some embodiments $X^{7'}$ is $C_{1-3}$ hydroxyalkyl.
In some embodiments $X^{7'}$ is $C_{1-3}$ aminoalkyl.
In some embodiments $X^{7'}$ is $C_{1-3}(O)NR^{15a}R^{15b}$.
In some embodiments both $X^7$ and $X^{7'}$ together form $C_{3-6}$ cycloalkyl having 3-6 carbons. In some embodiments both $X^7$ and $X^{7'}$ together form $C_{3-6}$ heterocycle ring having 3-6 carbons and 1 oxygen, sulphur or nitrogen atom in the ring. In some embodiments both $X^7$ and $X^{7'}$ together form $C_{3-6}$ heterocycle ring having 3-6 carbons and 1 oxygen atom in the ring. In some embodiments both $X^7$ and $X^{7'}$ together form $C_{3-6}$ heterocycle ring having 3-6 carbons and 1 sulphur atom in the ring. In some embodiments both $X^7$ and $X^{7'}$ together form $C_{3-6}$ heterocycle ring having 3-6 carbons and 1 nitrogen atom in the ring. In some embodiments no carbon ring atom of the $C_{3-6}$ cycloalkyl or the heterocycle is substituted (except with hydrogen). In some embodiments, 1, 2 or 3 (or 4, 5 or 6, if present) carbon ring atoms of the $C_{3-6}$ cycloalkyl or the heterocycle is substituted with $C_{1-3}$ alkyl, hydroxyl, halogen, amino, $C_{1-3}$ haloalkyl, $C_{1-3}$ alkoxy, $C_{1-3}$ hydroxyalkyl or $C_{1-3}(O)NR^{15a}R^{15b}$. In some embodiments, the halogen is fluorine.

In some embodiments both $X^7$ and $X^{7'}$ together form

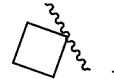

In some embodiments both $X^7$ and $X^{7'}$ together form

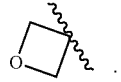

In some embodiments both $X^7$ and $X^{7'}$ together form

wherein R is H or $C_{1-3}$ alkyl.

In some embodiments both $X^7$ and $X^{7'}$ together form

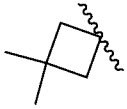

In some embodiments both $X^7$ and $X^{7'}$ together form

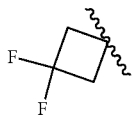

In some embodiments both $X^7$ and $X^{7'}$ together form

In some embodiments both $X^7$ and $X^{7'}$ together form

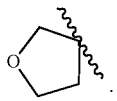

In some embodiments both $X^7$ and $X^{7'}$ together form

wherein R is H or $C_{1-3}$ alkyl.

In some embodiments both $X^7$ and $X^{7'}$ together form

In some embodiments both $X^7$ and $X^{7'}$ together form

In some embodiments both $X^7$ and $X^{7'}$ together form

In some embodiments both $X^7$ and $X^{7'}$ together form

wherein R is H or $C_{1-3}$ alkyl.

In some embodiments both $X^7$ and $X^{7'}$ together form

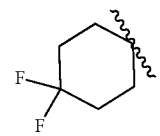

In some embodiments $R^{15a}$ is hydrogen.
In some embodiments $R^{15a}$ is $C_{1-3}$ alkyl.
In some embodiments $R^{15a}$ is $C_3$ branched alkyl.
In some embodiments $R^{15b}$ is hydrogen.
In some embodiments $R^{15b}$ is $C_{1-3}$ alkyl.
In some embodiments $R^{15b}$ is $C_3$ branched alkyl.

In some embodiments, the compound excludes any compound having formula (Ia)

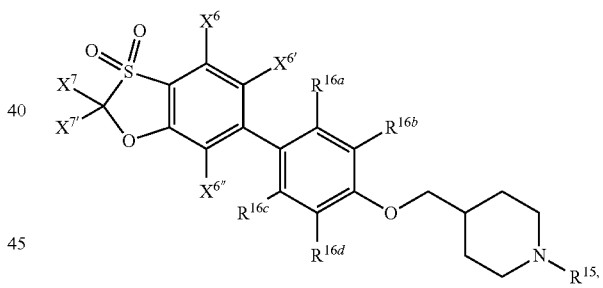

(Ia)

wherein:
$X^6$, $X^{6'}$, $X^{6''}$, $X^7$ and $X^{7'}$ are as defined for any embodiments defined above or elsewhere herein;

$R^{15}$ is: hydrogen; $C_1$-$C_5$ alkyl; halogen-substituted $C_1$-$C_5$ alkyl; acyl selected from the group $C_1$-$C_5$ alkyl(C=O) and phenyl(C=O); substituted heteroaryl representing a monocyclic aromatic group with two nitrogen atoms which is substituted by a halogen or ($C_1$-$C_5$) alkyl; ($C_1$-$C_3$) alkylsulphonyl; or phenylsulphonyl; and $R^{16a}$, $R^{16b}$, $R^{16c}$ and $R^{16d}$ are hydrogen or one or two substitutents simultaneously selected from the group consisting of halogen, ($C_1$-$C_3$) alkyl, halogen-substituted ($C_1$-$C_3$)alkyl, ($C_1$-$C_3$)alkylsulphonyl or cyano.

In some embodiments, the compounds have formula (XVIIIa) or an enantiomer, diastereomer, hydrate, solvate, or pharmaceutically acceptable salt of formula (XVIIIa), or a complex thereof:

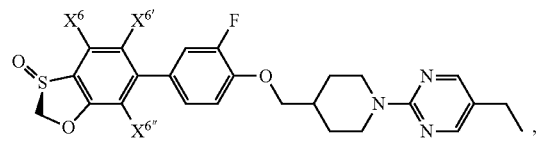

(XVIIIa)

wherein one of $X^6$, $X^{6'}$ and $X^{6''}$ is fluorine and two of $X^6$, $X^{6'}$ and $X^{6''}$ are hydrogen. In some such embodiments, $X^6$ is F. In some such embodiments, $X^{6'}$ is F. In some such embodiments, $X^{6''}$ is F.

Exemplary embodiments include compounds having the formula (XXX) or an enantiomer, diastereomer, hydrate, solvate, prodrug, complex, or pharmaceutically acceptable salt form thereof:

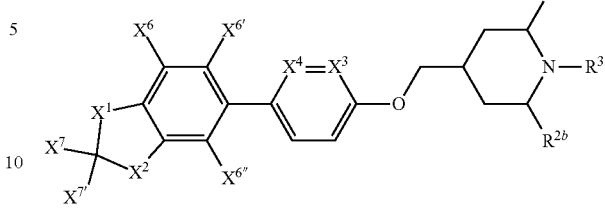

(XXX)

wherein non-limiting examples of $X^1$, $X^2$, $X^3$, $X^4$, $R^{2a}$, $R^{2b}$ and $R^3$ are defined in Table 1A and for each of the 80 entries in Table 1A, non-limiting examples of $X^6$, $X^{6'}$, $X^{6''}$, $X^7$, $X^{7'}$ are defined in Table 1B.

TABLE 1A

Exemplary definitions for $X^1$, $X^2$, $X^3$, $X^4$, $R^{2a}$, $R^{2b}$ and $R^3$ in exemplary compounds of the formula (XXX)

| Entry | $X^1$ | $X^2$ | $X^3$ | $X^4$ | $R^{2a}$ | $R^{2b}$ | $R^3$ |
|---|---|---|---|---|---|---|---|
| 1 | $SO_2$ | O | N | N | H | H | pyrimidin-2-yl, 5-Cl |
| 2 | $SO_2$ | O | N | N | $CH_3$ | H | pyrimidin-2-yl, 5-Cl |
| 3 | $SO_2$ | O | N | N | $CH_3$ | $CH_3$ | pyrimidin-2-yl, 5-Cl |
| 4 | O | $SO_2$ | N | N | $CH_3$ | $CH_3$ | pyrimidin-2-yl, 5-Cl |
| 5 | O | $SO_2$ | N | N | H | H | pyrimidin-2-yl, 5-Cl |
| 6 | O | $SO_2$ | N | N | $CH_3$ | H | pyrimidin-2-yl, 5-Cl |
| 7 | $SO_2$ | O | CF | N | H | H | pyrimidin-2-yl, 5-ethyl |
| 8 | $SO_2$ | O | CF | N | H | $CH_3$ | pyrimidin-2-yl, 5-ethyl |
| 9 | $SO_2$ | O | CF | N | $CH_3$ | $CH_3$ | pyrimidin-2-yl, 5-ethyl |

TABLE 1A-continued
Exemplary definitions for $X^1$, $X^2$, $X^3$, $X^4$, $R^{2a}$, $R^{2b}$ and $R^3$ in exemplary compounds of the formula (XXX)
| Entry | $X^1$ | $X^2$ | $X^3$ | $X^4$ | $R^{2a}$ | $R^{2b}$ | $R^3$ |
|---|---|---|---|---|---|---|---|
| 10 | O | SO$_2$ | CF | N | H | H | 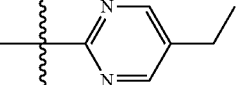 |
| 11 | O | SO$_2$ | CF | CH | H | CH$_3$ | 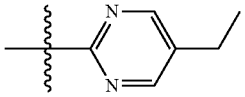 |
| 12 | O | SO$_2$ | CF | CH | CH$_3$ | CH$_3$ | 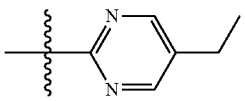 |
| 13 | SO$_2$ | O | N | N | H | H | 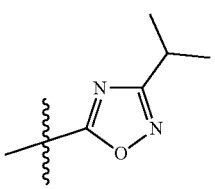 [SMILES: *c1nc(C(C)C)no1] |
| 14 | SO$_2$ | O | N | N | CH$_3$ | H | 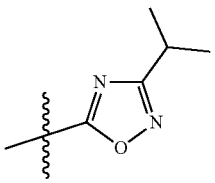 [SMILES: *c1nc(C(C)C)no1] |
| 15 | SO$_2$ | O | N | N | CH$_3$ | CH$_3$ | 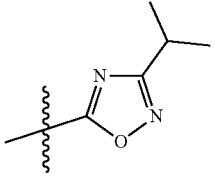 [SMILES: *c1nc(C(C)C)no1] |
| 16 | SO$_2$ | O | CF | N | CH$_3$ | CH$_3$ | 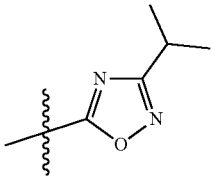 [SMILES: *c1nc(C(C)C)no1] |
| 17 | SO$_2$ | O | CF | N | H | H | 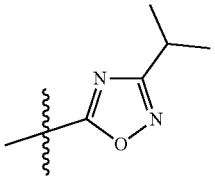 [SMILES: *c1nc(C(C)C)no1] |
| 18 | SO$_2$ | O | CF | N | H | CH$_3$ | 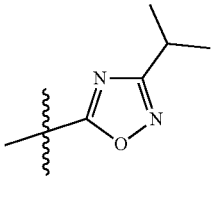 [SMILES: *c1nc(C(C)C)no1] |

TABLE 1A-continued
Exemplary definitions for $X^1$, $X^2$, $X^3$, $X^4$, $R^{2a}$, $R^{2b}$ and $R^3$ in exemplary compounds of the formula (XXX)
| Entry | $X^1$ | $X^2$ | $X^3$ | $X^4$ | $R^{2a}$ | $R^{2b}$ | $R^3$ |
|---|---|---|---|---|---|---|---|
| 19 | $SO_2$ | O | CF | H | H | H | 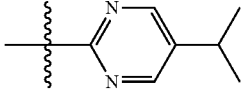 |
| 20 | $SO_2$ | O | CF | N | H | H | 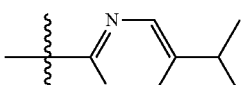 |
| 21 | $SO_2$ | O | N | N | $CH_3$ | H | 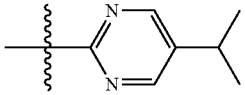 [SMILES: *c1ncc(C(C)C)cn1] |
| 22 | $SO_2$ | O | CF | CH | $CH_3$ | $CH_3$ | 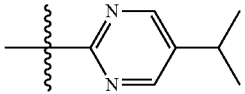 |
| 23 | $SO_2$ | O | CF | CH | H | H | 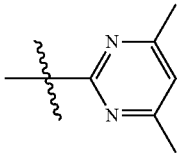 [SMILES: *c1nc(C)cc(C)n1] |
| 24 | $SO_2$ | O | CF | CH | H | H | 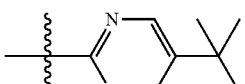 |
| 25 | $SO_2$ | O | CF | CH | H | H | 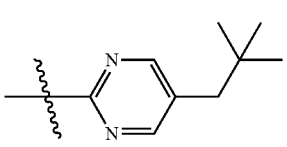 [SMILES: *c1ncc(CC(C)(C)C)cn1] |
| 26 | $SO_2$ | O | CF | CH | H | H | 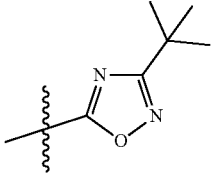 [SMILES: *c1nc(C(C)(C)C)no1] |
| 27 | $SO_2$ | O | CF | H | H | H | 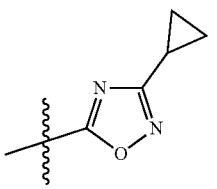 [SMILES: *c1nc(C2CC2)no1] |

TABLE 1A-continued
Exemplary definitions for $X^1$, $X^2$, $X^3$, $X^4$, $R^{2a}$, $R^{2b}$ and $R^3$ in exemplary compounds of the formula (XXX)
| Entry | $X^1$ | $X^2$ | $X^3$ | $X^4$ | $R^{2a}$ | $R^{2b}$ | $R^3$ |
|---|---|---|---|---|---|---|---|
| 28 | $SO_2$ | O | CF | N | H | H | 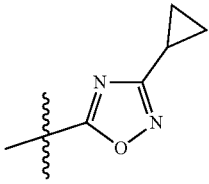 [SMILES: *c1nc(C2CC2)no1] |
| 29 | $SO_2$ | O | CF | CH | $CH_3$ | $CH_3$ | 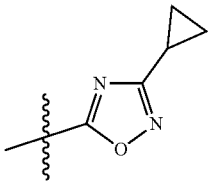 [SMILES: *c1nc(C2CC2)no1] |
| 30 | $SO_2$ | O | N | N | H | H | 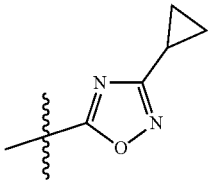 [SMILES: *c1nc(C2CC2)no1] |
| 31 | $SO_2$ | O | CF | CH | $CH_3$ | H | 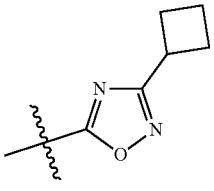 [SMILES: *c1nc(C2CCC2)no1] |
| 32 | $SO_2$ | O | CF | CH | $CH_3$ | $CH_3$ | 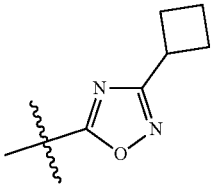 [SMILES: *c1nc(C2CCC2)no1] |
| 33 | O | $SO_2$ | CF | CH | H | H | 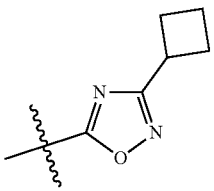 [SMILES: *c1nc(C2CCC2)no1] |
| 34 | O | $SO_2$ | CF | CH | $CH_3$ | H | 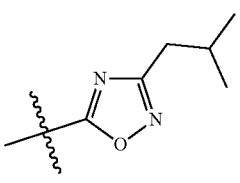 [SMILES: *c1nc(CC(C)C)no1] |
| 35 | $SO_2$ | O | CF | CH | H | H | 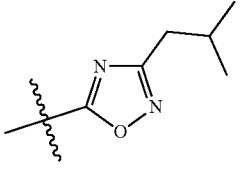 [SMILES: *c1nc(CC(C)C)no1] |

TABLE 1A-continued
Exemplary definitions for $X^1$, $X^2$, $X^3$, $X^4$, $R^{2a}$, $R^{2b}$ and $R^3$ in exemplary compounds of the formula (XXX)
| Entry | $X^1$ | $X^2$ | $X^3$ | $X^4$ | $R^{2a}$ | $R^{2b}$ | $R^3$ |
|---|---|---|---|---|---|---|---|
| 36 | O | SO$_2$ | CF | CH | H | H | 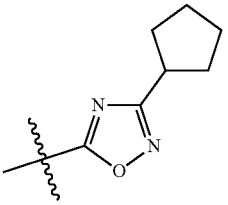 [SMILES: *c1nc(C2CCCC2)no1] |
| 37 | O | SO$_2$ | N | N | H | H | 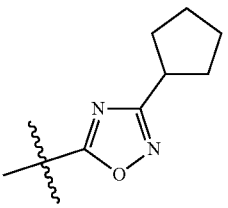 |
| 38 | O | SO$_2$ | CF | CH | CH$_3$ | CH$_3$ | 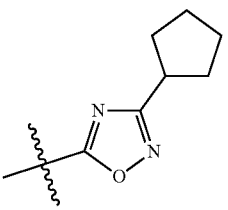 [SMILES: *c1nc(C2CCCC2)no1] |
| 39 | O | SO$_2$ | CF | CH | H | H | 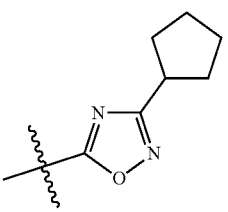 [SMILES: *c1nc(C2CCCC2)no1] |
| 40 | SO$_2$ | O | CF | CH | CH$_3$ | H | 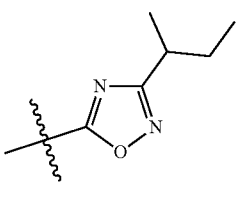 [SMILES: *c1nc(C(C)CC)no1] |
| 41 | S | O | N | CH | H | H | 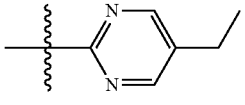 [SMILES: *c1ncc(CC)cn1] |
| 42 | S | O | CF | CH | CH$_3$ | H | 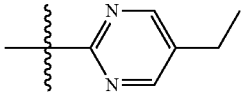 |
| 43 | S | O | CF | CH | H | CH$_2$CH$_3$ | 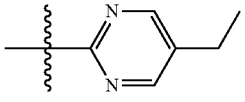 |
| 44 | S | O | CF | CH | CH$_3$ | CH$_3$ | 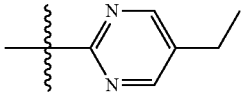 [SMILES: *c1ncc(CC)cn1] |

TABLE 1A-continued
Exemplary definitions for $X^1$, $X^2$, $X^3$, $X^4$, $R^{2a}$, $R^{2b}$ and $R^3$ in exemplary compounds of the formula (XXX)
| Entry | $X^1$ | $X^2$ | $X^3$ | $X^4$ | $R^{2a}$ | $R^{2b}$ | $R^3$ |
|---|---|---|---|---|---|---|---|
| 45 | O | S | N | CH | H | H | 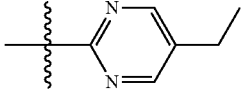 [SMILES: *c1ncc(CC)cn1] |
| 46 | O | S | CF | CH | CH$_3$ | H | 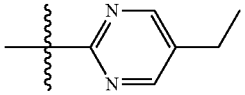 [SMILES: *c1ncc(CC)cn1] |
| 47 | O | S | CF | CH | H | CH$_2$CH$_3$ | 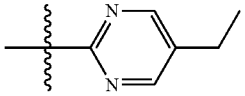 |
| 48 | O | S | CF | CH | CH$_3$ | CH$_3$ | 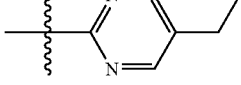 |
| 49 | SO | O | N | CH | H | H | 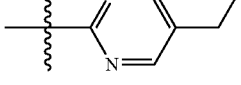 |
| 50 | SO | O | CF | CH | CH$_3$ | H | 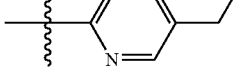 |
| 51 | SO | O | CF | CH | H | CH$_2$CH$_3$ | 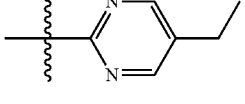 |
| 52 | SO | O | CF | CH | CH$_3$ | CH$_3$ | 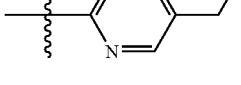 |
| 53 | O | SO | N | CH | H | H | 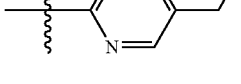 |
| 54 | O | SO | CF | CH | CH$_3$ | H | 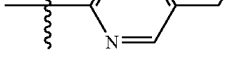 |
| 55 | O | SO | CF | CH | H | CH$_2$CH$_3$ | 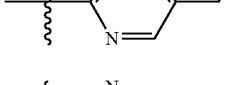 |
| 56 | O | SO | CF | CH | CH$_3$ | CH$_3$ | 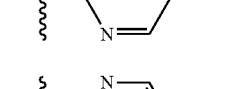 |
| 57 | S | O | N | N | H | H | 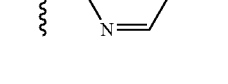 |

TABLE 1A-continued
Exemplary definitions for $X^1$, $X^2$, $X^3$, $X^4$, $R^{2a}$, $R^{2b}$ and $R^3$ in exemplary compounds of the formula (XXX)
| Entry | $X^1$ | $X^2$ | $X^3$ | $X^4$ | $R^{2a}$ | $R^{2b}$ | $R^3$ |
|---|---|---|---|---|---|---|---|
| 58 | SO | O | N | N | H | H | 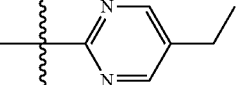 |
| 59 | O | S | N | N | H | H | 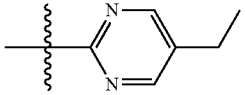 |
| 60 | O | SO | N | N | H | H | 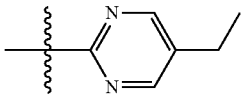 [SMILES: *c1ncc(CC)cn1] |
| 61 | SO | O | CF | CH | H | H | 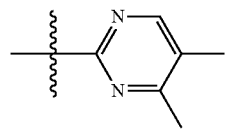 |
| 62 | SO | O | CF | CH | H | H | 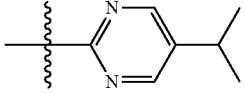 |
| 63 | SO | O | N | CH | H | H | 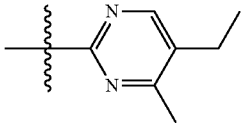 [SMILES: *c1ncc(CC)c(C)n1] |
| 64 | SO | O | CF | CH | H | H | 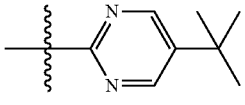 |
| 65 | SO | O | CF | CH | H | H | 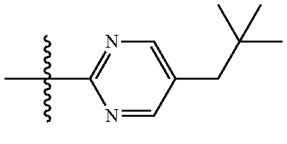 [SMILES: *c1ncc(CC(C)(C)C)cn1] |
| 66 | SO | O | CF | CH | H | H | 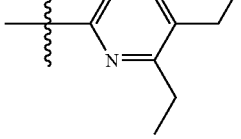 |
| 67 | SO | O | CF | CH | H | H | 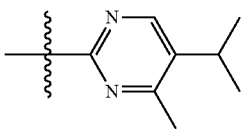 [SMILES: *c1ncc(C(C)C)c(C)n1] |
| 68 | SO | O | N | CH | H | H | 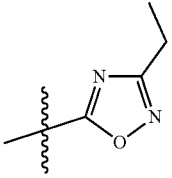 [SMILES: *c1nc(CC)no1] |

TABLE 1A-continued

Exemplary definitions for $X^1$, $X^2$, $X^3$, $X^4$, $R^{2a}$, $R^{2b}$ and $R^3$ in exemplary compounds of the formula (XXX)

| Entry | $X^1$ | $X^2$ | $X^3$ | $X^4$ | $R^{2a}$ | $R^{2b}$ | $R^3$ |
|---|---|---|---|---|---|---|---|
| 69 | SO | O | CF | CH | H | H | isopropyl-1,2,4-oxadiazole |
| 70 | SO | O | N | N | H | H | isopropyl-1,2,4-oxadiazole |
| 71 | SO | O | CF | CH | CH$_3$ | H | isopropyl-1,2,4-oxadiazole |
| 72 | SO | O | CF | CH | H | CH$_2$CH$_3$ | isopropyl-1,2,4-oxadiazole |
| 73 | SO | O | CF | CH | CH$_3$ | CH$_3$ | isopropyl-1,2,4-oxadiazole |
| 74 | O | SO | CF | CH | CH$_3$ | CH$_3$ | isopropyl-1,2,4-oxadiazole |
| 75 | SO | O | CF | CH | H | H | cyclopropyl-1,2,4-oxadiazole |
| 76 | SO | O | CF | CH | H | H | tert-butyl-1,2,4-oxadiazole |

TABLE 1A-continued

Exemplary definitions for $X^1$, $X^2$, $X^3$, $X^4$, $R^{2a}$, $R^{2b}$ and $R^3$ in exemplary compounds of the formula (XXX)

| Entry | $X^1$ | $X^2$ | $X^3$ | $X^4$ | $R^{2a}$ | $R^{2b}$ | $R^3$ |
|---|---|---|---|---|---|---|---|
| 77 | SO | O | CF | CH | H | H | 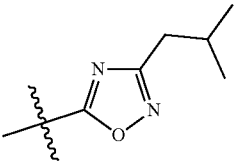 [SMILES: *c1nc(CC(C)C)no1] |
| 78 | SO | O | CF | CH | H | H | 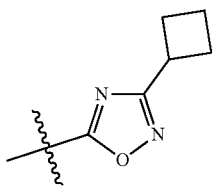 [SMILES: *c1nc(C2CCC2)no1] |
| 79 | SO | O | CF | CH | H | H | 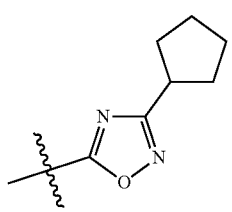 [SMILES: *c1nc(C2CCCC2)no1] |
| 80 | SO | O | CF | CH | H | H | 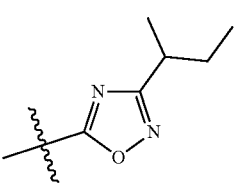 [SMILES: *c1nc(C(C)CC)no1] |

TABLE 1B

Exemplary definitions for $X^6$, $X^{6'}$, $X^{6''}$, $X^7$ and $X^{7'}$ in exemplary compounds of the formula (XXX)

| Entry | $X^6$ | $X^{6'}$ | $X^{6''}$ | $X^7$ | $X^{7'}$ |
|---|---|---|---|---|---|
| 1 | H | H | H | H | F |
| 2 | H | H | H | F | H |
| 3 | H | H | H | F | F |
| 4 | H | H | F | H | H |
| 5 | H | F | H | H | H |
| 6 | F | H | H | H | H |
| 7 | H | H | H | $CH_3$ | $CH_3$ |
| 8 | H | H | F | $CH_3$ | $CH_3$ |
| 9 | H | F | H | $CH_3$ | $CH_3$ |
| 10 | F | H | H | $CH_3$ | $CH_3$ |
| 11 | H | H | H | $CH_2CH_3$ | $CH_3$ |
| 12 | H | H | F | $CH_2CH_3$ | $CH_3$ |
| 13 | H | F | H | $CH_2CH_3$ | $CH_3$ |
| 14 | F | H | H | $CH_2CH_3$ | $CH_3$ |
| 15 | H | H | H | $CH_3$ | $CH_2CH_3$ |
| 16 | H | H | F | $CH_3$ | $CH_2CH_3$ |
| 17 | H | F | H | $CH_3$ | $CH_2CH_3$ |
| 18 | F | H | H | $CH_3$ | $CH_2CH_3$ |
| 19 | H | H | H | $CH_2CH_3$ | $CH_2CH_3$ |
| 20 | H | H | F | $CH_2CH_3$ | $CH_2CH_3$ |
| 21 | H | F | H | $CH_2CH_3$ | $CH_2CH_3$ |
| 22 | F | H | H | $CH_2CH_3$ | $CH_2CH_3$ |
| 23 | H | H | H | $CH_2CF_3$ | $CH_2CF_3$ |
| 24 | H | H | H | $CH_2CF_3$ | $CH_3$ |
| 25 | H | H | H | $CH_2CF_3$ | $CH_2CH_3$ |
| 26 | H | H | H | $CH_3$ | $CH_2CF_3$ |
| 27 | H | H | H | $CH_2CH_3$ | $CH_2CF_3$ |
| 28 | H | H | H |  | |
| 29 | H | H | F |  | |
| 30 | H | F | H |  | |
| 31 | F | H | H |  | |
| 32 | H | H | H |  | |

TABLE 1B-continued

Exemplary definitions for $X^6$, $X^{6'}$, $X^{6''}$, $X^7$ and $X^{7'}$ in exemplary compounds of the formula (XXX)

| Entry | $X^6$ | $X^{6'}$ | $X^{6''}$ | $X^7$ | $X^{7'}$ |
|---|---|---|---|---|---|
| 33 | H | H | F |  | |
| 34 | H | F | H |  | |
| 35 | F | H | H |  | |
| 36 | H | H | H | 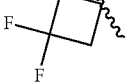 | |
| 37 | H | H | H | 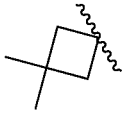 | |
| 38 | H | H | F | 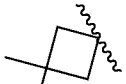 | |
| 39 | H | F | H |  | |
| 40 | F | H | H |  | |
| 41 | H | H | H | , where R is H or $C_{1-3}$ alkyl | |
| 42 | H | H | F | 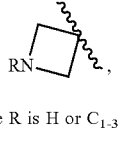, where R is H or $C_{1-3}$ alkyl | |
| 43 | H | F | H | , where R is H or $C_{1-3}$ alkyl | |

TABLE 1B-continued

Exemplary definitions for $X^6$, $X^{6'}$, $X^{6''}$, $X^7$ and $X^{7'}$ in exemplary compounds of the formula (XXX)

| Entry | $X^6$ | $X^{6'}$ | $X^{6''}$ | $X^7$ | $X^{7'}$ |
|---|---|---|---|---|---|
| 44 | F | H | H | 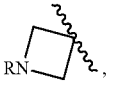, where R is H or $C_{1-3}$ alkyl | |
| 45 | H | H | H | 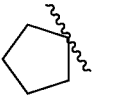 | |
| 46 | H | H | F | 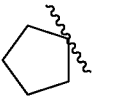 | |
| 47 | H | F | H | 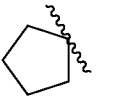 | |
| 48 | F | H | H | 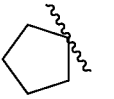 | |
| | H | H | H |  | |
| 50 | H | H | F |  | |
| 51 | H | F | H |  | |
| 52 | F | H | H |  | |
| 53 | H | H | H | , where R is H or $C_{1-3}$ alkyl | |
| 54 | H | H | F | 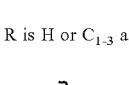, where R is H or $C_{1-3}$ alkyl | |

TABLE 1B-continued

Exemplary definitions for $X^6$, $X^{6'}$, $X^{6''}$, $X^7$ and $X^{7'}$ in exemplary compounds of the formula (XXX)

| Entry | $X^6$ | $X^{6'}$ | $X^{6''}$ | $X^7$ and $X^{7'}$ |
|---|---|---|---|---|
| 55 | H | F | H |  where R is H or $C_{1-3}$ alkyl |
| 56 | F | H | H |  where R is H or $C_{1-3}$ alkyl |
| 57 | H | H | H |  |
| 58 | H | H | H |  |
| 59 | H | H | F |  |
| 60 | H | F | H | 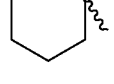 |
| 61 | F | H | H | 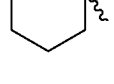 |
| 62 | H | H | H | 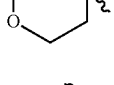 |
| 63 | H | H | F | 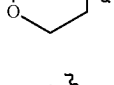 |
| 64 | H | F | H | 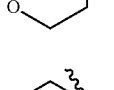 |
| 65 | F | H | H | 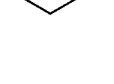 |
| 66 | H | H | H | 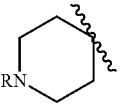 where R is H or $C_{1-3}$ alkyl |
| 67 | H | H | F | 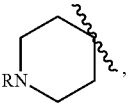 where R is H or $C_{1-3}$ alkyl |
| 68 | H | F | H | 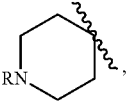 where R is H or $C_{1-3}$ alkyl |
| 69 | F | H | H |  where R is H or $C_{1-3}$ alkyl |
| 70 | H | H | H | 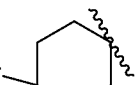 |

In some embodiments, the compound is a pharmaceutically acceptable salt of formula (I), (II), (III), (IV), (V), (VI), (VII), (VIII), (IX), (X), (XI), (XII), (XIII), (XIV), (XV), (XVI), (XVII), (XVIII), (XIX), (XX), (XXI), (XXII), (XXIII), (XXIV), (XXV), (XXVI), (XXVII), (XXVIII), (XXIX) or (XXX).

For the purposes of demonstrating the manner in which the compounds of the present disclosure are named and referred to herein, the compound having the formula:

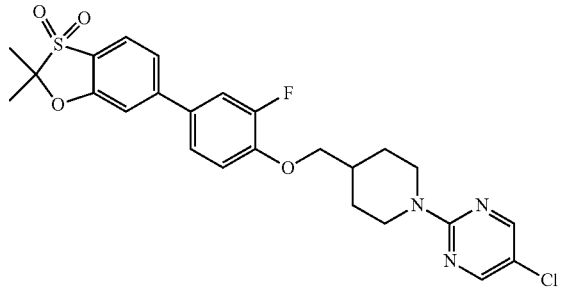 [SMILES: CC1(C)Oc2cc(-c3ccc(OCC4CCN(c5ncc(Cl)cn5)CC4)c(F)c3)ccc2S1(=O)=O]

has the chemical name 5-chloro-2-(4-{[4-(2,2-dimethyl-3,3-dioxido-1,3-benzoxathiol-6-yl)-2-fluorophenoxy]methyl}piperidin-1-yl)pyrimidine.

For the purposes of demonstrating the manner in which the compounds of the present disclosure are named and referred to herein, the compound having the formula:

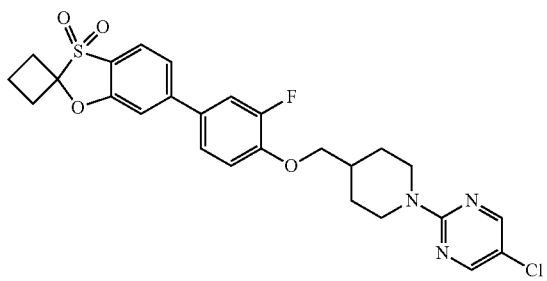 [SMILES: O=S1(=O)c2ccc(-c3ccc(OCC4CCN(c5ncc(Cl)cn5)CC4)c(F)c3)cc2OC12CCC2]

has the chemical name 5-chloro-2-(4-{[4-(3,3-dioxidospiro[1,3-benzoxathiole-2,1'-cyclobutan]-6-yl)-2-fluorophenoxy]methyl}piperidin-1-yl)pyrimidine.

For the purposes of demonstrating the manner in which the compounds of the present disclosure are named and referred to herein, the compound having the formula:

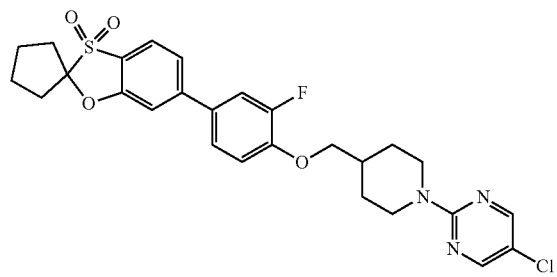 [SMILES: O=S1(=O)c2ccc(-c3ccc(OCC4CCN(c5ncc(Cl)cn5)CC4)c(F)c3)cc2OC12CCCC2]

has the chemical name 5-chloro-2-(4-{[4-(3,3-dioxidospiro[1,3-benzoxathiole-2,1'-cyclopentan]-6-yl)-2-fluorophenoxy]methyl}piperidin-1-yl)pyrimidine.

For the purposes of demonstrating the manner in which the compounds of the present disclosure are named and referred to herein, the compound having the formula:

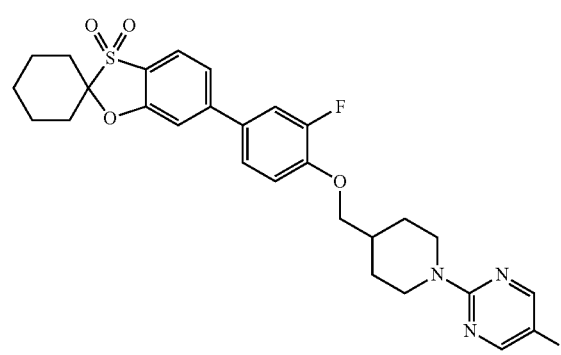

has the chemical name 5-chloro-2-(4-{[4-(3,3-dioxidospiro[1,3-benzoxathiole-2,1'-cyclohexan]-6-yl)-2-fluorophenoxy]methyl}piperidin-1-yl)pyrimidine.

For the purposes of the present disclosure, a compound depicted by the racemic formula, for example:

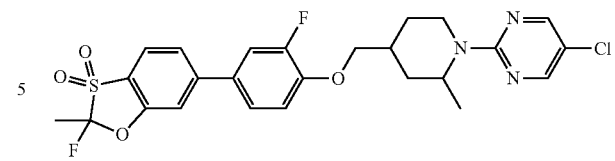

will stand equally well for either of the four stereoisomers having the formula

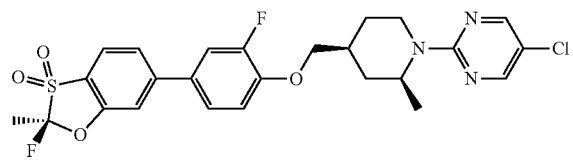 [SMILES: C[C@H]1C[C@@H](COc2ccc(-c3ccc4c(c3)O[C@@](C)(F)S4(=O)=O)cc2F)CCN1c1ncc(Cl)cn1]

or the formula

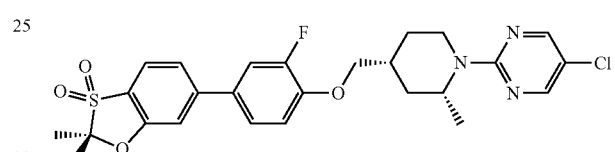

or the formula

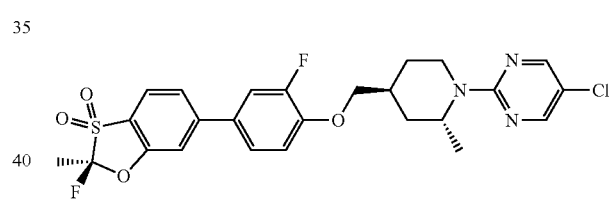

or the formula

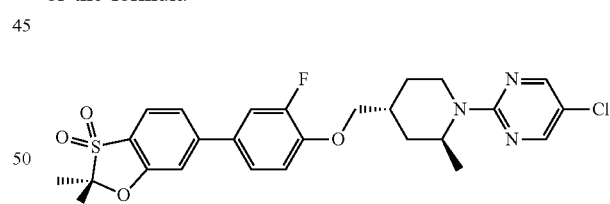

or the formula

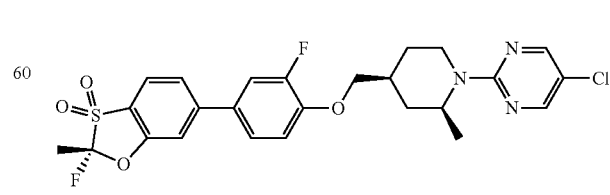

or the formula

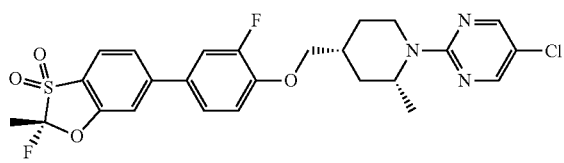 [SMILES: C[C@@H]1C[C@H](COc2ccc(-c3ccc4c(c3)O[C@](C)(F)S4(=O)=O)cc2F)CCN1c1ncc(Cl)cn1]

or the formula

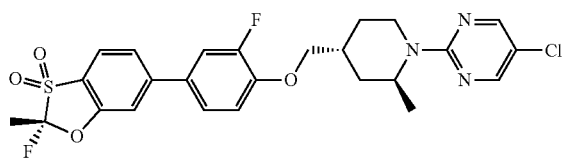 [SMILES: C[C@H]1C[C@H](COc2ccc(-c3ccc4c(c3)O[C@](C)(F)S4(=O)=O)cc2F)CCN1c1ncc(Cl)cn1]

or the formula

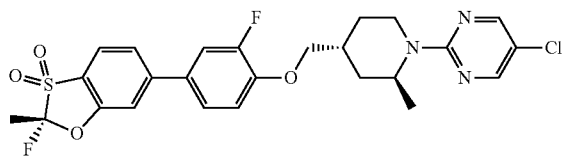 [SMILES: C[C@H]1C[C@H](COc2ccc(-c3ccc4c(c3)O[C@](C)(F)S4(=O)=O)cc2F)CCN1c1ncc(Cl)cn1]

or mixtures thereof, or in the case where more than one chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

It will also be appreciated by those of skilled in the art, may be administered to a mammal and thereafter metabolized in the body to form compounds of the invention which are pharmacologically active. Such derivatives may therefore be described as "prodrugs". All prodrugs of compounds of formula (I) are included within the scope of this invention.

It is understood that one skilled in the art would be able to make compounds of the disclosure by similar methods as shown below, or by methods known to one skilled in the art. It is also understood that one skilled in the art would be able to make in a similar manner as described below other compounds of formula (I) not specifically illustrated below by using appropriate starting components and modifying the parameters of the synthesis as needed. In general, starting materials may be obtained from sources such as Sigma Aldrich, TCI and the like, or synthesized according to sources known to those of skill in the art (see Smith, M. B. and J. March, *Advanced Organic Chemistry: Reactions, Mechanisms and Structure*, 5$^{th}$ edition (Wiley, December 2000).

III. Combination Therapy

In another embodiment of the invention, a compound of the disclosure may be combined with one or more additional compounds of the disclosure for the treatment of tyrosine kinases-mediated disease and conditions. The compound of the disclosure may be administered simultaneously, sequentially or separately with the one or more additional compounds of the disclosure for the treatment of tyrosine kinases-mediated disease and conditions. In a further embodiment of the invention, a compound of the disclosure may be combined with one or more additional compounds of the disclosure and an excipient for the treatment of tyrosine kinases-mediated disease and conditions.

In another embodiment of the invention, a compound of the disclosure may be combined with an anti-diabetic agent for the treatment of type 2 diabetes mellitus-mediated disease and conditions. Said agents include but not limited to metformin, sulfonylureas such as glimepiride, glyburide and glipizide. Glitazones such as pioglitazone and rosiglitazone and glucagon-like peptide-1 (GLP-1) analogues and receptor agonists such as liraglutide, albiglutide, exenatide, exenatide-LAR, CJC 1134, AVE 0010, R-51077, taspoglutide. DPP-4 inhibitors such as sitagliptin, vildagliptin, linagliptin, saxagliptin, alogliptin, BI 1356 BS, melogliptin, AMG 222, MP 513, PHX 1149, PSN 9301, R 1579, SYR 472, TA 6666, denagliptin GPR agonists such as TAK-875, AMG 837 and related FFAR1 agonists. Combination therapy also includes GPR119 agonists such as APD668, APD597, BMS-903452, HD047703, GSK1292263 and MBX-2982. The compounds of the disclosure may be administered simultaneously, sequentially or separately with for the treatment of tyrosine-mediated disease and conditions.

IV. Preparation of the Compounds of the Invention

The present invention further relates to a process for preparing the compounds of the disclosure. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC). Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

V. General Synthetic Schemes for Preparation of Compounds

Reagents used in the preparation of the compounds disclosed herein, including those of formulas (I) to (XXX), can be either commercially obtained or can be prepared by standard procedures described in the literature. Compounds disclosed herein may be produced using one or more of the following reaction schemes.

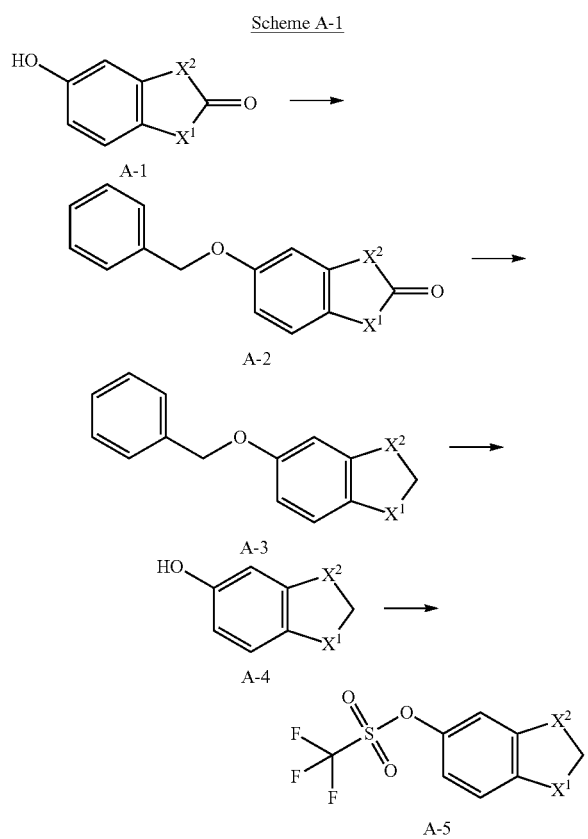

A compound of the formula (A-1), a known compound or compound prepared by known methods, is reacted with benzyl bromide in the presence of a base such as potassium carbonate, cesium carbonate, trimethylamine, pyridine, 2,6-lutidine, and the like, in a solvent such as acetonitrile, tetrahydrofuran, 1,4-dioxane, methylene chloride, N,N-dimethylformamide and the like, optionally with heating, optionally with microwave irradiation to provide a compound of the formula (A-2). A compound of formula (A-2) is reacted with methylene bromide in the presence of a base such as potassium carbonate, cesium carbonate, trimethylamine, pyridine, 2,6-lutidine, and the like, in a solvent such as acetonitrile, tetrahydrofuran, 1,4-dioxane, methylene chloride, N,N-dimethylformamide, and the like, optionally in the presence of a crown ether such as 18-crown-6, 12-crown-4, and the like optionally with heating, optionally with microwave irradiation to provide a compound of the formula (A-3). A compound of formula (A-3) is oxidized with an oxidizing agent such as hydrogen peroxide in an acid such as acetic acid, formic acid, trifluoroacetic acid, and the like, optionally in the presence of a solvent such as methanol, ethanol, tetrahydrofuran, 1,4-dioxane, N,N-dimethylformamide, and the like, optionally with heating, optionally with microwave. The resulting material is reacted with hydrogen on a catalyst such as palladium on charcoal, palladium on carbon, tris(dibenzylideneacetone)dipalladium, palladium, tetrakis(triphenylphosphine), palladium acetate, palladium chloride, (tridibenzylideneacetone) dipalladium(0), raney nickel, and the like, in a solvent such as tetrahydrofuran, 1,4-dioxane, t-butyl methyl ether, methanol, ethanol, and the like optionally with heating, optionally with microwave irradiation to provide a compound of the formula (A-4). A compound of the formula (A-4) is reacted with trifluoromethanesulfonic anhydride in the presence of a base such as pyridine, 2,6-lutidine, 2-picoline, 3-picoline, 4-picoline, N,N-dimethylaminopyridine, diisopropylethyl amine, trimethylamine and the like in a solvent such as methylene chloride, 1,2-dichloroethane, chloroform, tetrahydrofuran, ether, 1,4-dioxane, acetone, acetonitrile, N,N-dimethylformamide and the like optionally with heating, optionally with microwave irradiation to provide compounds of the formula (A-5).

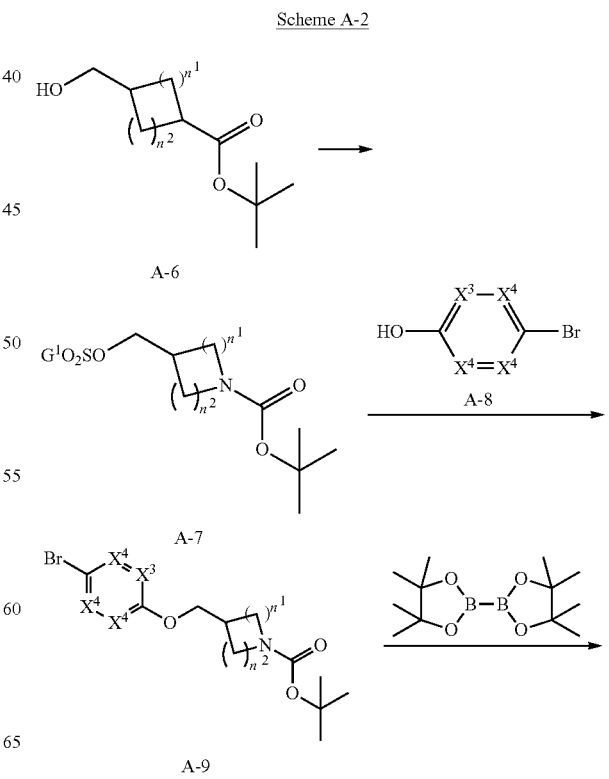

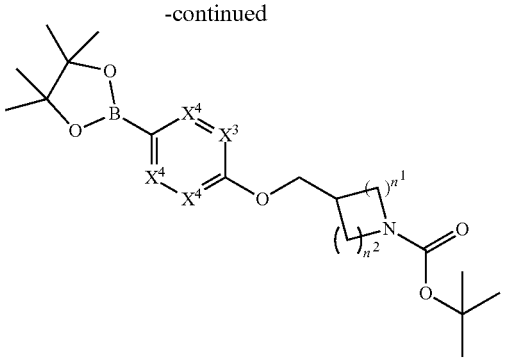

A-10

A compound of the formula (A-6), a known compound or compound prepared by known methods, is reacted with a sulfonyl chloride such as methylsulfonyl chloride, toluene sulfonyl chloride, p-nitrophenyl sulfonyl chloride in the presence of a base such as sodium carbonate, cesium carbonate, lithium carbonate, potassium carbonate, potassium hydroxide, sodium hydroxide, lithium hydroxide, triethylamine, diisopropylethylamine and the like, in a solvent such as acetone, acetonitrile, tetrahydrofuran, 1,4-dioxane, methylene chloride, 1,2-dichloroethane, and the like, optionally with heating, optionally with microwave irradiation to provide a compound of the formula (A-7) wherein G1 is selected from the group consisting of methyl, tolyl and p-nitrophenyl. A compound of the formula (A-7), is reacted with a compound of the formula (A-8), a known compound prepared by known methods in the presence of a base such as sodium carbonate, cesium carbonate, lithium carbonate, potassium carbonate, potassium hydroxide, sodium hydroxide, lithium hydroxide, triethylamine, diisopropylethylamine and the like, in a solvent such as dimethylsulfoxide, N,N-dimethylformamide, acetone, acetonitrile, tetrahydrofuran, 1,4-dioxane, methylene chloride, 1,2-dichloroethane, and the like, optionally with heating, optionally with microwave irradiation to provide a compound of the formula (A-9). A compound of the formula (A-9), is reacted with a 4,4,4',4',5,5,5',5'-octamethyl-2,2'-bi-1,3,2-dioxoborolane, a known compound prepared by known methods, in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium (0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, N,N-dimethylformamide, and the like, optionally with heating, optionally with microwave irradiation to provide a compound of the formula (A-10).

Scheme A-3

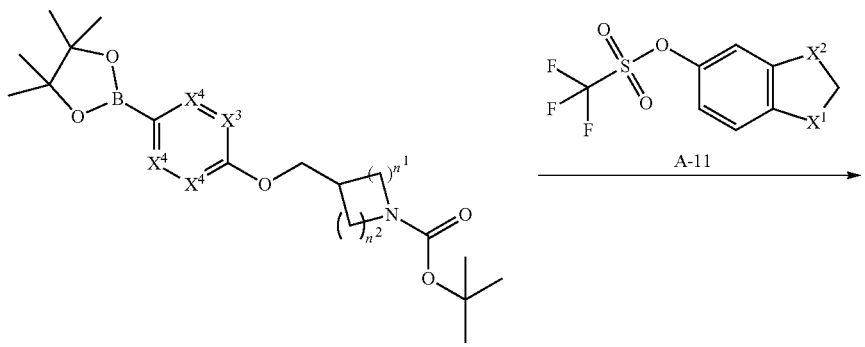

A-10    A-11

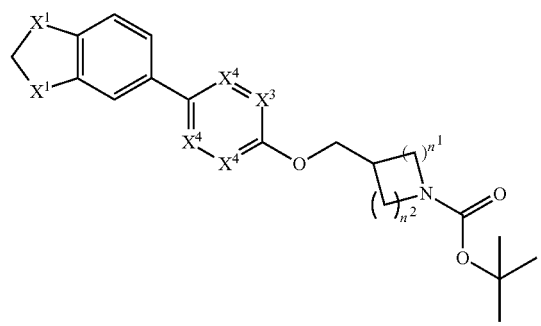

A-12

A compound of the formula (A-10), is reacted with a compound of the formula (A-11), a known compound prepared by known methods in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium(0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-12).

Scheme A-4

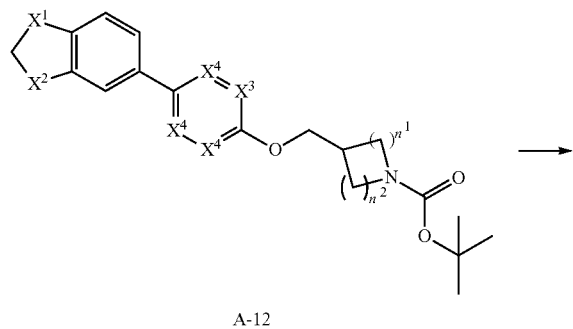

A-12

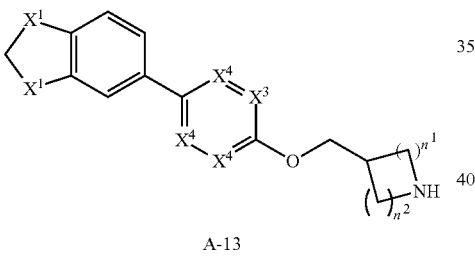

A-13

A compound of the formula (A-12), is reacted with an acid such as formic acid, trifluoroacetic acid, trichloroacetic acid, hydrochloric acid, sulfuric acid and the like, in the presence of a solvent such as 1,4-dioxane, tetrahydrofuran, methylene chloride, N,N-dimethylformamide, acetonitrile, and the like, optionally with heating, optionally with microwave irradiation to provide a compound of the formula (A-13).

Scheme A-5

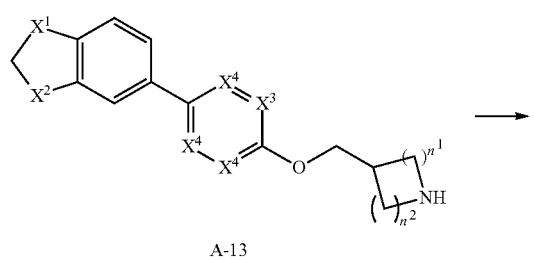

A-13

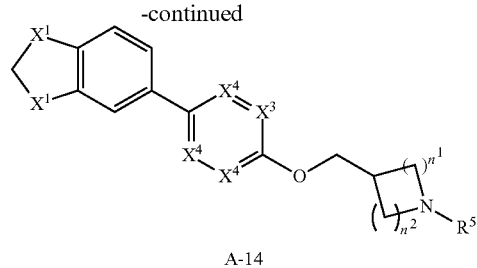

A-14

A compound of the formula (A-13), is reacted with an aldehyde in the presence of a reducing agent such as sodium triacetoxyborohydride, lithium triacetoxyborohydride, sodium borohydride, lithium borohydride, and the like, optionally in the presence of an acid such as acetic acid, trifluoroacetic acid, hydrochloric acid, and the like, in the presence of a solvent such as 1,4-dioxane, tetrahydrofuran, N,N-dimethylformamide, and the like, optionally with heating, optionally with microwave irradiation to provide a compound of the formula (A-14). Alternatively, a compound of the formula (A-13), is reacted with a ketone in the presence of a reducing agent such as sodium triacetoxyborohydride, lithium triacetoxyborohydride, sodium borohydride, lithium borohydride, and the like, optionally in the presence of an acid such as acetic acid, trifluoroacetic acid, hydrochloric acid, and the like, in the presence of a solvent such as 1,4-dioxane, tetrahydrofuran, N,N-dimethylformamide, and the like, optionally with heating, optionally with microwave irradiation to provide a compound of the formula (A-14).

Scheme A-6

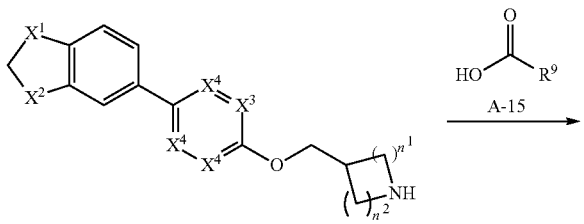

A-13

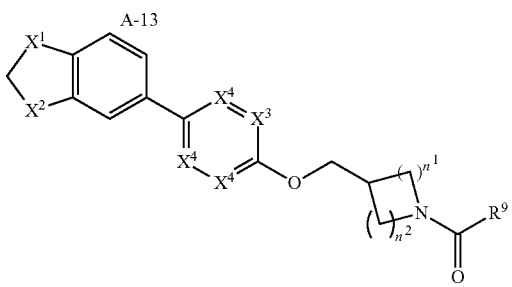

A-16

Alternatively, A compound of the formula (A-13), is reacted with a compound of the formula (A-15), a known compound or a compound prepared by known methods, in the presence of a coupling agent such as O-(benzotriazol-1-yl)-N,N,N',N'-tetramethyluronium hexafluorophosphate, N,N-dicyclohexyl carbodiimide, 1-ethyl-3-(3-dimethylaminopropyl) carbodiimide, 1-[bis(dimethylamino) methylene]-1H-1,2,3-triazolo[4,5-b]pyridinium 3-oxid hexafluorophosphate, 1-hydroxy-7-azabenzotriazole N-[(1H-1,2,3-benzotriazol-1-yloxy)(dimethylamino)methylene]-N- methyl methanaminium hexafluorophosphate, 1-ethyl-3-(3-dimethylaminopropyl)carbodiimide and the like, in the presence of a base such as trimethylamine, pyridine, 2,6-lutidine, diisopropylethylamine, N-methylmorpholine, and the like in a solvent such as acetonitrile, N,N-dimethylformamide, 1,4-dioxane, tetrahydrofuran, and the like, optionally with heating, optionally with microwave irradiation to provide a compound of the formula (A-16).

A compound of the formula (A-13), is reacted with isocyanotrimethylsilane in the presence of a base such as trimethylamine, pyridine, 2,6-lutidine and the like, in a solvent such as acetonitrile, N,N-dimethylformamide, 1,4-dioxane, tetrahydrofuran, and the like, optionally with heating, optionally, with microwave irradiation to provide a compound of the formula (A-18).

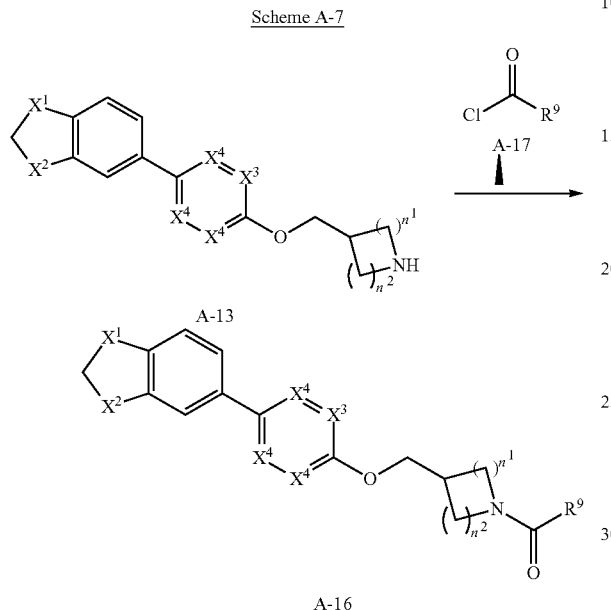

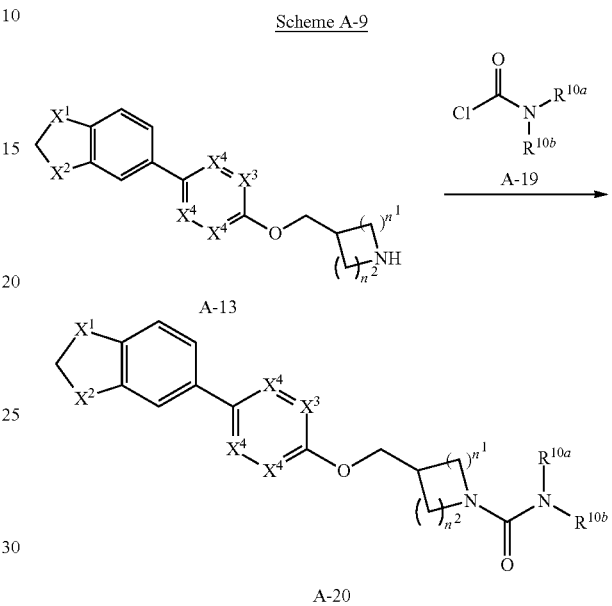

Alternatively, a compound of formula (A-13) is reacted with a compound of the formula (A-17), a known compound or a compound prepared by known methods, in the presence of a base such as trimethylamine, pyridine, 2,6-lutidine and the like, in a solvent such as acetonitrile, N,N-dimethylformamide, 1,4-dioxane, tetrahydrofuran, and the like, optionally with heating, optionally with microwave irradiation to provide a compound of the formula (A-16).

A compound of the formula (A-13), is reacted with a compound of the formula (A-19) in the presence of a base such as trimethylamine, pyridine, 2,6-lutidine and the like in a solvent such as acetonitrile, N,N-dimethylformamide, 1,4-dioxane, tetrahydrofuran, and the like, optionally with heating, optionally with microwave irradiation to provide a compound of the formula (A-20).

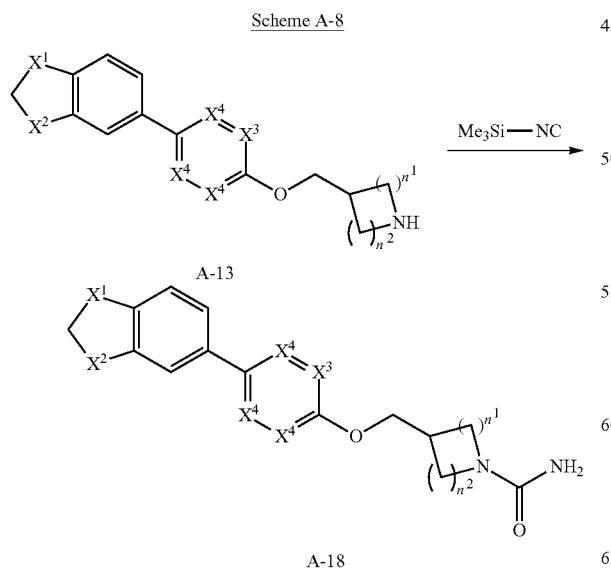

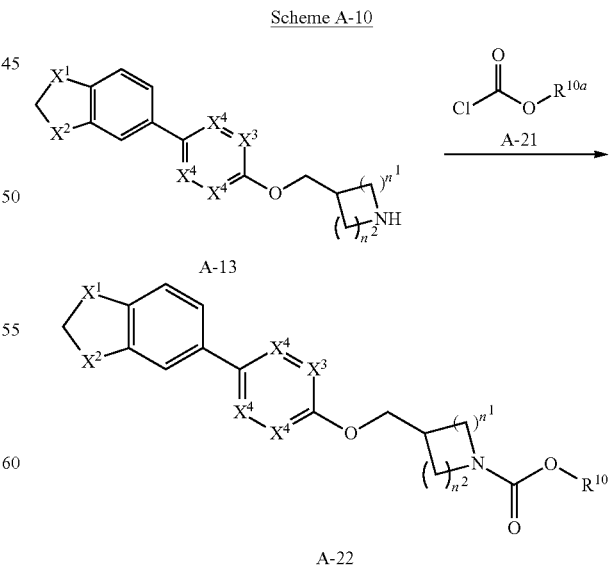

A compound of the formula (A-13), is reacted with a compound of the formula (A-21) in the presence of a base such as trimethylamine, pyridine, 2,6-lutidine and the like in a solvent such as acetonitrile, N,N-dimethylformamide, 1,4-dioxane, tetrahydrofuran, and the like optionally with heating, optionally with microwave irradiation to provide a compound of the formula (A-22).

Scheme A-11

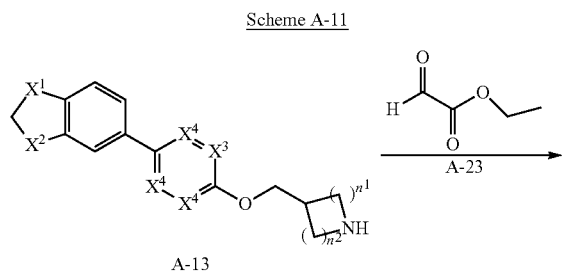

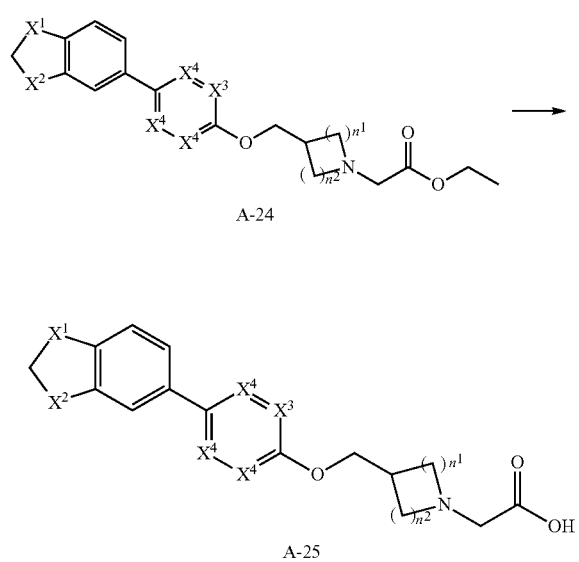

A compound of the formula (A-13) is reacted with a compound of the formula (A-23), a known compound or a compound prepared by known methods, in the presence of sodium triacetoxyborohydride in the presence of a solvent such as dichloromethane, dioxane, tetrahydrofuran, and the like, optionally with heating, optionally with microwave irradiation to provide a compound of the formula (A-24). A compound of formula (A-24) is hydrolyzed in the presence of a base such as potassium hydroxide, sodium hydroxide, potassium carbonate, cesium carbonate, lithium carbonate optionally with heating, optionally with microwave irradiation to provide a compound of the formula (A-25).

Scheme A-12

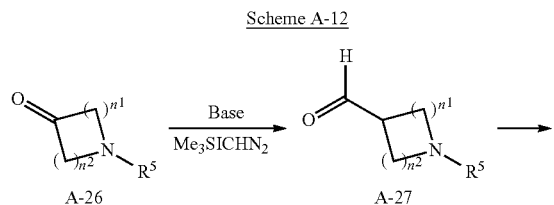

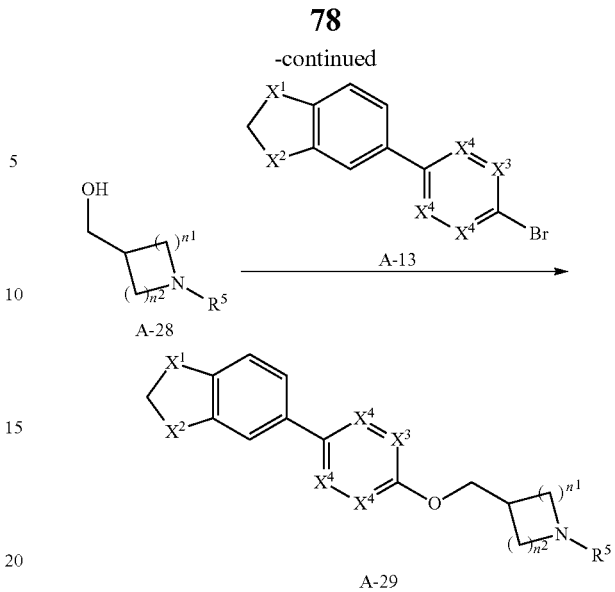

A compound of formula (A-26) is reacted with trimethylsilyldiazomethane in hexanes in the presence of a base such as lithium diisopropylamide, sodium diisopropylamide, potassium diisopropylamide, lithium hexamethyldisilazide, sodium hexamethyldisilazide, potassium hexamethyldisilazide, and the like, in the presence of a solvent such as 1,4-dioxane, tetrahydrofuran, methylene chloride, 1,2-dichloroethane, and the like, optionally with cooling to −78° C. to provide a compound of formula (A-27). A compound of formula (A-27) is reacted with a reducing hydride reagent such as sodium borohydride, lithium borohydride, lithium aluminum hydide, and the like, in a solvent such as methanol, ethanol, 1,4-dioxane, tetrahydrofuran, and the like, optionally with heating, optionally with microwave irradiation to provide a compound of the formula (A-28). A compound of formula (A-28) is reacted with a compound of formula (A-13) a known compound or compound prepared by known methods, in the presence of a phosphine such as triphenylphosphine, tri(o-tolyl)phosphine, resin-bound triphenylphosphine, and the like, in the presence of an azodicarboxylate such as diethyl azodicarboxylate, diisopropyl azodicarboxylate, di-t-butylazodicarboxylate, di-(4-chlorobenzyl)azodicarboxylate, and the like, in the presence of a solvent such as tetrahydrofuran, diethyl ether, 1,4-dioxane, methylene chloride, and the like, optionally with heating, optionally with microwave irradiation to provide a compound of the formula (A-29).

Scheme A-13

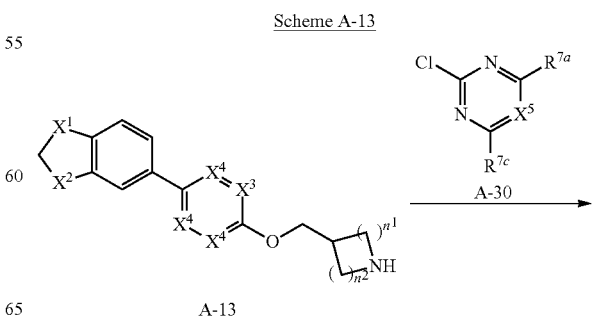

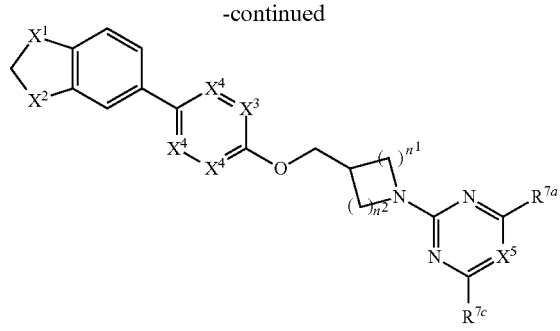

A-31

A compound of formula (A-13) which is reacted with a compound of the formula (A-30), a known compound or a compound prepared by known methods, in the presence of a base such as potassium acetate, sodium carbonate, cesium carbonate, lithium carbonate, potassium carbonate, potassium hydroxide, sodium hydroxide, lithium hydroxide, in a solvent such as acetonitrile, dimethylformamide, dioxane, tetrahydrofuran and the like, optionally with heating, optionally with microwave irradiation to provide a compound of the formula (A-31).

Scheme A-14

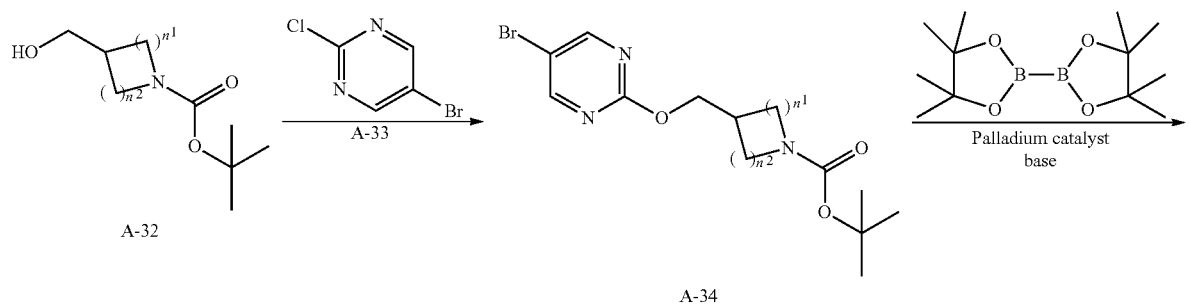

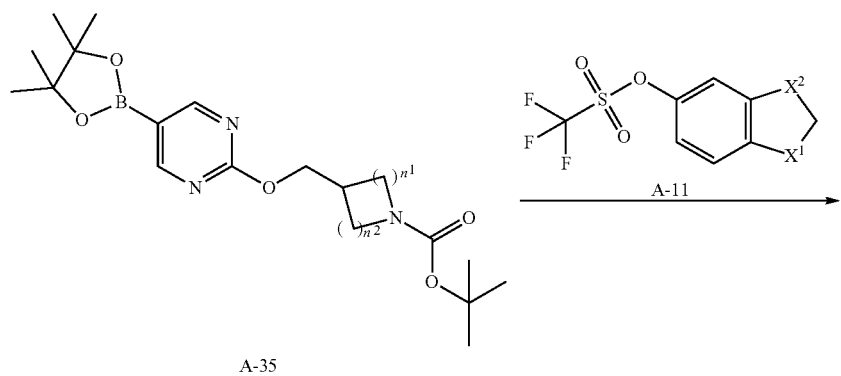

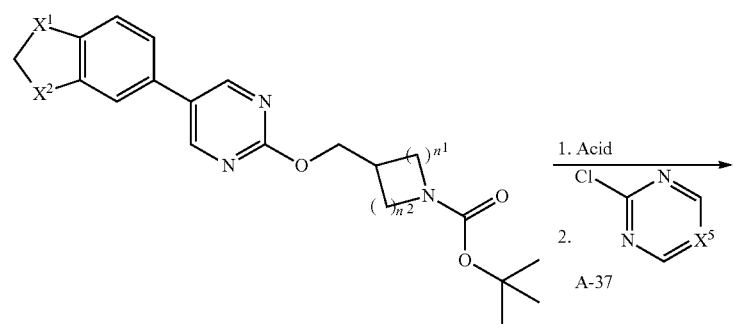

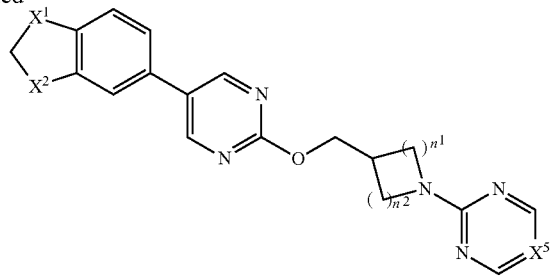

A-38

A compound of the formula (A-32), a known compound or compound prepared by known methods, is reacted with a compound of formula (A-33), in the presence of a base such as sodium hydride, carbonate, cesium carbonate, lithium carbonate, potassium carbonate, triethylamine, diisopropylethylamine and the like, in a solvent such as tetrahydrofuran, ethyl ether, acetonitrile acetonitrile, tetrahydrofuran, 1,4-dioxane, and the like, optionally with heating, optionally with microwave irradiation to provide a compound of the formula (A-34). A compound of the formula (A-34), is reacted with a 4,4,4',4',5,5,5',5'-octamethyl-2,2'-bi-1,3,2-dioxoborolane, in the presence of abase such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis (triphenylphosphine)palladium(0), bis(triphenylphosphine) palladium(II)dichloride, (1,1'-bis(diphenylphosphino)ferrocene)palladium(II) dichloride and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-35). A compound of the formula (A-35), is reacted with a compound of the formula (A-11), a known compound or a compound prepared by known methods, in the presence of a base such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis (triphenylphosphine)palladium(0), bis(triphenylphosphine) palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-36). A compound of the formula (A-36), is reacted with an acid such as formic acid, trifluoroacetic acid, trichloroacetic acid, hydrochloric acid, sulfuric acid and the like in the presence of a solvent such as 1,4-dioxane, tetrahydrofuran, methylene chloride, methanol, ethanol, and the like, optionally with heating, optionally with microwave irradiation. The resulting material is reacted with a compound of the formula (A-37), a known compound or a compound prepared by known methods, in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-38).

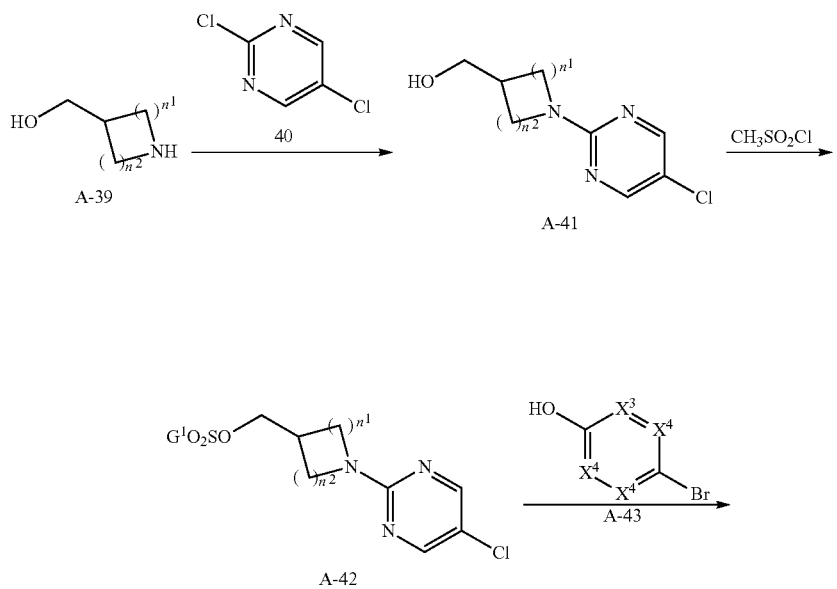

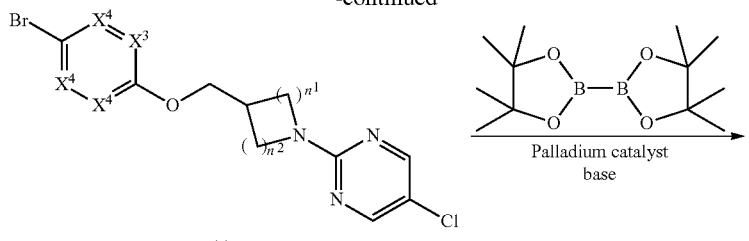

A-44

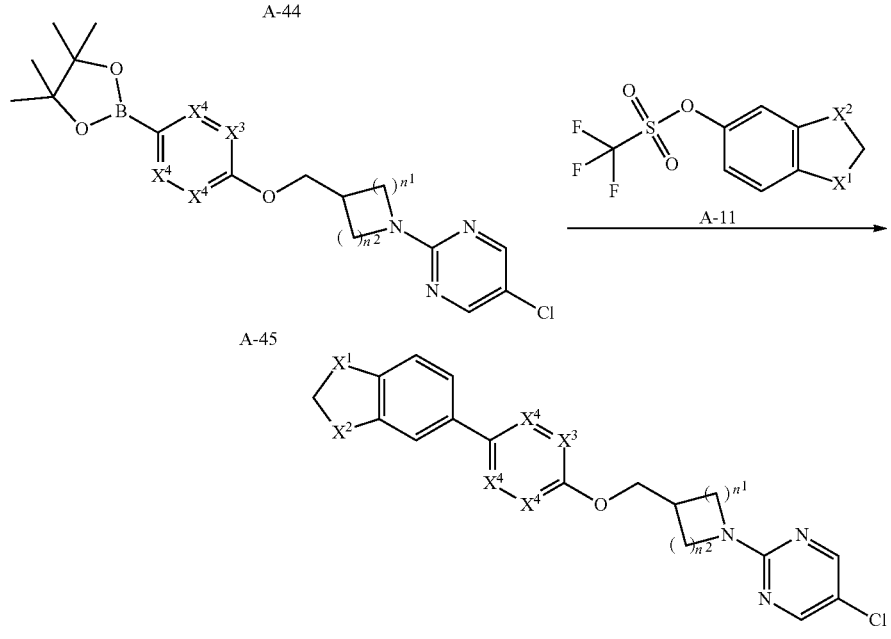

A-45 n = 1, 2
A-46

A compound of the formula (A-39), a known compound or compound prepared by known methods, is reacted with a compound of formula (A-40), in the presence of a base such as sodium hydride, carbonate, cesium carbonate, lithium carbonate, potassium carbonate, triethylamine, diisopropylethylamine and the like, in a solvent such as tetrahydrofuran, ethyl ether, acetonitrile acetonitrile, tetrahydrofuran, 1,4-dioxane, and the like, optionally with heating, optionally with microwave irradiation to provide a compound of the formula (A-41). A compound of the formula (A-41), is reacted with a sulfonyl chloride such as methylsulfonyl chloride, toluene sulfonyl chloride, p-nitrophenyl sulfonyl chloride, and the like, in the presence of a base such as sodium carbonate, cesium carbonate, lithium carbonate, potassium carbonate, potassium hydroxide, sodium hydroxide, lithium hydroxide, triethylamine, diisopropylethylamine and the like in a solvent such as acetone, acetonitrile, tetrahydrofuran, 1,4-dioxane, methylene chloride, 1,2-dichloroethane, and the like, optionally with heating, optionally with microwave irradiation to provide a compound of the formula (A-42) wherein $G^1$ is selected from the group consisting of methyl, tolyl and p-nitrophenyl. A compound of the formula (A-42), is reacted with a compound of the formula (A-43), a known compound or a compound prepared by known methods, in the presence of a base such as sodium carbonate, cesium carbonate, lithium carbonate, potassium carbonate, potassium hydroxide, sodium hydroxide, lithium hydroxide, triethylamine, diisopropylethylamine and the like, in a solvent such as acetone, acetonitrile, tetrahydrofuran, 1,4-dioxane, methylene chloride, 1,2-dichloroethane, and the like, optionally with heating, optionally with microwave irradiation to provide a compound of the formula (A-44). A compound of the formula (A-44), is reacted with a 4,4,4',4',5,5,5',5'-octamethyl-2,2'-bi-1,3,2-dioxoborolane in the presence of a base such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis (triphenylphosphine)palladium(0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-45). A compound of the formula (A-45), is reacted with a compound of the formula (A-11) in the presence of a base such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis(triphenylphosphine)palladium(0), bis(triphenylphosphine)palladium(II)dichloride, (1,1'-bis(diphenylphosphino)ferrocene) palladium(II) dichloride and the like, in the presence of a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-46).

Scheme A-16

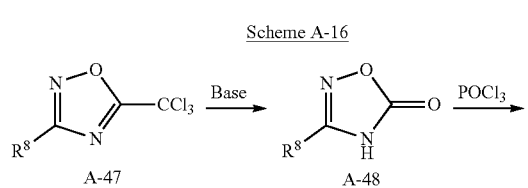

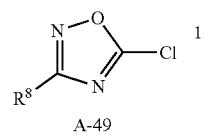

A compound of formula (A-47), a known compound or a compound prepared by known. methods is reacted with a base such potassium hydroxide, lithium hydroxide, sodium hydroxide and the like, in the presence of a solvent such as ethanol, methanol, isopropanol and the like, optionally with heating, optionally with microwave irradiation to provide a compound of the formula (A-48). A compound of formula (A-48), a known compound or a compound prepared by known methods is reacted with phosphoyl chloride in a base such pyridine, trimethylamine, 2,6-lutidine, picoline and the like, optionally with heating, optionally with microwave irradiation to provide a compound of the formula (A-49).

Scheme A-17

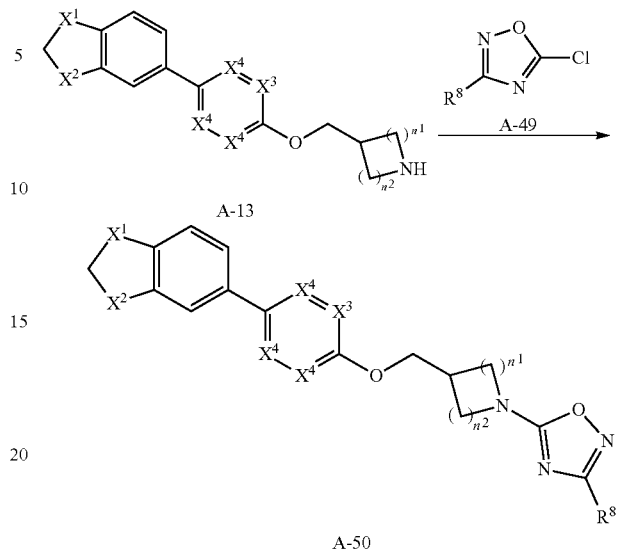

A compound of formula (A-13) is reacted with a compound of the formula (A-49) in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-50).

Scheme A-18

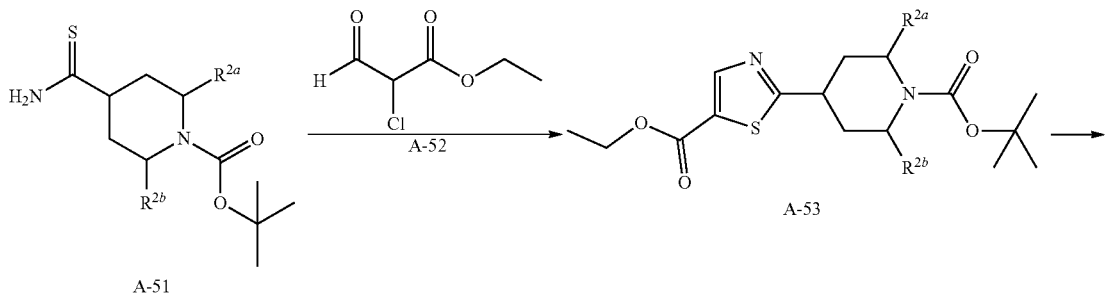

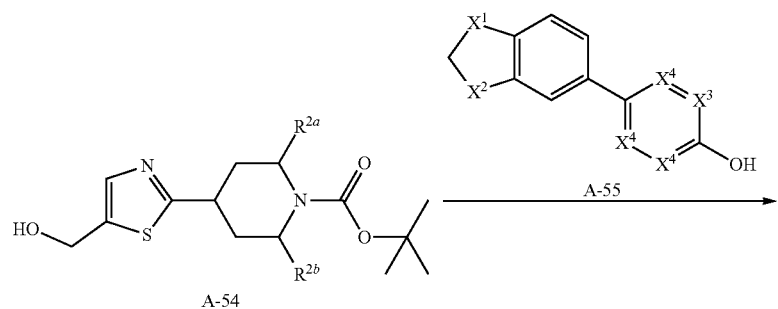

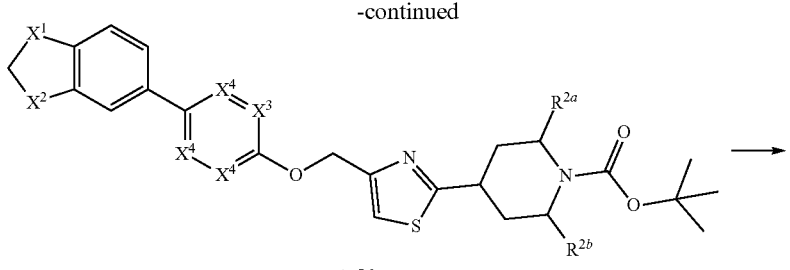

A-56

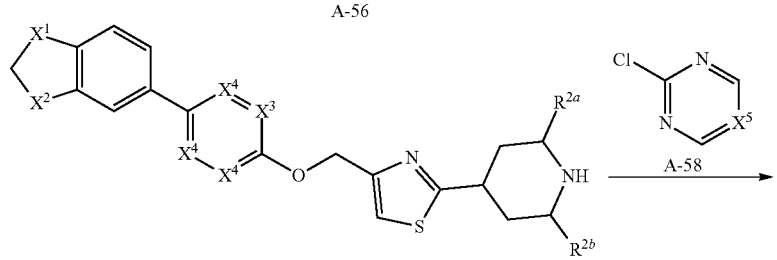

A-57

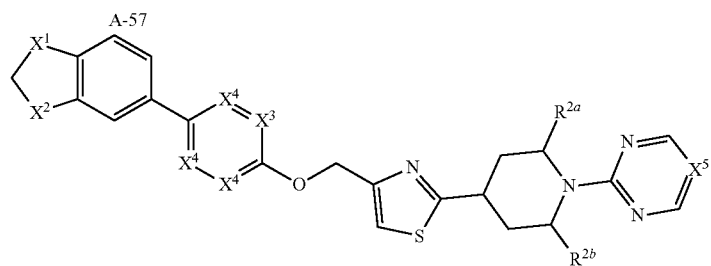

A-59

A compound of formula (A-51), a known compound or a compound prepared by known methods, is reacted with a compound of formula (A-52) in the presence of a base such as trimethylamine, pyridine, diisopropylethylamine and the like, in a solvent such as toluene, benzene, and the like to provide a compound of formula (A-53). A compound of formula (A-53) is reacted with a reducing agent such as lithium aluminum hydride, diisobutyl aluminum hydride, and the like, in a solvent such as tetrahydrofuran, ethyl ether, 1,4-dioxane and the like, to provide a compound of formula (A-54). A compound of formula (A-54) is reacted with a compound of formula (A-55), a known compound or a compound prepared by known methods, in the presence of a phosphine such as triphenylphosphine, tri(o-tolyl)phosphine, resin-bound triphenylphosphine, and the like, in the presence of an azodicarboxylate such as diethyl azodicarboxylate, diisopropyl azodicarboxylate or di-t-butylazodicarboxylate, di-(4-chlorobenzyl)azodicarboxylate, and the like, in the presence of a solvent such as tetrahydrofuran, diethyl ether, 1,4-dioxane and the like, optionally with heating, optionally with microwave irradiation to provide a compound of the formula (A-56). A compound of the formula (A-56), is reacted with an acid such as formic acid, trifluoroacetic acid, trichloroacetic acid, hydrochloric acid, sulfuric acid and the like, in the presence of a solvent such as 1,4-dioxane, tetrahydrofuran, methanol, ethanol, methylene chloride, and the like, optionally with heating, optionally with microwave irradiation to provide a compound of formula (A-57). A compound of formula (A-57) is reacted with a compound of the formula (A-58), a known compound or a compound prepared by known methods, in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-59).

Scheme A-19

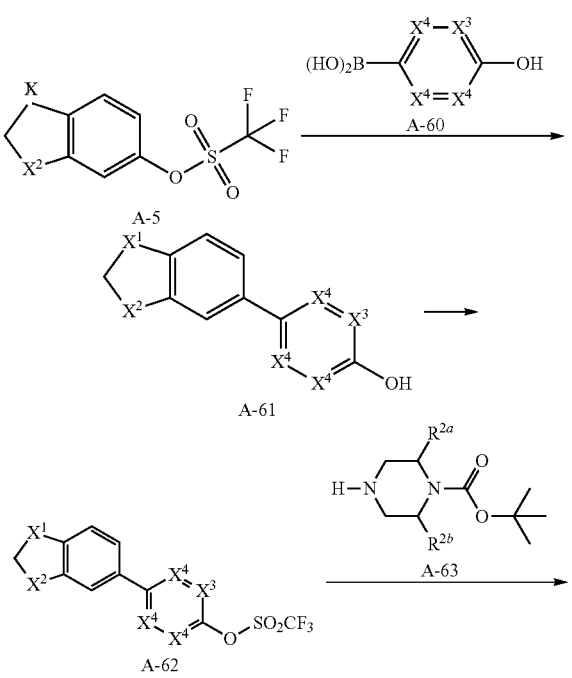

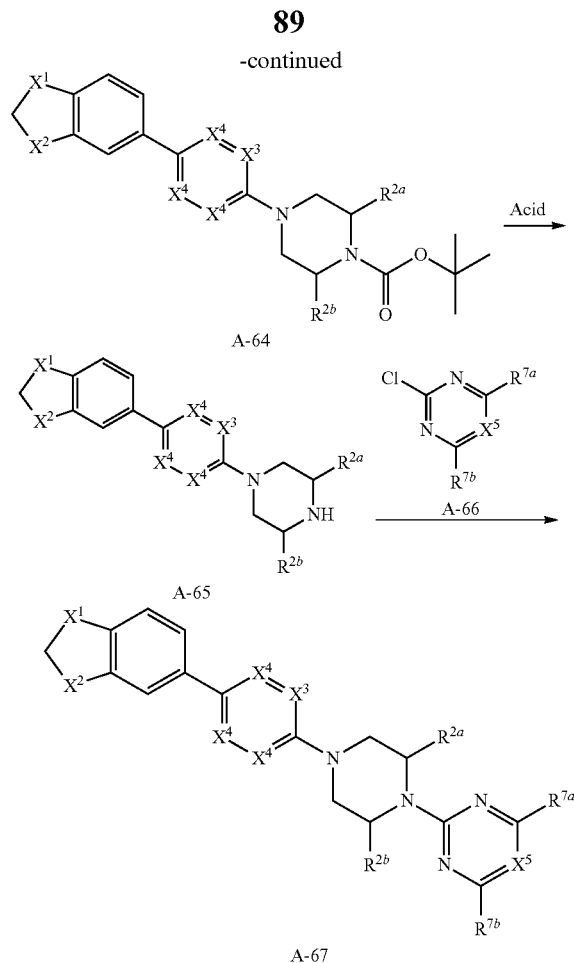

A-64

A-65

A-67

A compound of the formula (A-5), is reacted with a compound of the formula (A-60), a known compound prepared by known methods in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium(0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-61). A compound of the formula (A-61) is reacted with trifluoromethanesulfonic anhydride in the presence of a base such as pyridine, 2,6-lutidine, 2-picoline, 3-picoline, 4-picoline, N,N-dimethylaminopyridine, diisopropylethyl amine, trimethylamine and the like in a solvent such as methylene chloride, 1,2-dichloroethane, chloroform, tetrahydrofuran, ether, 1,4-dioxane, acetone, acetonitrile, N,N-dimethylformamide and the like, optionally with heating, optionally with microwave irradiation to provide compounds of the formula (A-62). A compound of formula (A-62) is reacted with a compound of formula (A-63), a known compound or a compound prepared by known methods, in the presence of an organophosphorus ligand such as 2,2'-bis(diphenylphosphino)-1,1'-binaphthyl, (R)-(+)-5,5'-bis(diphenylphosphino)-4,4'-bi-1,3-benzodioxole, [4(R)-(4,4'-bi-1,3-benzodioxole)-5,5'-diyl]bis[diphenylphosphine], (S)-(+)-5,5'-Bis (diphenylphosphino)-4,4'-bi-1,3-benzodioxole, [4(S)-(4,4'-bi-1,3-benzodioxole)-5,5'-diyl]bis[diphenylphosphine], (R)-(+)-2,2'-bis(diphenylphosphino)-5,5',6,6',7,7',8,8'-octahydro-1,1'-binaphthyl, [(1R)-5,5',6,6',7,7',8,8'-octahydro-[1,1'-binaphthalene]-2,2'-diyl]bis [diphenylphosphine], (S)-(+)-5,5'-bis(diphenylphosphino)-4,4'-bi-1,3-benzodioxole, [4(S)-(4,4'-bi-1,3-benzodioxole)-5,5'-diyl]bis[diphenylphosphine], (R)-(+)-2,2'-bis(di-p-tolylphosphino)-1,1'-binaphthyl, (S)-(−)-2,2'-bis(di-p-tolylphosphino)-1,1'-binaphthyl, and the like, in the presence of a palladium catalyst such as palladium acetate, palladium chloride, tetrakis(triphenylphosphine)palladium (0), bis(triphenylphosphine)palladium(II) dichloride, and the like, in a solvent such as toluene, benzene, xylene, tetrahydrofuran, 1,4-dioxane, acetonitrile, and the like, optionally in the presence of a base such as trimethylamine, pyridine, diisopropylethylamine and the like, optionally with heating, optionally with microwave irradiation, to provide a compound of formula (A-64). A compound of the formula (A-64), is reacted with an acid such as formic acid, trifluoroacetic acid, trichloroacetic acid, hydrochloric acid, sulfuric acid and the like in the presence of a solvent such as 1,4-dioxane, tetrahydrofuran, methanol, ethanol, methylene chloride, and the like, optionally with heating, optionally with microwave irradiation to provide a compound of formula (A-65). A compound of formula (A-65) is reacted with a compound of the formula (A-66) a known compound or a compound prepared by known methods, in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (A-67).

Scheme A-20

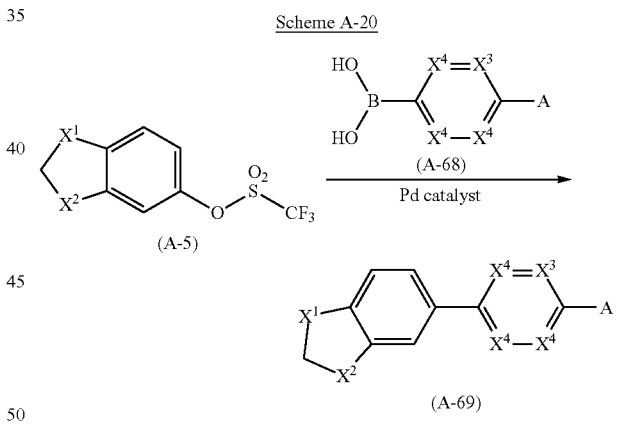

A compound of the formula (A-5), a known compound or a compound prepared by known methods, is reacted with a compound of the formula (A-68), a know compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (A-69).

Scheme A-21

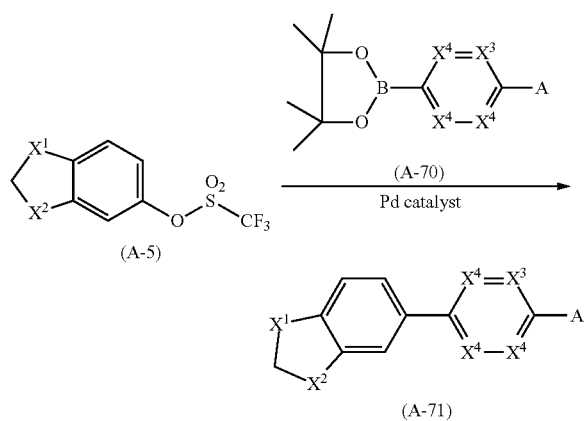

A compound of the formula (A-5), a known compound or a compound prepared by known methods, is reacted with a compound of the formula (A-70), a know compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (A-71).

Scheme A-22
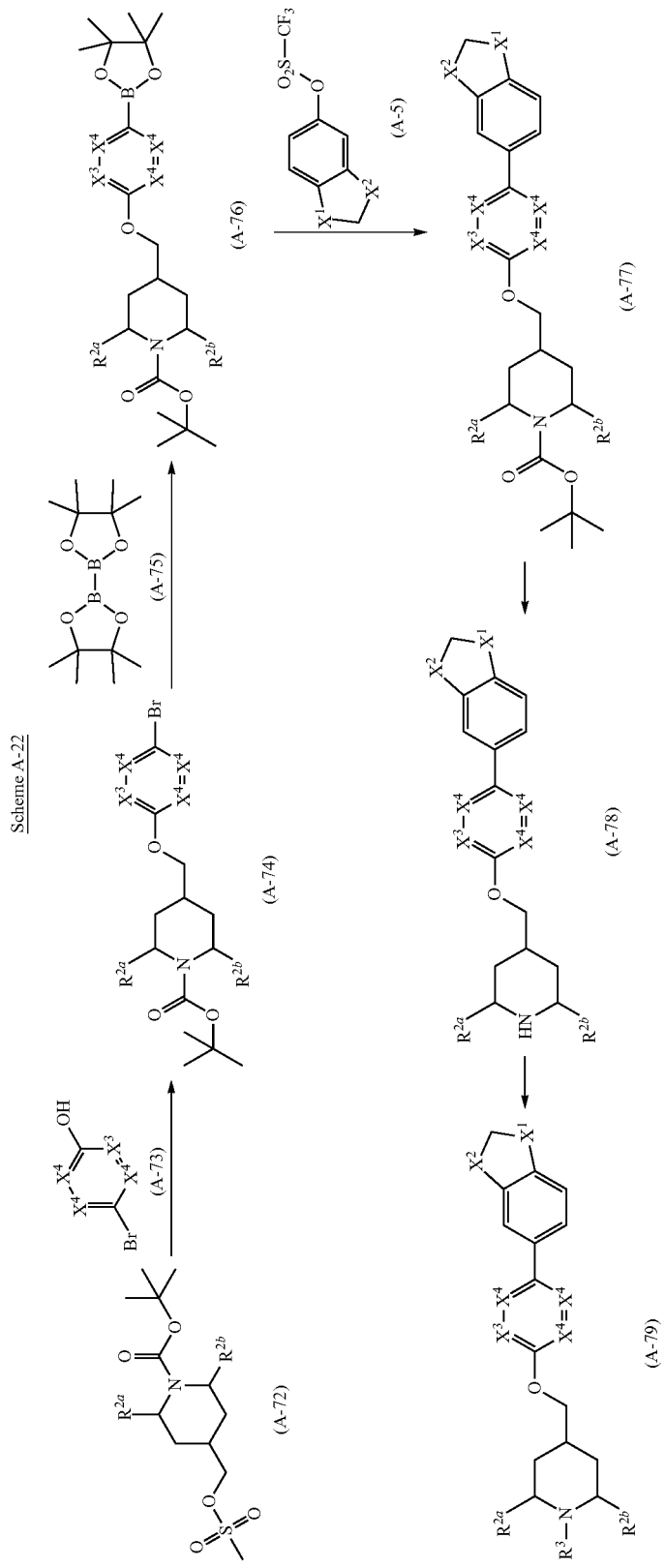

A compound of the formula (A-72), a known compound or a compound prepared by known methods, is reacted with a compound of the formula (A-73), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N,N-dimethyl formamide, dimethyl sulfoxide, methanol, ethanol, and the like, optionally with heating, optionally with microwave irradiation to provide a compound of the formula (A-74). A compound of the formula (A-74) is reacted with a compound of the formula (A-75) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N, N-dimethyl formamide, and the like, optionally with heating, optionally with microwave irradiation to provide a compound of the formula (A-76). A compound of the formula (A-76) is reacted with a compound of the formula (A-5), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (A-77). A compound of the formula (A-77) is then reacted with an acid such as hydrochloric acid, hydrobromic acid, trifluoroacetic acid, acetic acid, formic acid, and the like, optionally with heating, optionally with microwave irradiation to provide a compound of the formula (A-78). A compound of the formula (A-78) is reacted with an aldehyde in the presence of a reducing agent such as sodium triacetoxy borohydride, sodium borohydride, and the like, optionally in the presence of an acid such as acetic acid, formic acid, hydrochloric acid, and the like, in a solvent such as tetrahydrofuran, 1,4-dioxane, methylene chloride, methanol, ethanol, and the like, optionally with heating, optionally with microwave irradiation to provide a compound of the formula (A-79). Alternatively, a compound of the formula (A-78) is reacted with a ketone in the presence of a reducing agent such as sodium triacetoxy borohydride, sodium borohydride, and the like, optionally in the presence of an acid such as acetic acid, formic acid, hydrochloric acid, and the like, in a solvent such as tetrahydrofuran, 1,4-dioxane, methylene chloride, methanol, ethanol, and the like, optionally with heating, optionally with microwave irradiation to provide a compound of the formula (A-79).

Scheme A-23

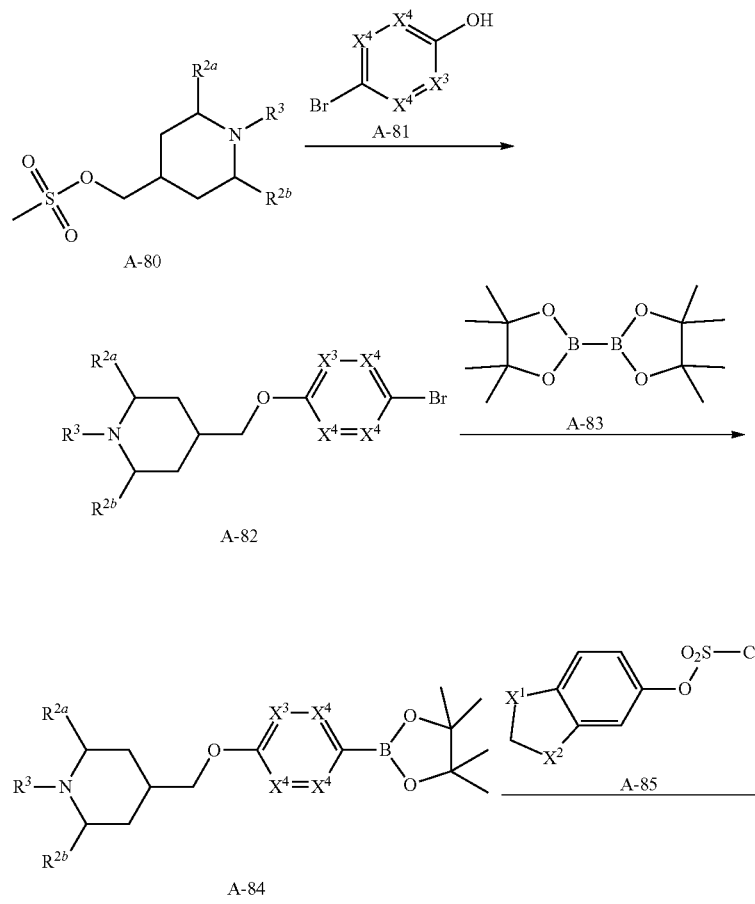

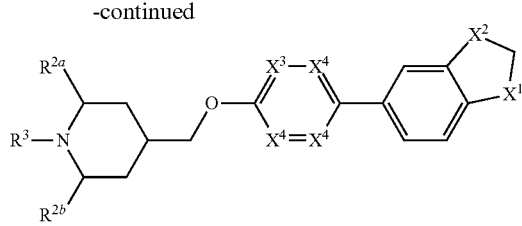

A-86

A compound of the formula (A-80), a known compound or a compound prepared by known methods, is reacted with a compound of the formula (A-81), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N,N-dimethyl formamide, dimethyl sulfoxide, methanol, ethanol, and the like, optionally with heating, optionally with microwave irradiation to provide a compound of the formula (A-82). A compound of the formula (A-82) is reacted with a compound of the formula (A-83) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N, N-dimethyl formamide, and the like, optionally with heating, optionally with microwave irradiation to provide a compound of the formula (A-84). A compound of the formula (A-84) is reacted with a compound of the formula (A-85), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (A-86).

Scheme A-24

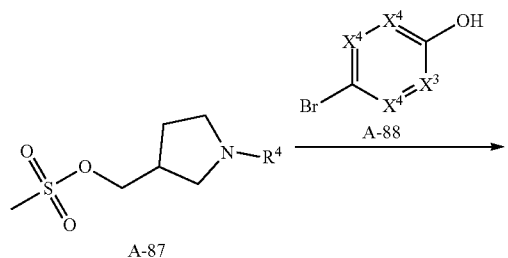

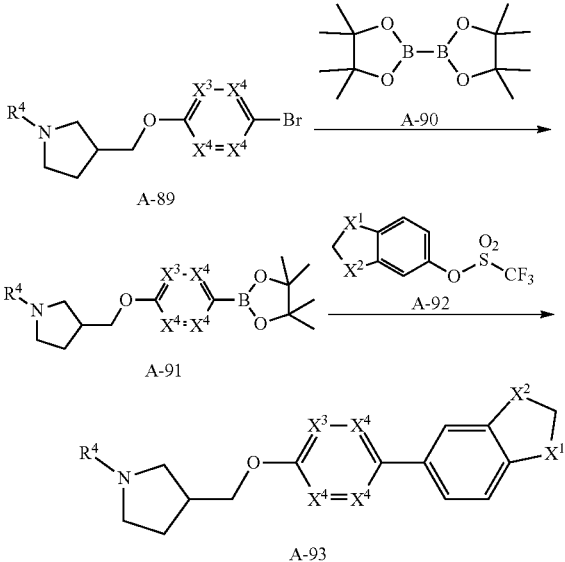

A compound of the formula (A-87), a known compound or a compound prepared by known methods, is reacted with a compound of the formula (A-88), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N, N-dimethyl formamide, dimethyl sulfoxide, methanol, ethanol, and the like, optionally with heating, optionally with microwave irradiation to provide a compound of the formula (A-89). A compound of the formula (A-89) is reacted with a compound of the formula (A-90) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N, N-dimethyl formamide, and the like, optionally with heating, optionally with microwave irradiation to provide a compound of the formula (A-91). A compound of the formula (A-91) is reacted with a compound of the formula (A-92), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (A-93).

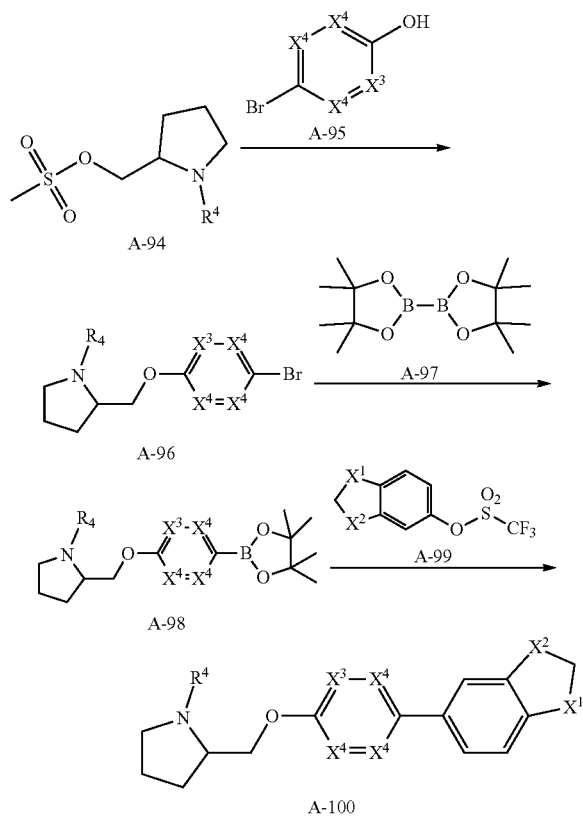

Scheme A-25

A compound of the formula (A-94), a known compound or a compound prepared by known methods, is reacted with a compound of the formula (A-95), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N,N-dimethyl formamide, dimethyl sulfoxide, methanol, ethanol, and the like, optionally with heating, optionally with microwave irradiation to provide a compound of the formula (A-96). A compound of the formula (A-96) is reacted with a compound of the formula (A-97) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N,N-dimethyl formamide, and the like, optionally with heating, optionally with microwave irradiation to provide a compound of the formula (A-98). A compound of the formula (A-98) is reacted with a compound of the formula (A-99), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (A-100).

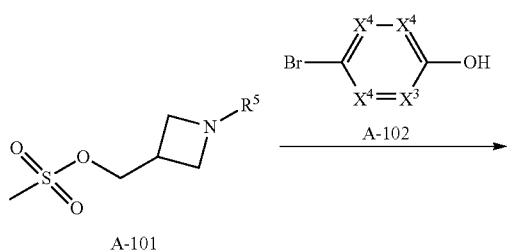

Scheme A-26

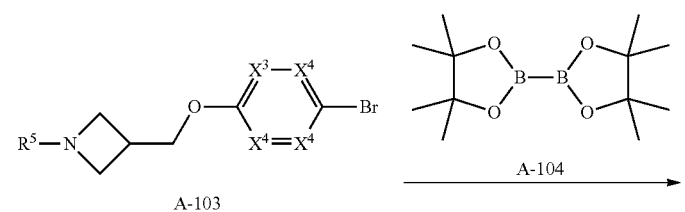

-continued

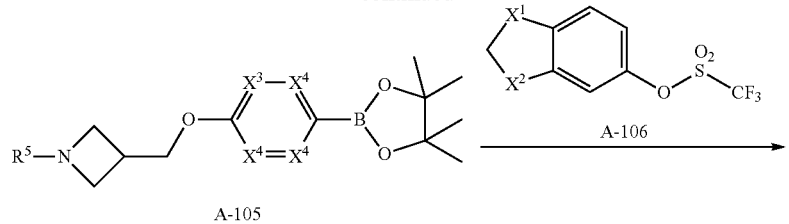

A-105 → A-106

A-107

A compound of the formula (A-101), a known compound or a compound prepared by known methods, is reacted with a compound of the formula (A-102), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N, N-dimethyl formamide, dimethyl sulfoxide, methanol, ethanol, and the like, optionally with heating, optionally with microwave irradiation to provide a compound of the formula (A-103). A compound of the formula (A-103) is reacted with a compound of the formula (A-104) in the presence of a palladium catalyst such as a 1,1' (bisdiphenylphosphino) ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N, N-dimethyl formamide, and the like, optionally with heating, optionally with microwave irradiation to provide a compound of the formula (A-105). A compound of the formula (A-105) is reacted with a compound of the formula (A-106), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (A-107).

Scheme A-27

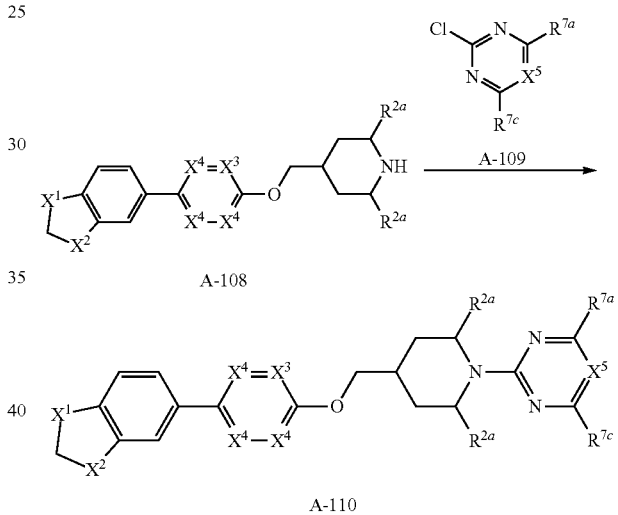

A compound of the formula (A-108) is reacted with a compound of the formula (A-109), a known compound or a compounds prepared by known methods, in the presence of a base such as triethylamine, diisopropylethyl amine, pyridine, 2,6-lutidine, and the like, in the presence of a solvent such as acetonitrile, tetrahydrofuran, 1,4-dioxane, N,N-dimethylformamide, and the like, optionally with heating, optionally with microwave irradiation to provide a compound of the formula (A-110).

Scheme A-28

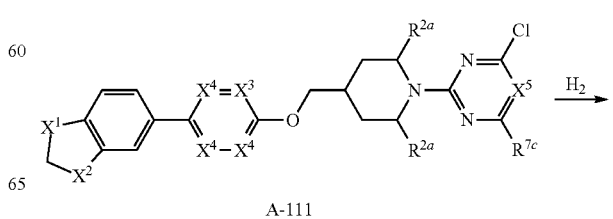

A-111

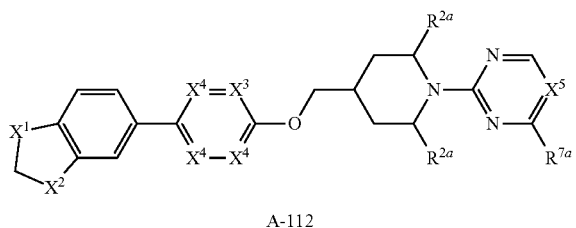

A-112

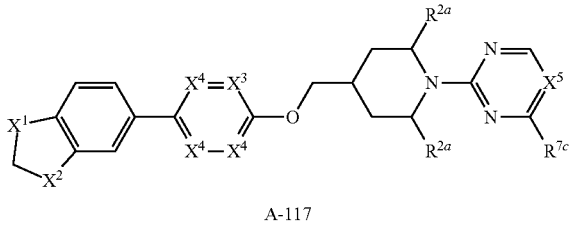

A-117

A compound of the formula (A-111) is reacted with hydrogen in the presence of a palladium catalyst such as palladium on carbon, tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methanol, ethanol, and the like, optionally with heating, optionally with microwave irradiation to provide a compound of the formula (A-112).

A compound of the formula (A-116) is reacted with hydrogen in the presence of a palladium catalyst such as palladium on carbon, tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methanol, ethanol, and the like, optionally with heating, optionally with microwave irradiation to provide a compound of the formula (A-117).

Scheme A-29

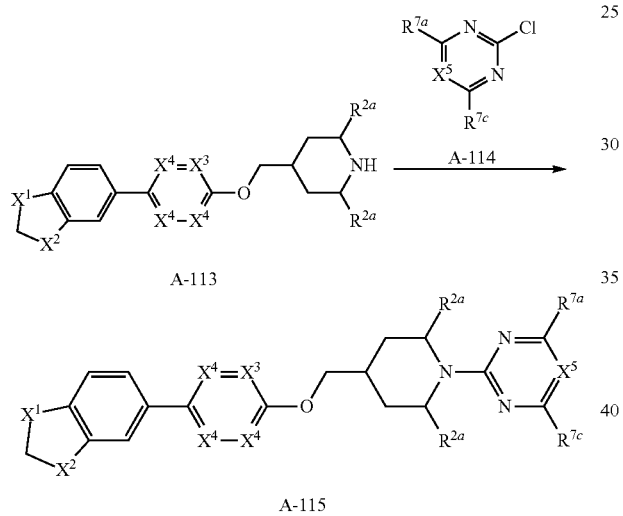

Scheme A-31

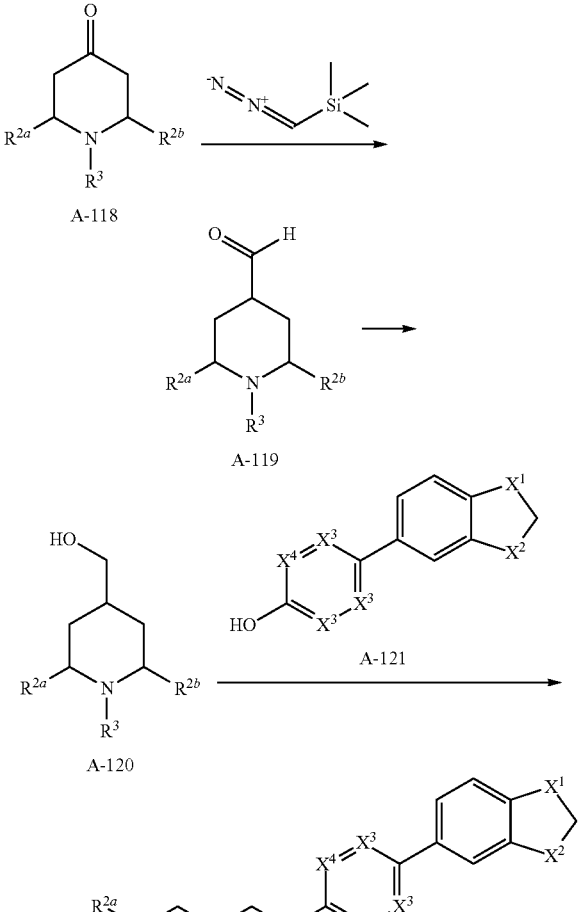

A compound of the formula (A-113) is reacted with a compound of the formula (A-114), a known compound or a compounds prepared by known methods, in the presence of a base such as triethylamine, diisopropylethyl amine, pyridine, 2,6-lutidine, and the like, in the presence of a solvent such as acetonitrile, tetrahydrofuran, 1,4-dioxane, N,N-dimethylformamide, and the like, optionally with heating, optionally with microwave irradiation to provide a compound of the formula (A-115).

Scheme A-30

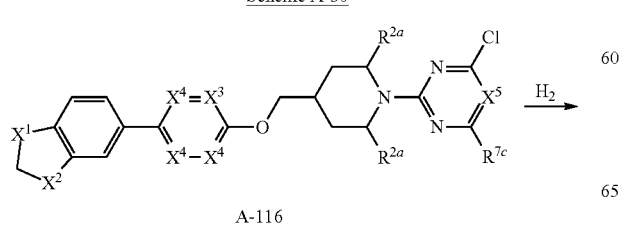

A-116

A compound of formula (A-118) is reacted with trimethylsilyldiazomethane in hexanes in the presence of a base such as lithium diisopropylamide, sodium diisopropylamide, potassium diisopropylamide, lithium hexamethyldisilazide, sodium hexamethyldisilazide, potassium hexamethyldisilazide, and the like, in the presence of a solvent such as 1,4-dioxane, tetrahydrofuran, methylene chloride, 1,2-dichloroethane, and the like, optionally with cooling to −78° C. to provide a compound of formula (A-119). A compound of formula (A-119) is reacted with a reducing hydride reagent such as sodium borohydride, lithium borohydride, lithium aluminum hydide, and the like, in a solvent such as methanol, ethanol, 1,4-dioxane, tetrahydrofuran, and the like, optionally with heating, optionally with microwave irradiation to provide a compound of the formula (A-120). A compound of formula (A-120) is reacted with a compound of formula (A-121) a known compound or compound prepared by known methods, in the presence of a phosphine such as triphenylphosphine, tri(o-tolyl)phosphine, resin-bound triphenylphosphine, and the like, in the presence of an azodicarboxylate such as diethyl azodicarboxylate, diisopropyl azodicarboxylate, di-t-butylazodicarboxylate, di-(4-chlorobenzyl)azodicarboxylate, and the like, in the presence of a solvent such as tetrahydrofuran, diethyl ether, 1,4-dioxane, methylene chloride, and the like, optionally with heating, optionally with microwave irradiation to provide a compound of the formula (A-122).

Scheme B-1

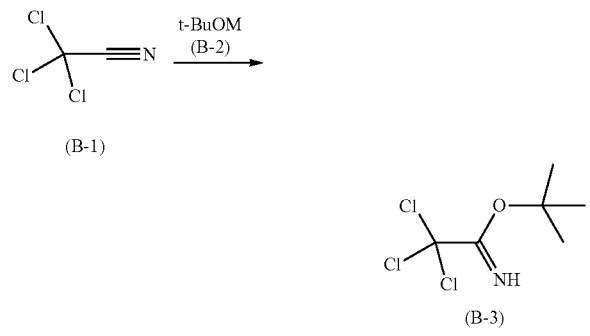

A compound of the formula (B-1), a known compound or compound prepared by known methods, is reacted with a compound of the formula (B-2) wherein M is a metal such as sodium, lithium, potassium, and the like, in a solvent such as methanol, ethanol, isopropanol, t-butanol, neopentanol, tetrahydrofuran, 1,4-dioxane, methylene chloride. and the like, optionally with heating, optionally with microwave irradiation to provide a compound of the formula (B-3).

Scheme B-2

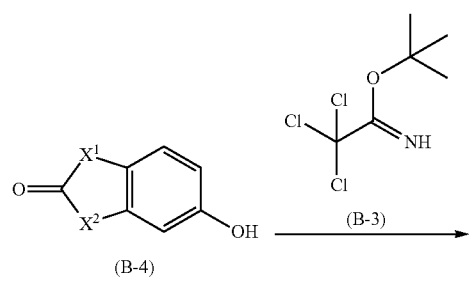

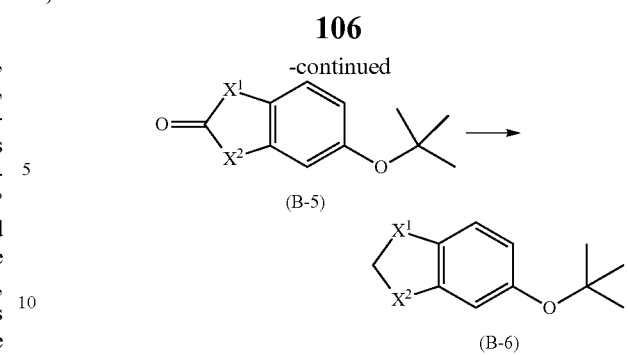

A compound of the formula (B-4), a known compound or compound prepared by known methods, is reacted with a compound of the formula (B-3), in the presence of a Lewis acid such as boron trifluoride etherate, boron trichloride, trimethyl borate, triethyl borate, aluminum chloride, iron chloride, magnesium chloride, chromium chloride, titanium tetramethoxide, titanium tetraethoxide, tin chloride, cobalt chloride and the like, in the presence of a solvent such as methylene chloride, tetrahydrofuran, 1,4-dioxane, N,N-dimethylformamide, and the like, optionally with heating, optionally with microwave irradiation to give a compound of formula (B-5). The compound of formula (B-5) is reacted with a base such as sodium carbonate, cesium carbonate, lithium carbonate, potassium carbonate, potassium hydroxide, sodium hydroxide, lithium hydroxide, and the like in a solvent such as, methylene chloride, acetone, acetonitrile, tetrahydrofuran, 1,4-dioxane, methylene chloride, 1,2-dichloroethane, and the like, optionally in the presence of a crown ether such as 18-crown-6, 12-crown-4, 15-crown-5, and the like, optionally with heating, optionally with microwave irradiation to provide a compound of the formula (B-6).

Scheme B-3

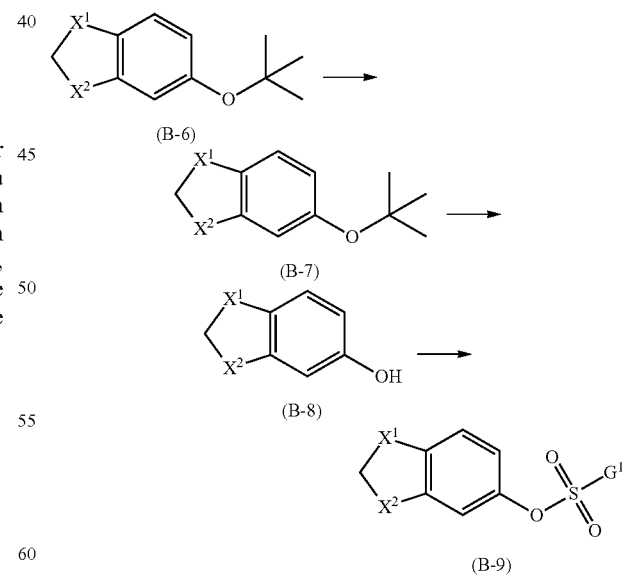

A compound of the formula (B-6) is reacted with an oxidizing agent such as m-chloroperoxybenzoic acid, monoperphthalic acid, peracetic acid, perpropionic acid, pertrifluoroacetic acid, potassium periodate, sodium metaperiodate, sodium perborate, potassium peroxymonosulfate (Oxone®), potassium peroxydisulfate, dimethyldioxirane, and the like, in the presence of a solvent such as tetrahydrofuran, ether, 1,4-dioxane, acetone, acetonitrile, methanol, ethanol, isopropanol, water, optionally with heating, optionally with microwave irradiation to provide compounds of the formula (B-7). Alternatively, a compound of the formula (B-6) is reacted with a sulfoxide such as diphenyl sulfoxide, dimethyl sulfoxide, and the like, in the presence of a rhenium catalyst such as $ReOCl_3(PPh_3)_2$, and the like, in a solvent such as methylene chloride, 1,2-dichloroethane, chloroform, tetrahydrofuran, ether, 1,4-dioxane, acetone, acetonitrile, and the like, optionally with heating, optionally with microwave irradiation to provide compounds of the formula (B-7). Alternatively, a compound of the formula (B-6) is reacted with urea hydrogen peroxide complex in the presence of a rhenium catalyst such as $ReOCl_3(PPh_3)_2$, and the like, in a solvent such as methylene chloride, 1,2-dichloroethane, chloroform, tetrahydrofuran, ether, 1,4-dioxane, acetone, acetonitrile, N,N-dimethylformamide, optionally with heating, optionally with microwave irradiation to provide compounds of the formula (B-7). Alternatively, a compound of the formula (B-6) is reacted with hydrogen peroxide in the presence titanium (IV) isopropoxide-diethyltartarate, optionally in the presence of an amino alcohol such as 2-amino-3-phenylpropan-1-ol, 2-amino-4-methylpentan-1-ol, 2-amino-4-(methylthio)butan-1-ol, 2-aminopropan-1-ol, and the like, in a solvent such as methylene chloride, 1,2-dichloroethane, chloroform, tetrahydrofuran, ether, 1,4-dioxane, acetone, acetonitrile, N,N-dimethylformamide optionally with heating, optionally with microwave irradiation to provide compounds of the formula (B-7). Alternatively, a compound of the formula (B-6) is reacted with an oxidoreductase such as Baeyer-Villiger monooxygenase, cytochrome P450 2C9, cytochrome P450 2C19, cytochrome P450 3A4 and, in a solvent such as water, methanol, ethanol, isopropanol, acetonitrile, acetone, and the like, optionally with heating, optionally with microwave irradiation to provide compounds of the formula (B-7). Alternatively, a compound of the formula (B-6) is electrochemically oxidized optionally in the presence of a buffer solution such as a sodium phosphate solution, a potassium phosphate solution, and the like to provide compounds of the formula (B-7). Alternatively, a compound of the formula (B-6) is photochemically oxidized in a solvent such as methylene chloride, 1,2-dichloroethane, chloroform, tetrahydrofuran, ether, 1,4-dioxane, acetone, acetonitrile, N,N-dimethylformamide, water, methanol, ethanol, isopropanol, and the like, optionally with heating, optionally with microwave irradiation to provide compounds of the formula (B-7). The compound of formula (B-7) is reacted with an acid such as trifluoacetic acid, hydrochloric acid, sulfuric acid, hydrogen bromide, and the like in a solvent such as, methylene bromide, acetone, acetonitrile, tetrahydrofuran, 1,4-dioxane, methylene chloride, 1,2-dichloroethane, and the like, optionally with heating, optionally with microwave irradiation to provide a compound of the formula (B-8). A compound of formula (B-8) is reacted with a sulfonyl anhydride such as methylsulfonyl anhydride, trifluoromethanesulfonic anhydride, and the like, in the presence of a base such as pyridine, 2,6-lutidine, 2-picoline, 3-picoline, 4-picoline, N,N-dimethylaminopyridine, diisopropylethyl amine, trimethylamine and the like in a solvent such as methylene chloride, 1,2-dichloroethane, chloroform, tetrahydrofuran, ether, 1,4-dioxane, acetone, acetonitrile, N,N-dimethylformamide and the like optionally with heating, optionally with microwave irradiation to provide a compound of the formula (B-9) wherein $G^1$ is selected from the group consisting of methyl and trifluoromethyl.

Scheme B-4

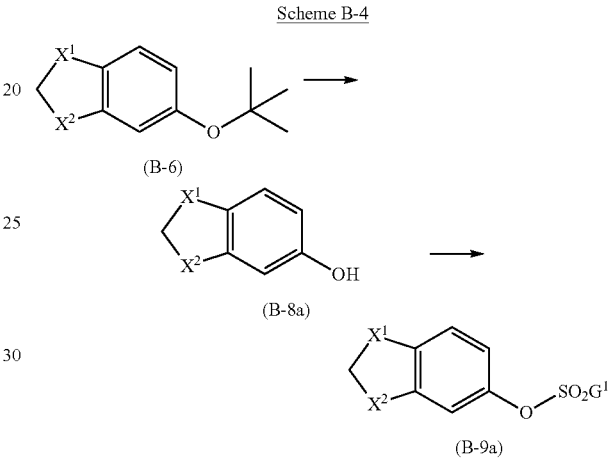

Alternatively, a compound of the formula (B-6) is reacted with an acid such as trifluoacetic acid, hydrochloric acid, sulfuric acid, hydrogen bromide, and the like in a solvent such as, methylene bromide, acetone, acetonitrile, tetrahydrofuran, 1,4-dioxane, methylene chloride, 1,2-dichloroethane, and the like, optionally with heating, optionally with microwave irradiation to provide a compound of the formula (B-8a). A compound of the formula (B-8a) is reacted with a sulfonyl anhydride such as methylsulfonyl anhydride, trifluoromethanesulfonic anhydride, and the like, in the presence of a base such as pyridine, 2,6-lutidine, 2-picoline, 3-picoline, 4-picoline, N,N-dimethylaminopyridine, diisopropylethyl amine, trimethylamine and the like in a solvent such as methylene chloride, 1,2-dichloroethane, chloroform, tetrahydrofuran, ether, 1,4-dioxane, acetone, acetonitrile, N,N-dimethylformamide and the like optionally with heating, optionally with microwave irradiation to provide a compound of the formula (B-9a) wherein $G^1$ is selected from the group consisting of methyl and trifluoromethyl.

Scheme B-5

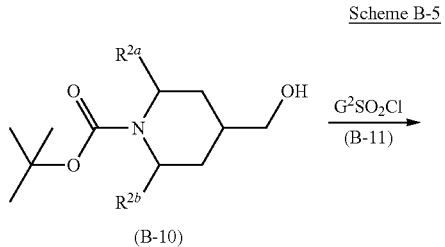

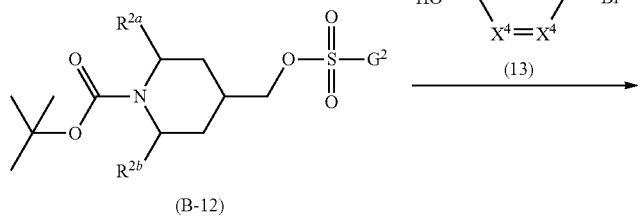

(B-12)

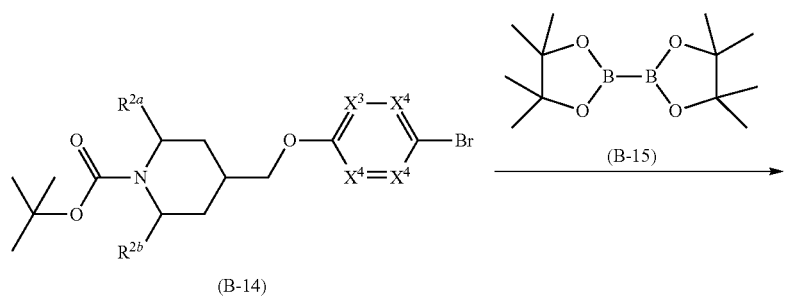

(B-14)

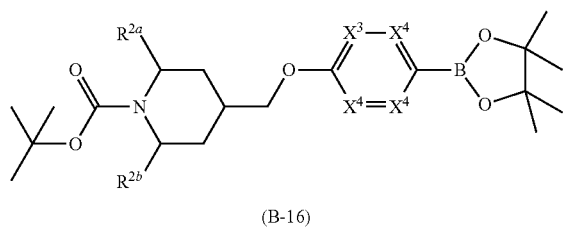

(B-16)

A compound of the formula (B-10), a known compound or compound prepared by known methods, is reacted with a compound of the formula (B-11), a known compound or a compound prepared by known methods wherein $G^2$ is selected from the group consisting of methyl, trifluoromethyl, tolyl, and p-nitrophenyl, in the presence of a base such as sodium carbonate, cesium carbonate, lithium carbonate, potassium carbonate, potassium hydroxide, sodium hydroxide, lithium hydroxide, triethylamine, diisopropylethylamine and the like in a solvent such as acetone, acetonitrile, tetrahydrofuran, 1,4-dioxane, methylene chloride, 1,2-dichloroethane, and the like, optionally with heating, optionally with microwave irradiation to provide a compound of the formula (B-12). A compound of the formula (B-12), is reacted with a compound of the formula (B-13), a known compound prepared by known methods in the presence of a base such as sodium carbonate, cesium carbonate, lithium carbonate, potassium carbonate, potassium hydroxide, sodium hydroxide, lithium hydroxide, triethylamine, diisopropylethylamine and the like, in a solvent such as acetone, acetonitrile, tetrahydrofuran, 1,4-dioxane, methylene chloride, 1,2-dichloroethane, dimethylsulfoxide, and the like, optionally with heating, optionally with microwave irradiation to provide a compound of the formula (B-14). A compound of the formula (B-14), is reacted with a compound of the formula (B-15) in the presence of a base such as potassium acetate, sodium carbonate, cesium carbonate, lithium carbonate, potassium carbonate, potassium hydroxide, sodium hydroxide, lithium hydroxide, potassium tert-butoxide, sodium tert-butoxide, lithium tert-butoxide, and the like, in the presence of a palladium catalyst such as palladium acetate, tetrakis(triphenylphosphine)palladium (0), bis(triphenylphosphine)palladium(II) dichloride, (1,1'-bis(diphenylphosphino)ferrocene)palladium(II) dichloride and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-16).

Scheme B-6

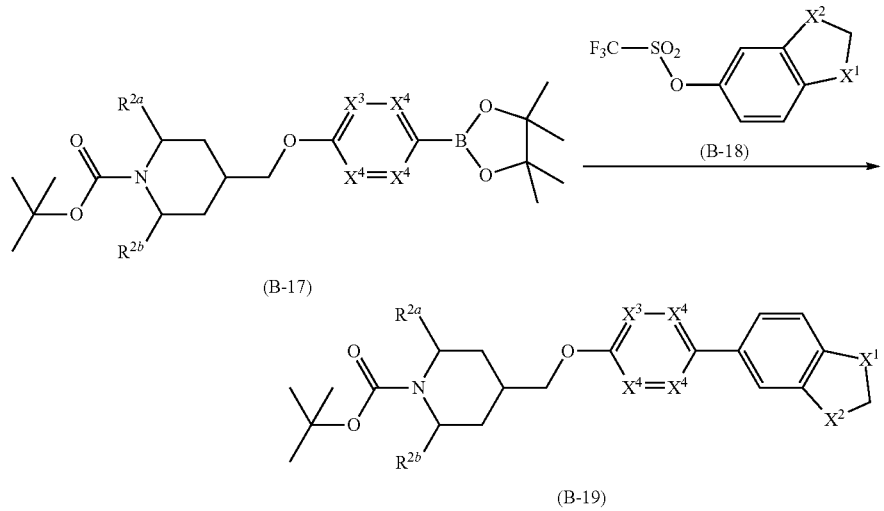

A compound of the formula (B-17), is reacted with a compound of the formula (B-18), a known compound prepared by known methods in the presence of a base such as potassium acetate, sodium carbonate, cesium carbonate, lithium carbonate, potassium carbonate, potassium hydroxide, sodium hydroxide, lithium hydroxide, potassium tert-butoxide, sodium tert-butoxide, lithium tert-butoxide, and the like in the presence of a palladium catalyst such as palladium acetate, tetrakis(triphenylphosphine)palladium (0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-19).

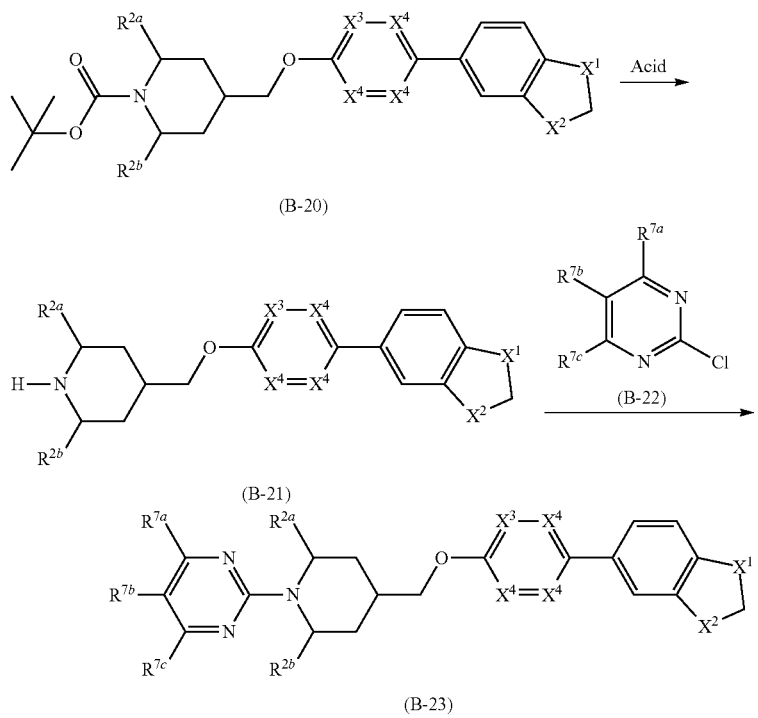

A compound of the formula (B-20), is reacted with an acid such as formic acid, trifluoroacetic acid, trichloroacetic acid, hydrochloric acid, sulfuric acid and the like, optionally in a solvent such as methanol, ethanol, methylene chloride, tetrahydrofuran, 1,4-dioxane and the like, optionally with heating, optionally with microwave irradiation, to give a compound of the formula (B-21). A compound of the formula (B-21) is reacted with a compound of the formula (B-22), a known compound or a compound prepared by known methods, in the presence of a base such as potassium acetate, sodium carbonate, cesium carbonate, lithium carbonate, potassium carbonate, potassium hydroxide, sodium hydroxide, lithium hydroxide, triethylamine, diisopropylethyl amine, and the like, in a solvent such as acetonitrile, N,N-dimethylformamide, 1,4-dioxane, tetrahydrofuran and the like, optionally with heating, optionally with microwave irradiation to provide a compound of the formula (B-23).

Scheme B-8

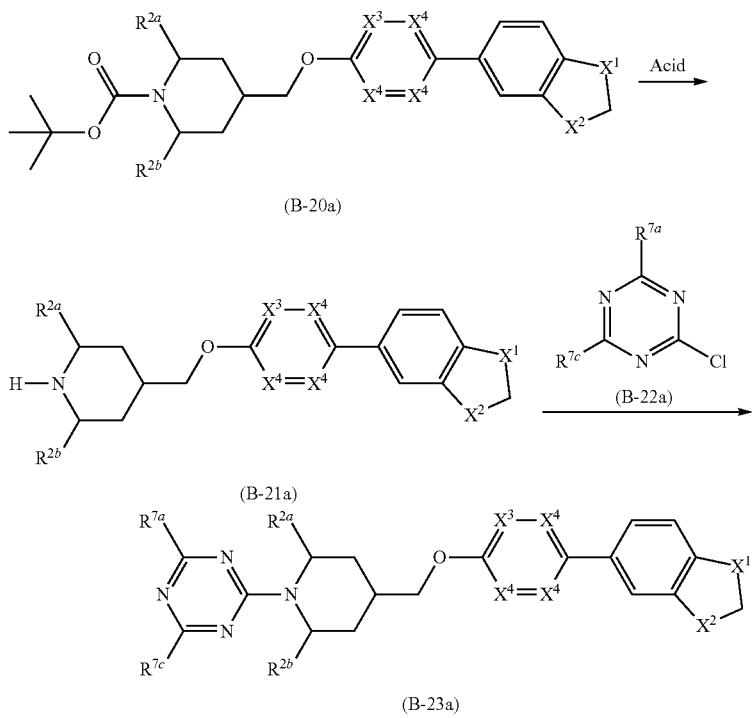

A compound of the formula (B-20a), is reacted with an acid such as formic acid, trifluoroacetic acid, trichloroacetic acid, hydrochloric acid, sulfuric acid and the like, optionally in a solvent such as methanol, ethanol, methylene chloride, tetrahydrofuran, 1,4-dioxane and the like, optionally with heating, optionally with microwave irradiation, to give a compound of the formula (B-21a). A compound of the formula (B-21a) is reacted with a compound of the formula (B-22a), a known compound or a compound prepared by known methods, in the presence of a base such as potassium acetate, sodium carbonate, cesium carbonate, lithium carbonate, potassium carbonate, potassium hydroxide, sodium hydroxide, lithium hydroxide, triethylamine, diisopropylethyl amine, and the like, in a solvent such as acetonitrile, N,N-dimethylformamide, 1,4-dioxane, tetrahydrofuran and the like, optionally with heating, optionally with microwave irradiation to provide a compound of the formula (B-23a).

Scheme B-9

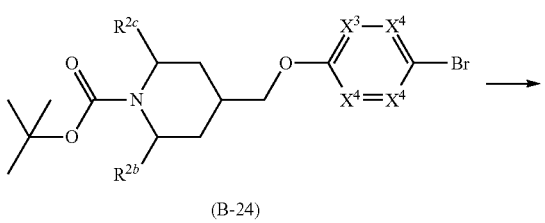

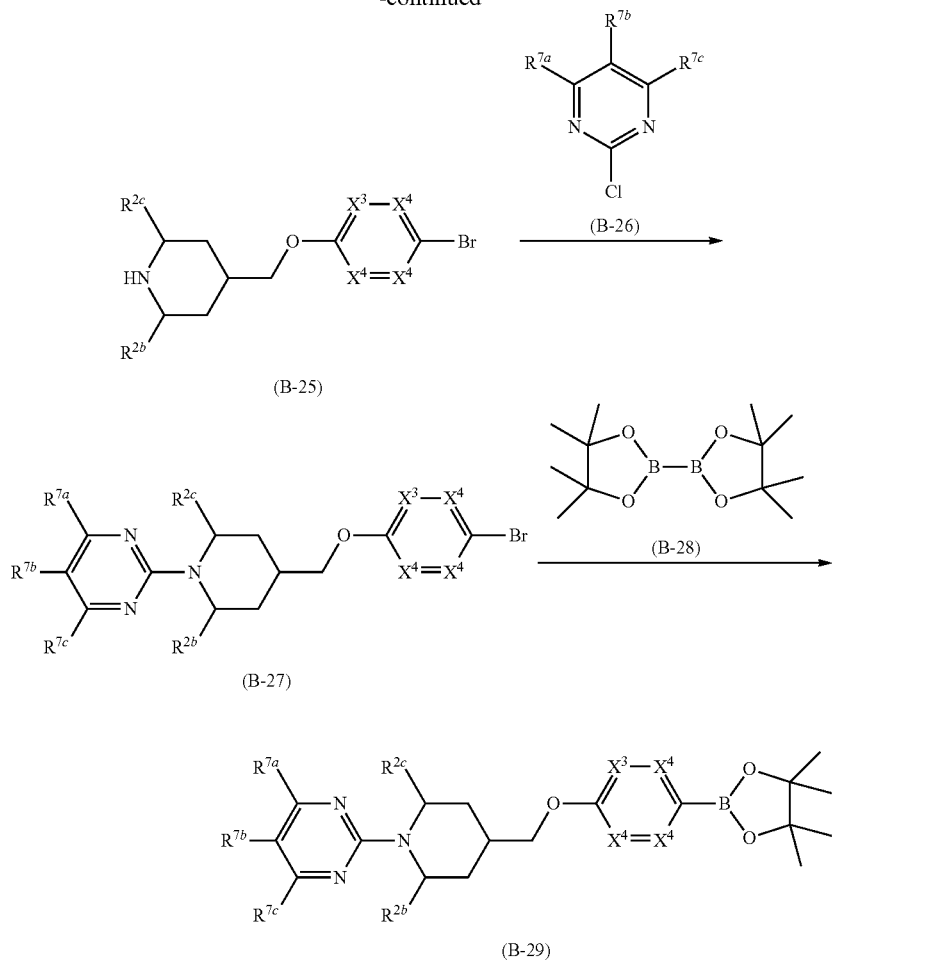

A compound of the formula (B-24), is reacted with an acid such as formic acid, trifluoroacetic acid, trichloroacetic acid, hydrochloric acid, sulfuric acid and the like, optionally in a solvent such as methanol, ethanol, methylene chloride, tetrahydrofuran, 1,4-dioxane and the like, optionally with heating, optionally with microwave irradiation, to give a compound of the formula (B-25). A compound of the formula (B-25) is reacted with a compound of the formula (B-26), a known compound or a compound prepared by known methods, in the presence of abase such as potassium acetate, sodium carbonate, cesium carbonate, lithium carbonate, potassium carbonate, potassium hydroxide, sodium hydroxide, lithium hydroxide, triethylamine, diisopropylethyl amine, and the like, optionally with heating, optionally with microwave irradiation to provide a compound of the formula (B-27). A compound of the formula (B-27), is reacted with a compound of the formula (B-28) in the presence of a base such as potassium acetate, sodium carbonate, cesium carbonate, lithium carbonate, potassium carbonate, potassium hydroxide, sodium hydroxide, lithium hydroxide, potassium tert-butoxide, sodium tert-butoxide, lithium tert-butoxide, and the like in the presence of a palladium catalyst such as palladium acetate, tetrakis(triphenylphosphine)palladium(0), bis(triphenylphosphine)palladium(II) dichloride, (1,1'-bis(diphenylphosphino)ferrocene) palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-29).

Scheme B-10

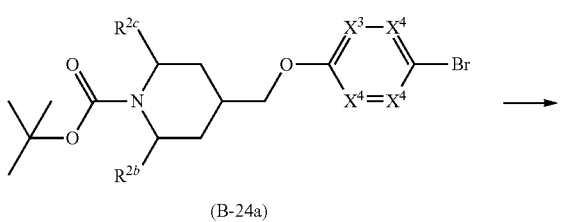

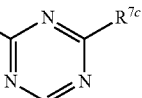
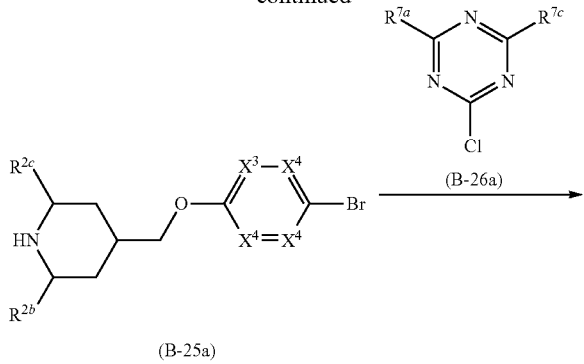

(B-26a)

(B-25a)

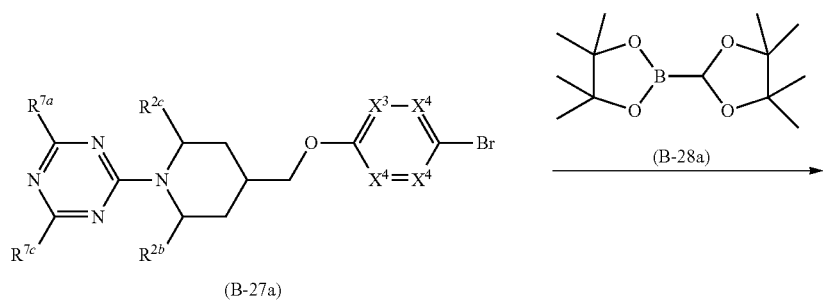

(B-28a)

(B-27a)

(B-29a)

A compound of the formula (B-24a), is reacted with an acid such as formic acid, trifluoroacetic acid, trichloroacetic acid, hydrochloric acid, sulfuric acid and the like, optionally in a solvent such as methanol, ethanol, methylene chloride, tetrahydrofuran, 1,4-dioxane and the like, optionally with heating, optionally with microwave irradiation, to give a compound of the formula (B-25a). A compound of the formula (B-25a) is reacted with a compound of the formula (B-26a), a known compound or a compound prepared by known methods, in the presence of a base such as potassium acetate, sodium carbonate, cesium carbonate, lithium carbonate, potassium carbonate, potassium hydroxide, sodium hydroxide, lithium hydroxide, triethylamine, diisopropylethyl amine, and the like, optionally with heating, optionally with microwave irradiation to provide a compound of the formula (B-27a). A compound of the formula (B-27a), is reacted with a compound of the formula (B-28a) in the presence of a base such as potassium acetate, sodium carbonate, cesium carbonate, lithium carbonate, potassium carbonate, potassium hydroxide, sodium hydroxide, lithium hydroxide, potassium tert-butoxide, sodium tert-butoxide, lithium tert-butoxide, and the like in the presence of a palladium catalyst such as palladium acetate, tetrakis(triphenylphosphine)palladium(0), bis(triphenylphosphine)palladium(II) dichloride, (1,1'-bis(diphenylphosphino)ferrocene) palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-29a).

Scheme B-11

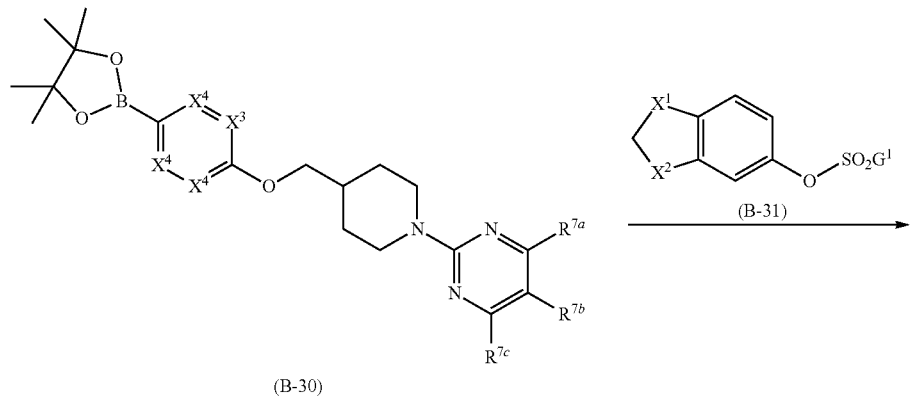

(B-30)

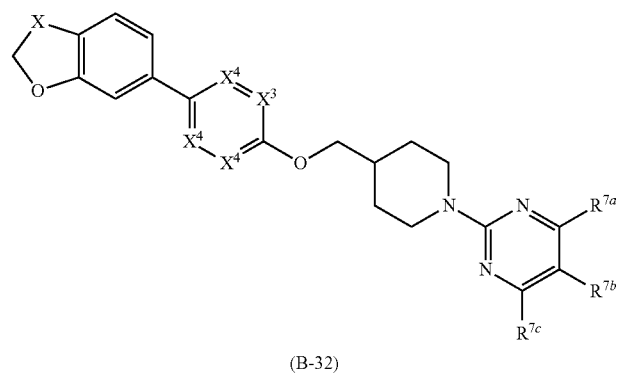

(B-32)

A compound of the formula (B-30), is reacted with a compound of the formula (B-31), a known compound prepared by known methods wherein $G^1$ is selected from the group consisting of methyl and trifluoromethyl, in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium (0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-32).

Scheme B-12

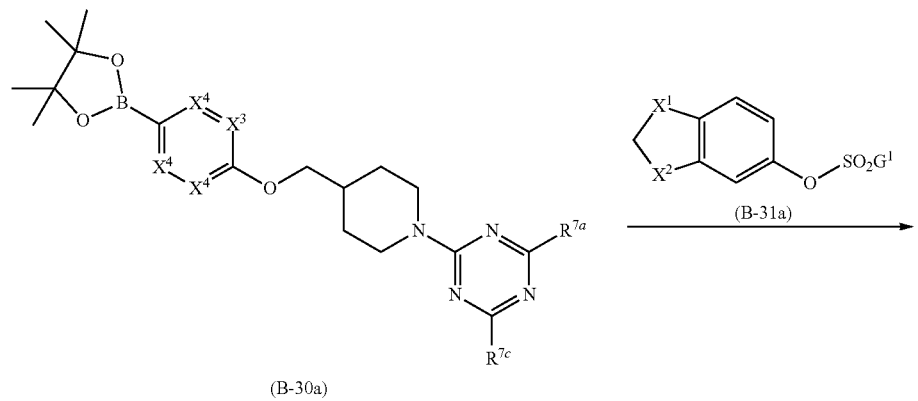

(B-30a)

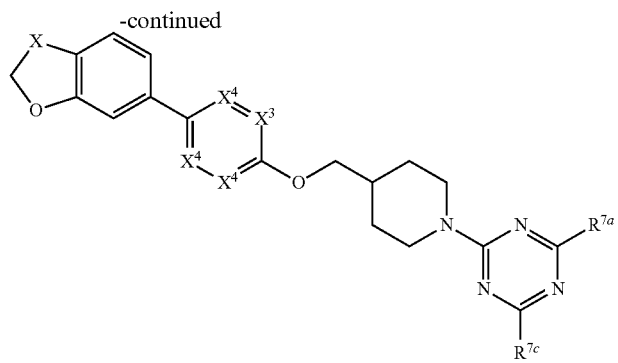

(B-32a)

A compound of the formula (B-30), is reacted with a compound of the formula (B-31), a known compound prepared by known methods wherein G¹ is selected from the group consisting of methyl and trifluoromethyl, in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium (0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-32).

dimethylformamide and the like, optionally with heating, optionally with microwave irradiation to provide compounds of the formula (B-34). A compound of formula (B-34) is reacted with methylene bromide in the presence of a base such as potassium carbonate, cesium carbonate, trimethylamine, pyridine, and the like, in a solvent such as acetonitrile, methylene chloride, N,N-dimethylformamide, and the like, optionally in the presence of a crown ether such as 18-crown-6, 12-crown-4, and the like, optionally with heating, optionally with microwave irradiation to provide a compound of the formula (B-35). A compound of formula (B-35) is oxidized with an oxidizing agent such as m-chlorobenzoic acid, hydrogen peroxide in an acid such as acetic acid, formic acid, trifluoroacetic acid, and the like, optionally in the presence of a solvent such as methanol, ethanol, tetrahydrofuran, 1,4-dioxane, N,N-dimethylformamide, and the like, optionally with heating, optionally with microwave irradiation to provide a compound of the formula (B-36).

Scheme B-13

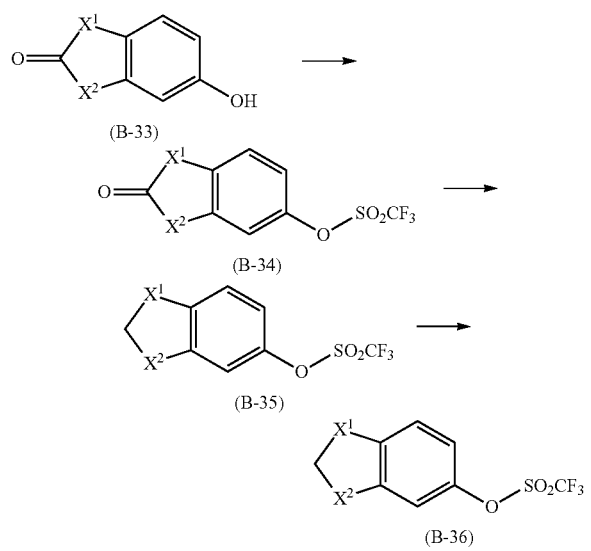

Scheme B-14

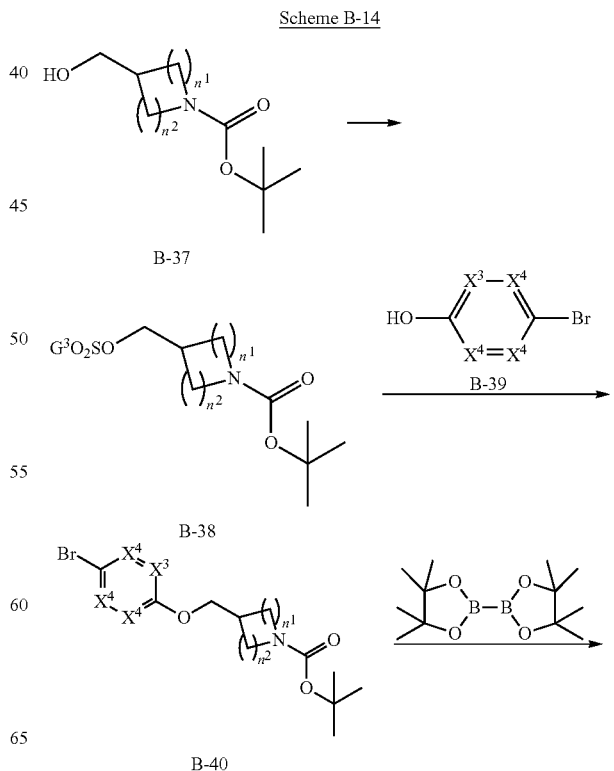

A compound of the formula (B-33), a known compound or compound prepared by known methods, is reacted with with trifluoromethanesulfonic anhydride in the presence of a base such as pyridine, 2,6-lutidine, 2-picoline, 3-picoline, 4-picoline, N,N-dimethylaminopyridine, diisopropylethyl amine, trimethylamine and the like, in a solvent such as methylene chloride, 1,2-dichloroethane, chloroform, tetrahydrofuran, ether, 1,4-dioxane, acetone, acetonitrile, N,N-

-continued

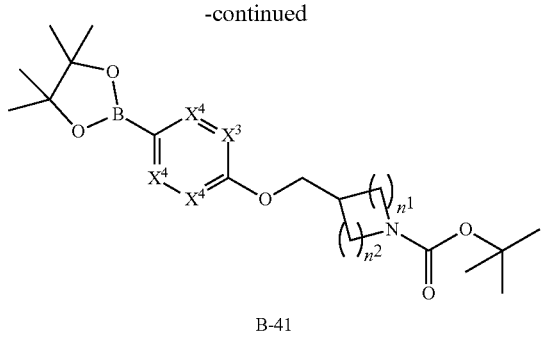

B-41

A compound of the formula (B-37), a known compound or compound prepared by known methods, is reacted with a sulfonyl chloride such as methylsulfonyl chloride, toluene sulfonyl chloride, p-nitrophenyl sulfonyl chloride in the presence of a base such as sodium carbonate, cesium carbonate, lithium carbonate, potassium carbonate, potassium hydroxide, sodium hydroxide, lithium hydroxide, triethylamine, diisopropylethylamine and the like, in a solvent such as acetone, acetonitrile, tetrahydrofuran, 1,4-dioxane, methylene chloride, 1,2-dichloroethane, and the like, optionally with heating, optionally with microwave irradiation to provide a compound of the formula (B-38) wherein $G^3$ is selected from the group consisting of methyl, tolyl and p-nitrophenyl. A compound of the formula (B-38), is reacted with a compound of the formula (B-39), a known compound prepared by known methods in the presence of a base such as sodium carbonate, cesium carbonate, lithium carbonate, potassium carbonate, potassium hydroxide, sodium hydroxide, lithium hydroxide, triethylamine, diisopropylethylamine and the like, in a solvent such as dimethylsulfoxide, N, N-dimethylformamide, acetone, acetonitrile, tetrahydrofuran, 1,4-dioxane, methylene chloride, 1,2-dichloroethane, and the like, optionally with heating, optionally with microwave irradiation to provide a compound of the formula (B-40). A compound of the formula (B-40), is reacted with a 4,4,4',4',5,5,5',5'-octamethyl-2,2'-bi-1,3,2-dioxoborolane, a known compound prepared by known methods, in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium(0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, N, N-dimethylformamide, and the like, optionally with heating, optionally with microwave irradiation to provide a compound of the formula (B-41).

Scheme B-15

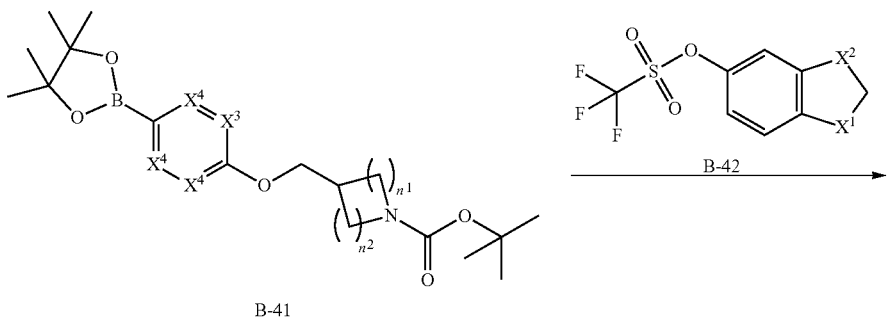

B-41

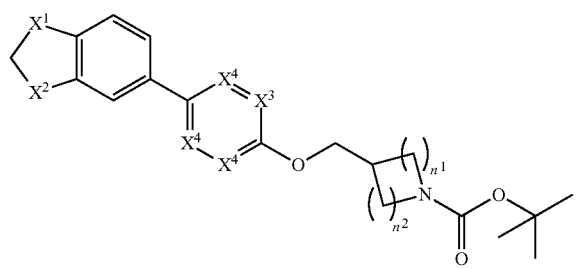

B-43

A compound of the formula (B-41), is reacted with a compound of the formula (B-42), a known compound prepared by known methods in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium(0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-43).

Scheme B-16

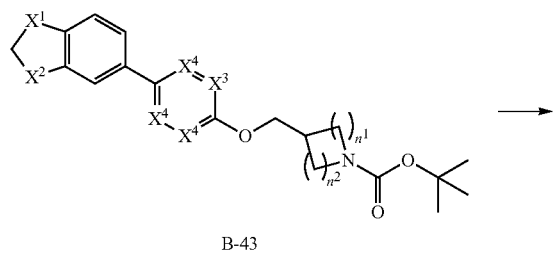

B-43

↓

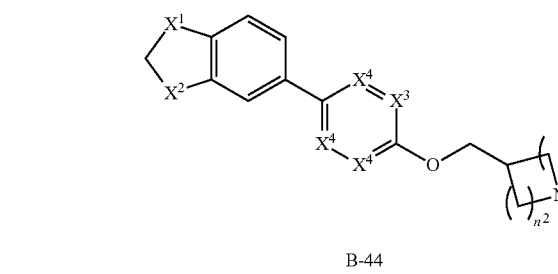

B-44

A compound of the formula (B-43), is reacted with an acid such as formic acid, trifluoroacetic acid, trichloroacetic acid, hydrochloric acid, sulfuric acid and the like, in the presence of a solvent such as 1,4-dioxane, tetrahydrofuran, methylene chloride, N,N-dimethylformamide, acetonitrile, and the like, optionally with heating, optionally with microwave irradiation to provide a compound of the formula (B-44).

Scheme B-17

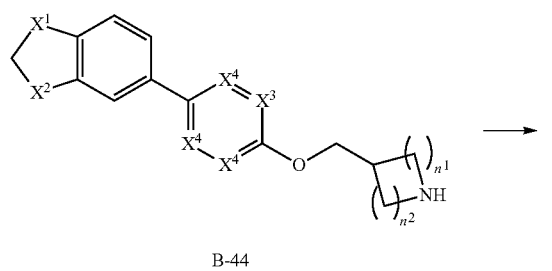

B-44

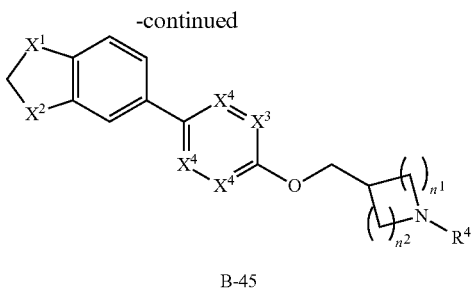

B-45

A compound of the formula (B-44), is reacted with an aldehyde in the presence of a reducing agent such as sodium triacetoxyborohydride, lithium triacetoxyborohydride, sodium borohydride, lithium borohydride, and the like, optionally in the presence of an acid such as acetic acid, trifluoroacetic acid, hydrochloric acid, and the like, in the presence of a solvent such as 1,4-dioxane, tetrahydrofuran, N,N-dimethylformamide, and the like, optionally with heating, optionally with microwave irradiation to provide a compound of the formula (B-45). Alternatively, a compound of the formula (B-44), is reacted with an ketone in the presence of a reducing agent such as sodium triacetoxyborohydride, lithium triacetoxyborohydride, sodium borohydride, lithium borohydride, and the like, optionally in the presence of an acid such as acetic acid, trifluoroacetic acid, hydrochloric acid, and the like, in the presence of a solvent such as 1,4-dioxane, tetrahydrofuran, N,N-dimethylformamide, and the like, optionally with heating, optionally with microwave irradiation to provide a compound of the formula (B-45).

Scheme B-18

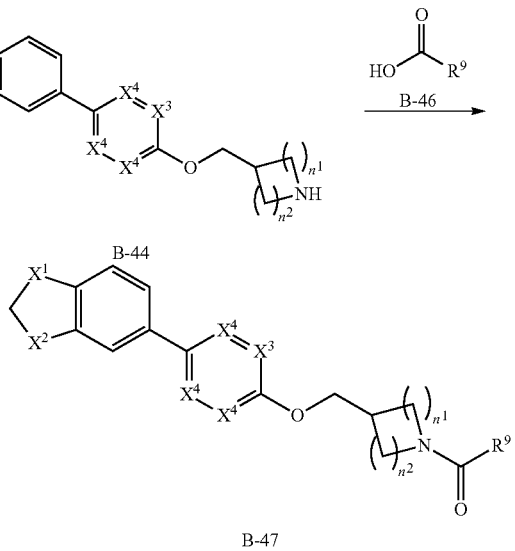

Alternatively, A compound of the formula (B-44), is reacted with a compound of the formula (B-46), a known compound or a compound prepared by known methods, in the presence of a coupling agent such as O-(benzotriazol-1-yl)-N,N,N',N'-tetramethyluronium hexafluorophosphate, N,N'-dicyclohexyl carbodiimide, 1-ethyl-3-(3-dimethylaminopropyl) carbodiimide, 1-[bis(dimethylamino) methylene]-1H-1,2,3-triazolo[4,5-b]pyridinium 3-oxide, hexafluorophosphate, 1-hydroxy-7-azabenzotriazole, N-[(1H-1,2,3- benzotriazol-1-yloxy)(dimethylamino)methylene]-N-methyl methanaminium hexafluorophosphate, 1-ethyl-3-(3-dimethylaminopropyl)carbodiimide and the like, in the presence of a base such as trimethylamine, pyridine, 2,6-lutidine, diisopropylethylamine, N-methylmorpholine, and the like in a solvent such as acetonitrile, N,N-dimethylformamide, 1,4-dioxane, tetrahydrofuran optionally with heating, optionally with microwave irradiation to provide a compound of the formula (B-47).

A compound of the formula (B-44), is reacted with a reagent of the formula (B-50) in the presence of a base such as trimethylamine, pyridine, 2,6-lutidine and the like, in a solvent such as acetonitrile, N,N-dimethylformamide, 1,4-dioxane, tetrahydrofuran optionally with heating, optionally, with microwave irradiation to provide a compound of the formula (B-51).

Scheme B-19

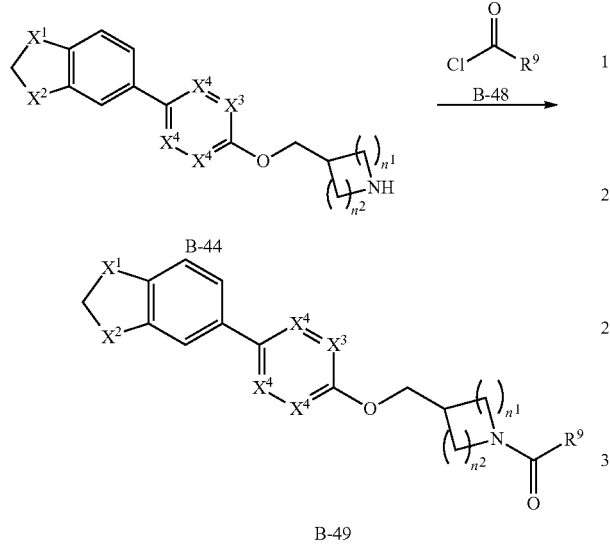

B-49

Alternatively, a compound of formula (B-44) is reacted with a compound of the formula (B-48), a known compound or a compound prepared by known methods, in the presence of a base such as trimethylamine, pyridine, 2,6-lutidine and the like, in a solvent such as acetonitrile, N,N-dimethylformamide, 1,4-dioxane, tetrahydrofuran, and the like, optionally with heating, optionally with microwave irradiation to provide a compound of the formula (B-49).

Scheme B-21

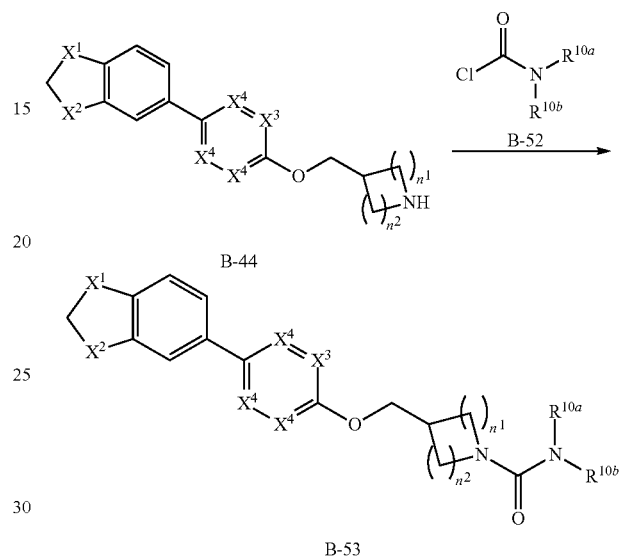

B-53

A compound of the formula (B-44), is reacted with a compound of the formula (B-52) in the presence of a base such as trimethylamine, pyridine, 2,6-lutidine and the like in a solvent such as acetonitrile, N,N-dimethylformamide, 1,4-dioxane, tetrahydrofuran optionally with heating, optionally with microwave irradiation to provide a compound of the formula (B-53).

Scheme B-20

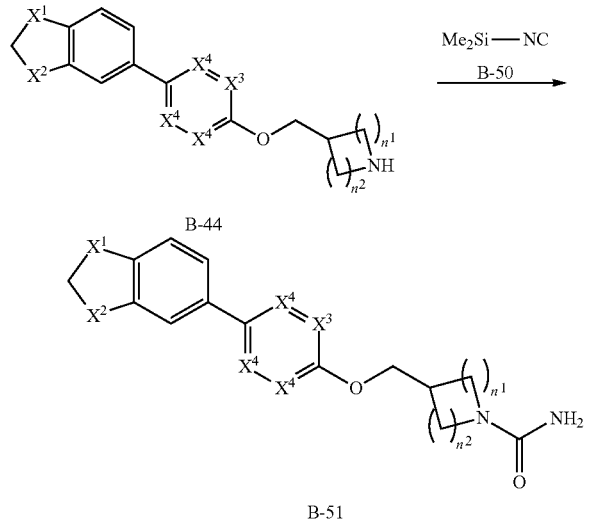

B-51

Scheme B-22

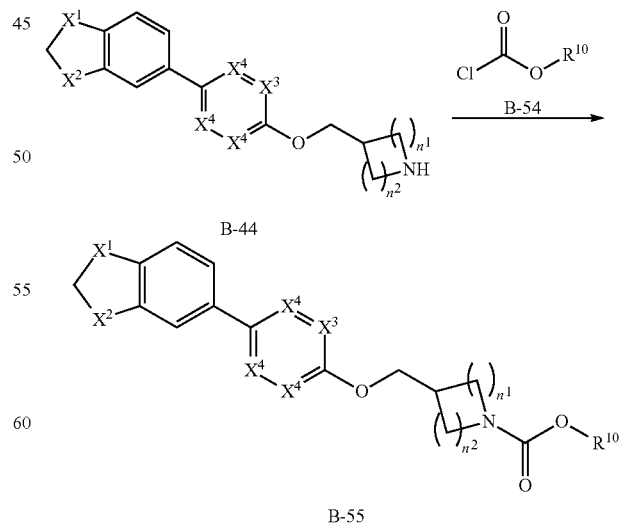

B-55

A compound of the formula (B-44), is reacted with a compound of the formula (B-54) in the presence of a base such as trimethylamine, pyridine, 2,6-lutidine and the like in a solvent such as acetonitrile, N,N-dimethylformamide, 1,4-dioxane, tetrahydrofuran optionally with heating, optionally with microwave irradiation to provide a compound of the formula (B-55).

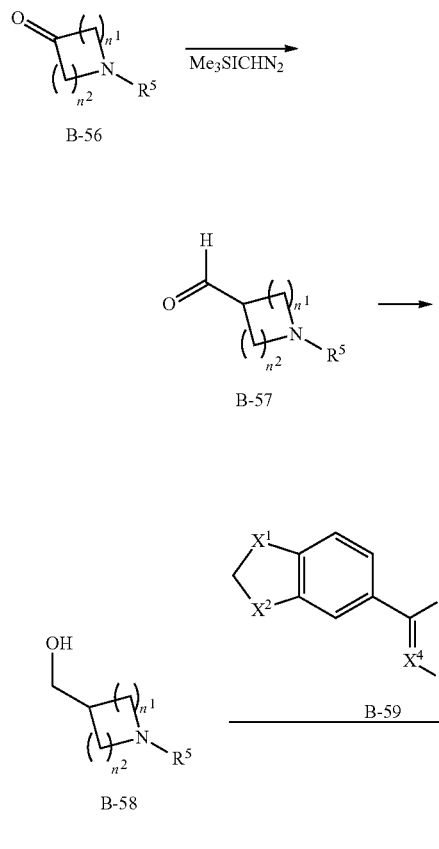

aluminum hydide, and the like, in a solvent such as methanol, ethanol, 1,4-dioxane, tetrahydrofuran, and the like, optionally with heating, optionally with microwave irradiation to provide a compound of the formula (B-58). A compound of formula (B-58) is reacted with a compound of formula (B-59) a known compound or compound prepared by known methods, in the presence of a phosphine such as triphenylphosphine, tri(o-tolyl)phosphine, resin-bound triphenylphosphine, and the like, in the presence of an azodicarboxylate such as diethyl azodicarboxylate, diisopropyl azodicarboxylate, di-t-butylazodicarboxylate, di-(4-chlorobenzyl)azodicarboxylate, and the like, in the presence of a solvent such as tetrahydrofuran, diethyl ether, 1,4-dioxane, methylene chloride, and the like, optionally with heating, optionally with microwave irradiation to provide a compound of the formula (B-60).

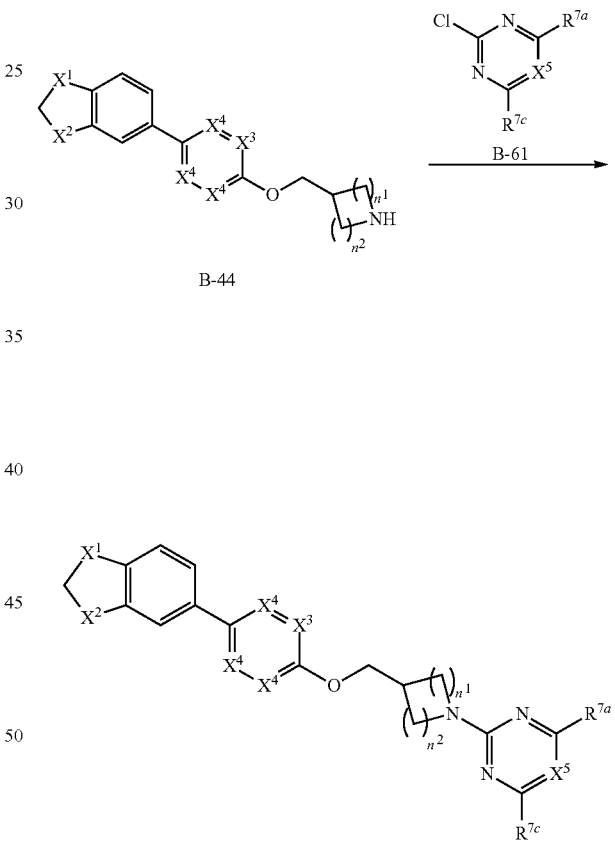

A compound of formula (B-56) is reacted with trimethylsilyldiazomethane in hexanes in the presence of a base such as lithium diisopropylamide, sodium diisopropylamide, potassium diisopropylamide, lithium hexamethyldisilazide, sodium hexamethyldisilazide, potassium hexamethyldisilazide, and the like, in the presence of a solvent such as 1,4-dioxane, tetrahydrofuran, methylene chloride, 1,2-dichloroethane, and the like, optionally with cooling to −78° C. to provide a compound of formula (B-57). A compound of formula (B-57) is reacted with a reducing hydride reagent such as sodium borohydride, lithium borohydride, lithium A compound of formula (B-44) which is reacted with a compound of the formula (B-61), a known compound or a compound prepared by known methods, in the presence of a base such as potassium acetate, sodium carbonate, cesium carbonate, lithium carbonate, potassium carbonate, potassium hydroxide, sodium hydroxide, lithium hydroxide, in a solvent such as acetonitrile, dimethylformamide, dioxane, tetrahydrofuran and the like, optionally with heating, optionally with microwave irradiation to provide a compound of the formula (B-62).

Scheme b-25
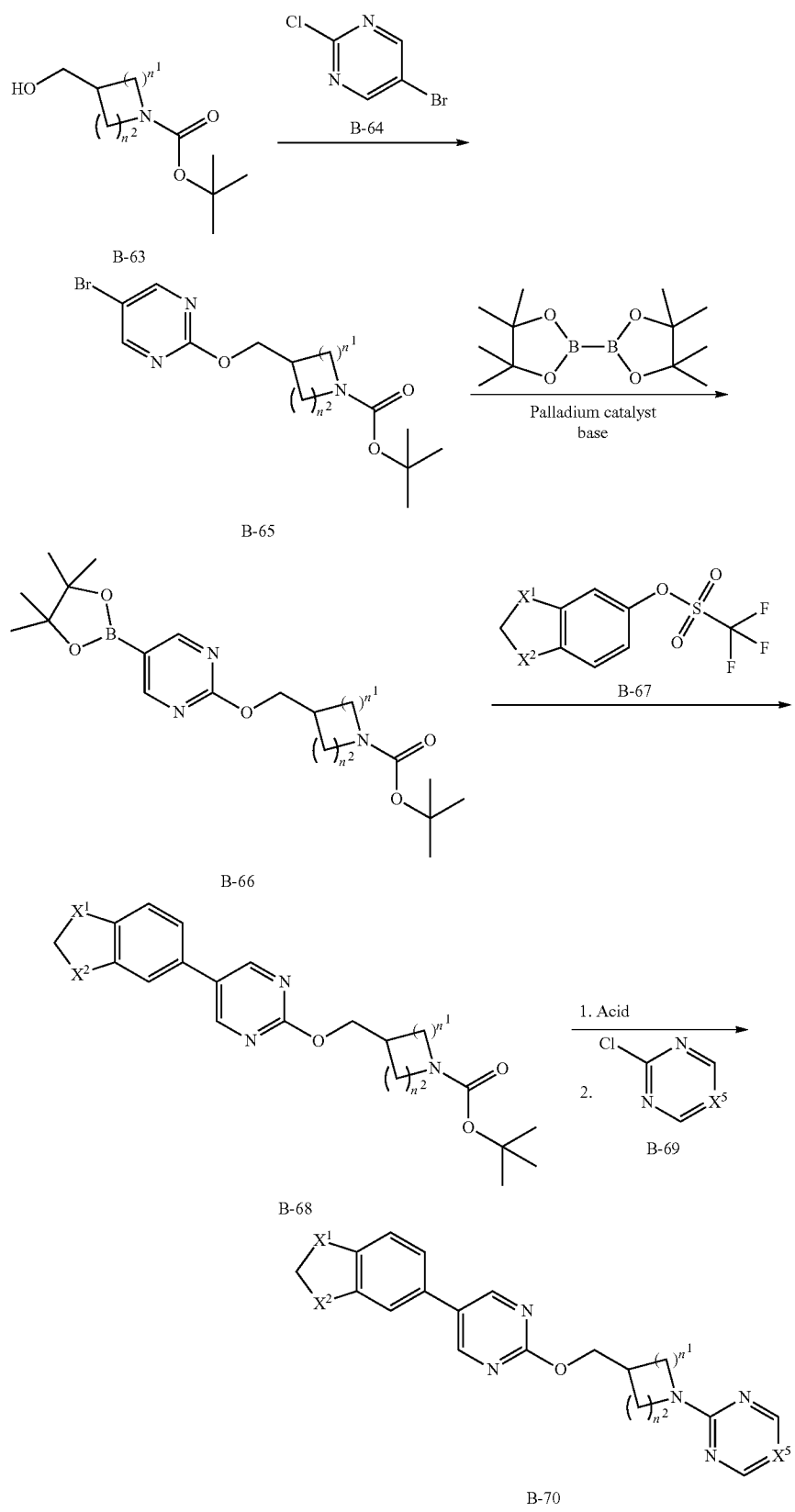

A compound of the formula (B-63), a known compound or compound prepared by known methods, is reacted with a compound of formula (B-64), in the presence of a base such as sodium hydride, carbonate, cesium carbonate, lithium carbonate, potassium carbonate, triethylamine, diisopropylethylamine and the like, in a solvent such as tetrahydrofuran, ethyl ether, acetonitrile acetonitrile, tetrahydrofuran, 1,4-dioxane, and the like, optionally with heating, optionally with microwave irradiation to provide a compound of the formula (B-65). A compound of the formula (B-65), is reacted with a 4,4,4',4',5,5,5',5'-octamethyl-2,2'-bi-1,3,2-dioxoborolane, in the presence of a base such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis (triphenylphosphine)palladium(0), bis(triphenylphosphine) palladium(II) dichloride, (1,1'-bis(diphenylphosphino)ferrocene)palladium(II) dichloride and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-66). A compound of the formula (B-66), is reacted with a compound of the formula (B-67), a known compound or a compound prepared by known methods, in the presence of a base such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis (triphenylphosphine)palladium(0), bis(triphenylphosphine) palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-68). A compound of the formula (B-68), is reacted with an acid such as formic acid, trifluoroacetic acid, trichloroacetic acid, hydrochloric acid, sulfuric acid and the like in the presence of a solvent such as 1,4-dioxane, tetrahydrofuran, methylene chloride, methanol, ethanol, and the like, optionally with heating, optionally with microwave irradiation. The resulting material is reacted with a compound of the formula (B-69), a known compound or a compound prepared by known methods, in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-70).

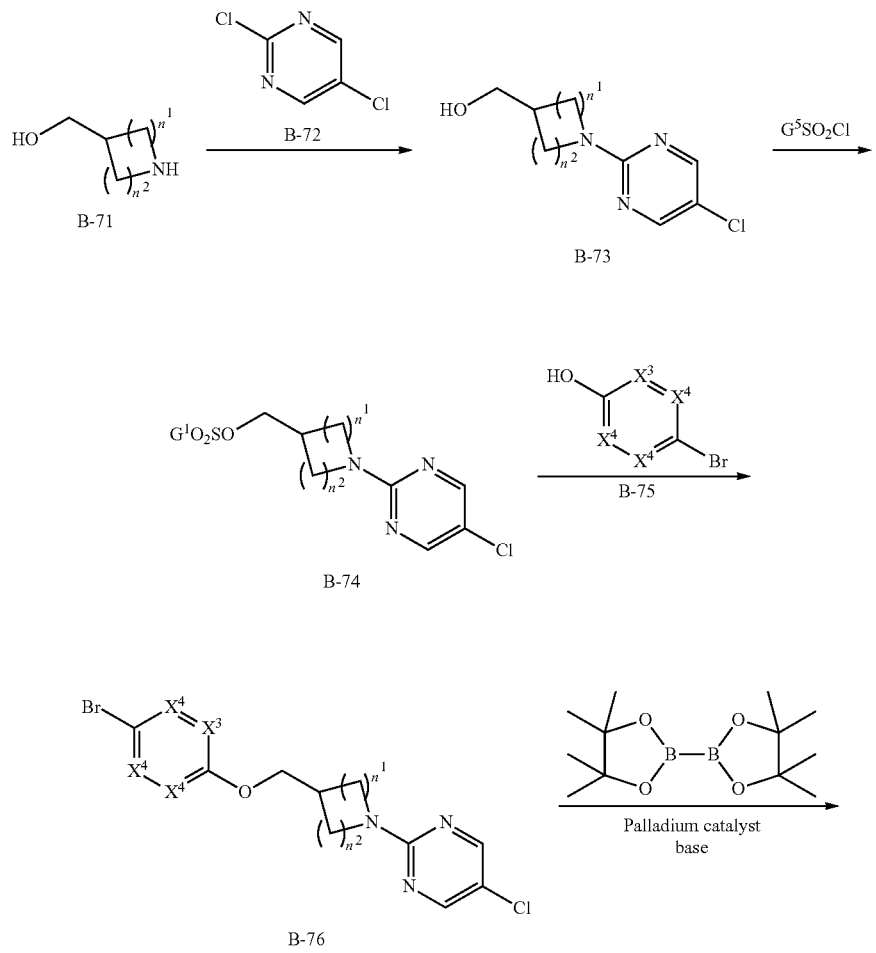

Scheme B-26

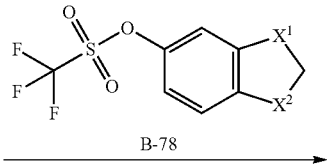

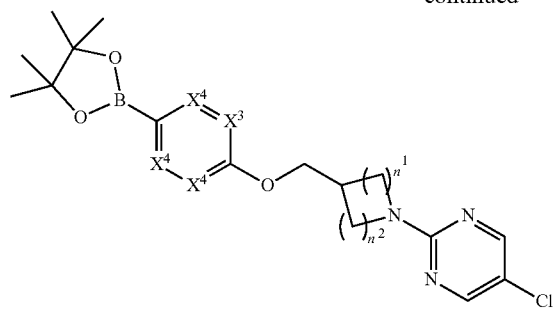

B-77

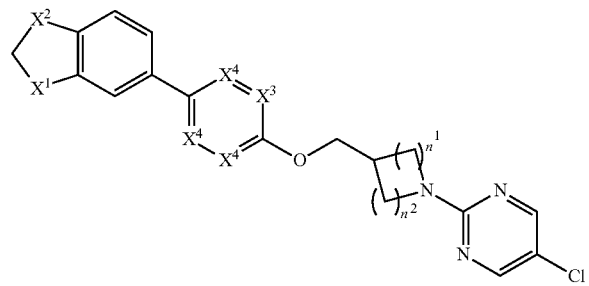

B-79

A compound of the formula (B-71), a known compound or compound prepared by known methods, is reacted with a compound of formula (B-72), in the presence of a base such as sodium hydride, carbonate, cesium carbonate, lithium carbonate, potassium carbonate, triethylamine, diisopropylethylamine and the like, in a solvent such as tetrahydrofuran, ethyl ether, acetonitrile acetonitrile, tetrahydrofuran, 1,4-dioxane, and the like, optionally with heating, optionally with microwave irradiation to provide a compound of the formula (B-73). A compound of the formula (B-73), is reacted with a sulfonyl chloride such as methylsulfonyl chloride, toluene sulfonyl chloride, p-nitrophenyl sulfonyl chloride, and the like, in the presence of a base such as sodium carbonate, cesium carbonate, lithium carbonate, potassium carbonate, potassium hydroxide, sodium hydroxide, lithium hydroxide, triethylamine, diisopropylethylamine and the like in a solvent such as acetone, acetonitrile, tetrahydrofuran, 1,4-dioxane, methylene chloride, 1,2-dichloroethane, and the like, optionally with heating, optionally with microwave irradiation to provide a compound of the formula (B-74) wherein $G^5$ is selected from the group consisting of methyl, tolyl and p-nitrophenyl. A compound of the formula (B-74), is reacted with a compound of the formula (B-75), a known compound or a compound prepared by known methods, in the presence of a base such as sodium carbonate, cesium carbonate, lithium carbonate, potassium carbonate, potassium hydroxide, sodium hydroxide, lithium hydroxide, triethylamine, diisopropylethylamine and the like, in a solvent such as acetone, acetonitrile, tetrahydrofuran, 1,4-dioxane, methylene chloride, 1,2-dichloroethane, and the like, optionally with heating, optionally with microwave irradiation to provide a compound of the formula (B-76). A compound of the formula (B-76), is reacted with a 4,4,4',4',5,5,5',5'-octamethyl-2,2'-bi-1,3,2-dioxoborolane in the presence of a base such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis (triphenylphosphine)palladium(0), bis(triphenylphosphine) palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-77). A compound of the formula (B-77), is reacted with a compound of the formula (B-78) in the presence of a base such as potassium acetate, sodium carbonate, cesium carbonate, lithium carbonate, potassium carbonate, potassium hydroxide, sodium hydroxide, lithium hydroxide, and the like, in the presence of a palladium catalyst such as palladium acetate, tetrakis(triphenylphosphine)palladium(0), bis(triphenylphosphine)palladium(II) dichloride, (1,1'-bis(diphenylphosphino)ferrocene) palladium(II) dichloride and the like, in the presence of a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-79).

Scheme B-27

A compound of formula (B-80), a known compound or a compound prepared by known. methods is reacted with a base such potassium hydroxide, lithium hydroxide, sodium hydroxide and the like, in the presence of a solvent such as ethanol, methanol, isopropanol and the like, optionally with heating, optionally with microwave irradiation to provide a compound of the formula (B-81). A compound of formula (B-81), a known compound or a compound prepared by known methods is reacted with phosphoyl chloride in a base such pyridine, trimethylamine, 2,6-lutidine, picoline and the like, optionally with heating, optionally with microwave irradiation to provide a compound of the formula (B-82).

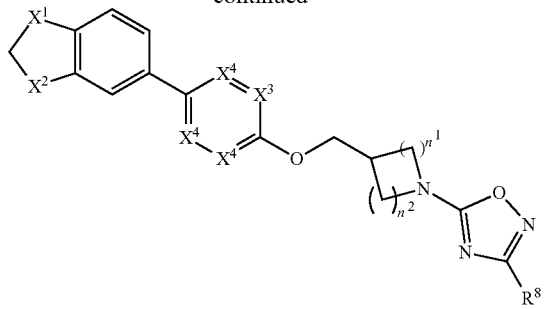

B-84

Scheme B-28

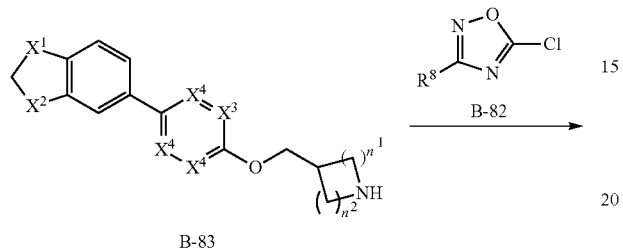

A compound of formula (B-83) is reacted with a compound of the formula (B-82) in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-84).

Scheme B-29

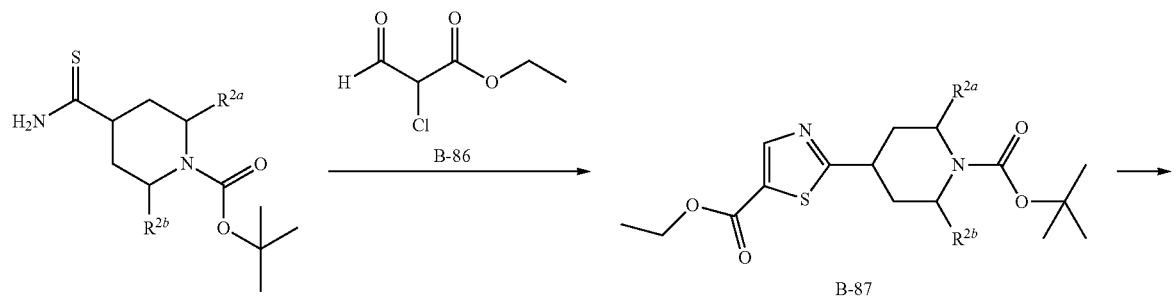

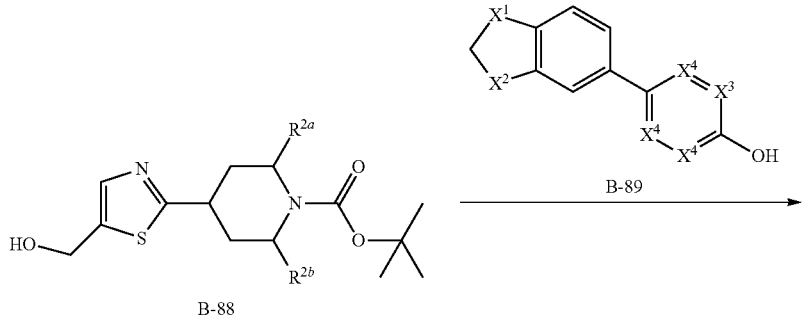

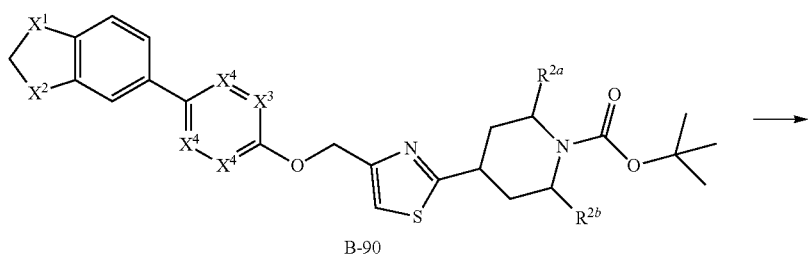

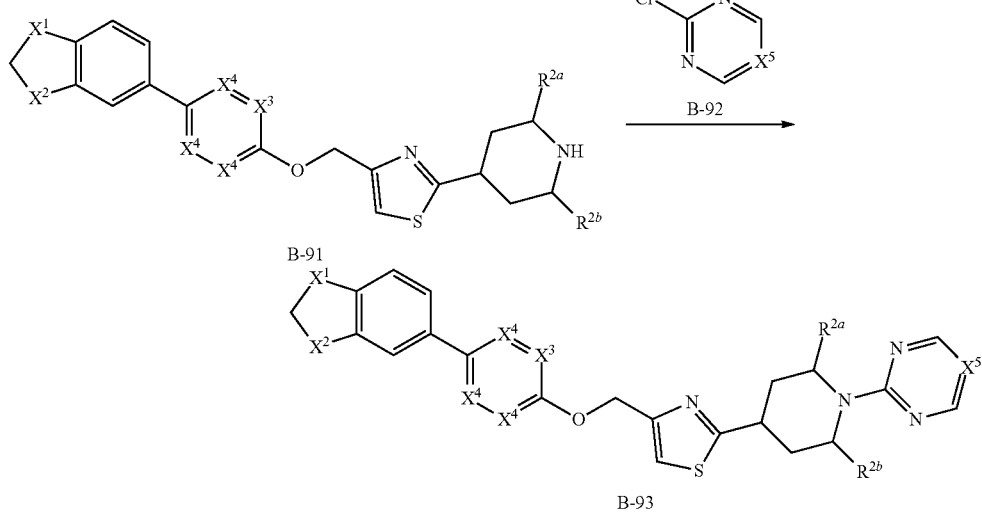

A compound of formula (B-85), a known compound or a compound prepared by known methods, is reacted with a compound of formula (B-86) in the presence of a base such as trimethylamine, pyridine, diisopropylethylamine and the like, in a solvent such as toluene, benzene, and the like to provide a compound of formula (B-87). A compound of formula (B-87) is reacted with a reducing agent such as lithium aluminum hydride, diisobutyl aluminum hydride, and the like, in a solvent such as tetrahydrofuran, ethyl ether, 1,4-dioxane and the like, to provide a compound of formula (B-88). A compound of formula (B-88) is reacted with a compound of formula (B-89), a known compound or a compound prepared by known methods, in the presence of a phosphine such as triphenylphosphine, tri(o-tolyl)phosphine, resin-bound triphenylphosphine, and the like, in the presence of an azodicarboxylate such as diethyl azodicarboxylate, diisopropyl azodicarboxylate or di-t-butylazodicarboxylate, di-(4-chlorobenzyl)azodicarboxylate, and the like, in the presence of a solvent such as tetrahydrofuran, diethyl ether, 1,4-dioxane and the like, optionally with heating, optionally with microwave irradiation to provide a compound of the formula (B-90). A compound of the formula (B-90), is reacted with an acid such as formic acid, trifluoroacetic acid, trichloroacetic acid, hydrochloric acid, sulfuric acid and the like, in the presence of a solvent such as 1,4-dioxane, tetrahydrofuran, methanol, ethanol, methylene chloride, and the like, optionally with heating, optionally with microwave irradiation to provide a compound of formula (B-91). A compound of formula (B-91) is reacted with a compound of the formula (B-92), a known compound or a compound prepared by known methods, in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-93).

Scheme B-30

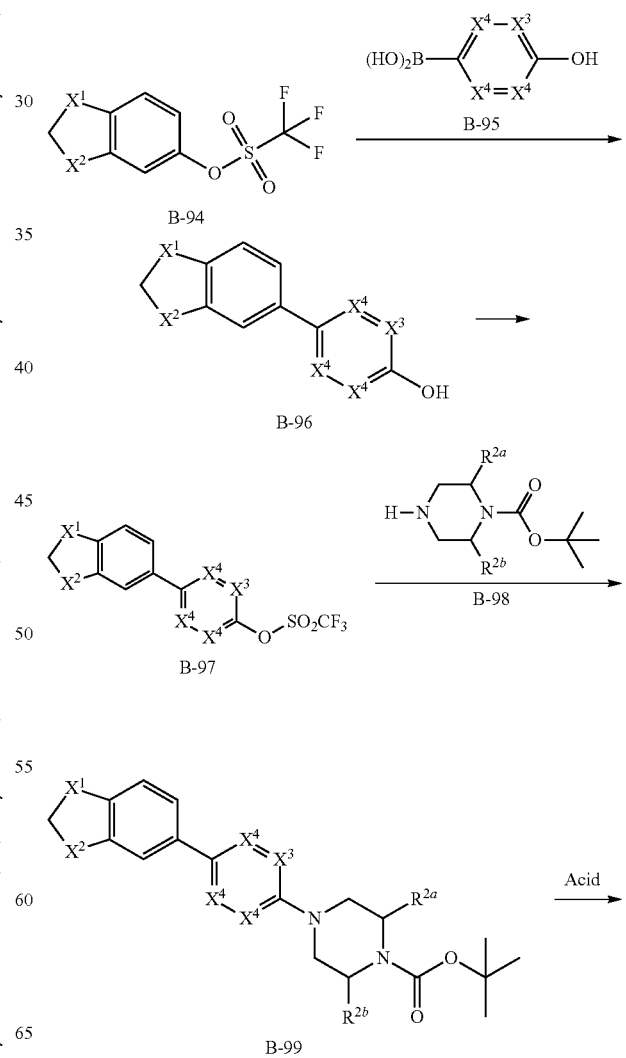

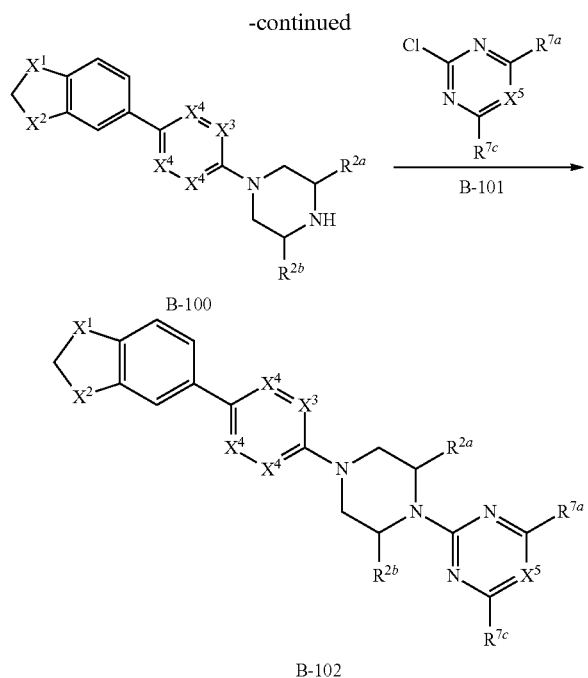

B-100

B-102 catalyst such as palladium acetate, palladium chloride, tetrakis(triphenylphosphine)palladium(0), bis(triphenylphosphine)palladium(II) dichloride, and the like, in a solvent such as toluene, benzene, xylene, tetrahydrofuran, 1,4-dioxane, acetonitrile, and the like, optionally in the presence of a base such as trimethylamine, pyridine, diisopropylethylamine and the like, optionally with heating, optionally with microwave irradiation, to provide a compound of formula (B-99). A compound of the formula (B-99), is reacted with an acid such as formic acid, trifluoroacetic acid, trichloroacetic acid, hydrochloric acid, sulfuric acid and the like in the presence of a solvent such as 1,4-dioxane, tetrahydrofuran, methanol, ethanol, methylene chloride, and the like, optionally with heating, optionally with microwave irradiation to provide a compound of formula (B-100). A compound of formula (B-100) is reacted with a compound of the formula (B-101) a known compound or a compound prepared by known methods, in the presence of a base such as trimethylamine, pyridine, diisopropylethyl amine and the like, in a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-102).

A compound of the formula (B-94), is reacted with a compound of the formula (B-95), a known compound prepared by known methods in the presence of a base such as potassium acetate, sodium carbonate, cesium carbonate, lithium carbonate, potassium carbonate, potassium hydroxide, sodium hydroxide, lithium hydroxide, and the like in the presence of a palladium catalyst such as palladium acetate, tetrakis(triphenylphosphine)palladium(0), bis(triphenylphosphine)palladium(II) dichloride, (1,1'-bis(diphenylphosphino)ferrocene)palladium(II) dichloride and the like a solvent such as acetonitrile, acetone, tetrahydrofuran, 1,4-dioxane, methylene chloride, 1,2-dichloroethane, and the like, optionally with heating, optionally with microwave irradiation to provide a compound of the formula (B-96). A compound of the formula (B-96) is reacted with trifluoromethanesulfonic anhydride in the presence of a base such as pyridine, 2,6-lutidine, 2-picoline, 3-picoline, 4-picoline, N,N-dimethylaminopyridine, diisopropylethyl amine, trimethylamine and the like in a solvent such as methylene chloride, 1,2-dichloroethane, chloroform, tetrahydrofuran, ether, 1,4-dioxane, acetone, acetonitrile, N,N-dimethylformamide and the like, optionally with heating, optionally with microwave irradiation to provide compounds of the formula (B-97). A compound of formula (B-97) is reacted with a compound of formula (B-98), a known compound or a compound prepared by known methods, in the presence of an organophosphorus ligand such as 2,2'-bis(diphenylphosphino)-1,1'-binaphthyl, (R)-(+)-5,5'-bis(diphenylphosphino)-4,4'-bi-1,3-benzodioxole, [4(R)-(4,4'-bi-1,3-benzodioxole)-5,5'-diyl]bis[diphenylphosphine], (S)-(+)-5,5'-bis(diphenylphosphino)-4,4'-bi-1,3-benzodioxole, [4(S)-(4,4'-bi-1,3-benzodioxole)-5,5'-diyl]bis[diphenylphosphine], (R)-(+)-2,2'-Bis(diphenylphospino)-5,5',6,6',7,7',8,8'-octahydro-1,1'-binaphthyl, [(1R)-5,5',6,6',7,7',8,8'-octahydro-[1,1'-binaphthalene]-2,2'-diyl]bis[diphenylphosphine], (S)-(+)-5,5'-bis(diphenylphosphino)-4,4'-bi-1,3-benzodioxole, [4(S)-(4,4'-bi-1,3-benzodioxole)-5,5'-diyl]bis[diphenylphosphine], (R)-(+)-2,2'-bis(di-p-tolylphosphino)-1,1'-binaphthyl, (S)-(–)-2,2'-Bis(di-p-tolylphosphino)-1,1'-binaphthyl, and the like, in the presence of a palladium Scheme B-31

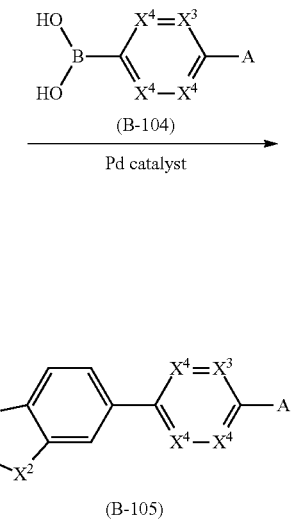

A compound of the formula (B-103), a known compound or a compound prepared by known methods, is reacted with a compound of the formula (B-104), a know compound or a compound prepared by known methods, in the presence of a base such as potassium carbonate, sodium carbonate, potassium hydroxide, sodium hydroxide, and the like, in the presence of a palladium catalyst such as 1,1'(bisdiphenylphosphino)ferrocene dichloropalladium (II), tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (B-105).

Scheme B-32

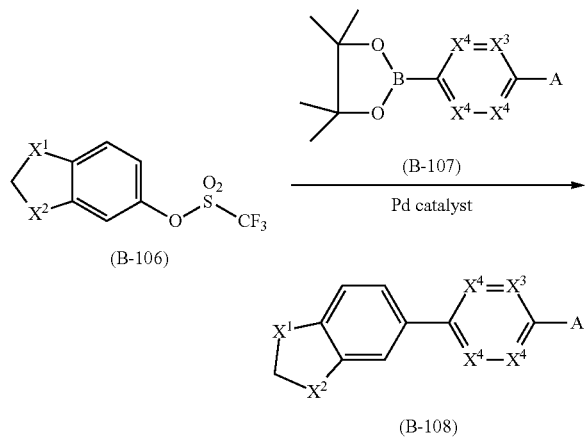

A compound of the formula (B-106), a known compound or a compound prepared by known methods, is reacted with a compound of the formula (B-107), a know compound or a compound prepared by known methods, in the presence of a base such as potassium carbonate, sodium carbonate, potassium hydroxide, sodium hydroxide, and the like, in the presence of a palladium catalyst such as 1,1'(bisdiphenylphosphino)ferrocene dichloropalladium (II), tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (B-108).

Scheme B-33
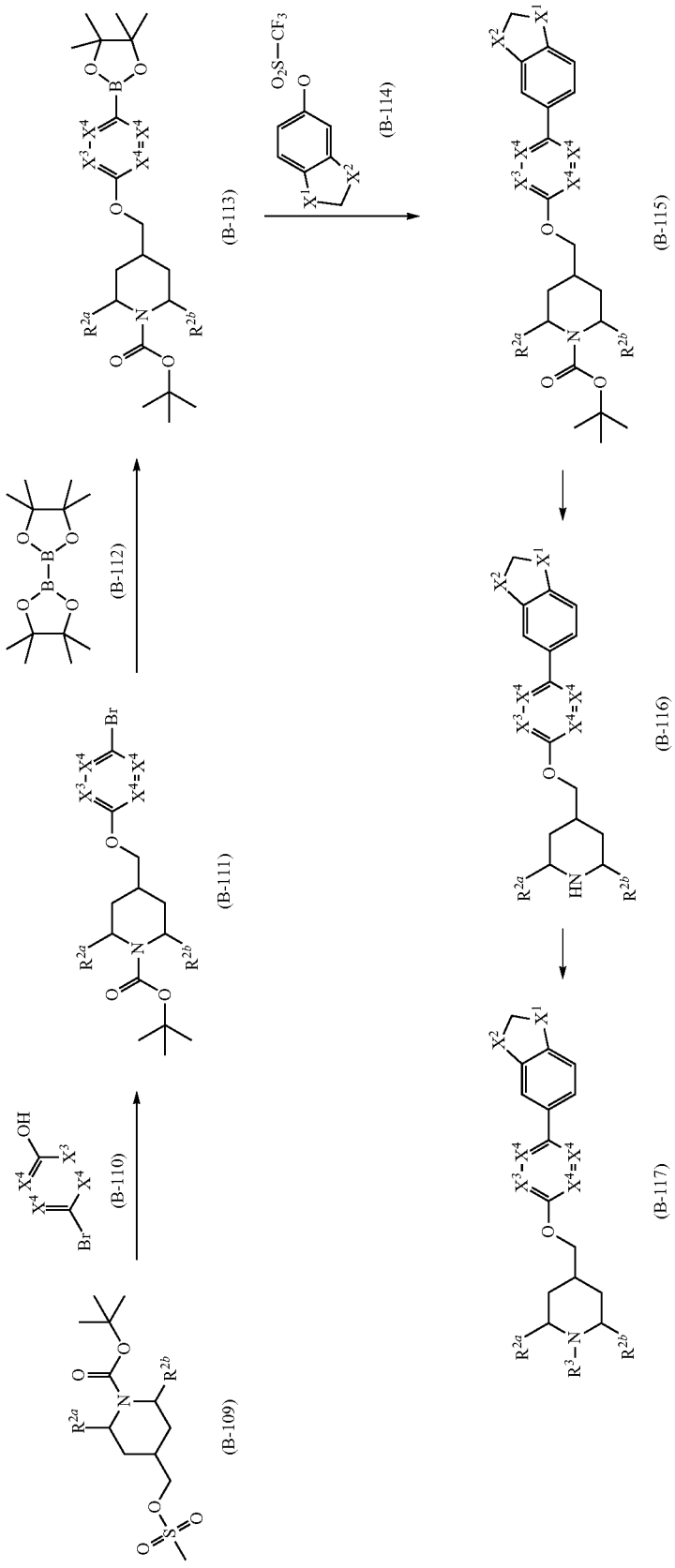

A compound of the formula (B-109), a known compound or a compound prepared by known methods, is reacted with a compound of the formula (B-110), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N,N-dimethyl formamide, dimethyl sulfoxide, methanol, ethanol, and the like, optionally with heating, optionally with microwave irradiation to provide a compound of the formula (B-111). A compound of the formula (B-111) is reacted with a compound of the formula (B-112) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N, N-dimethyl formamide, and the like, optionally with heating, optionally with microwave irradiation to provide a compound of the formula (B-113). A compound of the formula (B-113) is reacted with a compound of the formula (B-114), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (B-115). A compound of the formula (B-115) is then reacted with an acid such as hydrochloric acid, hydrobromic acid, trifluoroacetic acid, acetic acid, formic acid, and the like, optionally with heating, optionally with microwave irradiation to provide a compound of the formula (B-116). A compound of the formula (B-116) is reacted with an aldehyde in the presence of a reducing agent such as sodium triacetoxy borohydride, sodium borohydride, and the like, optionally in the presence of an acid such as acetic acid, formic acid, hydrochloric acid, and the like, in a solvent such as tetrahydrofuran, 1,4-dioxane, methylene chloride, methanol, ethanol, and the like, optionally with heating, optionally with microwave irradiation to provide a compound of the formula (B-117). Alternatively, a compound of the formula (B-116) is reacted with a ketone in the presence of a reducing agent such as sodium triacetoxy borohydride, sodium borohydride, and the like, optionally in the presence of an acid such as acetic acid, formic acid, hydrochloric acid, and the like, in a solvent such as tetrahydrofuran, 1,4-dioxane, methylene chloride, methanol, ethanol, and the like, optionally with heating, optionally with microwave irradiation to provide a compound of the formula (B-117).

Scheme B-34

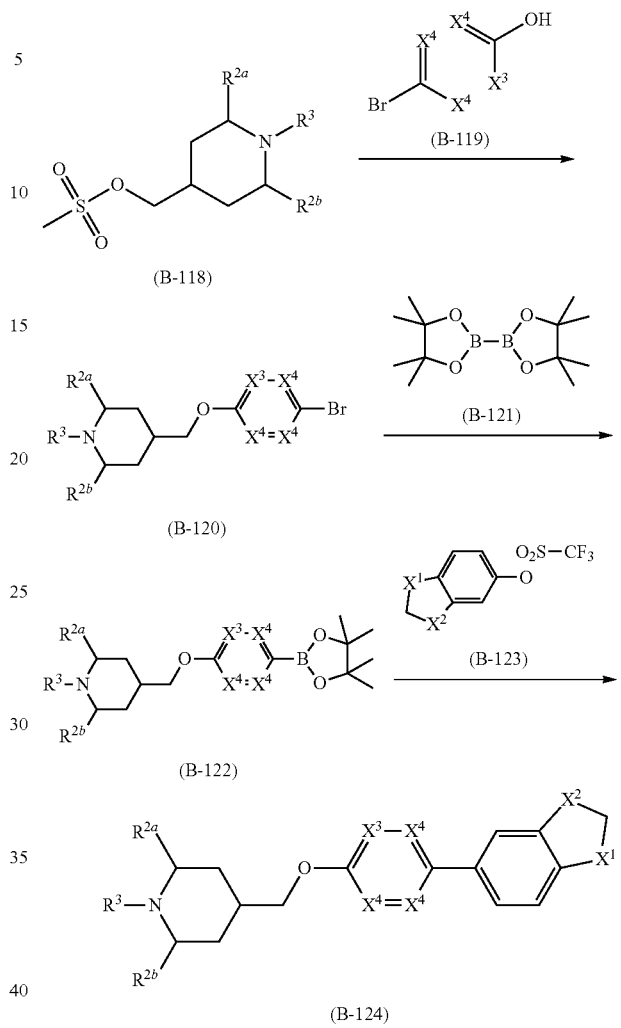

A compound of the formula (B-118), a known compound or a compound prepared by known methods, is reacted with a compound of the formula (B-119), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N,N-dimethyl formamide, dimethyl sulfoxide, methanol, ethanol, and the like, optionally with heating, optionally with microwave irradiation to provide a compound of the formula (B-120). A compound of the formula (B-120) is reacted with a compound of the formula (B-121) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N,N-dimethyl formamide, and the like, optionally with heating, optionally with microwave irradiation to provide a compound of the formula (B-122). A compound of the formula (B-122) is reacted with a compound of the formula (B-123), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (B-124).

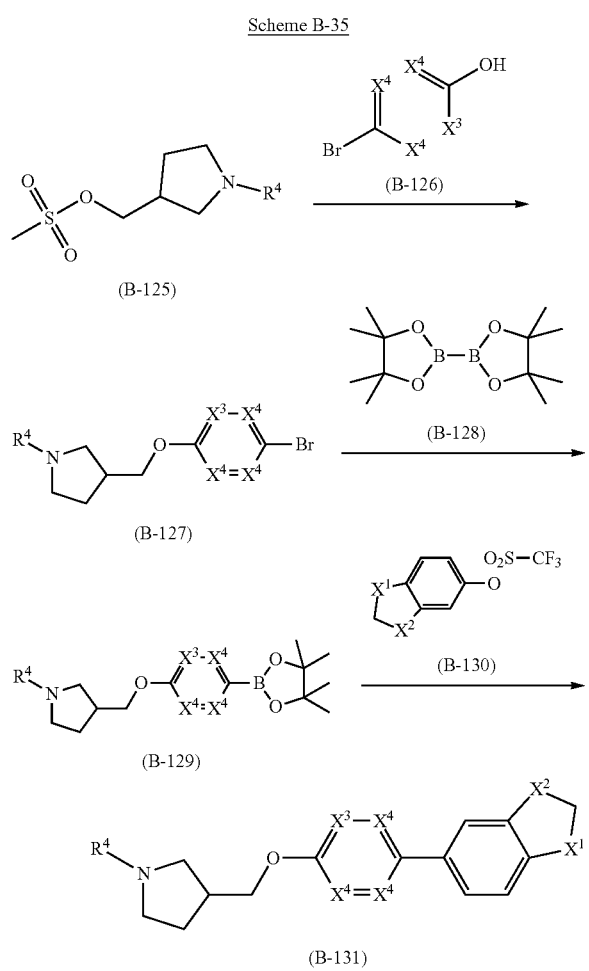

acetate, palladium chloride, (tridibenzylideneacetone) dipalladium(0), and the like, in the presence of potassium acetate, in the presence of a solvent such as acetonitrile, tetrahydrofuran, 1,4-dioxane, N, N-dimethyl formamide, and the like, optionally with heating, optionally with microwave irradiation to provide a compound of the formula (B-129). A compound of the formula (B-129) is reacted with a compound of the formula (B-130), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenyl phosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (B-131).

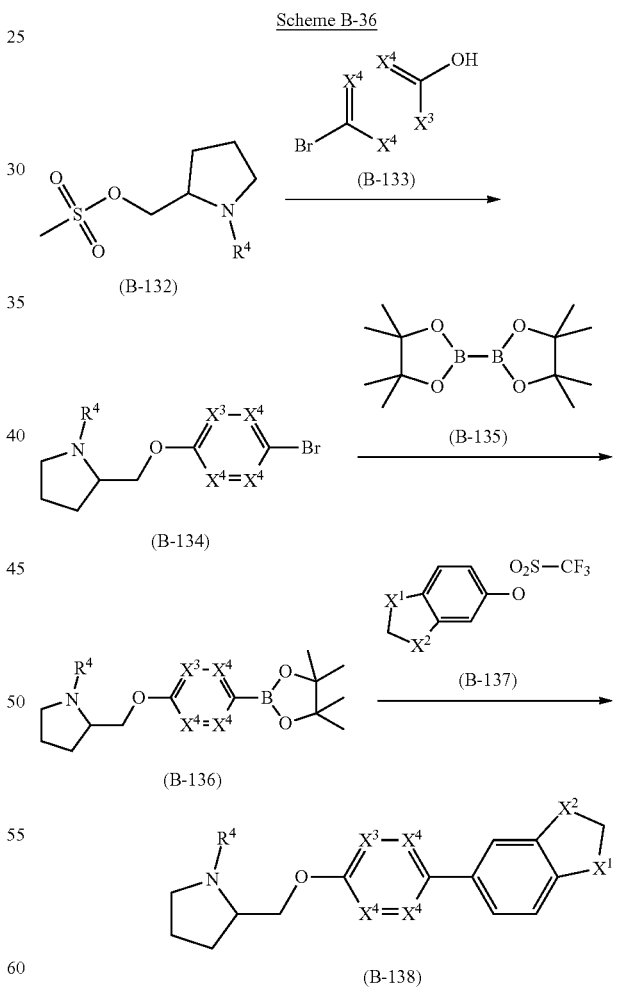

A compound of the formula (B-125), a known compound or a compound prepared by known methods, is reacted with a compound of the formula (B-126), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N, N-dimethyl formamide, dimethyl sulfoxide, methanol, ethanol, and the like, optionally with heating, optionally with microwave irradiation to provide a compound of the formula (B-127). A compound of the formula (B-127) is reacted with a compound of the formula (B-128) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium A compound of the formula (B-132), a known compound or a compound prepared by known methods, is reacted with a compound of the formula (B-133), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N,N-dimethyl formamide, dimethyl sulfoxide, methanol, ethanol, and the like, optionally with heating, optionally with microwave irradiation to provide a compound of the formula (B-134). A compound of the formula (B-134) is reacted with a compound of the formula (B-135) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N,N-dimethyl formamide, and the like, optionally with heating, optionally with microwave irradiation to provide a compound of the formula (B-136). A compound of the formula (B-136) is reacted with a compound of the formula (B-137), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (B-138).

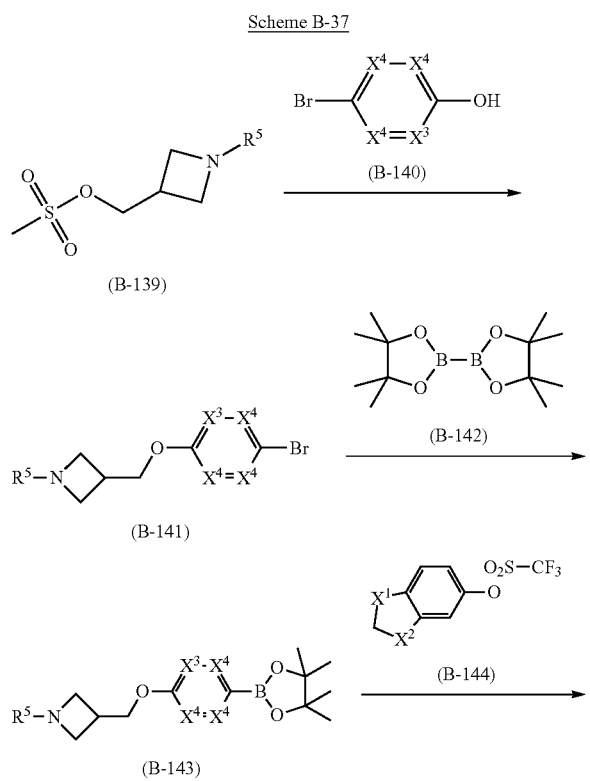

Scheme B-37

(B-139)

(B-140)

(B-141)

(B-142)

(B-143)

(B-144)

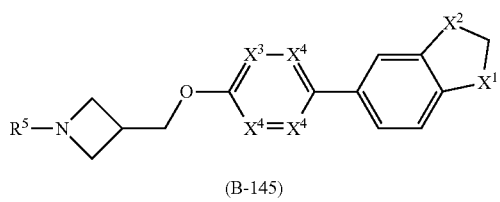

(B-145)

A compound of the formula (B-139), a known compound or a compound prepared by known methods, is reacted with a compound of the formula (B-140), a known compound or a compounds prepared by known methods, in the presence of a base such as potassium carbonate, sodium carbonate, potassium hydroxide, sodium hydroxide, and the like, in a solvent such as tetrahydrofuran, 1,4-dioxane, N, N-dimethyl formamide, dimethyl sulfoxide, methanol, ethanol, and the like, optionally with heating, optionally with microwave irradiation to provide a compound of the formula (B-141). A compound of the formula (B-141) is reacted with a compound of the formula (B-142) in the presence of a palladium catalyst such as a 1,1' (bisdiphenylphosphino)ferrocene dichloropalladium (II), tris(dibenzylideneacetone) dipalladium, palladium tetrakis(triphenylphosphine), palladium acetate, palladium chloride, (tridibenzylideneacetone) dipalladium(0), and the like, in the presence of potassium acetate, in the presence of a solvent such as acetonitrile, tetrahydrofuran, 1,4-dioxane, N,N-dimethyl formamide, and the like, optionally with heating, optionally with microwave irradiation to provide a compound of the formula (B-143). A compound of the formula (B-143) is reacted with a compound of the formula (B-144), known compound or a compound prepared by known methods, in the presence of a base such as potassium carbonate, sodium carbonate, potassium hydroxide, sodium hydroxide, and the like, in the presence of a palladium catalyst such as 1,1' (bisdiphenylphosphino)ferrocene dichloropalladium (II), tris(dibenzylideneacetone)dipalladium, palladium tetrakis(triphenylphosphine), palladium acetate, palladium chloride, (tridibenzylideneacetone) dipalladium(0), and the like, in the presence of a solvent such as tetrahydrofuran, 1,4-dioxane, methylene chloride, acetonitrile, and the like, optionally in the presence of water, optionally with heating, optionally with microwave irradiation to provide a compound of the formula (B-145).

Scheme B-38

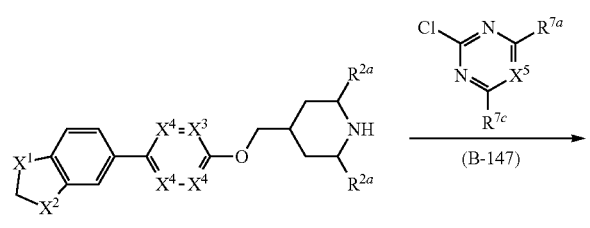

(B-146)

(B-147)

153

-continued

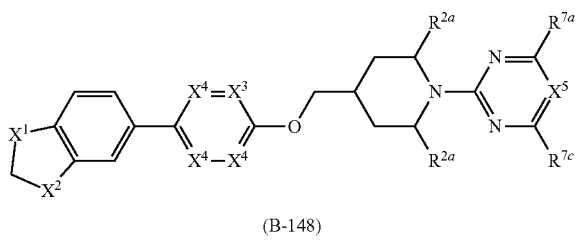

(B-148)

A compound of the formula (B-146) is reacted with a compound of the formula (B-147), a known compound or a compounds prepared by known methods, in the presence of a base such as triethylamine, diisopropylethyl amine, pyridine, 2,6-lutidine, and the like, in the presence of a solvent such as acetonitrile, tetrahydrofuran, 1,4-dioxane, N,N-dimethylformamide, and the like, optionally with heating, optionally with microwave irradiation to provide a compound of the formula (B-148).

Scheme B-39

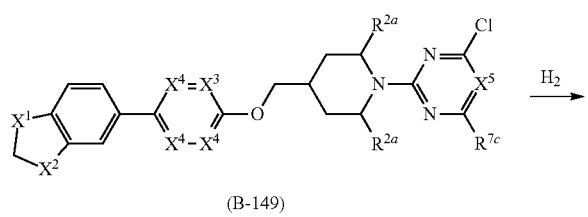

(B-149)

(B-150)

A compound of the formula (B-149) is reacted with hydrogen in the presence of a palladium catalyst such as palladium on carbon, tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methanol, ethanol, and the like, optionally with heating, optionally with microwave irradiation to provide a compound of the formula (B-150).

Scheme B-40

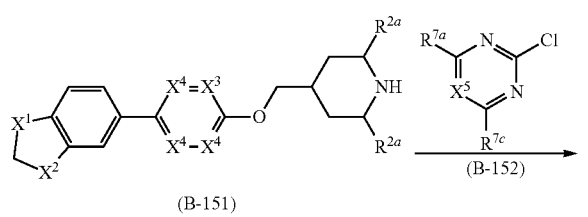

(B-151)

154

-continued

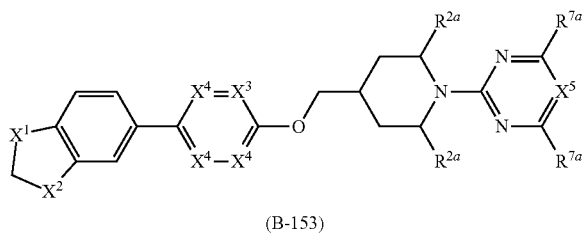

(B-153)

A compound of the formula (B-151) is reacted with a compound of the formula (B-152), a known compound or a compounds prepared by known methods, in the presence of a base such as triethylamine, diisopropylethyl amine, pyridine, 2,6-lutidine, and the like, in the presence of a solvent such as acetonitrile, tetrahydrofuran, 1,4-dioxane, N,N-dimethylformamide, and the like, optionally with heating, optionally with microwave irradiation to provide a compound of the formula (B-153).

Scheme B-41

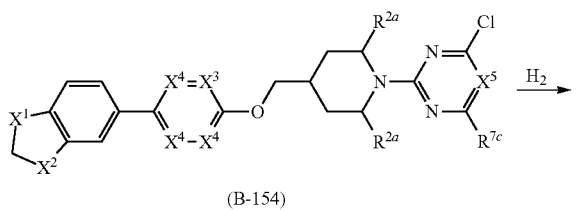

(B-154)

(B-155)

A compound of the formula (B-154) is reacted with hydrogen in the presence of a palladium catalyst such as palladium on carbon, tris(dibenzylideneacetone)dipalladium, palladium, tetrakis(triphenylphosphine), palladium acetate, palladium chloride, (tridibenzylideneacetone) dipalladium(0), and the like, in the presence of a solvent such as tetrahydrofuran, 1,4-dioxane, methanol, ethanol, and the like, optionally with heating, optionally with microwave irradiation to provide a compound of the formula (B-155).

Scheme B-42

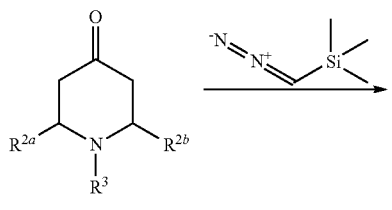

(B-156)

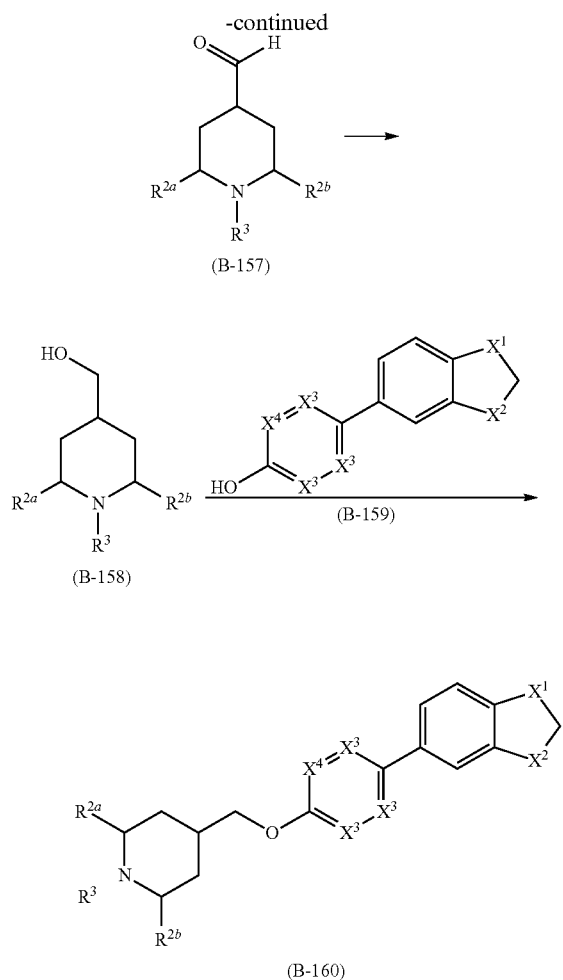

(B-157)

(B-158)

(B-159)

(B-160)

A compound of formula (B-156) is reacted with trimethylsilyldiazomethane in hexanes in the presence of a base such as lithium diisopropylamide, sodium diisopropylamide, potassium diisopropylamide, lithium hexamethyldisilazide, sodium hexamethyldisilazide, potassium hexamethyldisilazide, and the like, in the presence of a solvent such as 1,4-dioxane, tetrahydrofuran, methylene chloride, 1,2-dichloroethane, and the like, optionally with cooling to −78° C. to provide a compound of formula (B-157). A compound of formula (B-157) is reacted with a reducing hydride reagent such as sodium borohydride, lithium borohydride, lithium aluminum hydide, and the like, in a solvent such as methanol, ethanol, 1,4-dioxane, tetrahydrofuran, and the like, optionally with heating, optionally with microwave irradiation to provide a compound of the formula (B-158). A compound of formula (B-158) is reacted with a compound of formula (B-159) a known compound or compound prepared by known methods, in the presence of a phosphine such as triphenylphosphine, tri(o-tolyl)phosphine, resin-bound triphenylphosphine, and the like, in the presence of an azodicarboxylate such as diethyl azodicarboxylate, diisopropyl azodicarboxylate, di-t-butylazodicarboxylate, di-(4-chlorobenzyl)azodicarboxylate, and the like, in the presence of a solvent such as tetrahydrofuran, diethyl ether, 1,4-dioxane, methylene chloride, and the like, optionally with heating, optionally with microwave irradiation to provide a compound of the formula (B-160).

Scheme B-43

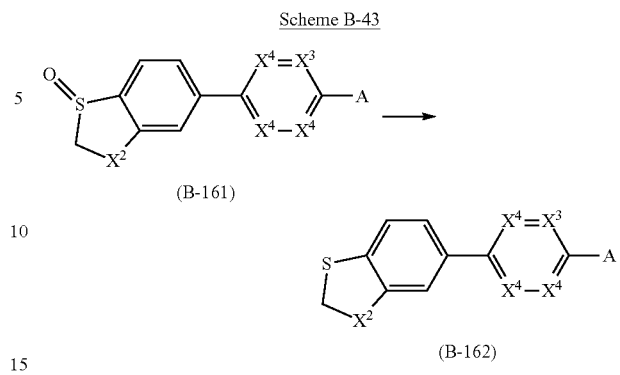

(B-161)

(B-162)

A compound of the formula (B-161), a known compound or a compound prepared by known methods, is reacted with borane dimethylsulfide in a solvent such as acetonitrile, N,N dimethylformamide, 1,4-dioxane, tetrahydrofuran, and the like, optionally with heating, optionally with microwave irradiation to provide a compound of the formula (B-162). Alternatively, a compound of the formula (B-161), a known compound or a compound prepared by known methods, is reacted with methylene dibromide in a solvent such as acetonitrile, dimethylformamide, 1,4-dioxane, tetrahydrofuran, and the like, optionally with heating, optionally with microwave irradiation to provide a compound of the formula (B-162).

Scheme B-44

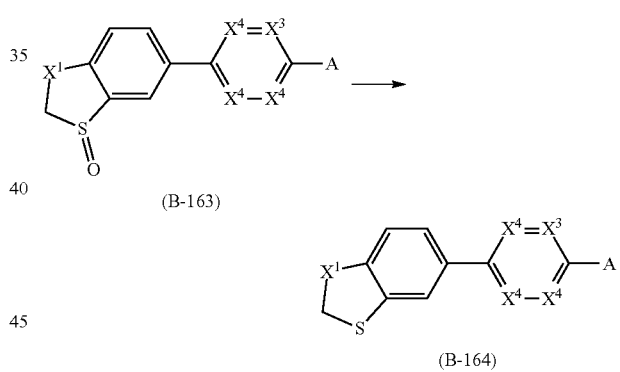

(B-163)

(B-164)

A compound of the formula (B-163), a known compound or a compound prepared by known methods, is reacted with borane dimethylsulfide in a solvent such as acetonitrile, N,N dimethylformamide, 1,4-dioxane, tetrahydrofuran, and the like, optionally with heating, optionally with microwave irradiation to provide a compound of the formula (B-164). Alternatively, a compound of the formula (B-163), a known compound or a compound prepared by known methods, is reacted with methylene dibromide in a solvent such as acetonitrile, dimethylformamide, 1,4-dioxane, tetrahydrofuran, and the like, optionally with heating, optionally with microwave irradiation to provide a compound of the formula (B-164).

The compounds of formula (I) differ from the compounds made using synthetic schemes A-1 to A-31 (see above) and/or schemes B-1 to B-44 (see above) in the substituents of the "head portion" that contains the benzo[d][1,3]oxathiole, benzo[d][1,3]oxathiole 3-oxide or benzo[d][1,3]oxathiole 3,3-dioxide (typically shown herein as the leftmost portion of the compound). Accordingly, synthesis of the compounds of formula (I) involves many of the same synthetic steps as shown in schemes A-1 to A-31 and schemes B-1 to B-44, e.g. for synthesizing the "tail portion" (typically shown herein as the rightmost portion of the compound) which does not include the benzo[d][1,3]oxathiole, benzo[d][1,3]oxathiole 3-oxide or benzo[d][1,3]oxathiole 3,3-dioxide. Exemplary synthetic schemes for producing compounds of formula (I) are shown below.

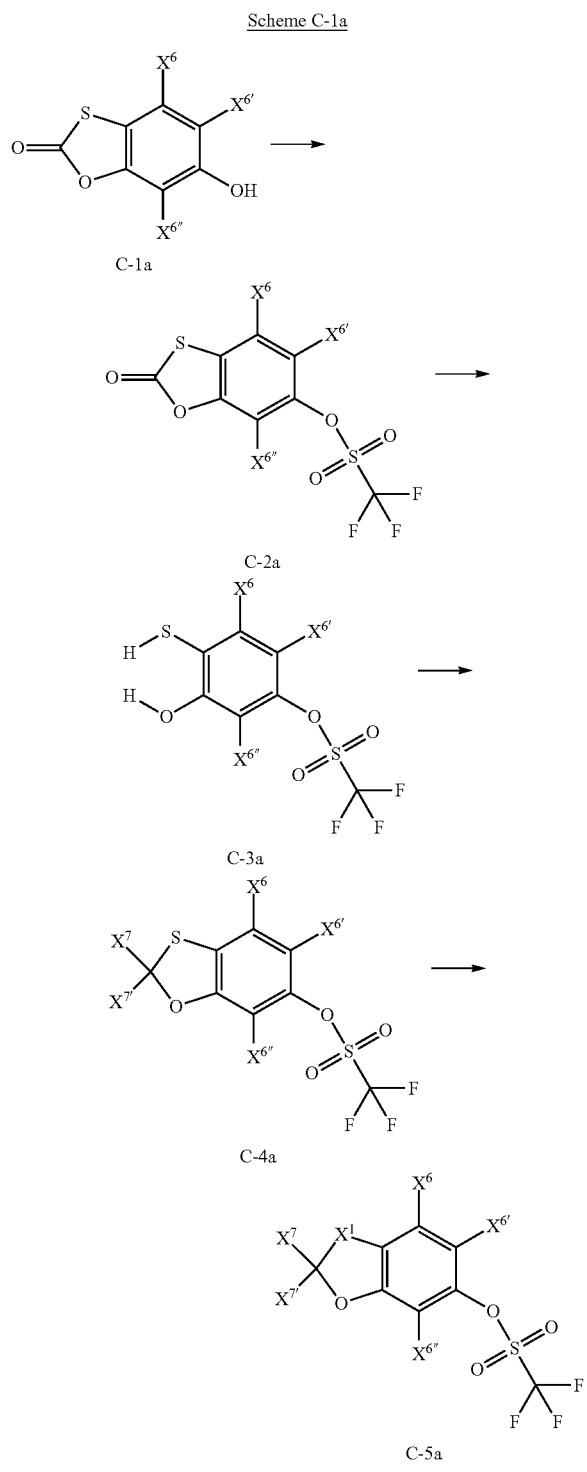

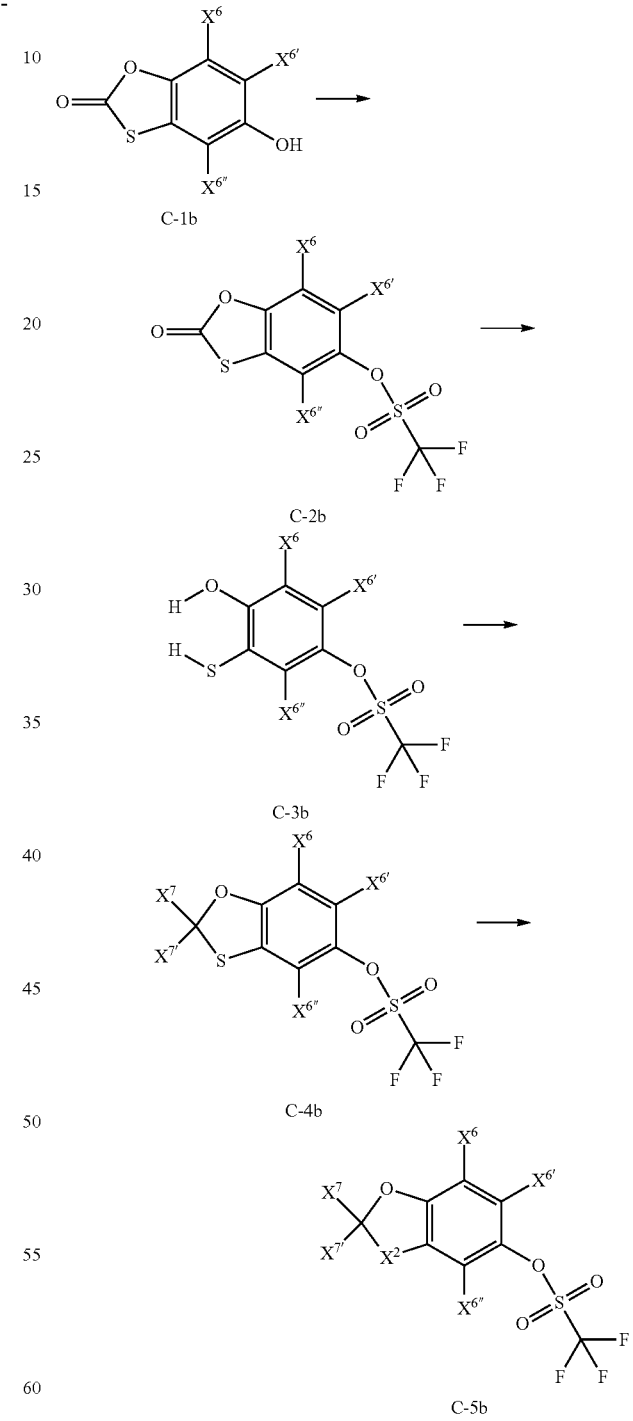

In Schemes C-1a and C-1b above, with $X^6$, $X^{6'}$, $X^{6''}$, $X^7$ and $X^{7'}$ as defined for the compounds of formula (I), compounds of formula (C-1a) or (C-1b) are commercially available or readily prepared by known methods. A compound of the formula (C-1a) or (C-1b) is reacted with triflic anhydride in the presence of a base (such as, pyridine, 2,6-lutidine, and the like) in a solvent (such as acetonitrile, tetrahydrofuran, 1,4-dioxane, methylene chloride, N,N-dimethylformamide and the like), optionally with heating, and optionally with microwave irradiation, to provide a compound of the formula (C-2a) or (C-2b), respectively. A compound of formula (C-2a) or (C-2b) is reacted with base (such as sodium hydroxide, potassium hydroxide, cesium hydroxide potassium carbonate, cesium carbonate, and the like) in a solvent (such as water, or a mixture of water with organic solvents, such as, tetrahydrofuran, 1,4-dioxane, and the like) with heating, optionally with microwave irradiation, to provide a compound of the formula (C-3a) or (C-3b), respectively. A compound of formula (C-3a) or (C-3b) is reacted with a ketone (such as acetone, cyclobutanone, cyclopentatone, 1,1,1,5,5,5-hexafluoropentan-3-one, and the like) in the presence of an acid (such as p-toluenesulfonic acid and the like) or alternatively, in the presence of a base (such as sodium hydroxide, potassium hydroxide, and the like), and in the presence of a solvent (such as benzene, toluene and the like) with heating, optionally with microwave, and optionally with Dean-Stark attachment to produce a compound of formula (C-4a) or (C-4b), respectively. Alternatively, for certain compounds of formula (I), a compound of formula (C-3a) or (C-3b) is reacted with mono- or difluorinated dihalogenomethane (e.g. difluorodibromomethane, dibromofluoromethane, and the like) in the presence of a base (such as potassium carbonate, cesium carbonate, trimethylamine, pyridine, and the like), in a solvent (such as acetonitrile, methylene chloride, N,N-dimethylformamide, and the like), optionally in the presence of a phase transfer catalyst (e.g. crown ether such as 18-crown-6, 12-crown-4, and the like), optionally with heating, and optionally with microwave irradiation to provide a compound of the formula (C-4a) or (C-4b), respectively. The resulting compound of formula (C-4a) or (C-4b) may be used in Scheme C-2 below or may be further reacted with hydrogen peroxide or meta-chloroperbenzoic acid, or the like, in a solvent (such as acetic acid, chloroform, dichloromethane, and the like), optionally with heating, and optionally with microwave irradiation, to provide a compound of the formula (C-5a) or (C-5b), respectively.

Synthesizing the tail portion can proceed as has already been described in schemes A-1 to A-31 (see above) and schemes B-1 to B-44 (see above). For example, with reference to Scheme C-2 above, a compound of the formula (C-6) in which $X^1$, $X^2$, $X^6$, $X^{6'}$, $X^{6''}$, $X^7$ and $X^{7'}$ are as defined for the compounds of formula (I) (e.g. a compound of formula, C-4a, C-4b, C-5a or C-5b) is reacted with a boronic acid/ester of formula (C-7), in which $X^3$, $X^4$ and A are as defined for the compounds of formula (I), in the presence of a base (such as potassium acetate, sodium carbonate, cesium carbonate, lithium carbonate, potassium carbonate, potassium hydroxide, sodium hydroxide, lithium hydroxide, and the like) in the presence of a palladium catalyst (such as palladium acetate, tetrakis(triphenylphosphine)palladium (0), bis(triphenylphosphine)palladium(II) dichloride, (1,1'-bis(diphenylphosphino)ferrocene)palladium(II) dichloride and the like) in the presence of a solvent (such as acetonitrile, acetone, tetrahydrofuran, 1,4-dioxane, methylene chloride, 1,2-dichloroethane, and the like), optionally with heating, and optionally with microwave irradiation, to provide a compound of formula (C-8). Exemplary compounds of formula (C-7) include, without limitation, a boronic acid/ester as already described above, e.g. compound A-10 (see schemes A-3 to A-13, A-16 and A-17), compound A-35 (see scheme A-14), compound A-45 (see scheme A-15), compound A-60 (see scheme A-19), compound A-68 (see scheme A-20), compound A-70 (see scheme A-21), compound A-76 (see scheme A-22), compound A-84 (see scheme A-23), compound A-91 (see scheme A-24), compound A-98 (see scheme A-25), compound A-105 (see scheme A-26), compound B-17 (see schemes B-6 to B-8), compound B-29 (see scheme B-9), compound B-29a (see scheme B-10), compound B-30 (see scheme B-11), compound B-30a (see scheme B-12), compound B-41 (see schemes B-15 to B-22, B-24 and B-28), compound B-66 (see scheme B-25), compound B-77 (see scheme B-26), compound B-95 (see scheme B-30), compound B-104 (see scheme B-31), compound B-107 (see scheme B-32), compound B-113 (see scheme B-33), compound B-122 (see scheme B-34), compound B-129 (see scheme B-35), compound B-136 (see scheme B-36) and compound B-143 (see scheme B-37), and the boronic acids/esters described in Examples A-7, A-26, A-39, A-45, A-60, A-70, A-73, A-79, A-85, A-88, A-91, B-8, B-11, B-49, B-55, B-74, B-80, B-83 and B-90 (shown below). In each case, the A group for the compounds of formula (C-8) would be identical to those indicated in the products shown for schemes A-1 to A-31 and schemes B-1 to B-44.

Scheme C-2

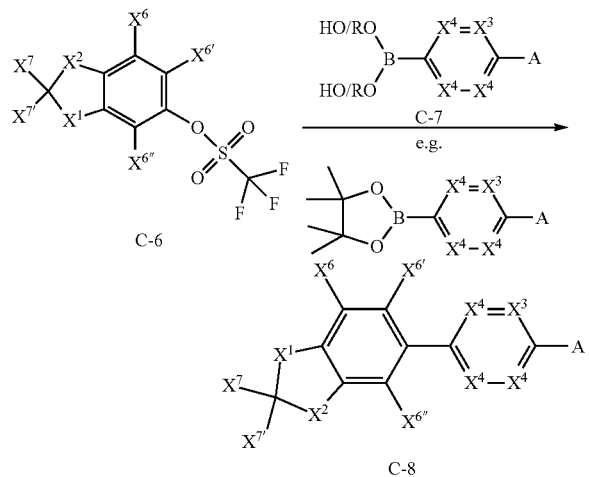

Scheme C-3

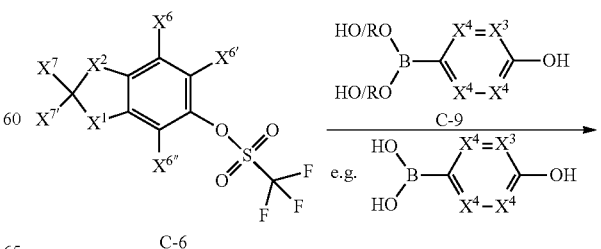

-continued

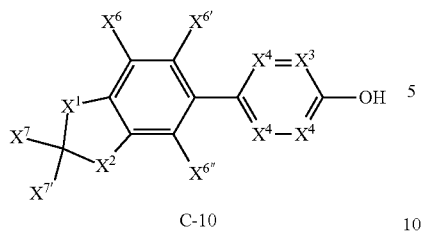

C-10

Alternatively, referring now to Scheme C-3, a compound of formula (C-6) (defined above) can be reacted with a compound of formula (C-9) under the same conditions described for Scheme C-2 to produce a compound of formula (C-10). The compound of formula (C-10) can be substituted for compound A-55 in scheme A-18 to produce further substituted derivatives of the products shown therein (e.g. derivatives of A-57 and A-59).

Scheme C-4

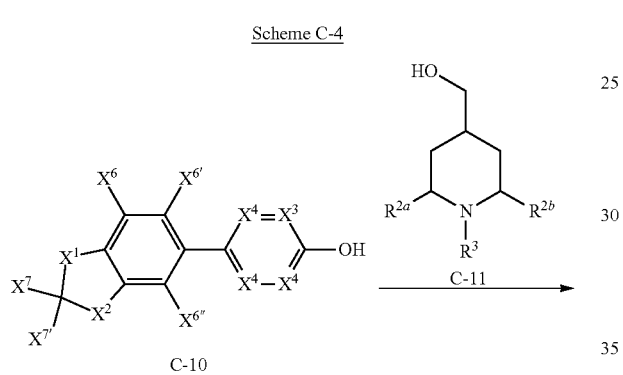

Referring now to Scheme C-4 above, a compound of formula (C-11) (e.g. see synthesis of A-120 in scheme A-31 above) is reacted with a compound of formula (C-10) (defined above) in the presence of a phosphine (such as triphenylphosphine, tri(o-tolyl)phosphine, resin-bound triphenylphosphine, and the like), in the presence of an azodicarboxylate (such as diethyl azodicarboxylate, diisopropyl azodicarboxylate, di-t-butylazodicarboxylate, di-(4-chlorobenzyl)azodicarboxylate, and the like), in the presence of a solvent (such as tetrahydrofuran, diethyl ether, 1,4-dioxane, methylene chloride, and the like), optionally with heating, and optionally with microwave irradiation, to provide a compound of formula (C-12).

Scheme C-5

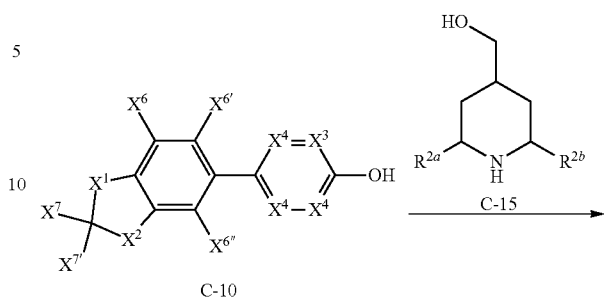

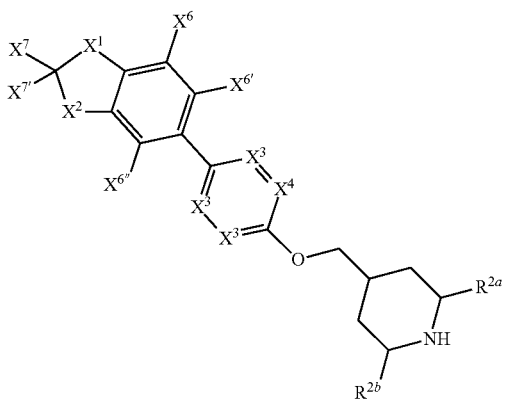

C-16

Referring now to Scheme C-5 above, a compound of formula (C-15), a known compound or a compounds prepared by known methods, is reacted with a compound of formula (C-10) (defined above) in the presence of a phosphine (such as triphenylphosphine, tri(o-tolyl)phosphine, resin-bound triphenylphosphine, and the like), in the presence of an azodicarboxylate (such as diethyl azodicarboxylate, diisopropyl azodicarboxylate, di-t-butylazodicarboxylate, di-(4-chlorobenzyl)azodicarboxylate, and the like), in the presence of a solvent (such as tetrahydrofuran, diethyl ether, 1,4-dioxane, methylene chloride, and the like), optionally with heating, and optionally with microwave irradiation, to provide a compound of formula (C-16).

Scheme C-6

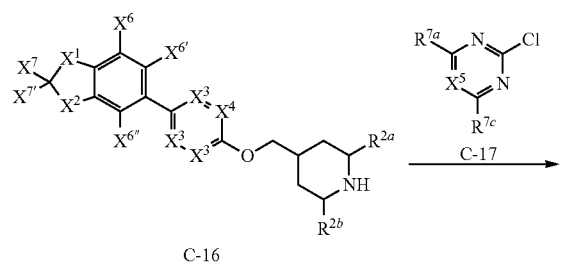

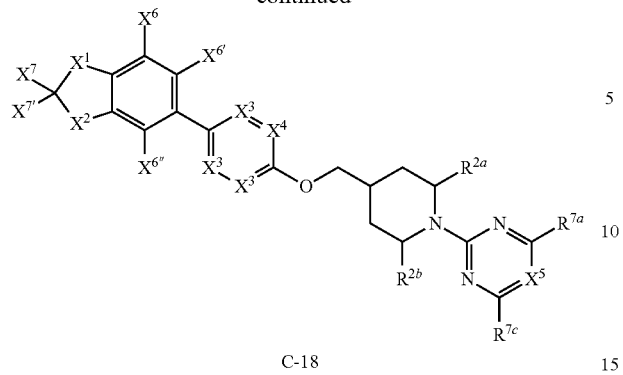

C-18

Referring now to Scheme C-6 above, a compound of the formula (C-16) (defined above) is reacted with a compound of the formula (C-17), a known compound or a compounds prepared by known methods, in the presence of a base (such as triethylamine, diisopropylethyl amine, pyridine, 2,6-lutidine, and the like), in the presence of a solvent (such as acetonitrile, tetrahydrofuran, 1,4-dioxane, N,N-dimethylformamide, and the like), optionally with heating, and optionally with microwave irradiation, to provide a compound of the formula (C-18).

Scheme C-7

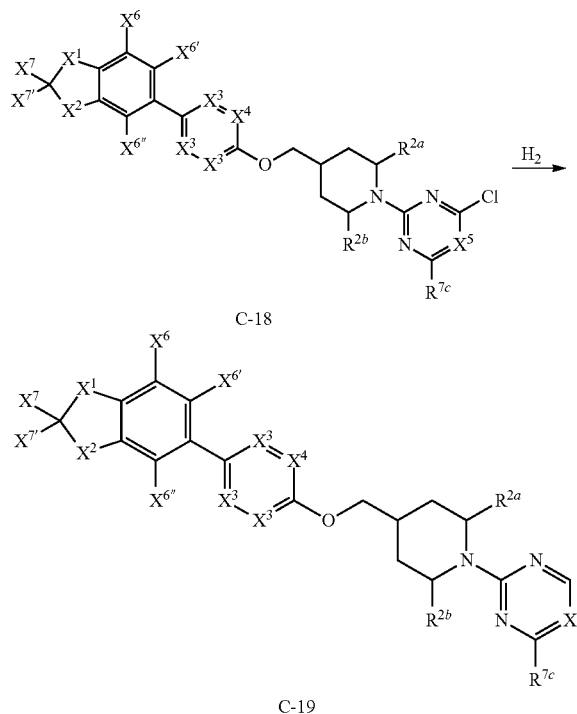

Referring now to Scheme C-7 above, a compound of formula (C-18) (defined above) is reacted with hydrogen in the presence of a palladium catalyst (such as palladium on carbon, tris(dibenzylideneacetone)dipalladium, palladium, tetrakis(triphenylphosphine), palladium acetate, palladium chloride, (tridibenzylideneacetone) dipalladium(0), and the like), in the presence of a solvent (such as tetrahydrofuran, 1,4-dioxane, methanol, ethanol, and the like,) optionally with heating, and optionally with microwave irradiation, to provide a compound of formula (C-19).

Scheme C-8

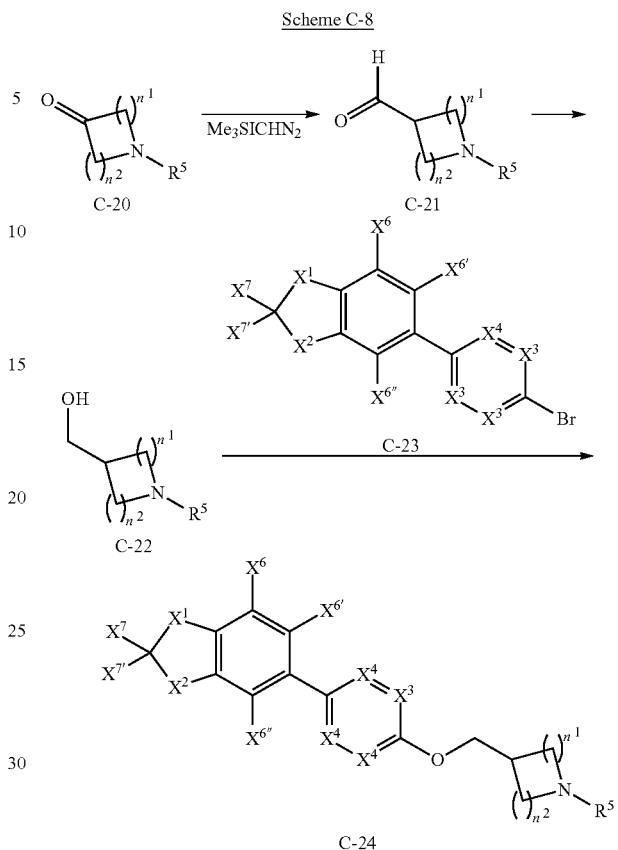

Referring now to Scheme C-8, a compound of formula (C-20) is reacted with trimethylsilyldiazomethane in hexanes in the presence of a base (such as lithium diisopropylamide, sodium diisopropylamide, potassium diisopropylamide, lithium hexamethyldisilazide, sodium hexamethyldisilazide, potassium hexamethyldisilazide, and the like), in the presence of a solvent (such as 1,4-dioxane, tetrahydrofuran, methylene chloride, 1,2-dichloroethane, and the like), optionally with cooling to −78° C., to provide a compound of formula (C-21). A compound of formula (C-21) is reacted with a reducing hydride reagent (such as sodium borohydride, lithium borohydride, lithium aluminum hydide, and the like), in a solvent (such as methanol, ethanol, 1,4-dioxane, tetrahydrofuran, and the like), optionally with heating, and optionally with microwave irradiation, to provide a compound of formula (C-22). A compound of formula (C-22) is reacted with a compound of formula (C-23), a known compound or compound prepared by known methods in which $X^3$, $X^4$, $X^6$, $X^{6'}$, $X^{6''}$, $X^7$ and $X^{7'}$ are as defined for compounds of formula (I), in the presence of a phosphine (such as triphenylphosphine, tri(o-tolyl)phosphine, resin-bound triphenylphosphine, and the like), in the presence of an azodicarboxylate (such as diethyl azodicarboxylate, diisopropyl azodicarboxylate, di-t-butylazodicarboxylate, di-(4-chlorobenzyl)azodicarboxylate, and the like), in the presence of a solvent (such as tetrahydrofuran, diethyl ether, 1,4-dioxane, methylene chloride, and the like), optionally with heating, and optionally with microwave irradiation, to provide a compound of the formula (C-24).

VI. Exemplary Compounds

Example A-1: 6-(Benzyloxy)benzo[d][1,3]oxa-thiole-2-one

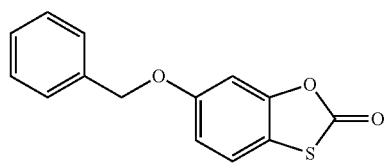 [SMILES: O=c1oc2cc(OCc3ccccc3)ccc2s1]

6-(Hydroxy)benzo[d][1,3]oxathiole-2-one (100 g, 0.6 mol) was dissolved in acetonitrile (1000 mL) and treated with potassium carbonate (165 g, 1.2 mol) and benzyl bromide (77.8 mL, 0.66 mol). The reaction mixture was stirred overnight at 70° C. Upon cooling to ambient temperature the inorganic precipitate was filtered off and the filtrate was concentrated under reduced pressure to a volume of 150 mL. Upon cooling, a precipitate was formed, filtered off and washed with diethyl ether to afford (123.3 g, 80%) of the title compound which was used in the next step without further purification.

Example A-2: 6-((Benzyloxy)benzo[d][1,3]oxa-thiole

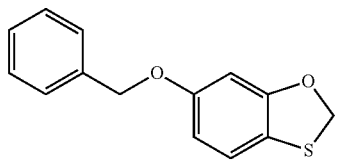 [SMILES: c1ccc(COc2ccc3c(c2)OCS3)cc1]

To a solution of 6-(benzyloxy)benzo[d][1,3]oxathiole-2-one (78.2 g, 0.3 mol) in dibromomethane (235 mL) and water (16 mL) was added potassium carbonate (125.5 g, 0.9 mol) 18-crown-6 (2.0 g, 7.5 mmol). The reaction mixture was heated to reflux under argon for 48 hours. Upon cooling to ambient temperature, an inorganic precipitate was formed and filtered off and the filtrate was concentrated under reduced pressure. The residual oil was treated with dichloromethane (400 mL) and the organic layer was separated, washed with brine (2×100 mL) and dried over magnesium sulfate and filtered. The filtrate was evaporated under reduced pressure and the residual oil was treated with dry diethyl ether (200 mL) with cooling in dry ice-acetone bath and starred for 30 minutes. The formed precipitate was filtered off and washed with cold diethyl ether (100 mL) to afford upon drying the title compound (62.5 g, 85%) which was used in the next step without further purification.

Example A-3: 6-(Benzyloxy)-2H-benzo[d][1,3]oxa-thiole 3,3-dioxide

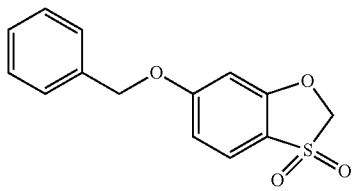 [SMILES: O=S1(=O)COc2cc(OCc3ccccc3)ccc21]

A solution of hydrogen peroxide (125 mL, 30% water) was added to a solution of 6-((benzyloxy)benzo[d][1,3] oxathiole (62.5 g, 0.26 mol) in acetic acid (625 mL) and the reaction mixture was stirred overnight at 70° C. Upon cooling to ambient temperature, the reaction mixture was quenched with water (625 mL) to form a precipitate which was filtered off and washed with water (2×100 mL) to afford upon drying 6-(benzyloxy)-2H-benzo[d][1,3]oxathiole 3,3-dioxide (61.7 g, 87%) which was used in the next step without further purification.

Example A-4: 6-Hydroxy-2H-benzo[d][1,3]oxa-thiole 3,3-dioxide

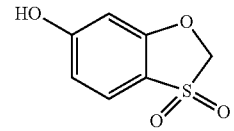

To a solution of 68 g (0.25 mol) of 6-(benzyloxy)-2H-benzo[d][1,3]oxathiole 3,3-dioxide (68 g, 0.25 mol) in tetrahydrofuran (816 mL) was added 10% Pd/C (6.8 g). The reaction mixture was stirred under hydrogen at ambient pressure and temperature overnight and then filtered through a pad of celite. The filtrate was evaporated under reduced pressure and the residual oil was triturated with diethyl ether (100 mL) and dried to afford 6-hydroxy-2H-benzo[d][1,3] oxathiole 3,3-dioxide (39.3 g, 86%) which was used in the next step without further purification.

Example A-5: 3,3-Dioxido-2H-benzo[d][1,3]oxa-thiol-6-yl Trifluoromethanesulfonate

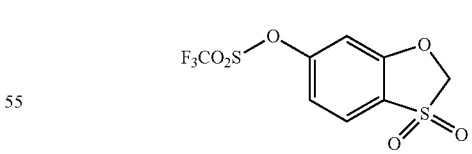

To a solution of 6-hydroxy-2H-benzo[d][1,3]oxathiole 3,3-dioxide (39.2 g, 0.21 mol) in pyridine (392 mL) was slowly added at 0° C. triflic anhydride (39 mL, 0.23 mol). The reaction mixture was then stirred for 40 minutes at 0° C. and overnight at ambient temperature. The solvents were evaporated under reduced pressure and the residual oil was stirred in ethyl acetate (400 mL) to form a suspension which was washed with an aqueous solution citric acid (100 mL, 10%) followed by brine (100 mL) and water (100 mL). The organic layer was separated, dried over magnesium sulfate and filtered. The filtrate was evaporated under reduced pressure to give an oil which was washed with diethyl ether (100 mL) and the solution was reduced in vacuo to give an oil which was purified by column chromatography eluting with dichloromethane to afford the title compound (6.8 g, 85%) as a white powder: $^1$H NMR (400 MHz, DMSO-$d_6$) δ 8.13 (d, J=8.7 Hz, 1H), 7.73 (d, J=2.1 Hz, 1H), 7.43 (dd, J=8.6, 2.08 Hz, 1H), 5.54 (s, 2H).

Example A-6: tert-Butyl-4-((4-bromo-2-fluorophenoxy)methyl)piperidine-1-carboxylate

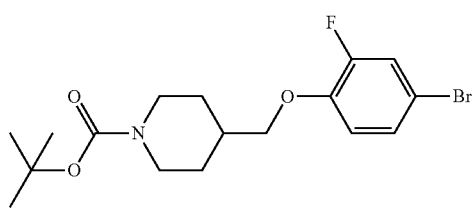 [SMILES: CC(C)(C)OC(=O)N1CCC(COc2ccc(Br)cc2F)CC1]

A suspension containing tert-butyl-4-((methylsulfonyloxy)methyl)piperidine-1-carboxylate (80.0 g, 0.27 mol), 4-bromo-2-fluorophenol (62.5 g, 0.33 mol) and potassium carbonate (75.4 g, 0.55 mol) in dimethylsulfoxide (800 mL) was stirred at 110° C. for 16 hours. Upon completion of reaction as evidenced by thin layer chromatography, dimethylsulfoxide was distilled off under reduced pressure. The residual oil was quenched with water (800 mL) and the resultant precipitate was filtered off and re-crystallized from iso-propanol to afford tert-butyl-4-((4-bromo-2-fluorophenoxy)methyl)pyperidine-1-carboxylate (88.0 g, 83.1%) as a white crystalline powder: $^1$H NMR (400 MHz, DMSO-$d_6$) δ 7.50 (dd, J=10.85, 2.3 Hz, 1H), 7.30 (m, 1H), 7.15 (m, 1H), 3.96 (d, J=10.7 Hz, 2H), 3.90 (d, J=6.4 Hz, 2H), 2.66-2.79 (m, 2H), 1.89-1.98 (m, 1H), 1.72 (d, J=10.9 Hz, 2H), 1.39 (s, 9H), 1.09-1.23 (m, 2H).

Example A-7: tert-Butyl-4-((2-fluoro-4-(4,4,5,5-tetramethyl-1,3,2-dioxoborolan-2-yl) phenoxy)methyl)piperidine-1-carboxylate

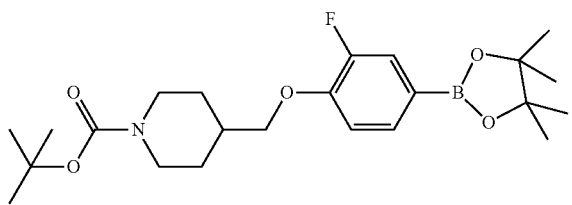 [SMILES: CC(C)(C)OC(=O)N1CCC(COc2ccc(B3OC(C)(C)C(C)(C)O3)cc2F)CC1]

To a mixture of tert-butyl-4-((4-bromo-2-fluorophenoxy)methyl)piperidine-1-carboxylate (60.0 g, 0.15 mol) and 4,4,4',4,5,5,5',5'-octamethyl-2,2'-bi-1,3,2-dioxoborolane (51.0 g, 0.2 mol) in acetonitrile (1000 mL) was added of 1,1' (bisdiphenylphosphino)ferrocene dichloropalladium (II) (Pd(dppf)Cl$_2$ (5.63 g, 8 mmol) and potassium acetate (45.5 g, 0.46 mol) and the solution was stirred under argon at 70° C. for 16 hours. Upon completion, the reaction mixture was diluted with ethyl acetate (1000 mL) and washed with brine (1000 mL). The organic layers were combined, dried over magnesium sulfate, filtered and the filtrate was evaporated under reduced pressure. The residue after evaporation was purified by column chromatography eluting with hexanes-ethyl acetate mixture (10:1) to afford the title compound (50.0 g, 74.3%) as a white powder. $^1$H NMR (400 MHz, DMSO-$d_6$) δ 7.42 (d, J=8.1 Hz, 1H), 7.31 (m, 1H), 7.15 (m, 1H), 3.91-4.02 (m, 4H), 2.66-2.80 (m, 2H), 1.89-2.02 (m, 1H), 1.73 (d, J=11.2 Hz, 2H), 1.39 (s, 9H), 1.27 (s, 12H), 1.07-1.22 (m, 2H).

Example A-8: Tert-Butyl-4-((4-(3,3-dioxido-2H-benzo[d][1,3]oxathiol-6-yl)-2-fluorophenoxy)methyl)piperidine-1-carboxylate

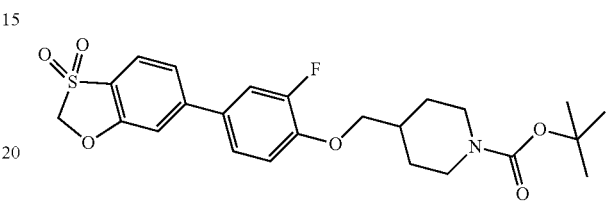

A mixture of tert-butyl-4-((2-fluoro-4-(4,4,5,5-tetramethyl-1,3,2-dioxoborolan-2-yl)phenoxy]methyl)piperidine-1-carboxylate (36.1 g, 83 mmol), 3,3-dioxido-1,3-benzoxythiol-6-yl trifluoromethane sulfonate (26.5 g, 83 mmol), potassium carbonate (69.0 g, 0.5 mmol) and of 1,1' (bisdiphenylphosphino)ferrocene dichloropalladium (II) Pd(dppf)Cl$_2$ (3.1 g, 4 mmol) in water-dioxane mixture (1000 mL, 1:1) was stirred under argon at ambient temperature for 1 hour. A precipitate was formed, filtered off and was subjected to purification by column chromatography on silica gel eluting with dichloromethane to afford crude product which was dissolved in dioxane (200 mL) and stirred with the Lewatit® MonoPlus SP 112 acidic resin (5.0 g) at ambient temperature for 2 hours. The solution was filtered and the filtrate was evaporated to afford the title compound (28.4 g, 71.5%). as a white powder. $^1$H NMR (400 MHz, DMSO-$d_6$) δ 7.89 (d, J=8.1 Hz, 1H), 7.71 (dd, J=12.9, 1.9 Hz, 1H), 7.62 (s, 1H), 7.58 (d, J=8.1 Hz, 2H), 7.28 (t, J=8.7 Hz, 1H), 5.43 (s, 2H), 3.94-4.02 (m, 4H), 2.67-2.85 (m, 2H), 1.93 (m, 1H), 1.74 (d, J=11.6 Hz, 2H), 1.40 (s, 9H), 1.11-1.24 (m, 2H).

Example A-9: 6-((3-Fluoro-4-piperidin-4-yl-methoxy)phenyl)-2H-benzo[d][1,3]oxathiole 3,3-dioxide Hydrochloride

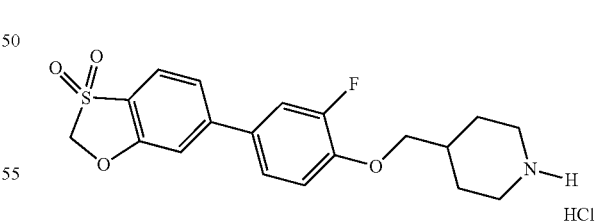

To a solution of tert-butyl-4-((4-(3,3-dioxido-2H-benzo[d][1,3]oxathiol-6-yl)-2-fluorophenoxy)methyl)piperidine-1-carboxylate (24.0 g, 50 mmol) in dioxane (350 mL) was added 50 mL of hydrochloride acid solution (4M) in dioxane and the resulting mixture was stirred at 70° C. for 24 hours. Upon cooling to ambient temperature a precipitate was formed which was filtered off to afford upon drying the title compound (19.5 g, 93.7%) as a white powder. $^1$H NMR (400 MHz, DMSO-$d_6$) δ 9.01 (br s, 1H), 8.69 (br s, 1H), 7.90 (d, J=8.1 Hz, 1H), 7.73 (dd, J=12.8, 2.3 Hz, 1H), 7.62 (s, 1H), 7.59 (d, J=8.1 Hz, 2H), 7.31 (t, J=8.8 Hz, 1H), 5.44 (s, 2H), 4.02 (d, J=6.3 Hz, 2H), 3.29 (d, J=12.5 Hz, 2H), 2.90 (m, 2H), 2.11 (br. s, 1H), 1.92 (d, J=12.7 Hz, 2H), 1.57 (m, 2H).

Example A-10: 6-((3-Fluoro-4-((1-isopropylpiperidin-4-ylmethoxy)phenyl)-2H-benzo[d][1,3]oxathiole 3,3-dioxide

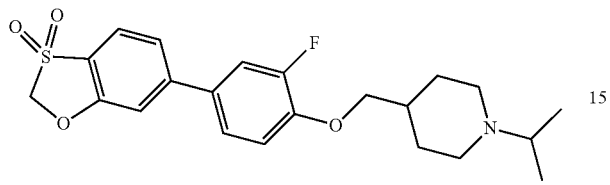

To a suspension of 6-((3-fluoro-4-piperidin-4-ylmethoxy)phenyl)-2H-benzo[d][1,3]oxathiole 3,3-dioxide hydrochloride (200 mg, 0.48 mmol) in acetone (20 mL) was added sodium triacetoxyborohydride (307 mg, 1.44 mmol) and the mixture was stirred at ambient temperature for 16 hours. Upon completion, the reaction mixture was evaporated under reduced pressure and the residual oil was treated with 10% aqueous solution of $K_2CO_3$ (30 mL) and stirred at ambient temperature for 30 minutes. A formed precipitate was filtered, dried and purified by column chromatography, eluting with a gradient $CH_2Cl_2$:MeOH:25% aq.$NH_4OH$ mixture (600:10:1-400:10:1-30:10:1-200:10:1) to afford the title compound as a white powder. $^1$H NMR (400 MHz, DMSO-$d_6$) δ 7.89 (d, J=8.0 Hz, 1H), 7.67-7.74 (m, 1H), 7.53-7.65 (m, 3H), 7.27 (t, J=8.8 Hz, 1H), 5.43 (s, 2H), 3.96 (d, J=5.6 Hz, 2H), 3.96 (d, J=5.6 Hz, 2H), 2.6-2.87 (m, 3H), 2.03-2.18 (m, 2H), 1.67-1.81 (m, 3H), 1.2-1.36 (m, 2H), 0.96 (d, J=6.4 Hz, 6H).

Example A-11: 1-tert-Butylpiperidine-4-carbaldehyde

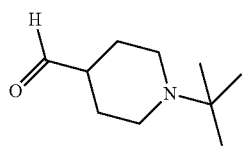

To a solution of diisopropylamine (19.65 g, 194.2 mmol) in tetrahydrofuran (72 mL) at −15° C. was added n-butyllithium (2.5M in hexanes, 9.36 mL, 23.4 mmol) and the mixture was cooled to −78° C. To the reaction mixture was added to trimethylsilyldiazomethane (2M in hexanes, 11.7 mL, 23.4 mmol) at −75° C., and the resulting mixture was stirred at −78° C. for 1 hour. To the reaction mixture was added a solution of 1-tert-butylpiperidine-4-one (3.0 g, 19.3 mmol) in tetrahydrofuran (10 mL) at −75° C., and the resulting mixture was stirred at −78° C. for 1.5 hours then allowed to warm up to ambient temperature and then stirred overnight under reflux. To the reaction mixture was added water (50 mL) and the volatiles were evaporated under reduced pressure and water (100 mL) was added and the resulting mixture was extracted with EtOAc (3×50 mL). The organic layer was separated, washed with brine (100 mL), dried over $Na_2SO_4$ and filtered. The filtrate was evaporated under reduced pressure and the residual oil was dissolved in EtOAc (120 mL) and silica gel (24 g) was added at room temperature. The mixture was stirred at ambient temperature for 1.5 h, filtered and the filtrate was evaporated under reduced pressure to afford the title compound. $^1$H-NMR (400 MHz, CDCl$_3$) δ 9.64 (s, 1H), 2.92-3.02 (m, 2H), 2.16-2.27 (m, 2H), 1.87-1.96 (m, 2H), 1.61-1.82 (m, 3H), 1.07 (s, 9H).

Example A-12: (1-tert-Butylpiperidin-4-yl)methanol

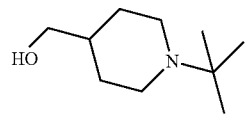

To a solution of 1-tert-butylpiperidine-4-carbaldehyde (2.1 g, 12.4 mmol) in methanol (50 mL) was added sodium borohydride (0.5 g, 12.4 mmol) and the mixture was stirred at ambient temperature for 30 minutes. Upon completion the reaction mixture was evaporated under reduced pressure and the residue was treated with 10% aq. solution of potassium carbonate (50 mL) and the resulting suspension was extracted with dichloromethane (3×30 mL). The combined extracts were washed with brine (50 mL), dried over sodium sulfate, filtered, and the filtrate was evaporated to afford the title compound. $^1$H-NMR (400 MHz, CDCl$_3$) δ 3.03-3.12 (m, 2H), 2.02-2.15 (m, 2H), 1.57-1.83 (m, 3H), 1.41-1.56 (m, 1H), 1.21-1.35 (m, 2H), 1.03-1.18 (m, 11H).

Example A-13: 6-((3-Fluoro-4-((1-tert-butylpiperidin-4-ylmethoxy)phenyl)-2H-benzo[d][1,3]oxathiole 3,3-dioxide

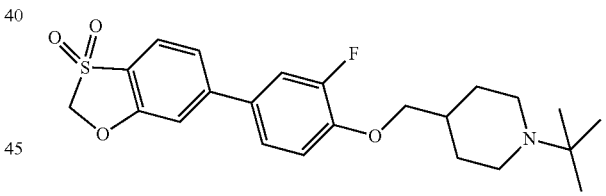

To a solution of (1-tert-butylpiperidin-4-yl)methanol (150 mg, 0.88 mmol), 4-(3,3-dioxido-1,3-benzoxathiol-6-yl)-2-fluorophenol (171 mg, 0.613 mmol) and triphenylphosphine (459 mg, 1.75 mmol) in tetrahydrofuran (9 mL) was added dropwise diisopropyl azodicarboxylate (354 mg, 1.75 mmol) at 0° C., and the resulting mixture was stirred at ambient temperature for 24 hours. Upon completion, water (40 mL) was added and the reaction mixture was extracted with ethyl acetate (2×50 mL). The organic layer was separated and washed with 1M aq. Solution of potassium hydroxide (30 mL), brine (50 mL) and dried over sodium sulfate. The reaction mixture was filtered and the filtrate was evaporated to give an oil which was purified by column chromatography on silica gel eluting with $CH_2Cl_2$:MeOH: 25% $NH_4OH$ mixture (20:1:0.1) to obtain a white solid which was purified further by preparative HPLC to afford the title compound (34.4 mg, 9%) as a white solid. $^1$H NMR (400 MHz, DMSO-$d_6$) δ 7.89 (d, J=8.0 Hz, 1H), 7.66-7.74 (m, 1H), 7.52-7.64 (m, 3H), 7.19-7.32 (m, 1H), 5.43 (s, 2H), 3.92-4.19 (m, 1H), 2.92-3.12 (m, 1H), 2.57-2.8 (m, 2H), 1.44-2.16 (m, 6H), 0.91-1.33 (m, 10H) LCMS retention time 5.3 minutes, [M+1]+ 434

Example A-14: 4-((4-3,3-Dioxido-2H-benzo[d][1,3]oxathiol-6-yl)-2-fluorophenyoxy)methyl)-N,N-dimethylpiperidine-1-carboxamide

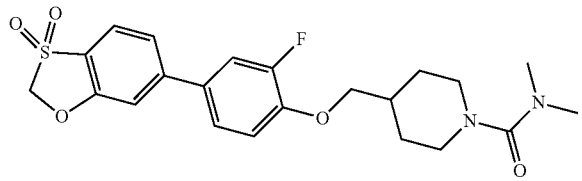 [SMILES: CN(C)C(=O)N1CCC(COc2ccc(-c3ccc4c(c3)OCS4(=O)=O)cc2F)CC1]

To a solution of 6-((3-fluoro-4-piperidin-4-ylmethoxy)phenyl)-2H-benzo[d][1,3]oxathiole 3,3-dioxide hydrochloride (0.25 g, 0.6 mmol) and triethylamine (0.15 g, 1.5 mmol) in acetonitrile (50.0 mL) at 0° C. was added dropwise dimethylcarbamic chloride (750 mg, 7.0 mmol). The reaction mixture was stirred at 70° C. for 24 hours. Upon completion, the reaction mixture was diluted with ethyl acetate (50 mL) and washed with 0.1N aq solution of hydrochloric acid (20 mL) and brine (20 mL). The organic layer was dried over sodium sulfate and concentrated in vacuo to afford the title compound (0.23 g, 85.5%) as a white solid. $^1$H NMR (400 MHz, DMSO-$d_6$) δ 7.89 (d, J=8.2 Hz, 2H), 7.72 (dd, J=12.9, 1.84 Hz, 1H), 7.62 (s, 1H), 7.58 (dd, J=8.1, 1.59 Hz, 2H), 7.29 (t, J=8.8 Hz, 1H), 5.43 (s, 2H), 3.99 (d, J=6.4 Hz, 3H), 3.56 (d, J=12.1 Hz, 2H), 2.72 (m, 8H), 1.96 (s, 1H), 1.75 (d, J=11.3 Hz, 2H), 1.27 (m, 2H).

Example A-15: 1-4-((4-3,3-Dioxido-2H-benzo[d][1,3]oxathiol-6-yl)-2-fluorophenyoxy) Methyl)-piperidin-1-yl)-2,2-dimethylpropan-1-one

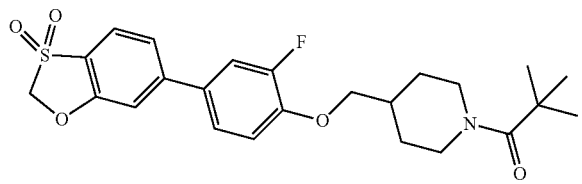 [SMILES: CC(C)(C)C(=O)N1CCC(COc2ccc(-c3ccc4c(c3)OCS4(=O)=O)cc2F)CC1]

To a suspension of 6-((3-fluoro-4-piperidin-4-ylmethoxy)phenyl)-2H-benzo[d][1,3]oxathiole 3,3-dioxide hydrochloride (0.25 g, 0.6 mmol) and pivalic acid (72 mg, 0.7 mmol) in acetonitrile (10 mL) was added triethylamine (0.18 mg, 1.8 mmol) followed by N-[(1H-1,2,3-benzotriazol-1-yloxy)(dimethylamino)methylene]-N-methylmethanaminium hexafluoro-phosphate (HBTU, 265 mg, 0.7 mmol). The resulting mixture was stirred at 40° C. for 24 hours. Upon cooling a precipitate was filtered off and dried to afford the title compound (156 mg, 56%) as a white solid. $^1$H NMR (400 MHz, DMSO-$d_6$) δ 7.89 (d, J=8.19 Hz, 1H), 7.74 (dd, J=12.84 Hz, J=2.1 Hz 1H), 7.62 (s, 1H), 7.58 (m, 2H), 7.29 (t, J=8.7 Hz, 1H), 5.44 (s, 2H), 4.30 (d, J=13.8 Hz, 2H), 4.00 (d, J=6.4 Hz, 2H), 2.82 (d, J=12.1 Hz, 2H), 2.08 (s, 1H), 1.80 (d, J=12.8 Hz, 2H), 1.2 (m, 12H).

Example A-16: Tert-Butyl (2-(4-((4-(3,3-dioxido-2H-benzo[d][1,3]oxathiol-6-yl)-2-fluorophenoxy)methyl)piperidin-1-yl)-2-oxoethyl)carbamate

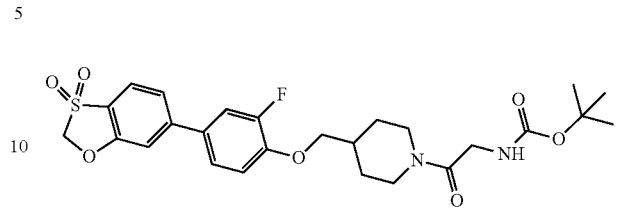

To a suspension of 6-((3-fluoro-4-piperidin-4-ylmethoxy)phenyl)-2H-benzo[d][1,3]oxathiole 3,3-dioxide hydrochloride (0.25 g, 0.6 mmol) and N-(tert-butoxycarbonyl)glycine (0.12 g, 0.7 mmol) in acetonitrile (10 mL) was added triethylamine (0.182 g, 1.8 mmol), followed by N-[(1H-1,2,3-benzotriazol-1-yloxy)(dimethylamino)methylene]-N-methylmethanaminium hexafluorophosphate (HBTU, 0.3 g, 0.8 mmol). The resulting mixture was stirred at 40° C. for 24 hours. Upon completion acetonitrile was removed under reduced pressure and the residue was treated with water (20 mL). A solid precipitate was filtered off and dried to afford the title compound (0.3 g, 93.5%) as a white solid. The product was used in the next step without further purification.

Example A-17: (2-(4-((4-(3,3-dioxido-2H-benzo[d][1,3]oxathiol-6-yl)-2-fluorophenoxy) Methyl)piperidin-1-yl)ethan-1-one

A solution of tert-butyl (2-(4-((4-(3,3-dioxido-2H-benzo[d][1,3]oxathiol-6-yl)-2-fluorophenoxy)methyl)piperidin-1-yl)-2-oxoethyl)carbamate (1.2 g, 2.3 mmol) of in dioxane (15 mL) was treated with 4M hydrochloric acid in dioxane (3 mL) and stirred at 70° C. for 24 hours. Upon cooling to ambient temperature a precipitate was formed which was filtered and suspended in 30 mL of 1 M solution of potassium carbonate in water. A precipitate was filtered to afford upon drying the title compound (0.17 g, 65%) as a white solid. $^1$H NMR (400 MHz, DMSO-$d_6$) δ 7.89 (d, J=8.2 Hz, 2H), 7.71 (dd, J=12.8, 2.0 Hz, 2H), 7.61 (s, 1H), 7.61 (s, 1H), 7.58 (dd, J=8.25, 7.28 (t, J=8.80 Hz, 2H), 5.43 (s, 2H), 1.14 (m, 2H), 4.40 (d, J=12.35 Hz, 1H), 3.99 (d, J=6.5 Hz, 3H), 3.76 (d, J=14.3 Hz, 2H), 3.32 (m, 3H), 2.97 (t, J=12.2 Hz, 1H), 2.62 (t, J=12.2 Hz, 1H), 2.06 (s, 1H), 1.78 (d, J=12.1 Hz 2H), 1.56 (s, 2H), 1.28 Hz, 2H).

Example A-18: tert-Butyl (S)-(1-(4-((4-(3,3-dioxido-2H-benzo[d][1,3]oxathiol-6-yl)-2-fluorophenoxy)methyl)piperidin-1-yl)-3-methyl-1-oxobutan-2-yl)carbamate

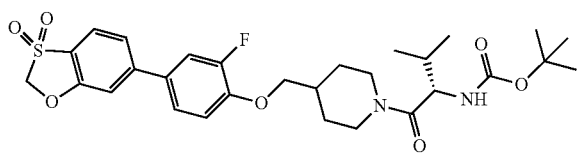 [SMILES: CC(C)[C@H](NC(=O)OC(C)(C)C)C(=O)N1CCC(COc2ccc(-c3ccc4c(c3)OCS4(=O)=O)cc2F)CC1]

A mixture of 6-((3-fluoro-4-piperidin-4-ylmethoxy)phenyl)-2H-benzo[1,3]oxathiole 3,3-dioxide hydrochloride (0.23 g, 0.57 mmol), N-(tert-butoxycarbonyl)-L-valine (0.12 g, 0.57 mmol), diisopropylethylamine (0.147 g, 1.14 mmol) and 1-ethyl-3-(3-dimethylaminopropyl)carbodiimide (EDCl, 1.11 g, 0.57 mmol) was stirred at ambient temperature for 12 hours. The solvent was then evaporated in vacuo and water (50 mL) was added. The product was extracted with dichloromethane (3×20 mL). The combined extracts were evaporated to give an oil which was subjected to column chromatography on silica gel eluting with dichloromethane to afford the title product (0.2 g, 61%) as a white solid. The material was used in the next step without further purification.

Example A-19: ((S)-2-Amino-1-(4-((4-(3,3-dioxido-2H-benzo[d][1,3]oxathiol-6-yl)-2-fluorophenoxy)methyl)piperidin-1-yl)-)-3-methylbutan-1-one

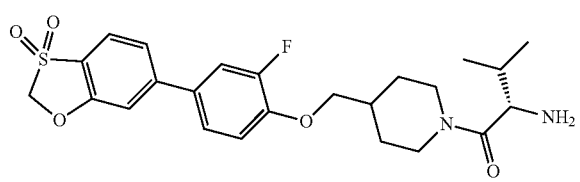 [SMILES: CC(C)[C@H](N)C(=O)N1CCC(COc2ccc(-c3ccc4c(c3)OCS4(=O)=O)cc2F)CC1]

A solution of tert-butyl (S)-(1-(4-((4-(3,3-dioxido-2H-benzo[d][1,3]oxathiol-6-yl)-2-fluorophenoxy)methyl)piperidin-1-yl)-3-methyl-1-oxobutan-2-yl)carbamate (0.2 g, 0.35 mmol) in methylene chloride (20 mL) was treated with 4M solution of HCl in dioxane (4 mL, 1.0 mmol) and the resulting mixture was stirred at ambient temperature for 3 hours. A precipitate was formed, filtered and washed with ether to afford upon drying the title compound (0.15 g, 84%) as a white solid. $^1$H NMR (400 MHz, DMSO-$d_6$) δ 8.10 (bs, 3H), 7.89 (d, J=8.2 Hz, 1H), 7.72 (d, J=12.7 Hz, 1H), 7.64-7.55 (m, 3H), 7.33-7.26 (m, 1H), 5.43 (s, 2H), 4.46 (t, J=14.3 Hz, 1H), 4.34-4.21 (m, 1H), 4.05-3.97 (m, 3H), 3.12 (t, J=12.4 Hz, 1H), 2.73 (t, J=12.3 Hz, 1H), 2.19-2.00 (m, 2H), 1.94-1.80 (m, 2H), 1.40-1.14 (m, 3H), 1.00 (m, 3H), 0.91 (m, 3H).

Example A-20: 4-((4-3,3,-Dioxido-2H-benzo[d][1,3]oxathiol-6-yl)-2-fluorophenyoxy)methyl)-piperidine-1-carboxamide

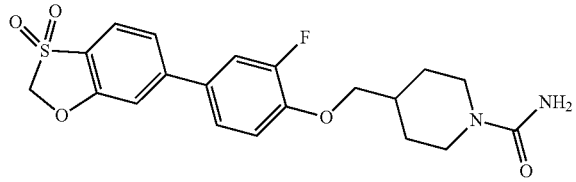 [SMILES: NC(=O)N1CCC(COc2ccc(-c3ccc4c(c3)OCS4(=O)=O)cc2F)CC1]

To a solution of 6-((3-fluoro-4-piperidin-4-ylmethoxy)phenyl)-2H-benzo[d][1,3]oxathiole 3,3-dioxide hydrochloride (0.25 g, 0.6 mmol) and triethylamine (0.15 g, 1.5 mmol) in acetonitrile (50.0 mL) at 0° C. was added dropwise isocyanato(trimethyl)silane (0.08 g, 7.0 mmol). The reaction mixture was stirred at 70° C. for 24 hours and then washed sequentially with 0.1 N aqueous hydrochloric acid (20 mL) and brine (40 mL). The organic layer was separated, dried over sodium sulfate, filtered and the filtrate was concentrated in vacuo to afford the title compound (0.18 g, 71%) as a white solid. $^1$H NMR (400 MHz, DMSO-$d_6$) δ 7.89 (d, J=8.1 Hz, 1H), 7.73 (s, 1H), 7.62 (m, 1H), 7.28 (t, J=8.7 Hz, 1H), 5.88 (s, 2H), 5.43 (s, 2H), 3.99 (d, J=6.0 Hz, 2H), 3.95 (s, 2H), 2.68 (t, J=12.2 Hz, 2H), 1.96 (m, 1H), 1.70 (d, J=12.2 Hz, 2H), 1.18 (m, 2H).

Example A-21: 1-4-((4-3,3,-Dioxido-2H-benzo[d][1,3]oxathiol-6-yl)-2-fluorophenyoxy) Methyl)-piperidin-1-yl)-2-methylpropan-1-one

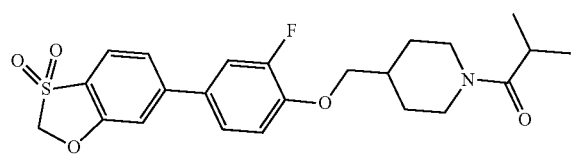 [SMILES: CC(C)C(=O)N1CCC(COc2ccc(-c3ccc4c(c3)OCS4(=O)=O)cc2F)CC1]

To a suspension of 6-((3-fluoro-4-piperidin-4-ylmethoxy)phenyl)-2H-benzo[d][1,3]oxathiole 3,3-dioxide hydrochloride (0.25 g, 0.6 mmol) and 2-methylpropanoic acid (0.062 g, 0.7 mmol) in acetonitrile (10 mL) was added triethylamine (0.182 g, 1.8 mmol). To a resulting solution was added N-[(1H-1,2,3-benzotriazol-1-yloxy)(dimethylamino)methylene]-N-methylmethanaminium hexafluoro phosphate (HBTU, 300 mg, 0.8 mmol). The resulting mixture was stirred at 40° C. for 24 hours. Upon cooling a formed precipitate was filtered off to afford upon drying the title compound (0.108 g, 40%) as an off-white solid. $^1$H NMR (400 MHz, DMSO-$d_6$) δ 7.89 (d, J=8.1 Hz, 1H), 7.69 (dd, J=12.9, J=2.0 Hz, 1H), 7.59 (m, 3H), 4.42 (d, J=13.2, 1H), 4.00 (m, 3H), 3.05 (t, J=11.9, 1H), 2.88 (q, J=6.9 Hz, 1H), 2.5 (m, 1H), 2.07 (m, 1H), 1.82 (m, 2H), 7.30 (t, J=8.7, 1H), 1.20 (m, 2H), 0.98 (d, J=5.9 Hz, 6H).

Example A-22: Ethyl-2-(4-((-(3,3-dioxido-2H-benzo[d][1,3]oxathiol-6-yl)-2-fluoropheny-oxy)methyl)-piperidin-1-yl)acetate

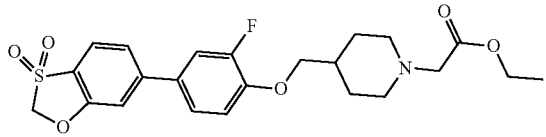 [SMILES: CCOC(=O)CN1CCC(COc2ccc(-c3ccc4c(c3)OCS4(=O)=O)cc2F)CC1]

To a solution of 6-((3-fluoro-4-piperidin-4-ylmethoxy)phenyl)-2H-benzo[d][1,3]oxathiole 3,3-dioxide hydrochloride (1000 mg, 2.4 mmol) and ethyl oxoacetate (271 mg, 2.6 mmol) and triethylamine (269 mg, 2.6 mmol) in dichloromethane (30 mL) at ambient temperature was added sodium triacetoxyborohydride (768 mg, 3.6 mmol) in small portions. The reaction mixture was stirred at room temperature for 15 hours and upon completion was washed with water (3×10 mL). The organic phase was separated and the volatiles were removed under reduced pressure. The oily residue after evaporation was triturated with acetonitrile (5 mL) to afford the title compound (716 mg, 65%) as an off-white solid. $^1$H NMR (400 MHz, DMSO-$d_6$) δ 7.89 (d, J=8.9 Hz, 1H), 7.71 (d, J=12.8 Hz, 1H, 5.43 (s, 2H), 1.19 (t, J=7.1 Hz, 3H), 7.54-7.63 (m, 3H), 7.27 (t, J=8.9 Hz, 1H), 4.08 (q, J=7.1 Hz, 2H), 3.98 (d, J=5.9 Hz, 2H), 3.19 (s, 2H), 1.27-1.41 (m, 2H), 2.86 (d, J=10.5 Hz, 2H), 2.18 (t, J=10.5 Hz, 2H), 1.67-1.83 (m, 3H).

Example A-23: 2-(4-((4-(3,3-Dioxido-2H-benzo[d][1,3]oxathiol-6-yl)-2-fluorophenyoxy) Methyl)-piperidin-1-yl)acetic Acid

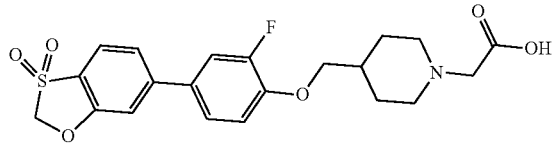 [SMILES: O=C(O)CN1CCC(COc2ccc(-c3ccc4c(c3)OCS4(=O)=O)cc2F)CC1]

To a suspension of ethyl-2-(4-((4-(3,3-dioxido-2H-benzo[d][1,3]oxathiol-6-yl)-2-fluorophenyoxy)methyl)-piperidin-1-yl)acetate (0.5 g, 1.1 mmol) in ethanol (2 mL) was added a solution of potassium hydroxide (73 mg, 1.3 mmol) in water (0.5 mL) and the reaction mixture was stirred at ambient temperature for 16 hours. Upon completion, the reaction mixture was acidified with 1N hydrochloric acid solution to pH 5. The solution was then filtered to remove a precipitate, washed with water (10 mL) and dried to afford the title compound (440 mg, 93%) as a white powder $^1$H NMR (400 MHz, DMSO-$d_6$) δ 7.89 (d, J=8.9 Hz, 1H), 7.72 (d, J=12.8 Hz, 1H), 7.55-7.63 (m, 3H), 7.29 (t, J=8.9 Hz, 1H), 5.43 (s, 2H), 4.00 (d, J=5.9 Hz, 2H), 3.21 (s, 2H), 1.43-1.58 (m, 2H), 3.19 (d, J=10.5 Hz, 2H), 2.57 (t, J=10.5 Hz, 2H), 1.76-1.98 (m, 3H).

Example A-24: 6-(4-((1-(5-Ethylpyrimidin-2-yl)piperidin-4-yl)methoxy-3-fluorophenyl)-2H-benzo[d][1,3]oxathiole 3,3-dioxide

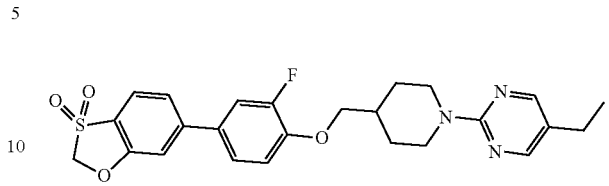

A solution of 6-((3-fluoro-4-piperidin-4-ylmethoxy)phenyl)-2H-benzo[d][1,3]oxathiole 3,3-dioxide hydrochloride (0.23 g, 0.57 mmol), 2-chloro-5-ethylpyrimidine (0.086 g, 0.6 mmol) and triethylamine (0.23 g, 2.3 mmol) in acetonitrile (50 mL) was stirred at reflux for 6 hours. Upon completion the reaction mixture was allowed to reach room temperature and filtered to remove a precipitate. The filtrate was washed consequently with water and hexanes and then purified by column chromatography eluting with dichloromethane to provide the title product (0.2 g, 74%). $^1$H NMR (400 MHz, DMSO-$d_6$) δ 8.24 (s, 2H), 7.89 (d, J=7.8 Hz, 1H), 7.71 (d, J=12.5 Hz, 1H), 7.64-7.55 (m, 3H), 7.29 (t, J=8.2 Hz, 1H), 5.44 (s, 2H), 4.67 (d, J=12.1 Hz, 2H), 4.01 (d, J=5.6 Hz, 2H), 2.89 (t, J=12.1 Hz, 2H), 2.46-2.39 (m, 2H), 2.10 (bs, 1H), 1.84 (d, J=11.7 Hz, 2H), 1.30-1.19 (m, 2H), 1.13 (t, J=7.3 Hz, 3H).

Example A-25: tert-Butyl 4-(((5-bromopyrimidin-2-yl)oxy)methyl)piperidine-1-carboxylate

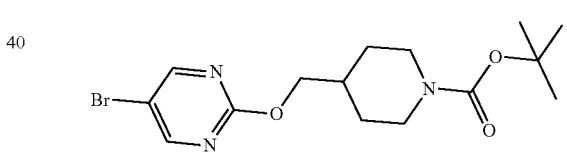

To a mixture of tert-butyl 4-(hydroxymethyl)piperidine-1-carboxylate (18.37 g, 0.085 mol) and 5-bromo-2-chloropyrimidine (15.0 g, 0.077 mol) in tetrahydrofuran (200 mL) was added a suspension (60%) of sodium hydride (3.07 g, 0.128 mol) in mineral oil and the resulting mixture was stirred under argon at 70° C. for 16 hours. Upon completion ethanol (15 mL) was slowly added to the reaction mixture and the reaction mixture was diluted with ethyl acetate (200 mL) and washed with brine (100 mL). The organic phase was separated, dried over magnesium sulfate, filtered and the filtrate was evaporated under reduced pressure. The residue after evaporation was subjected to column chromatography eluting with hexanes-ethyl acetate mixture 5:1 by volume to afford 15.13 g (52.4%) of tert-butyl 4-(((5-bromopyrimidin-2-yl) oxy)methyl)piperidine-1-carboxylate as a white powder. The product was used in the next step without further purification.

Example A-26: Tert-Butyl 4-(((5-(4,4,5,5-tetramethyl-1,3,2-dioxaborolan-2-yl)pyrimidin-2-yl)oxy)methyl)piperidine-1-carboxylate

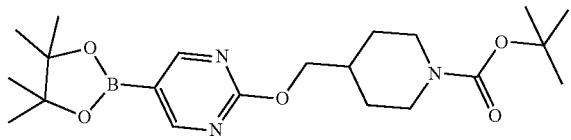 [SMILES: CC(C)(C)OC(=O)N1CCC(COc2ncc(B3OC(C)(C)C(C)(C)O3)cn2)CC1]

A mixture of tert-butyl 4-(((5-bromopyrimidin-2-yl)oxy)methyl)piperidine-1-carboxylate (11.0 g, 0.03 mol), 4,4,4',4',5,5,5',5'-octamethyl-2,2'-bi-1,3,2-dioxoborolane (7.5 g, 0.03 mol) and 1,1' (bisdiphenylphosphino)ferrocene dichloropalladium (II) Pd(dppf)Cl$_2$ (1.0 g, 1.3 mmol) and potassium acetate (8.7 g, 0.09 mol) in acetonitrile (300 mL) was stirred under argon at 70° C. for 16 hours. Upon completion, the reaction mixture was diluted with ethyl acetate (200 mL) and washed with brine (100 mL). The organic phase was separated, dried over magnesium sulfate, filtered and the filtrate was evaporated under reduced pressure. The residue after evaporation was subjected to column chromatography eluting with hexanes-ethyl acetate mixture 8:1 by volume to afford the title compound (4.5 g, 36.4%) as a white powder. $^1$H NMR (400 MHz, CDCl$_3$) δ 8.81 (s, 2H), 1.27 (m, 2H), 4.26 (s, J=6.7 Hz, 2H), 4.14 (m, 2H), 2.74 (t, J=12.9 Hz, 2H), 2.02 (m, 1H), 1.84 (d, J=13.2 Hz, 2H), 1.46 (s, 9H), 1.35 (s, 12H).

Example A-27: Tert-Butyl 4-(((5-(3,3-dioxido-2H-benzo[d][1,3]oxathiol-6-yl)pyrimidin-2-yl)oxy)methyl)piperidine-1-carboxylate

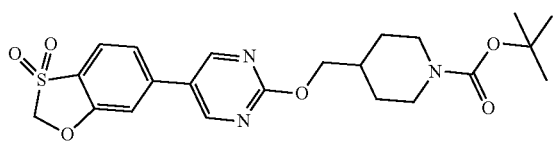 [SMILES: CC(C)(C)OC(=O)N1CCC(COc2ncc(-c3ccc4c(c3)OCS4(=O)=O)cn2)CC1]

A mixture of tert-butyl 4-(((5-(4,4,5,5-tetramethyl-1,3,2-dioxaborolan-2-yl)pyrimidin-2-yl)oxy}methyl)piperidine-1-carboxylate (2.77 g, 6.7 mmol), 3,3-dioxido-1,3-benzoxythiol-6-yl trifluoromethane sulfonate (1.57 g, 4.9 mmol), potassium carbonate (4.0 g, 29.4 mmol) and 1,1' (bisdiphenylphosphino)ferrocene dichloropalladium (II) Pd(dppf)Cl$_2$ (0.36 g, 0.5 mmol) in water-dioxane mixture 1:1 by volume (50 mL) was stirred under argon at ambient temperature for 1 hour and then filtered. The solid was purified by column chromatography on silica gel eluting with dichloromethane to afford the crude product. This material was dissolved in dioxane (30 mL) and stirred with the Lewatit® MonoPlus SP-112 resin (0.5 g) for 2 hours and then filtered. The solvent was distilled off to afford the title compound (1.66 g, 73.4%) as a white powder. $^1$H NMR (400 MHz, DMSO-d$_6$) δ 9.02 (s, 2H), 7.97 (d, J=8.1 Hz, 1H), 7.74 (s, 1H), 7.66 (d, J=8.16 Hz, 1H), 5.45 (s, 2H), 4.24 (d, J=6.5 Hz, 2H), 3.97 (d, J=11.8, Hz, 2H), 2.74 (m, 2H), 1.98 (m, 1H), 1.98 (m, 1H), 1.72 (m, J=12.4 Hz, 2H), 1.17 (m, 2H) 1.40 (s, 9H).

Example A-28: 6-(2-(Piperidin-4-ylmethoxy)pyrimidin-5-yl)-2H-benzo[d][1,3]oxathiole 3,3-dioxide Hydrochloride

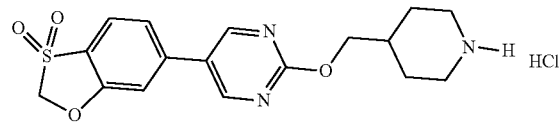 [SMILES: O=S1(=O)COc2cc(-c3cnc(OCC4CCNCC4)nc3)ccc21 ; Cl]

A solution of tert-butyl 4-(((5-(3,3-dioxido-1,3-benzoxathiol-6-yl)-pyrimidin-2-yl]oxy}methyl)piperidine-1-carboxylate (1.66 g, 3.6 mmol) in dioxane (30 mL) was treated with hydrochloric acid solution (4M) in dioxane (5 mL) and stirred at 70° C. for 24 hours. Upon cooling a precipitate was filtered off to afford title compound (1.3 g, 91%) as an off-white solid. $^1$H NMR (400 MHz, DMSO-d$_6$) δ 9.11 (br. s, 1H), 9.03 (s, 2H), 8.76 (br. s, 1H), 7.98 (d, J=8.1 Hz, 1H), 7.76 (s, 1H), 7.66 (d, J=8.1 Hz, 1H), 5.46 (s, 2H), 4.27 (d, J=6.5 Hz, 2H), 3.29 (d, J=12.4 Hz, 2H), 2.90 (m, 2H), 2.12 (m, 1H), 1.89 (d, J=13.2 Hz, 2H), 1.55 (m, 2H).

Example A-29: 6-(2-((1-(5-Chloropyrimidin-2-yl)piperidin-4-yl)methoxy)pyrimidin-5-yl)-2H-benzo[d][1,3]oxathiole 3,3-dioxide

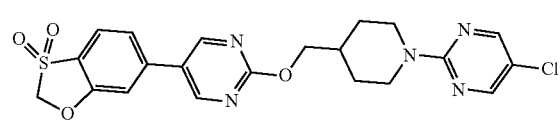 [SMILES: O=S1(=O)COc2cc(-c3cnc(OCC4CCN(c5ncc(Cl)cn5)CC4)nc3)ccc21]

To a suspension of 6-(2-(piperidin-4-ylmethoxy)pyrimidin-5-yl)-2H-benzo[d][1,3]oxathiole 3,3-dioxide hydrochloride (0.6 g, 1.5 mmol) and 2,5-dichloropyrimidine (0.22 g, 0.63 mmol) in aceonitrile (20 mL) was added triethylamine (0.6 g, 2 mmol) and the resulting mixture was heated under reflux for 16 hours. The volatile compounds were removed under reduced pressure and a residue was triturated with water (20 mL) to give a solid which was filtered off, washed with ether (10 mL) and air-dried to afford the title compound (0.24 g, 33.8%) as a white powder. $^1$H NMR (400 MHz, DMSO-d$_6$) δ 8.74 (s, 2H), 8.24 (s, 2H), 7.80 (d, J=8.1 Hz, 1H), 7.38 (dd, J=8.1, 1.1 Hz, 1H), 7.38 (dd, J=8.1, 1.1 Hz, 1H), 7.27 (s, 2H), 1.39 (m, 2H), 5.12 (s, 2H), 4.79 (d, J=13.7 Hz, 2H),), 4.33 (d, J=6.7 Hz, 2H), 2.95 (t, J=12.6 Hz, 2H), 2.22 (m, 1H), 1.98 (d, J=11.6 Hz, 2H).

Example A-30: 5-Hydroxybenzo[d][1,3]oxathiol-2-one

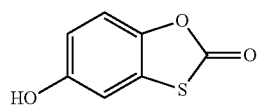

To a solution of thiourea (30 g, 0.39 mol) in 2 N aqueous hydrochloric acid (200 mL) was added a solution of quinine (28.4 g, 0.26 mol) in glacial acetic acid (28.4 g, 0.26 mol)). The resulting mixture was stirred at room temperature for 30 minutes, during which time a mass of crystalline thiouronium salt precipitated. Upon heating on a steam bath, the salt was re-dissolved to give a clear solution. The mixture was heated for 1 hour, and then chilled in an ice bath until crystallization was complete. The solid precipitate was collected, washed with water, and dried to give the title compound (55 g, 83%) as a white solid. The product was used in the next step without further purification.

Example A-31: 5-Benzyloxybenzo[d][1,3]oxathiol-2-one

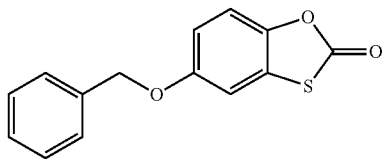 [SMILES: O=c1oc2ccc(OCc3ccccc3)cc2s1]

A solution of 5-hydroxybenzo[d][1,3]oxathiol-2-one (10 g, 0.06 mol) in acetonitrile (100 mL) was treated with potassium carbonate (16.5 g, 0.12 mol) of and benzyl bromide (7.8 mL, 0.07 mol). The reaction mixture was stirred at 70° C. for 16 hours. Upon cooling to ambient temperature, the solution was filtered to remove inorganic salts and the filtrate was concentrated under reduced pressure to a volume of 150 mL. A precipitate was formed, filtered off and washed with ether to afford the title product (11.8 g, 77%) as a white powder. The material used in the next step without further purification.

Example A-32: 5-Benzyloxybenzo[d][1,3]oxathiole

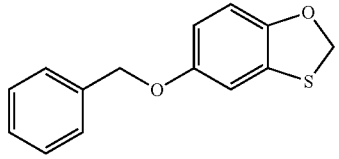 [SMILES: c1ccc(COc2ccc3c(c2)SCO3)cc1]

A mixture of 5-benzyloxybenzo[d][1,3]oxathiol-2-one (11.8 g, 0.046 mol), potassium carbonate (11.8 g, 0.046 mol) and 18-crown-6 (0.2 g, 0.8 mmol) in dibromomethane (100 mL) and water (4 mL) was stirred at reflux under argon for 48 hours. Upon cooling, the inorganic salts were removed by filtration and the filtrate was concentrated under reduced pressure. The residue after evaporation was treated with dichloromethane (150 mL). The organic layer was separated, washed with brine (2×50 mL) and dried over magnesium sulfate. The solution was filtered and the filtrate was evaporated under reduced pressure. The residue after evaporation was treated with dry ether (50 mL) with cooling in dry ice-acetone bath and starred for 30 minutes. A formed precipitate was filtered off and washed on filter with cold dry ether (20 mL) to afford the title compound (9.0 g, 81.5%) as a white powder. The product was used in the next step without further purification.

Example A-33: 5-Benzyloxybenzo[d][1,3]oxathiole 3,3-dioxide

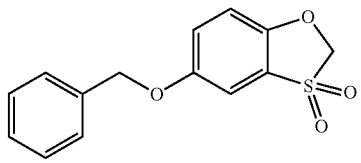 [SMILES: O=S1(=O)COc2ccc(OCc3ccccc3)cc21]

Into solution of 5-benzyloxybenzo[d][1,3]oxathiole (9 g, 0.037 mol) in acetic acid (100 mL) was added hydrogen peroxide (25 mL of 30% water solution) and the reaction mixture was stirred overnight at 70° C. Upon cooling to ambient temperature the reaction mixture was diluted with water (100 mL). A formed precipitate was filtered off and washed with water (2×30 mL) to afford upon drying on air 6.2 g (63%) of 5-(benzyloxy)-1,3-benzoxathiole 3,3-dioxide. The product was used in the next step without further purification.

Example A-34: 5-Hydroxy-2H-benzo[d][1,3]oxathiole 3,3-dioxide

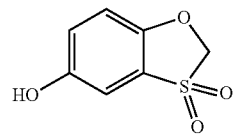 [SMILES: O=S1(=O)COc2ccc(O)cc21]

To a mixture of 5-benzyloxybenzo[d][1,3]oxathiole 3,3-dioxide (5.0 g, 0.018 mol) and palladium on charcoal (Pd/C, 0.7 g) in 10% mineral oil was added tetrahydrofuran (70 mL) and stirred under hydrogen at ambient pressure and temperature for 16 hours. The reaction mixture was then filtered through a pad of celite and the filtrate was evaporated under reduced pressure. The residue after evaporation was washed with ether (30 mL) to afford the title compound (3.01 g, 89%) as a white solid. The product was used in the next step without further purification.

Example A-35: 3,3-Dioxido-2H-benzo[d][1,3]oxathiol-5-yl trifluoromethanesulfonate

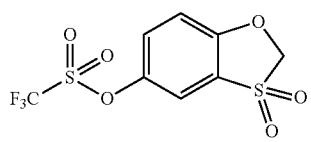 [SMILES: O=S1(=O)COc2ccc(OS(=O)(=O)C(F)(F)F)cc21]

A solution of 5-hydroxy-2H-benzo[d][1,3]oxathiole 3,3-dioxide (3.01 g, 0.016 mol) in pyridine (30 mL) at 0° C. was treated with triflic anhydride (5.2 g, 0.019 mol). The reaction mixture was stirred for 40 minutes at 0° C. and 16 hours at ambient temperature. The volatiles were removed under reduced pressure and the solution was concentrated to give an oil which was treated with ethyl acetate (70 mL). The suspension was washed with 10% aqueous solution of citric acid (70 mL) followed by brine (50 mL) and water (50 mL). The organic layer was separated, dried over magnesium sulfate and filtered. The filtrate was evaporated under reduced pressure and the residue after evaporation was subjected to column chromatography elution with dichloromethane to afford the title product (3.4 g, 66%) as a white powder. The product was used in the next step without further purification.

Example A-36: (1-(5-Chloropyrimidin-2-yl)piperidin-4-yl)methanol

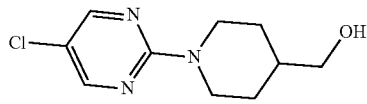 [SMILES: OCC1CCN(c2ncc(Cl)cn2)CC1]

A solution containing (piperidin-4-yl)methanol (124.6 g, 1.08 mol), 2,5-dichloropyrimidine (161.2 g, 1.08 mol) and triethylamine (438 g, 4.3 mol) in acetonitrile (1000 mL) was heated under reflux for 16 hours. The reaction mixture was allowed to cool to room temperature and filtered. The solid was washed with ether (300 mL) and dried to afford the title compound (203.2 g, 82.4%) as a beige powder. $^1$H NMR (400 MHz, DMSO-$d_6$) δ 8.36 (s, 2H), 4.58 (d, J=13.3 Hz, 2H), 4.47 (t, J=5.3 Hz, 1H), 3.26 (t, J=5.7 Hz, 2H), 2.87 (td, J=12.7, 2.2 Hz, 2H), 1.67 (m, 3H), 1.05 (m, 2H).

Example A-37: (1-(5-Chloropyrimidin-2-yl)piperidin-4-yl)methyl Methanesulfonate

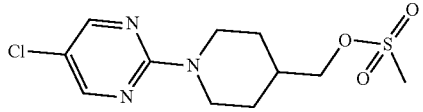 [SMILES: CS(=O)(=O)OCC1CCN(c2ncc(Cl)cn2)CC1]

To a solution of (1-(5-chloropyrimidin-2-yl)piperidin-4-yl)methyl methanesulfonate (203 g, 0.89 mol) and triethylamine (180.4 g, 1.78 mol) in dichloromethane (1500 mL) at 0° C. was added methanesulfonyl chloride (112.3 g, 0.98 mol). The reaction mixture was stirred at ambient temperature for 4 hours and washed sequentially with 0.1N hydrochloric acid (500 mL) and brine (300 mL). The organic layer was extracted and dried over sodium sulfate, filtered and the filtrate was concentrated in vacuo to afford the title product (120.1 g, 88%) as a white solid. $^1$H NMR (400 MHz, CDCl$_3$) δ 8.22 (s, 2H), 4.76 (d, J=13.5 Hz, 2H), 4.10 (d, J=6.6 Hz, 2H), 3.02 (s, 3H), 2.90 (td, J=12.9, 2.52 Hz, 2H), 2.06 (m, 1H), 1.84 (d, J=12.5 Hz, 2H), 1.30 (m, 2H).

Example A-38: 2-(4-((4-Bromo-2-fluorophenoxy)methyl]piperidin-1-yl)-5-chloro Pyrimidine

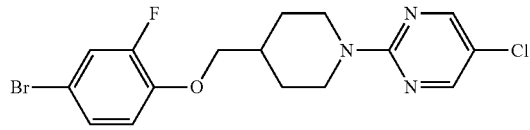 [SMILES: Fc1cc(Br)ccc1OCC1CCN(c2ncc(Cl)cn2)CC1]

A suspension of (1-(5-chloropyrimidin-2-yl)piperidin-4-yl)methyl methanesulfonate (244.3 g, 0.8 mol), 4-bromo-2-fluorophenol (206.0 g, 1.07 mol) and potassium carbonate (331.0 g, 2.4 mol) in dimethylsulfoxide (2.5 L) was heated at 110° C. for 16 hours. After cooling to room temperature, dimethylsulfoxide was removed under reduced pressure and the resultant residue was treated with water (2.0 L). A solid precipitated out and was filtered and recrystallized from isopropanol (1.5 L) to afford the title product (246.1 g, 77%) as a white crystalline powder: $^1$H NMR (400 MHz, CDCl$_3$) δ 8.22 (s, 2H), 7.24 (dd, J=10.5, 2.3 Hz, 1H), 7.18 (dt, J=8.7, 1.9 Hz, 1H), 6.83 (t, J=8.8 Hz, 1H), 4.77 (d, J=13.4 Hz, 2H), 3.87 (d, J=6.5 Hz, 2H),), 2.94 (td, J=12.9, 2.6 Hz, 2H), 2.14 (m, 1H), 1.93 (d, J=12.4 Hz, 2H), 1.34 (qd, J=12.5, 4.28 Hz, 2H).

Example A-39: 5-Chloro-2-(4-((2-fluoro-4-(4,4,5,5-tetramethyl-1,3,2-dioxaborolan-2-yl) phenoxy) methyl}piperidin-1-yl)pyrimidine

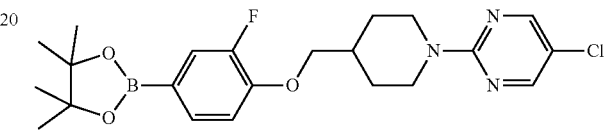

A mixture of 2-(4-((4-bromo-2-fluorophenoxy)methyl) piperidin-1-yl)-5-chloropyrimidine (246.0 g, 0.6 mol), 4,4, 4',4,5,5,5',5'-octamethyl-2,2'-bi-1,3,2-dioxoborolane (187.0 g, 0.746 mol), 1,1' (bisdiphenylphosphino)ferrocene dichloropalladium (II) Pd(dppf)Cl$_2$ (22.5 g, 0.05 mol) and potassium acetate (241.0 g, 2.45 mol) in acetonitrile (2.5 L) was stirred under argon at 70° C. for 16 hours. The reaction mixture was cooled to room temperature and diluted with ethyl acetate (2.0 L) and washed with brine (1.0 L). The organic phase was separated, dried over magnesium sulfate, filtered and the filtrate was evaporated under reduced pressure. The residue was purified by column chromatography eluting with hexanes-ethyl acetate mixture 10:1 by volume to afford the title product (234.8 g, 85.4%) as a white powder. $^1$H NMR (400 MHz, DMSO-$d_6$) δ 8.38 (s, 2H), 7.42 (d, J=8.2 Hz, 1H), 7.31 (d, J=11.74, 1.85 Hz, 1H), 1.27 (s, 12H), 7.15 (t, J=8.2 Hz, 1H), 4.61 (d, J=13.5 Hz, 2H), 3.96 (d, J=6.5 Hz, 2H), 2.94 (t, J=14.0 Hz, 2H), 2.06 (m, 1H), 1.82 (d, J=13.5 Hz, 2H).

Example A-40: 5-(4-((1-5-Chloropyrimidin-2-yl) piperidin-4-yl)methoxy)-3-fluorophenyl)-2H-benzo [d][1,3]oxathiole 3,3-dioxide

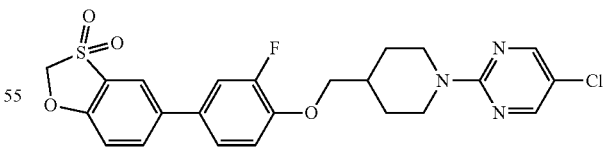

A mixture of 5-chloro-2-(4-((2-fluoro-4-(4,4,5,5-tetramethyl-1,3,2-dioxaborolan-2-yl)phenoxy)methyl}piperidin-1-yl)pyrimidine (1.0 g, 3.1 mmol), 3,3-dioxido-2H-benzo [d][1,3]oxathiol-5-yl trifluoromethanesulfonate (1.4 g, 3.1 mmol), potassium carbonate (1.28 g, 9.3 mmol) and 1,1' (bisdiphenylphosphino)ferrocene dichloropalladium (II) Pd(dppf)Cl$_2$ (0.15 g, 0.2 mmol) in (1:1) water-dioxane mixture (34 mL) was stirred under argon at ambient temperature for 1 hour. The solution was filtered and the solid was purified by column chromatography on silica gel eluting with dichloromethane to afford crude product. This material was dissolved in dioxane (20 mL) and stirred with Lewatit® MonoPlus SP-112 resin (0.5 g) for 2 hour. The mixture was filtered and the filtrate was evaporated in vacuo to afford the title product (0.15 g, 10%) as a white solid. $^1$H NMR (400 MHz, DMSO-d$_6$) δ 8.39 (s, 1H), 1.27 (m, 2H), 7.98 (dd, J=8.8, 1.84, 1H), 7.65 (dd, J=12.8, 2.0, 1H), 7.36 (d, J=8.8 Hz, 1H), 7.22 (t, J=8.9, 1H), 5.44 (s, 2H), 4.62 (d, J=13.3 Hz, 2H), 3.99 (d, J=6.4 Hz, 2H), 2.97 (t, J=12.7 Hz, 2H), 2.12 (m, 1H), 1.84 (d, J=13.1 Hz, 2H).

Example A-41: 6-(4-((1-(4-Chloro-1,3,5-triazin-2-yl)piperidin-4-yl)methoxy)-3-fluorophenyl)-2H-benzo[d][1,3]oxathiole 3,3-dioxide

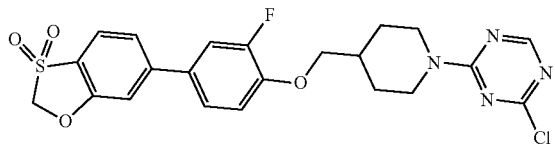 [SMILES: O=S1(=O)COc2cc(-c3ccc(OCC4CCN(c5ncnc(Cl)n5)CC4)c(F)c3)ccc21]

A suspension 6-((3-fluoro-4-piperidin-4-ylmethoxy)phenyl)-2H-benzo[1,3]oxathiole 3,3-dioxide hydrochloride (500 mg, 1.2 mmol), 2,4-dichloro-1,3,5-triazine (217 mg, 1.4 mmol) and triethylamine (390 mg, 3.0 mmol) in acetonitrile (20 mL) was heated under reflux for 16 hours. The volatiles were removed under reduced pressure and the residue was triturated with water (20 mL). A solid precipitate was filtered off, washed with cold methanol (10 mL) of MeOH and dried to afford the title product (540 mg, 91%) as a white solid. The material was used in the next step without further purification.

Example A-42: 6-(4-((1-(1,3,5-Triazin-2-yl)piperidin-4-yl)methoxy)-3-fluorophenyl)-2H-benzo[d][1,3]oxathiole 3,3-dioxide

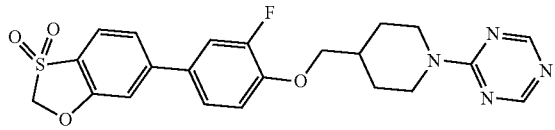 [SMILES: O=S1(=O)COc2cc(-c3ccc(OCC4CCN(c5ncncn5)CC4)c(F)c3)ccc21]

A mixture of 6-(4-((1-(4-chloro-1,3,5-triazin-2-yl)piperidin-4-yl)methoxy)-3-3-fluorophenyl)-2H-benzo[d][1,3]oxathiole 3,3-dioxide (500 mg, 1.0 mmol) and 10% palladium over charcoal (Pd/C, 11 mg) in THF (150 mL) was stirred under hydrogen at ambient temperature and pressure for 16 hours. The reaction mixture was filtered through a pad of celite and the solvents were evaporated to give an oil which was triturated with methanol (50 mL) to form a precipitate. This precipitate was filtered off and dried to afford the title compound (396 mg, 85%) as a white powder. $^1$H NMR (400 MHz, DMSO-d$_6$) δ 8.55 (s, 2H), 7.89 (d, J=8.9 Hz, 1H), 5.43 (s, 2H), 7.72 (d, J=12.8 Hz, 1H), 7.55-7.64 (m, 3H), 1.18-1.34 (m, 2H), 7.29 (t, J=8.9 Hz, 1H), 1.90 (d, J=13.2 Hz, 2H) 2.11-2.24 (m, 1H), 3.01 (t, J=13.2 Hz, 2H), 4.02 (d, J=6.6 Hz, 2H), 4.71 (d, J=13.2 Hz, 2H).

Example A-43: tert-Butyl 3-(((methylsulfonyl)oxy)methyl)azetidine-1-carboxylate

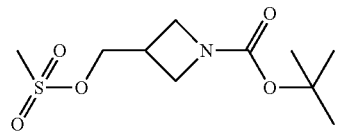 [SMILES: CC(C)(C)OC(=O)N1CC(COS(C)(=O)=O)C1]

To a stirring solution containing tert-butyl 3-(hydroxymethyl)azetidine-1-carboxylate (5.0 g, 26.7 mmol) and triethylamine (7.4 mL, 53.4 mmol) in dichloromethane (50.0 mL) at 0° C. was added methanesulfonyl chloride (2.3 mL, 29.4 mmol). The reaction mixture was stirred at ambient temperature for 4 hours and washed sequentially with 0.1N hydrochloric acid (30 mL) and brine (30 mL). The organic layer collected, dried over Na$_2$SO$_4$ and concentrated in vacuo to afford the title compound (6.6 g, 93%) as a white solid. $^1$H NMR (400 MHz, DMSO-d$_6$) δ 4.34 (d, J=6.7 Hz, 1H), 3.86-3.96 (m, 2H), 3.57-3.67 (m, 2H), 3.21 (s, 1H), 2.84-2.96 (m, 1H), 1.38 (s, 9H).

Example A-44: Tert-Butyl 3-((4-bromo-2-fluorophenoxy)methyl)azetidine-1-carboxylate

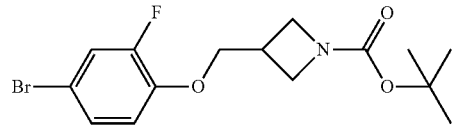 [SMILES: CC(C)(C)OC(=O)N1CC(COc2ccc(Br)cc2F)C1]

A suspension of tert-butyl 3-(((methylsulfonyl)oxy)methyl)azetidine-1-carboxylate (6.6 g, 24.9 mmol), 4-bromo-2-fluorophenol (5.7 g, 29.9 mmol) and potassium carbonate (6.9 g, 49.8 mmol) in dimethylsulfoxide (100 mL) was stirred at 110° C. for 16 hours. Upon cooling to room temperature, dimethylsulfoxide was removed in vacuo and the residue was triturated with water (100 mL). A solid precipitate was formed, filtered off and dried to afford the title compound (7.9 g, 88%) as a white powder. $^1$H NMR (400 MHz, DMSO-d$_6$) δ 7.54 (d, J=8.9 Hz, 1H), 7.37 (d, J=8.9 Hz, 1H), 7.17 (t, J=8.9 Hz, 1H), 4.18 (d, J=6.7 Hz, 1H), 3.87-4.03 (m, 2H), 3.61-3.75 (m, 2H), 2.89-3.02 (m, 1H), 1.38 (s, 9H).

Example A-45: Tert-Butyl 3-((2-fluoro-4-(4,4,5,5-tetramethyl-1,3,2-dioxaborolan-2-yl) phenoxy)methyl)azetidine-1-carboxylate

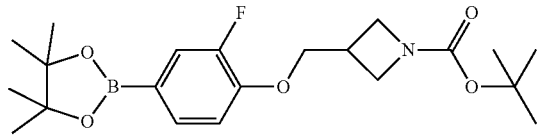 [SMILES: CC(C)(C)OC(=O)N1CC(COc2ccc(B3OC(C)(C)C(C)(C)O3)cc2F)C1]

A mixture of tert-butyl 3-((4-bromo-2-fluorophenoxy)methyl)azetidine-1-carboxylate (7.9 g, 21.9 mmol), 4,4,4',4',5,5,5',5'-octamethyl-2,2'-bi-1,3,2-dioxoborolane (6.7 g, 26.3 mmol), (bisdiphenylphosphino)ferrocene dichloropalladium (II) Pd(dppf)Cl$_2$ (0.64 g, 0.85 mmol) and potassium acetate in acetonitrile (100 mL) was stirred under argon at 70° C. for 16 hours. Upon completion the reaction mixture was diluted with ethyl acetate (100 mL) and washed with brine (100 mL). The organic phase was separated, dried over magnesium sulfate, filtered and the filtrate was evaporated under reduced pressure to afford the title compound (8.9 g, 100%) as a white powder. The product was used in the next step without further purification. $^1$H NMR (400 MHz, DMSO-$d_6$) δ 7.43 (d, J=8.9 Hz, 1H), 7.32 (d, J=8.9 Hz, 1H), 7.19 (t, J=8.9 Hz, 1H), 4.20 (d, J=6.7 Hz, 1H), 3.88-4.03 (m, 2H), 3.59-3.76 (m, 2H), 2.90-3.04 (m, 1H), 1.37 (s, 9H), 1.15 (s, 12H).

Example A-46: Tert-butyl 3-((4-(3,3-dioxido-2H-benzo[d][1,3]oxathiol-6-yl)-2-fluorophenoxy)methyl)azetidine-1-carboxylate

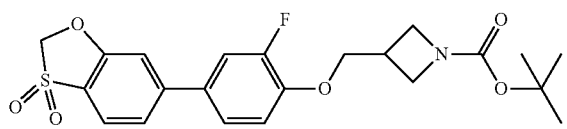 [SMILES: CC(C)(C)OC(=O)N1CC(COc2ccc(-c3ccc4c(c3)OCS4(=O)=O)cc2F)C1]

A solution containing tert-butyl 3-((2-fluoro-4-(4,4,5,5-tetramethyl-1,3,2-dioxaborolan-2-yl)phenoxy)methyl)azetidine-1-carboxylate (8.9 g, 21.9 mmol), 3,3-dioxido-2H-benzo[d][1,3]oxathiol-5-yl trifluoromethanesulfonate (6.95 g, 21.9 mmol), potassium carbonate (18.1 g, 131.4 mmol) and (bisdiphenylphosphino)ferrocene dichloropalladium (II) Pd(dppf)Cl$_2$ (0.8 g, 1.1 mmol) in a 1:1 water-dioxane mixture (260 mL) was stirred under argon at ambient temperature for 1 hour. A precipitate was formed, filtered and was purified by column chromatography on silica gel eluting with dichloromethane to afford an oil. This material was dissolved in dioxane (50 mL) and stirred with with Lewatit® MonoPlus SP-112 resin (1.2 g) for 2 hours. The reaction mixture was then filtered and the solvent was removed under reduced pressure to afford the title compound (2.6 g, 26%) as a white solid. $^1$H NMR (400 MHz, DMSO-$d_6$) δ 7.89 (d, J=8.9 Hz, 1H), 7.73 (d, J=12.8 Hz, 1H), 7.56-7.64 (m, 3H), 7.31 (t, J=8.9 Hz, 1H), 5.44 (s, 2H), 4.26 (d, J=6.7 Hz, 1H), 3.88-4.05 (m, 2H), 3.62-3.78 (m, 2H), 2.92-3.06 (m, 1H), 1.38 (s, 9H).

Example A-47: 6-(4-(Azetidin-3-ylmethoxy)-3-fluorophenyl)-2H-benzo[d][1,3]oxathiole 3,3-dioxide Hydrochloride

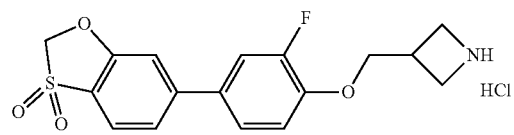 [SMILES: O=S1(=O)COc2cc(-c3ccc(OCC4CNC4)c(F)c3)ccc21 ; Cl]

A solution of tert-butyl 3-((4-(3,3-dioxido-2H-benzo[d][1,3]oxathiol-6-yl)-2-fluorophenoxy)methyl)azetidine-1-carboxylate (1.2 g, 2.3 mmol) in dioxane (15 mL) was treated with 4M hydrochloric acid solution in dioxane (3 mL) and stirred at 70° C. for 24 hours. After cooling to room temperature, a solid was formed which was filtered to afford the title compound (1.0 g, 97%) as a white powder. $^1$H NMR (400 MHz, DMSO-$d_6$) δ 8.25 (br.s, 2H), 7.90 (d, J=8.9 Hz, 1H), 7.76 (d, J=12.8 Hz, 1H), 7.56-7.68 (m, 3H), 7.33 (t, J=8.9 Hz, 1H), 5.44 (s, 2H), 4.33 (d, J=6.7 Hz, 1H), 4.01-4.12 (m, 2H), 3.80-3.91 (m, 2H), 3.19-3.30 (m, 1H).

Example A-48: 6-(4-((1-(5-Chloropyrimidin-2-yl)azetidin-3-yl)methoxy)-3-fluorophenyl)-2H-benzo[d][1,3]oxathiole 3,3-dioxide

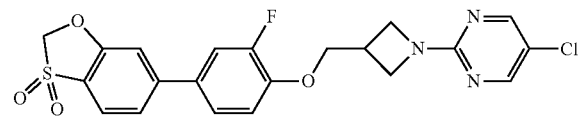 [SMILES: O=S1(=O)COc2cc(-c3ccc(OCC4CN(c5ncc(Cl)cn5)C4)c(F)c3)ccc21]

To a suspension of 6-(4-(azetidin-3-ylmethoxy)-3-fluorophenyl)-2H-benzo[d][1,3]oxathiole 3,3-dioxide hydrochloride (200 mg, 0.52 mmol) and 2,5-dichloropyrimidine (93 mg, 0.63 mmol) in acetonitrile (10 mL) was added triethylamine (209 mg, 2.08 mmol) and the resulting mixture was heated under reflux overnight. The volatiles were evaporated under reduced pressure and the residue was triturated with water (20 mL). A solid precipitate was filtered off, washed with methanol (10 mL) and dried to afford the title compound (63 mg, 26%) as a white powder. $^1$H NMR (400 MHz, DMSO-$d_6$) δ 8.41 (s, 2H). 3.12-3.25 (m, 1H), 7.89 (d, J=8.9 Hz, 1H), 7.72 (d, J=12.8 Hz, 1H), 7.54-7.66 (m, 3H), 7.33 (t, J=8.9 Hz, 1H), 5.43 (s, 2H), 4.36 (d, J=6.7 Hz, 1H), 4.15-4.26 (m, 2H), 3.86-3.99 (m, 2H).

Example A-49: 3-Isopropyl-5-(trichloromethyl)-1,2,4-oxadiazole

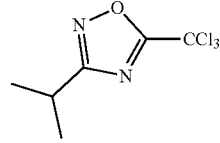

A solution of N-hydroxyisobutyramidine (7 g, 48 mmol), trichloroacetic anhydride (42 g, 137 mmol) in toluene (40 mL) was refluxed for 1 hour. The reaction was quenched with water (200 mL) and the resultant mixture was extracted with dichloromethane (2×150 mL). The combined organic layers were dried, filtered, and concentrated to afford the title compound (15.7 g, 100%). The product was used in the next step without further purification Example A-50: 3-Isopropyl-1,2,4-oxadiazol-5-ol

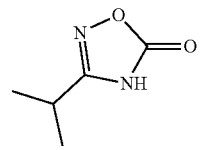

A solution of 3-isopropyl-5-(trichloromethyl)-1,2,4-oxadiazole (50 g, 219 mmol) and potassium hydroxide (24.0 g, 428 mmol) in ethanol (300 mL) was stirred at 80° C. for 10 minutes. The reaction mixture was then concentrated and diluted with water (500 mL) and the pH value was adjusted to 5 with 33% hydrochloric acid. The aqueous layer was extracted with ethyl acetate (2×300 mL) and the combined organic extracts were dried over magnesium sulfate, filtered, and the filtrate was evaporated to afford crude product. The crude product was re-crystallized from ethyl acetate-hexanes mixture (250 mL, 1:10 by volume) to afford the title compound (24.0 g, 87%) as a white solid. $^1$H NMR (400 MHz, DMSO-$d_6$) δ 12.18 (br.s, 1H), 2.76-2.90 (m, 1H), 1.18 (d, J=7.0 Hz, 6H).

Example A-51:
5-Chloro-3-isopropyl-1,2,4-oxadiazole

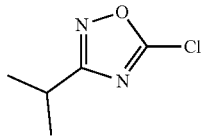

A solution of 3-isopropyl-1,2,4-oxadiazol-5-ol (300 mg, 2.23 mmol), phosphoryl chloride (1.02 g, 6.71 mmol) in pyridine (10 mL) was heated to 100° C. for 1 hour. The reaction was then quenched with water (50 mL) and the aqueous phase was extracted with EtOAc (2×50 mL). The organic layers were combined, dried over magnesium sulfate, filtered and the filtrate was concentrated to afford the title compound (103 mg, 30%) as a white solid. $^1$H NMR (400 MHz, DMSO-$d_6$) δ 1.27 (d, J=7.0 Hz, 6H), 3.05-3.19 (m, 1H).

Example A-52: 6-(3-Fluoro-4-((1-(3-isopropyl-1,2,4-oxadiazol-5-yl)azetidin-3-yl)methoxy)phenyl)-2H-benzo[d][1,3]oxathiole 3,3-dioxide

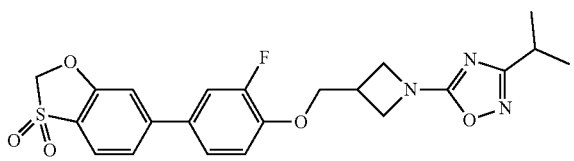 [SMILES: CC(C)c1noc(N2CC(COc3ccc(-c4ccc5c(c4)OCS5(=O)=O)cc3F)C2)n1]

To a suspension of of 6-(4-(azetidin-3-ylmethoxy)-3-fluorophenyl)-2H-benzo[d][1,3]oxathiole 3,3-dioxide hydrochloride (300 mg, 0.78 mmol) and 5-chloro-3-isopropyl-1,2,4-oxadiazole (171 mg, 1.17 mmol) in acetonitrile (10 mL) was added triethylamine (157 mg, 1.56 mmol) and the resulting mixture was heated under reflux for 16 hours. The volatiles were evaporated under reduced pressure and the residue was triturated with water (20 mL). A precipitate was filtered off, washed with cold methanol (10 mL) and dried to afford the title compound (28 mg, 8%) as a white powder. $^1$H NMR (400 MHz, DMSO-$d_6$) δ 1.18 (d, J=7.0 Hz, 6H), 2.77-2.87 (m, 1H), 3.21-3.30 (m, 1H), 3.99-4.07 (m, 2H), 3.27-4.34 (m, 2H), 4.35 (d, J=6.7 Hz, 1H), 5.44 (s, 2H), 7.32 (t, J=8.9 Hz, 1H), 7.56-7.65 (m, 3H), 7.73 (d, J=12.8 Hz, 1H), 7.90 (d, J=8.9 Hz, 1H)

Example A-53: Ethyl 2-chloro-3-oxopropanoate

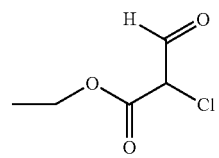

To a solution of ethyl chloroacetate (50.0 g, 0.409 mol) and ethyl formate (30.3 g, 0.409 mol) in toluene (500 mL) at 0° C. was added sodium ethoxide (33.0 g, 0.49 mol). The reaction mixture was stirred at 0° C. for 5 hours and then at ambient temperature for 12 hours. The reaction mixture was quenched with water (250 mL), and extracted with ether (2×250 mL). The aqueous layer was cooled to 0° C. and acidified to pH 4 with 5N hydrochloric acid solution. The aqueous layer was then extracted with ether (3×300 mL) and the combined organic extracts were dried over sodium sulfate, filtered, and concentrated under reduced pressure to furnish the title compound (20.0 g, 19%) as a light brown oil. The compound was used in the next step without further purification. $^1$H NMR (400 MHz, DMSO-$d_6$) δ 1.21 (t, J=7.1 Hz, 3H), 4.14 (q, J=7.1 Hz, 2H), 7.94 (s, 1H), 11.74 (br.s, 1H).

Example A-54: Tert-Butyl 4-(5-(ethoxycarbonyl)-1,3-thiazol-2-yl)piperidine-1-carboxylate

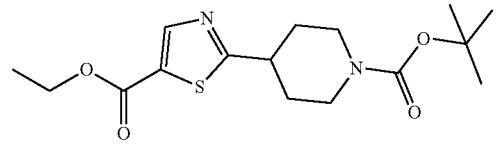 [SMILES: CCOC(=O)c1cnc(C2CCN(C(=O)OC(C)(C)C)CC2)s1]

A mixture of tert-butyl 4-(aminocarbonothioyl)piperidine-1-carboxylate (1.0 g, 8.2 mmol) and ethyl 2-chloro-3-oxopropanoate (2.5 g, 16.4 mmol) in toluene (40 mL) was heated at 90° C. for 2 hours. The reaction mixture was cooled and partitioned between saturated aqueous sodium bicarbonate and ethyl acetate (200 mL, 1:1 by volume). The organics were washed with water (50 mL) and brine (50 mL). The organic extract was dried over sodium sulfate, filtered and the filtrate was evaporated. The oily residue after evaporation was subjected to column chromatography on silica gel eluting with 3:7 by volume mixture ethyl acetate-hexanes mixture to afford the title compound (2.0 g, 72%) as an yellow oil. $^1$H NMR (400 MHz, DMSO-$d_6$) δ 1.28 (t, J=7.1 Hz, 3H), 1.40 (s, 9H), 1.49-1.62 (m, 2H), 2.03 (d, J=13.2 Hz, 2H), 2.80-2.99 (m, 2H), 3.21-3.30 (m, 1H), 4.00 (d, J=13.2 Hz, 2H), 8.33 (s, 1H)

Example A-55: tert-Butyl 4-(5-(hydroxymethyl)-1,3-thiazol-2-yl)piperidine-1-carboxylate

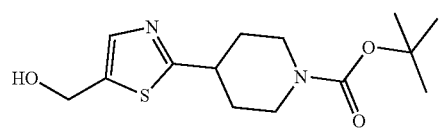 [SMILES: CC(C)(C)OC(=O)N1CCC(c2ncc(CO)s2)CC1]

A solution of tert-butyl 4-(5-(ethoxycarbonyl)-1,3-thiazol-2-yl)piperidine-1-carboxylate (1.70 g; 6.58 mmol) in tetrahydrofuran (30 mL) at 0° C. was treated with 1M solution of lithium aluminum hydride in tetrahydrofuran (7.60 mL, 7.60 mmol). The reaction mixture was stirred at room temperature for 1 hour, then was cooled to 0° C. and carefully quenched with water (0.76 mL). After stirring for 10 minutes, a solution of aqueous solution sodium hydroxide (5N, 0.38 mL) was added and was stirred again for another 10 minutes and filtered through a pad of celite. The filtrate was concentrated in vacuo to afford the title compound (0.8 g, 46%) as a white solid which was used in the next step without further purification. $^1$H NMR (400 MHz, DMSO-$d_6$) δ 7.51 (s, 1H), 5.46 (t, J=5.7 Hz, 2H), 4.62 (d, J=5.7 Hz, 2H), 3.99 (d, J=13.2 Hz, 2H), 3.09-3.20 (m, 1H), 2.79-2.99 (m, 2H), 1.45-1.58 (m, 2H), 1.99 (d, J=13.2 Hz, 2H), 1.40 (s, 9H).

Example A-56: Tert-Butyl 4-(5-((4-(3,3-dioxido-2H-benzo[d][1,3]oxathiol-6-yl)-2-fluoro phenoxy) methyl)thiazol-2-yl)piperidine-1-carboxylate

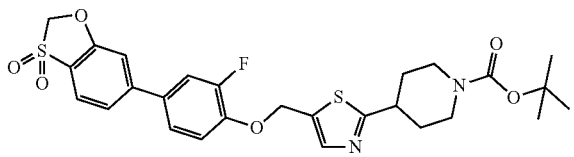 [SMILES: CC(C)(C)OC(=O)N1CCC(c2ncc(COc3ccc(-c4ccc5c(c4)OCS5(=O)=O)cc3F)s2)CC1]

To a solution of tert-butyl 4-(5-(hydroxymethyl)-1,3-thiazol-2-yl)piperidine-1-carboxylate (233 mg, 0.78 mmol), 4-(3,3-dioxido-1,3-benzoxathiol-6-yl)-2-fluorophenol (219 mg, 0.78 mmol), triphenylphosphine (225 mg, 0.85 mmol) in tetrahydrofuran (10 mL) at 0° C. was added dropwise diisopropyl azodicarboxylate (174 mg, 0.85 mmol) and the reaction mixture was stirred at ambient temperature for 24 hours. Water (40 mL) was then added and the reaction mixture was extracted with ethyl acetate (50 mL). The organic layer was washed with 1M aqueous solution potassium hydroxide (20 mL), brine (20 mL) and dried over Na$_2$SO$_4$ and filtered. The filtrate was evaporated to give an oil which was purified by column chromatography on silica gel eluting with 10:1 mixture by volume chloroform-tetrahydrofuran to afford the title compound (410 mg, 67%) as a white solid. $^1$H NMR (400 MHz, DMSO-$d_6$) δ 7.90 (d, J=8.9 Hz, 1H), 1.40 (s, 9H), 7.83 (s, 1H), 7.74 (d, J=12.8 Hz, 1H), 7.56-7.67 (m, 3H), 7.44 (t, J=8.9 Hz, 1H), 5.48 (s, 2H), 5.43 (s, 2H), 3.99 (d, J=13.2 Hz, 2H), 3.14-3.24 (m, 1H), 2.79-2.98 (m, 2H), 2.01 (d, J=13.2 Hz, 2H), 1.47-1.61 (m, 2H).

Example A-57: 6-(3-Fluoro-4-((2-piperidin-4-yl) thiazol-5-yl)methoxy)phenyl)-2H-benzo[d][1,3]oxathiole-3,3-dioxide

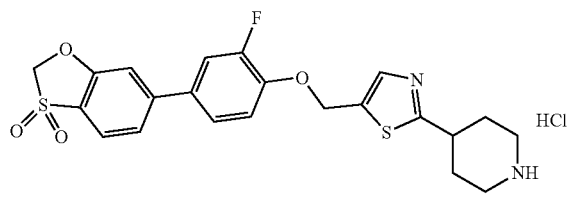 [SMILES: O=S1(=O)COc2cc(-c3ccc(OCc4cnc(C5CCNCC5)s4)c(F)c3)ccc21 ; Cl]

A solution of tert-butyl 4-(5-((4-(3,3-dioxido-2H-benzo[d][1,3]oxathiol-6-yl)-2-fluoro phenoxy)methyl)thiazol-2-yl)piperidine-1-carboxylate (0.41 g, 0.73 mmol) in dioxane (10 mL) was treated with 4M solution of hydrochloric acid in dioxane (1 mL) and stirred at 70° C. for 24 hours. A was filtered and dried to afford the title compound (0.26 g, 72%) as a white solid. $^1$H NMR (400 MHz, DMSO-$d_6$) δ 9.07 (br s, 1H), 8.89 (brs, 1H), 7.90 (d, J=8.9 Hz, 1H), 7.86 (s, 1H), 7.74 (d, J=12.8 Hz, 1H), 7.56-7.65 (m, 3H), 7.56-7.65 (m, 3H), 7.45 (t, J=8.9 Hz, 1H), 5.50 (s, 2H), 5.44 (s, 2H), 3.27-3.40 (m, 3H), 2.94-3.07 (m, 2H), 2.18 (d, J=13.2 Hz, 2H), 1.85-1.99 (m, 2H).

Example A-58: 6-(4-((2-(1-(5-Chloropyrimidin-2-yl) piperidin-4-yl)thiazol-5-yl)methoxy)-3-fluorophenyl)-2H-benzo[d][1,3]oxathiole-3,3-dioxide

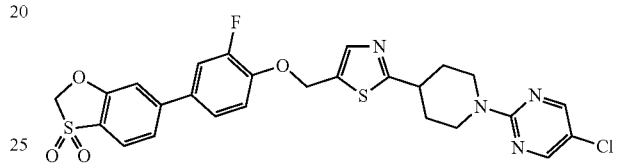

To a suspension of 6-(3-fluoro-4-((2-piperidin-4-yl)thiazol-5-yl)methoxy)phenyl)-2H-benzo[d][1,3]oxathiole-3,3-dioxide hydrochloride (130 mg, 0.26 mmol) and 2,5-dichloropyrimidine (43 mg, 0.29 mmol) in acetonitrile (10 mL) was added triethylamine (66 mg, 0.65 mmol) and the reaction mixture was heated under reflux for 16 hours. The reaction mixture was then cooled and filtered to give a solid which was washed with ether (10 mL) and dried to afford the title compound (96 mg, 64%) as a beige powder. $^1$H NMR (400 MHz, DMSO-$d_6$) δ 8.41 (s, 1H), 7.89 (d, J=8.9 Hz, 1H), 7.83 (s, 1H), 7.73 (d, J=12.8 Hz, 1H), 7.55-7.65 (m, 3H), 7.44 (t, J=8.9 Hz, 1H), 5.48 (s, 2H), 5.44 (s, 2H), 4.63 (d, J=13.2 Hz, 2H), 3.27-3.41 (m, 1H), 3.11 (t, J=13.2 Hz, 2H), 2.11 (d, J=13.2 Hz, 2H), 1.56-1.70 (m, 2H).

Example A-59: 6-(3-Fluoro-4-((1-(3-isopropyl-1,2,4-oxadiazol-5-yl)piperidin-4-yl) methoxy) phenyl)-2H-benzo[d][1,3]oxathiole 3,3-dioxide

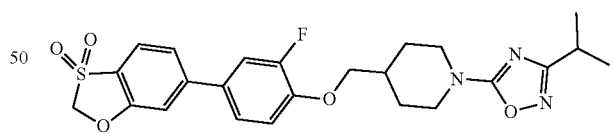

To a suspension of 6-((3-fluoro-4-piperidin-4-ylmethoxy) phenyl)-2H-benzo[1,3]oxathiole 3,3-dioxide hydrochloride (145 mg, 0.35 mmol) and 5-chloro-3-isopropyl-1,2,4-oxadiazole (103 mg, 0.70 mmol) in acetonitrile (10 mL) was added triethylamine (124 mg, 1.22 mmol) and the reaction mixture was heated under reflux for 16 hours. After cooling, the reaction mixture was concentrated under reduced pressure and the residue was triturated with water (20 mL). A solid precipitate was filtered off, washed with cold methanol (10 mL) and dried to afford the title compound (41 mg, 24%) as a beige powder. $^1$H NMR (400 MHz, DMSO-$d_6$) δ 7.89 (d, J=8.9 Hz, 1H), 7.72 (d, J=12.8 Hz, 1H), 7.54-7.64 (m, 3H), 7.29 (t, J=8.9 Hz, 1H), 5.43 (s, 2H), 4.01 (d, J=13.2 Hz, 2H), 4.03 (d, J=6.6 Hz, 2H), 3.15 (t, J=13.2 Hz, 2H), 2.74-2.88 (m, 1H), 2.01-2.16 (m, 1H), 1.88 (d, J=13.2 Hz, 2H), 1.29-1.43 (m, 2H), 1.19 (d, J=7.0 Hz, 6H).

Example A-60: 2-Fluoro-4-(4,4,5,5-tetramethyl-1,3,2-dioxaborolan-2-yl)phenol

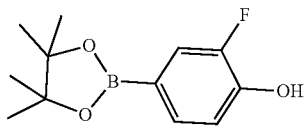 [SMILES: CC1(C)OB(c2ccc(O)c(F)c2)OC1(C)C]

To a solution of 4-bromo-2-fluorophenol (5.0 g, 26.2 mmol), 4,4,4',4',5,5,5',5'-octamethyl-2,2'-bi-1,3,2-dioxaborolane (7.97 g, 31.4 mmol) and (bisdiphenylphosphino) ferrocene dichloropalladium (II) Pd(dppf)Cl$_2$ (1.32 g, 1.8 mmol) in acetonitrile (200 mL) was added potassium acetate (10.3 g, 104.8 mmol) and the resulting mixture was stirred at 67° C. for 16 hours. After cooling to room temperature, the reaction mixture was filtered through celite and the filtrate was evaporated. The residue after evaporation was treated with water (300 mL) and the mixture was extracted with ethyl acetate (3×150 mL). The combined extracts were washed with brine (50 mL), dried over Na$_2$SO$_4$, filtered and the filtrate was evaporated. The residue after evaporation was taken up in hexanes (150 mL) and the resulting mixture was heated at reflux for 1 hour and the solution was filtered hot and the filtrate was evaporated to dryness to afford the title compound (5.8 g, 93%) as a yellow oil. $^1$H NMR (400 MHz, CDCl$_3$) δ 7.46-7.55 (m, 2H), 6.99 (t, J=8.8 Hz, 1H), 5.79 (br.s, 1H), 1.34 (s, 12H), Example A-61: 6-(3-Fluoro-4-hydroxyphenyl)-2H-benzo[d][1,3]oxathiole 3,3-dioxide

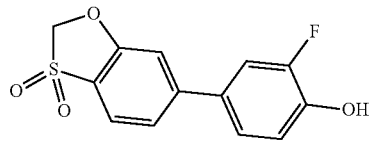 [SMILES: O=S1(=O)COc2cc(-c3ccc(O)c(F)c3)ccc21]

To a suspension of 3,3-dioxido-2H-benzo[d][1,3]oxathiol-6-yl trifluoromethanesulfonate (1.0 g, 3.1 mmol), 2-fluoro-4-(4,4,5,5-tetramethyl-1,3,2-dioxaborolan-2-yl) phenol (1.1 g, 4.6 mmol), 2M aqueous (4.7 mL, 9.3 mmol) solution in toluene (50 mL) was added (bisdiphenylphosphino)ferrocene dichloropalladium (II) Pd(dppf)Cl$_2$ (150 mg, 0.2 mmol) under argon and the reaction mixture was stirred at 80° C. for 3 hours. Upon completion, the reaction was quenched with water (20 mL) and the reaction mixture was extracted with ethyl acetate (3×50 mL). The combined extracts were dried over magnesium sulfate, filtered and the filtrate was evaporated to give an oil which was purified by column chromatography eluting with hexane-ethyl acetate mixture (gradient 4:1-2:1) to afford the title compound (300 mg, 35%) as a white solid. $^1$H NMR (400 MHz, DMSO-d$_6$) δ 10.26 (br.s, 1H), 7.86 (d, J=8.4 Hz, 1H), 7.6-7.67 (m, 1H), 7.51-7.59 (m, 2H), 7.41-7.48 (m, 1H), 7.05 (t, J=8.8 Hz, 1H), 5.42 (s, 2H).

Example A-62: 4-(3,3-Dioxido-2H-benzo[d][1,3] oxathiol-6-yl)-2-fluorophenyl Trifluoro Methanesulfonate

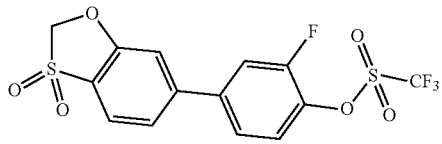 [SMILES: O=S1(=O)COc2cc(-c3ccc(OS(=O)(=O)C(F)(F)F)c(F)c3)ccc21]

To a suspension of 6-(3-fluoro-4-hydroxyphenyl)-2H-benzo[d][1,3]oxathiole 3,3-dioxide (1.0 g, 3.57 mmol) in pyridine (6 mL) at 0° C. was added dropwise triflic anhydride (1.1 g, 3.92 mmol). The mixture was stirred at ambient temperature for 17 hours and then the reaction mixture was diluted with ethyl acetate (40 mL) and washed with 10% aqueous solution citric acid (40 mL), water (40 mL), brine (50 mL), dried over Na$_2$SO$_4$, and filtered. The filtrate was evaporated under reduced pressure and the residual oil was sonicated with ether (10 mL) to form precipitate which was filtered, and dried to afford the title compound (1.05 g, 71%) as a white solid. H NMR (400 MHz, DMSO-d$_6$) δ 8.05-8.11 (m, 1H). 7.99 (d, J=8.2 Hz, 1H), 7.72-7.88 (m, 3H), 7.66 (d, J=8.0 Hz, 1H), 5.47 (s, 2H).

Example A-63: Tert-Butyl 4-[4-(3,3-dioxido-2H-benzo[d][1,3]oxathiol-6-yl)-2-fluorophenyl) Piperazine-1-carboxylate

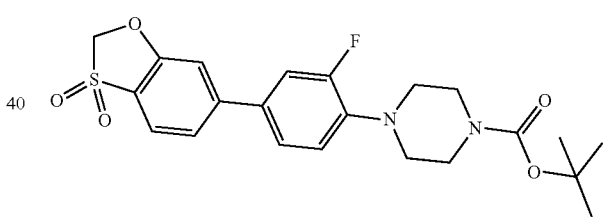

A mixture of 4-(3,3-Dioxido-2H-benzo[d][1,3]oxathiol-6-yl)-2-fluorophenyl trifluoro methanesulfonate (515 mg, 1.25 mmol), tert-butyl 1-piperazinecarboxylate (279 mg, 1.5 mmol), cesium carbonate (610 mg, 1.87 mmol), 2,2'-bis (diphenylphosphino)-1,1'-binaphthyl (BINAP, 93 mg, 0.14 mmol), palladium acetate (23 mg, 0.1 mmol) in toluene (15 mL) was stirred under argon at 100° C. for 16 hours. The reaction mixture was cooled to ambient temperature and quenched with water (10 mL) and extracted with ethyl acetate (3×30 mL). The combined extracts were washed with brine (30 mL), dried over Na$_2$SO$_4$, filtered and the filtrate was concentrated in vacuo to give an oil. This oil was purified by column chromatography eluting with hexanes-ethyl acetate mixture, gradient (5:1-3:1) to afford the title compound (350 mg, 63%) as a white powder. $^1$H NMR (400 MHz, DMSO-d$_6$) δ 7.88 (d, J=8.0 Hz, 1H), 7.53-7.69 (m, 4H), 7.14 (t, J=8.8 Hz, 1H), 5.43 (s, 2H), 3.45-3.53 (m, 4H), 3.0-3.08 (m, 4H), 1.43 (s, 9H).

Example A-64: 6-(3-Fluoro-4-(piperazine-1-yl)phenyl)-2H-benzo[d][1,3]oxathiole 3,3-dioxide

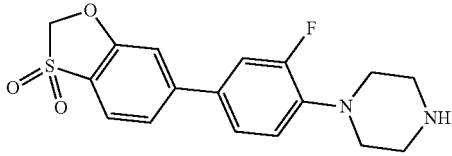 [SMILES: O=S1(=O)COc2cc(-c3ccc(N4CCNCC4)c(F)c3)ccc21]

To a solution of tert-butyl 4-(4-(3,3-dioxido-2-benzo[d][1,3]oxathiol-6-yl)-2-fluorophenyl)piperazine-1-carboxylate (250 mg, 0.56 mmol) in dichloromethane (30 mL) was added trifluoroacetic acid (15 mL) and the mixture was stirred at ambient temperature for 20 minutes and then evaporated to dryness to afford the title compound (190 mg, 97%) as a white powder. $^1$H NMR (400 MHz, DMSO-$d_6$) δ 7.84-7.91 (m, 1H), 7.51-7.66 (m, 4H), 7.05-7.14 (m, 1H), 5.42 (s, 2H), 2.97-3.03 (m, 4H), 2.81-2.88 (m, 4H).

Example A-65: 6-(4-(5-Chloropyrimidin-2-yl)piperazin-1-yl)-3-fluorophenyl-2H-benzo[d][1,3]oxathiole 3,3-dioxide

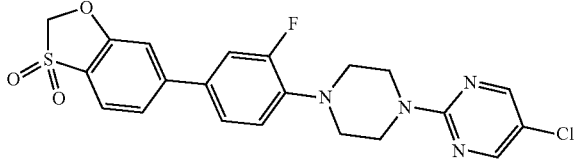 [SMILES: O=S1(=O)COc2cc(-c3ccc(N4CCN(c5ncc(Cl)cn5)CC4)c(F)c3)ccc21]

To a suspension of 6-(3-fluoro-4-(piperazine-1-yl)phenyl)-2H-benzo[d][1,3]oxathiole 3,3-dioxide (200 mg, 0.57 mmol) and 2,5-dichloropyrimidine (94.1 mg, 0.63 mmol) in acetonitrile (30 mL) was added triethylamine (116 mg, 1.14 mmol) and the reaction mixture was heated to reflux for 16 hours. Upon completion, the volatiles were evaporated and the residue was washed with water (50 mL). To the residue after washing was added acetone (15 mL) and the solution was heated at reflux for 30 minutes, stirred at ambient temperature for 20 minutes to furnish a solid which was filtered and dried to afford the title compound (80 mg, 30%) as a white powder. $^1$H NMR (400 MHz, DMSO-$d_6$) δ 8.46 (s, 2H), 7.88 (d, J=8.3 Hz, 1H), 7.88 (d, J=8.3 Hz, 1H), 7.52-7.72 (m, 4H), 7.16 (t, J=9.4 Hz, 1H), 5.43 (s, 2H), 3.85-3.95 (m, 4H), 3.11-3.21 (m, 4H).

Example A-66: 6-(3-Fluoro-4-(1-(5-isopropylpyrimidin-2-yl)piperidin-4-yl)methoxy)phenyl-2H-benzo[d][1,3]oxathiole 3,3-dioxide

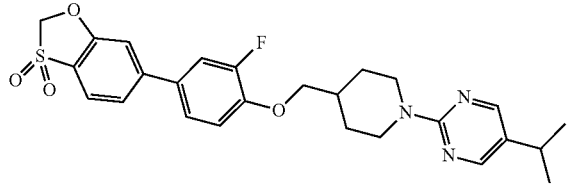 [SMILES: CC(C)c1cnc(N2CCC(COc3ccc(-c4ccc5c(c4)OCS5(=O)=O)cc3F)CC2)nc1]

To a suspension of 6-(3-fluoro-4(piperidin-4-ylmethoxy)phenyl)-2H-benzo[d][1,3]oxathiole 3,3-dioxide (230 mg, 0.57 mmol) and 2-chloro-5-isopropylpyrimidine (94.1 mg, 0.63 mmol) in acetonitrile (50 mL) was added triethylamine (230 mg, 2.3 mmol) and the reaction mixture was heated to reflux for 6 hours. Upon completion, the reaction mixture was cooled to ambient temperature. A white precipitate was formed which was filtered which was filtered off, washed with cold water and hexanes and then purified by column chromatography on silica gel, eluting with dichloromethane-ether mixture (1:1) to give the title compound (190 mg, 67%) as a white powder. $^1$H NMR (400 MHz, DMSO-$d_6$) δ 8.27 (s, 2H), 7.88 (d, J=8.3 Hz, 1H), 7.88 (d, J=8.2 Hz, 1H), 7.71 (d, J=12.8 Hz, 1H) 7.64-7.55 (m, 3H), 7.29 (t, J=8.7 Hz, 1H), 5.44 (s, 2H), 5.44 (s, 2H), 4.67 (d, J=12.6 Hz, 2H), 4.02 (d, J=6.4 Hz, 2H), 2.89 (J=12.1 Hz, 2H), 2.79-2.72 (m, 1H), 2.10 (bs, 1H), 1.83 (d, J=12.6 Hz, 2H), 1.30-1.19 (m, 2H), 1.18 (d, J=6.8 Hz, 6H).

Example A-67: 6-(3-Fluoro-4-(1-(5-methoxypyrimidin-2-yl)piperidin-4-yl)methoxy)phenyl-2H-benzo[d][1,3]oxathiole 3,3-dioxide

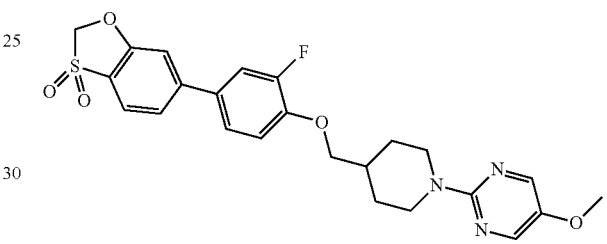

To a suspension of 6-(3-fluoro-4-(piperidin-4-yl)phenyl)-2H-benzo[d][1,3]oxathiole 3,3-dioxide (290 mg, 0.7 mmol) and 2-chloro-5-methoxypyrimidine (115 mg, 0.85 mmol) in acetonitrile (20 mL) was added triethylamine (63 mg, 0.6 mmol) and the reaction mixture was heated to reflux for 6 hours. Upon completion, the reaction mixture was cooled to ambient temperature. A white precipitate was formed which was filtered which was filtered off, washed with cold water and hexanes and then the crude product was purified by column chromatography on silica gel, eluting with dichloromethane to give the title compound (76 mg, 22%) as a white powder. $^1$H NMR (400 MHz, DMSO-$d_6$) δ 8.39 (s, 1H), 8.39 (s, 1H), 8.16 (d, J=1.8 Hz, 1H), 7.98 (d, J=8.82 Hz, 1H), 7.65 (d, J=12.8 Hz, 1H), 7.36 (d, J=8.8 Hz, 1H) 7.21 (t, J=8.93 Hz, 1H), 5.45 (s, 2H), 4.62 (d, J=13.23 Hz, 2H), 3.99 (d, J=6.36 Hz, 2H), 3.76 (s, 3H), 2.97 (t, J=12.71 Hz, 2H), 2.12 (m, 1H), 1.84 (d, J=13.08 Hz, 2H), 1.27 (m, 2H).

Example A-68: (R)-1-(5-Ethylpyrimidin-2-yl)pyrrolidin-2-yl)methanol

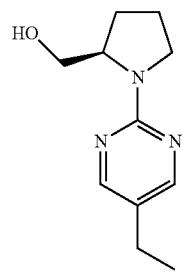

To a mixture of (R)-pyrrolidin-2-ylmethanol (1.0 g, 9.9 mmol), 2-chloro-5-ethylpyrimidine (2.8 g, 19.8 mmol) and diisopropylethylamine (4.2 g, 32.7 mmol) was added copper iodide CuI (60 mg, 0.3 mmol) and the mixture was stirred at ambient temperature for 5 minutes. The reaction mixture was then heated in a conventional CEM microwave system at 80° C. for 20 hours. Upon completion, the reaction mixture was cooled and water (50 mL) was carefully added followed by the addition of a 5% aqueous solution of citric acid until pH-6-7. A solution of brine was added and the organic layer was extracted with ethyl acetate (3×100 mL). The combined organic layer was dried over $Na_2SO_4$, filtered and the filtrate was evaporated in vacuo to give an oily residue which was purified by column chromatography eluting with hexanes:ethyl acetate gradient mixture (4:1 to 1:1) to give the title product as a colorless oil (1.3 g, 63%). $^1$H NMR (400 MHz, $CDCl_3$) δ 8.16 (s, 2H), 6.2 (br.s, 1H), 4.29-4.17 (m, 1H), 3.84-3.51 (m, 4H), 2.47 (q, J=7.6 Hz, 2H), 2.21-2.07 (m, 1H), 2.06-1.84 (m, 2H), 1.77-1.65 (m, 1H), 1.19 (t, J=7.6 Hz, 3H).

Example A-69: (R)-2-(2-((4-Bromo-2-fluorophenoxy)methyl)pyrrolidine-1-yl)-5-ethylpurimidine

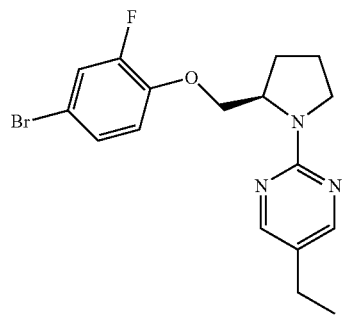 [SMILES: CCc1cnc(N2CCC[C@@H]2COc2ccc(Br)cc2F)nc1]

To a solution of (R)-1-(5-ethylpyrimidin-2-yl)pyrrolidin-2-yl]methanol (1.3 g, 6.3 mmol), 4-bromo-2-fluorophenol (1.2 g, 6.3 mmol), triphenylphosphine (3.3 g, 12.6 mmol) in tetrahydrofuran (40 mL) was added diethyl azodicarboxylate (2.6 g, 12.6 mmol) dropwise at 0° C. and the reaction mixture was stirred at ambient temperature overnight. Upon completion, the solvents were then evaporated to dryness and to the residue was extracted with ethyl acetate (200 mL). The organic layer was washed with saturated solution of $NaHCO_3$, brine, dried over $Na_2SO_4$ and filtered. The filtrate was evaporated to dryness to give a crude product which was purified by column chromatography on silica gel eluting with hexanes:ethyl acetate mixture (1:1) to afford the title compound as a white solid (1.1 g, 46%). $^1$H NMR (400 MHz, DMSO-$d_6$) δ 8.27 (s, 2H), 7.54-7.46 (m, 1H), 7.36-7.28 (m, 2H), 4.41-4.32 (m, 1H), 4.29-4.21 (m, 1H), 4.02 (t, J=9.2 Hz, 1H), 3.59-3.5 (m, 1H), 3.46-3.36 (m, 1H), 2.47-2.38 (q, J=7.6 Hz, 2H), 2.14-1.89 (m, 4H), 1.13 (t, J=7.6 Hz, 3H).

Example A-70: (R)-5-Ethyl-2-(2-((2-fluoro-4-(4,4,5,5,-tetramethyl-1,3,2-dioxaborolan-2-yl)phenoxy)methyl)pyrrolidine-1-yl)pyrimidine

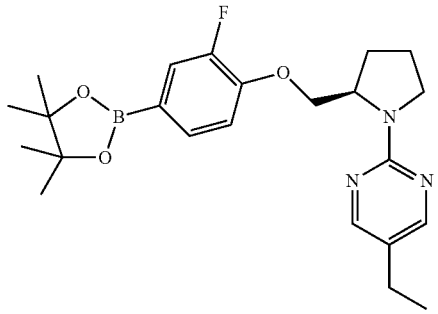 [SMILES: CCc1cnc(N2CCC[C@@H]2COc2ccc(B3OC(C)(C)C(C)(C)O3)cc2F)nc1]

To a solution of (R)-2-(2-((4-bromo-2-fluorophenoxy)methyl)pyrrolidine-1-yl)-5-ethylpurimidine (1.1 g, 2.9 mmol), 4,4,4',4',5,5,5',5'-octamethyl-2,2'-bi-1,3,2-dioxaborolane (0.89 g, 3.5 mmol), (bisdiphenylphosphino)ferrocene dichloropalladium (II) Pd(dppf)$Cl_2$ (150 mg, 0.2 mmol) in 1,4-dioxane (40 mL) was added potassium acetate (1.2 g, 11.6 mmol) and the resulting mixture was stirred and heated to 90° C. overnight. Upon cooling, the reaction mixture was poured into a 1:1 mixture of ethyl acetate (100 mL) and water (100 mL). The solution was filtered through a pad of celite (1 cm in length) and the organic layer was washed with water, brine, dried over $Na_2SO_4$ and evaporated in vacuo to dryness. To the residue was added hexanes (50 mL) and the resultant solution was heated to reflux and then filtered while keeping it hot. The precipitate formed upon cooling was filtered off and purified by column chromatography on silica gel eluting with hexanes:ethyl acetate to afford the title compound as colorless oil (1.0 g, 81%). $^1$H NMR (400 MHz, $CDCl_3$) δ 8.21 (s, 2H), 7.56-7.43 (m, 2H), 7.23 (t, J=8.3 Hz, 1H), 4.59-4.50 (m, 1H), 4.45-4.37 (m, 1H), 4.03 (t, J=8.3 Hz, 1H), 3.77-3.65 (m, 1H), 3.58-3.47 (m, 1H), 2.48 (q, J=7.6 Hz, 2H), 2.30-1.97 (m, 4H), 1.34 (s, 12H), 1.21 (t, J=7.6 Hz, 3H).

Example A-71. (R)-6-(4-((1-(5-Ethylpyrimidin-2-yl)pyrrolidin-2-yl)methoxy)-3-fluorophenyl-2H-benzo[d]oxathiole 3,3-dioxide

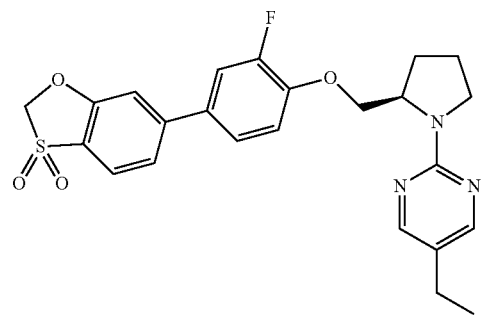 [SMILES: CCc1cnc(N2CCC[C@@H]2COc2ccc(-c3ccc4c(c3)OCS4(=O)=O)cc2F)nc1]

To a solution of (R)-5-ethyl-2-(2-((2-fluoro-4-(4,4,5,5,-tetramethyl-1,3,2-dioxaborolan-2-yl)phenoxy)methyl)pyrrolidine-1-yl)pyrimidine (470 mg, 1.1 mmol) in dioxane (20 mL) was added 3,3-dioxido-2H-benzo[d][1,3]oxathiol-6-yl trifluoromethanesulfonate (350 mg, 1.1 mmol), a solution of Na$_2$CO$_3$ (2M, 1.7 mL) and (bisdiphenylphosphino)ferrocene dichloropalladium (II) Pd(dppf)Cl$_2$ (40 mg, 0.06 mmol). The resulting mixture was to 85° C. for 2 hours and then stirred at ambient temperature overnight. Water (70 mL) was added to the solution with stirring followed by the addition of ethyl acetate (50 mL) and then the solution was filtered through a pad of celite. The organic solution was collected and washed with water, brine, dried over Na$_2$SO$_4$, filtered and evaporated in vacuo. The residual oil was purified by column chromatography on silica gel eluting with hexanes:ethyl acetate mixture. The crude product obtained was triturated with ether (20 mL) filtered and dried on standing to give the title compound as a white solid (280 mg, 54%). $^1$H NMR (400 MHz, DMSO-d6) δ 8.28 (s, 2H), 7.88 (d, J=8.1 Hz, 1H), 7.76-7.68 (m, 1H), 7.64-7.54 (m, 3H), 7.47 (t, J=8.8 Hz, 1H), 5.43 (s, 2H), 4.45-4.3 (m, 2H), 4.08 (t, J=8.4 Hz, 1H), 3.62-3.52 (m, 1H), 3.48-3.38 (m, 1H), 2.44 (q, J=7.6 Hz, 2H), 2.18-1.9 (m, 4H), 1.13 (t, J=7.6 Hz, 3H).

Example A-72: tert-Butyl 4-(((2-chloropyrimidin-5-yl)oxy)methyl)piperidine-1-carboxylate

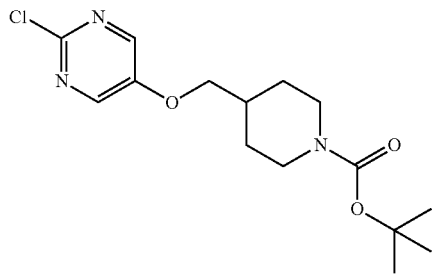 [SMILES: CC(C)(C)OC(=O)N1CCC(COc2cnc(Cl)nc2)CC1]

A suspension of tert-butyl 4-(((trifluoromethylsulfonyl)oxy)piperidine-1-carboxylate (6.2 g, 21.1 mmol), 2-chloropyrimidin-5-ol (2.5 g, 19.2 mmol) and potassium carbonate (13.3 g, 96 mmol) in dimethylsulfoxide (100 mL) was stirred at 110° C. for 16 hours. The reaction mixture was cooled to room temperature and dimethylsulfoxide was distilled off under reduced pressure. The residue was then treated with water (50 mL) and precipitate was formed, filtered off and purified by column chromatography eluting with hexanes:ethyl acetate mixture (3:2) by volume to afford the title compound (2.0 g, 31.7%) as a white crystalline powder: 1H NMR (400 MHz, DMSO-d6) δ 8.53 (s, 2H), 4.02 (d, J=6.4 Hz, 2H), 3.96 (d, J=12.4 Hz, 2H), 3.24-3.23 (m, 1H), 2.74 (s, 2H), 2.02-1.85 (m, 1H), 1.73 (d, J=11.1 Hz, 2H), 1.39 (s, 9H), 1.24-1.02 (m, 2H).

Example A-73: 6-(4,4,5,5-Tetramethyl-1,3,2-dioxaborolan-2-yl)-2H-benzo[d]oxathiole 3,3-dioxide

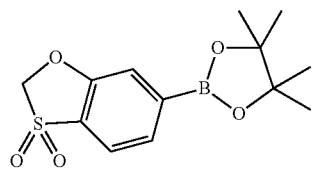 [SMILES: CC1(C)OB(c2ccc3c(c2)OCS3(=O)=O)OC1(C)C]

To a mixture of 3,3-dioxido-2H-benzo[d][1,3]oxathiol-6-yl trifluoromethanesulfonate (2.0 g, 6.3 mmol) and 4,4,4',4',5,5,5',5'-octanethyl-2,2'-bi-1,3,2-dioxoborolane (1.93 g, 7.6 mmol) in acetonitrile (30 mL) were added 1,1' (bisdiphenylphosphino)ferrocene dichloropalladium (II) (Pd(dppf)Cl$_2$ (0.22 g, 0.3 mmol) and potassium acetate (2.5 g, 25 mmol) and the reaction mixture was stirred under argon at 70° C. for 16 hours. Upon completion, the reaction mixture was diluted with ethyl acetate (50 mL) and washed with brine (50 mL). The organic layer was collected and dried over magnesium sulfate, filtered and the filtrate was evaporated under reduced pressure. The residue after evaporation was purified by column chromatography eluting with hexanes:ethyl acetate mixture (10:1) to afford the title compound (0.65 g, 35%) as a white powder. $^1$H NMR (400 MHz, DMSO-d$_6$) δ 7.84 (d, J=7.6 Hz, 1H), 7.52 (d, J=7.6 Hz, 1H), 7.43 (s, 1H), 5.40 (s, 2H), 1.3 (s, 12H).

Example A-74: tert-Butyl 4-(((2-(3,3-dioxido-2H-benzo[d][1,3]oxathiol-6-yl)pyrimidin-5-yl)oxy)methyl)piperidine-1-carboxylate

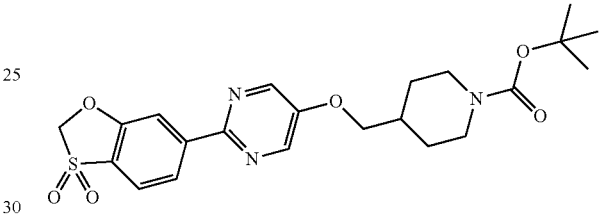

A mixture of of 6-(4,4,5,5-tetramethyl-1, 3, 2-dioxaborolan-2-yl)-2H-benzo[d]oxathiole 3,3-dioxide (0.95 g, 3.2 mmol), tert-butyl-4-(((2-chloropyrimidin-5-yl)oxy)methyl)piperidine-1-carboxylate (1.05 g, 3.2 mmol), sodium carbonate (2.65 g, 19.2 mmol) and 1,1' (bisdiphenylphosphino)ferrocene dichloropalladium (II) (Pd(dppf)Cl$_2$ (0.22 g, 0.3 mmol) in a 1:1 water:dioxane mixture (50 mL) was stirred under argon at 70° C. for 12 hours. A precipitate was formed, filtered and purified by column chromatography on silica gel eluting with hexanes:ethyl acetate mixture (4:1) to afford the title compound (0.5 g, 33.8%). 1H NMR (300 MHz, DMSO-d6) δ 8.71 (s, 2H), 8.20 (d, J=8.2 Hz, 1H), 8.05 (s, 1H), 7.97 (d, J=8.2 Hz, 1H), 5.47 (s, 2H), 4.11 (d, J=6.4 Hz, 2H), 3.98 (d, J=13.3 Hz, 2H), 2.76 (s, 2H), 1.99 (s, 1H), 1.77 (d, J=11.9 Hz, 2H), 1.40 (s, 9H), 1.27-1.10 (m, 2H).

Example A-75: 6-(5-(Piperidin-4-ylmethoxy)pyrimidin-2-yl)-2H-benzo[d][1,3]oxathiole 3,3-dioxide Hydrochloride

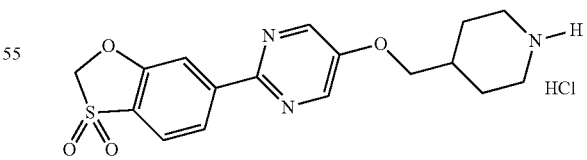

A solution of tert-butyl 4-(((2-(3,3-dioxido-2H-benzo[d][1,3]oxathiol-6-yl)pyrimidin-5-yl)oxy)methyl)piperidine-1-carboxylate (0.5 g, 1.1 mmol) in dioxane (30 mL) was treated with 4M hydrogen chloride in dioxane (5 mL) and stirred at 70° C. for 24 hours. Upon cooling a precipitate was filtered off and dried to afford the title product as a white solid (0.29 g, 66.3%).

Example A-76: 6-(5-((1-(5-Ethylpyrimidin-2-yl)piperidin-4-yl)methoxy)pyrimidin-2-yl)-2H-benzo[d][1,3]oxathiole 3,3-dioxide

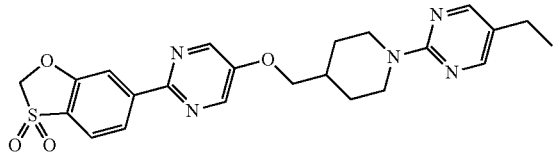 [SMILES: CCc1cnc(N2CCC(COc3cnc(-c4ccc5c(c4)OCS5(=O)=O)nc3)CC2)nc1]

To a suspension of 6-(5-(piperidin-4-ylmethoxy)pyrimidin-2-yl)-2H-benzo[d][1,3]oxathiole 3,3-dioxide hydrochloride (290 mg, 0.7 mmol) and 2-chloro-5-ethylpyrimidine (128 mg, 0.7 mmol) in acetonitrile (20 mL) was added triethylamine (210 mg, 2.1 mmol) and the mixture was heated under reflux overnight. The solvent was then removed under reduced pressure and the residue was triturated with water (20 mL). A solid precipitate was formed and filtered off, washed with ether (10 mL) and air-dried to afford the title product (56 mg, 17.1%) as a white powder. $^1$H NMR (300 MHz, CDCl$_3$) δ 8.49 (s, 2H), 8.26 (d, J=8.2 Hz, 1H), 8.20 (s, 2H), 8.14 (s, 1H), 7.75 (d, J=8.2 Hz, 1H), 7.28 (s, 1H), 5.10 (s, 2H), 4.83 (d, J=13.4 Hz, 2H), 4.01 (d, J=6.3 Hz, 2H), 2.94 (t, J=12.8 Hz, 2H), 2.48 (q, J=7.8 Hz, 2H), 2.17 (s, 1H), 1.96 (d, J=12.8 Hz, 2H), 1.53-1.31 (m, 2H), 1.21 (t, J=7.6 Hz, 3H).

Example A-77: (S)-1-(5-Ethylpyrimidin-2-yl)pyrrolidin-2-yl)methanol

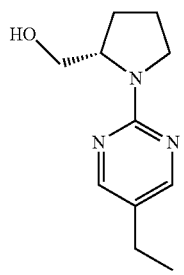

To a mixture of (R)-pyrrolidin-2-ylmethanol (2.0 g, 19.8 mmol), 2-chloro-5-ethylpyrimidine (3.7 g, 25.7 mmol) and diisopropylethylamine (7.7 g, 59.4 mmol) was added copper iodide CuI (380 mg, 2.0 mmol) and the mixture was stirred at ambient temperature for 5 minutes. The reaction mixture was then heated in a conventional CEM microwave system at 80° C. for 20 hours. Upon completion, the reaction mixture was cooled and water (50 mL) was carefully added followed by the addition of a 5% aqueous solution of citric acid until pH-6-7. A solution of brine was added and the organic layer was extracted with ethyl acetate (3×100 mL). The combined organic layer was dried over Na$_2$SO$_4$, filtered and the filtrate was evaporated in vacuo to give an oily residue which was purified by column chromatography eluting with hexanes:ethyl acetate gradient mixture (4:1 to 1:1) to give the title product as a colorless oil (1.3 g, 63%). $^1$H NMR (400 MHz, CDCl$_3$) δ 8.16 (s, 2H), 6.2 (br.s, 1H), 4.29-4.17 (m, 1H), 3.84-3.51 (m, 4H), 2.47 (q, J=7.6 Hz, 2H), 2.21-2.07 (m, 1H), 2.06-1.84 (m, 2H), 1.77-1.65 (m, 1H), 1.19 (t, J=7.6 Hz, 3H).

Example A-78: (S)-2-(2-((4-Bromo-2-fluorophenoxy)methyl)pyrrolidine-1-yl)-5-ethylpyrimidine

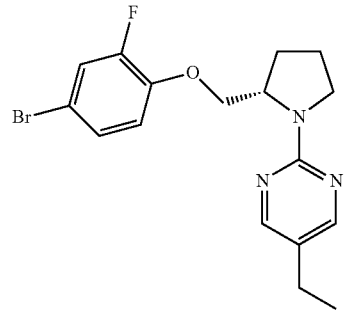 [SMILES: CCc1cnc(N2CCC[C@H]2COc2ccc(Br)cc2F)nc1]

To a solution of (S)-1-(5-ethylpyrimidin-2-yl)pyrrolidin-2-yl)methanol (1.7 g, 8.2 mmol), 4-bromo-2-fluorophenol (1.7 g, 9.0 mmol), triphenylphosphine (2.4 g, 9.0 mmol) in tetrahydrofuran (40 mL) was added diethyl azodicarboxylate (1.8 g, 9.0 mmol) dropwise at 0° C. and the reaction mixture was stirred at ambient temperature overnight. Upon completion, the solvents were then evaporated to dryness and to the residue was extracted with ethyl acetate (200 mL). The organic layer was washed with saturated solution of NaHCO$_3$, brine, dried over Na$_2$SO$_4$ and filtered. The filtrate was evaporated to dryness to give a crude product which was purified by column chromatography on silica gel eluting with hexanes:ethyl acetate mixture (1:1) to afford the title compound as a white solid (420 mg, 13%). H NMR (400 MHz, DMSO-d$_6$) δ 8.27 (s, 2H), 7.54-7.46 (m, 1H), 7.36-7.28 (m, 2H), 4.41-4.32 (m, 1H), 4.29-4.21 (m, 1H), 4.02 (t, J=9.2 Hz, 1H), 3.59-3.5 (m, 1H), 3.46-3.36 (m, 1H), 2.47-2.38 (q, J=7.6 Hz, 2H), 2.14-1.89 (m, 4H), 1.13 (t, J=7.6 Hz, 3H).

Example A-79: (S)-5-Ethyl-2-(2-((2-fluoro-4-(4,4,5,5,-tetramethyl-1,3,2-dioxaborolan-2-yl)phenoxy)methyl)pyrrolidine-1-yl)pyrimidine

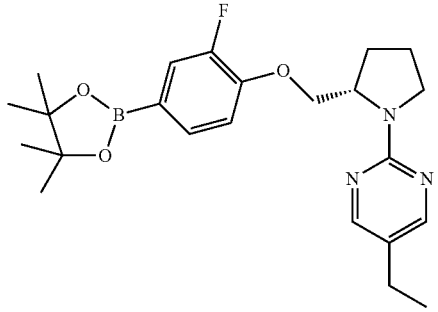 [SMILES: CCc1cnc(N2CCC[C@H]2COc2ccc(B3OC(C)(C)C(C)(C)O3)cc2F)nc1]

To a solution containing (S)-2-(2-((4-bromo-2-fluorophenoxy)methyl)pyrrolidine-1-yl)-5-ethylpurimidine (420 mg, 1.1 mmol), 4,4,4',4',5,5,5',5'-octamethyl-2,2'-bi-1,3,2-dioxaborolane (336 mg, 1.3 mmol), (bisdiphenylphosphino)ferrocene dichloropalladium (II) Pd(dppf)Cl$_2$ (56 mg, 0.08 mmol) in 1,4-dioxane (40 mL) was added potassium acetate (433 mg, 4.4 mmol) and the resulting mixture was stirred and heated to 90° C. overnight. Upon cooling, the reaction mixture was poured into a 1:1 mixture of ethyl acetate (50 mL) and water (50 mL). The solution was filtered through a pad of celite (1 cm in length) and the organic layer was washed with water, brine, dried over Na$_2$SO$_4$ and evaporated in vacuo to dryness. To the residue was added hexanes (50 mL) and the resultant solution was heated to reflux and then filtered while keeping it hot. The precipitate formed upon cooling was filtered off and purified by column chromatography on silica gel eluting with hexanes:ethyl acetate to afford the title compound as colorless oil (395 mg, 83%). $^1$H NMR (400 MHz, CDCl$_3$) δ 8.21 (s, 2H), 7.56-7.43 (m, 2H), 7.23 (t, J=8.3 Hz, 1H), 4.59-4.50 (m, 1H), 4.45-4.37 (m, 1H), 4.03 (t, J=8.3 Hz, 1H), 3.77-3.65 (m, 1H), 3.58-3.47 (m, 1H), 2.48 (q, J=7.6 Hz, 2H), 2.30-1.97 (m, 4H), 1.34 (s, 12H), 1.21 (t, J=7.6 Hz, 3H).

Example A-80: (S)-6-(4-((1-(5-Ethylpyrimidin-2-yl)pyrrolidin-2-yl)methoxy)-3-fluorophenyl-2H-benzo[d]oxathiole 3,3-dioxide

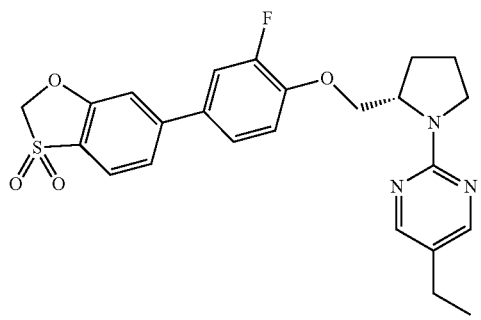 [SMILES: CCc1cnc(N2CCC[C@H]2COc2ccc(-c3ccc4c(c3)OCS4(=O)=O)cc2F)nc1]

To a solution of (S)-5-ethyl-2-(2-((2-fluoro-4-(4,4,5,5,-tetramethyl-1,3,2-dioxaborolan-2-yl)phenoxy)methyl)pyrrolidine-1-yl)pyrimidine (197 mg, 0.46 mmol) in dioxane (5 mL) was added 3,3-dioxido-2H-benzo[d][1,3]oxathiol-6-yl trifluoromethanesulfonate (147 mg, 0.46 mmol), a solution of Na$_2$CO$_3$ (2M, 0.8 mL) and (bisdiphenylphosphino)ferrocene dichloropalladium (II) Pd(dppf)Cl$_2$ (23 mg, 0.03 mmol). The resulting mixture was to 85° C. for 2 hours and then stirred at ambient temperature overnight. Water (35 mL) was added to the solution with stirring followed by the addition of ethyl acetate (50 mL) and then the solution was filtered through a pad of celite. The organic solution was collected and washed with water, brine, dried over Na$_2$SO$_4$, filtered and evaporated in vacuo. The residual oil was purified by column chromatography on silica gel eluting with hexanes:ethyl acetate mixture. The crude product obtained was triturated with ether (10 mL) filtered and dried on standing to give the title compound as a white solid (92 mg, 42%). $^1$H NMR (400 MHz, DMSO-d$_6$) δ 8.28 (s, 2H), 7.88 (d, J=8.1 Hz, 1H), 7.76-7.68 (m, 1H), 7.64-7.54 (m, 3H), 7.47 (t, J=8.8 Hz, 1H), 5.43 (s, 2H), 4.45-4.3 (m, 2H), 4.08 (t, J=8.4 Hz, 1H), 3.62-3.52 (m, 1H), 3.48-3.38 (m, 1H), 2.44 (q, J=7.6 Hz, 2H), 2.18-1.9 (m, 4H), 1.13 (t, J=7.6 Hz, 3H).

Example A-81: tert-Butyl-(S)-3-((methylsulfonyl)oxy)methyl)pyrrolidine-1-carboxylate

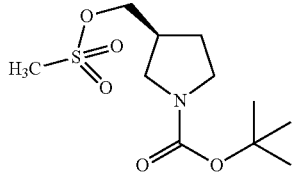 [SMILES: CC(C)(C)OC(=O)N1CC[C@H](COS(C)(=O)=O)C1]

To a solution of tert-butyl (S)-3-(hydroxymethyl)pyrrolidine-1-carboxylate (2.0 g, 9.9 mmol) and triethylamine (2.8 mL, 19.8 mmol) in methylene chloride (50.0 mL) at 0° C. was dropwise added methanesulfonyl chloride (0.85 mL, 10.9 mmol). The reaction mixture was stirred at ambient temperature for 4 hours and then washed sequentially with 0.1 N hydrogen chloride and brine. The organic layer was dried over Na$_2$SO$_4$ filtered, and concentrated in vacuo to yield 2.5 g (90%) of the title product as an oil. [M+1]$^+$ 280.

Example A-82: tert-Butyl-(S)-3-((4-bromo-2-fluorophenoxy)methyl)pyrrolidine-1-carboxylate

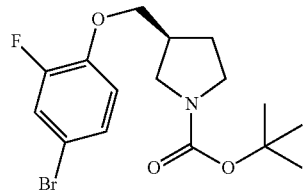 [SMILES: CC(C)(C)OC(=O)N1CC[C@H](COc2ccc(Br)cc2F)C1]

Method A: A solution of tert-butyl-(S)-3-((methylsulfonyl)oxy)methyl)pyrrolidine-1-carboxylate (2.2 g, 7.9 mmol), 4-bromo-2-fluorophenol (1.8 g, 9.5 mmol) and potassium carbonate (2.2 g, 15.8 mmol) in dimethylformamide (100 mL) was stirred at 100° C. overnight. After cooling to ambient temperature, the solvent was removed under reduced pressure. The residue was treated with acetonitrile (100 mL) and the resultant suspension was filtered through a pad of celite. The filtrate was evaporated to dryness and the residue was treated with water (50 mL). The mixture was extracted with ethyl acetate (2×50 mL), dried over sodium sulfate and filtered. The filtrate was evaporated, and purified by chromatography on a silica gel pad (3 cm) eluting with a mixture of hexanes:ethyl acetate (4:1) to give the title product (2.9 g, 98%) as a light yellow liquid. $^1$H-NMR (400 MHz, DMSO-d$_6$,) δ 7.52 (d, J=8.7 Hz, 1H), 7.32 (d, J=8.7 Hz, 1H), 7.16 (t, J=8.7 Hz, 1H), 4.08-3.96 (m, 2H), 3.56-3.06 (m, 4H), 2.75-2.59 (m, 1H), 2.09-1.95 (m, 1H), 1.81-1.64 (m, 1H), 1.40 (s, 9H).

Method B: To a solution of tert-butyl-(S)-3-((methylsulfonyl)oxy)methyl)pyrrolidine-1-carboxylate (8.3 g, 29.7 mmol), 4-bromo-2-fluorophenol (6.8 g, 35.6 mmol) in acetonitrile (200 mL) were added potassium carbonate (12.3 g, 89.1 mmol), 18-crown-6 (300 mg) and tetra n-butylammonium bromide (0.48 g, 1.5 mmol). The reaction mixture was stirred and heated to reflux overnight. Upon cooling, water (300 mL) and ethyl acetate (300 mL) were added. The organic phase was separated, washed with 5% aq. Solution of potassium carbonate, brine, dried over Na$_2$SO$_4$, filtered and the filtrate was evaporated to dryness. The product was purified by column chromatography on silica gel eluting with hexanes:ethyl acetate mixture to afford the title product as a white solid (9.9 g, 89%). ¹H NMR (400 MHz, CDCl₃) δ 7.27-7.15 (m, 2H), 6.84 (t, J=8.6 Hz, 1H), 3.96 (d, J=6.7 Hz, 2H), 3.66-3.31 (m, 3H), 3.28-3.16 (m, 1H), 2.79-2.63 (m, 1H), 2.17-2.02 (m, 1H), 1.89-1.73 (m, 1H), 1.48 (s, 9H).

Example A-83: (S)-3-((4-Bromo-2-fluorophenoxy)methyl)pyrrolidine Hydrochloride

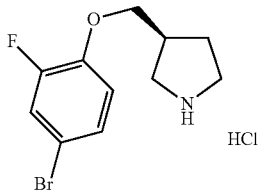 [SMILES: Fc1cc(Br)ccc1OC[C@H]1CCNC1 ; Cl]

To a stirred solution of tert-butyl-(S)-3-((4-bromo-2-fluorophenoxy)methyl)pyrrolidine-1-carboxylate (9.9 g, 26.5 mmol) in dioxane (30 mL) was added 3M solution of hydrogen chloride in dioxane (80 mL) and the mixture was stirred at 40° C. overnight. Upon completion dioxane was evaporated to the residual volume of 10 mL, and diethyl ether (150 mL) was added. A precipitate was formed, stirred for 20 minutes then, filtered off and air-dried to give the title product (8.2 g, 99%). as a white powder. ¹H-NMR (400 MHz, DMSO-d₆,) δ 9.48 (br.s, 2H), 7.52 (d, J=8.7 Hz, 1H), 7.32 (d, J=8.7 Hz, 1H), 7.16 (t, J=8.7 Hz, 1H), 4.15-4.03 (m, 2H), 3.40-3.10 (m, 3H), 3.03-2.94 (m, 1H), 2.80-2.66 (m, 1H), 2.15-2.02 (m, 1H), 1.81-1.67 (m, 1H).

Example A-84: (S)-2-(3-((4-Bromo-2-fluorophenoxy)methyl)pyrrolidin-1-yl)-5-ethylpyrimidine

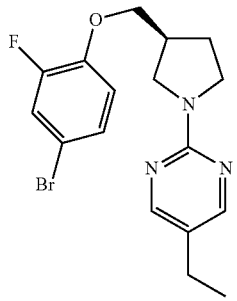 [SMILES: CCc1cnc(N2CC[C@H](COc3ccc(Br)cc3F)C2)nc1]

A mixture of (S)-3-((4-bromo-2-fluorophenoxy)methyl)pyrrolidine hydrochloride (1.70 g, 5.5 mmol), 2-chloro-5-ethylpyrimidine (0.85 g, 6.1 mmol) and diisopropylethylamine (1.77 g, 13.8 mmol) in dimethylformamide (150 mL) was stirred at 130° C. overnight. After cooling to ambient temperature, dimethylformamide was removed under reduced pressure and the residue was treated with water (200 mL). A brown precipitate was formed which was filtered and re-dissolved in methylene chloride until the solution was clear. This was then dried over sodium sulfate, and filtered through a 3 cm silica gel pad. The solution was then evaporated in vacuo and the residue was purified by column chromatography by eluting with hexanes-ethyl acetate mixture (4:1) to obtain the title product (1.3 g, 62%) as colorless crystals. ¹H-NMR (400 MHz, DMSO-d₆) δ 8.21 (s, 2H), 7.52 (d, J=8.7 Hz, 1H), 7.32 (d, J=8.7 Hz, 1H), 7.19 (t, J=8.7 Hz, 1H), 4.17-4.02 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example A-85: (S)-5-Ethyl-2-(3-((2-fluoro-4-(4,4,5,5-tetramethyl-1,3,2-dioxaborolan-2-yl)phenoxy)methyl)pyrrolidin-1-yl)pyrimidine

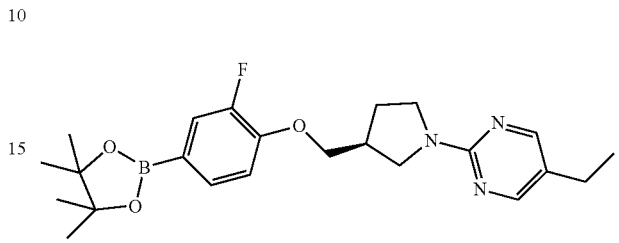

To a solution of (S)-2-(3-((4-bromo-2-fluorophenoxy)methyl]pyrrolidin-1-yl}-5-ethylpyrimidine (1.3 g, 3.4 mmol), 4,4,4',4',5,5,5',5'-octamethyl-2,2'-bi-1,3,2-dioxaborolane (1.0 g, 4.1 mmol),) and potassium acetate (1.3 g, 12 mmol) in dioxane (50 mL) under argon atmosphere was added (bisdiphenylphosphino)ferrocene dichloropalladium (II) Pd(dppf)Cl₂ (170 mg, 0.2 mmol) and the mixture was heated to 85° C. and stirred at that temperature overnight. The mixture was cooled and filtered through a pad of celite. The celite pad was washed with hot (50° C.) dioxane (100 mL) and the washings were combined with the filtrate and evaporated to dryness. The residue was subjected to column chromatography eluting with ether to obtain the crude product as a light yellow oil. This oil was dissolved in hexanes (100 mL) and placed into freezer for three days. White crystals were formed, filtered off and dried to afford the title compound (0.83 g, 56%). ¹H-NMR (400 MHz, DMSO-d₆) δ 8.21 (s, 2H), 7.43 (d, J=8.7 Hz, 1H), 7.34 (d, J=8.7 Hz, 1H), 7.21 (t, J=8.7 Hz, 1H), 4.19-4.05 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.16 (s, 12H), 1.12 (t, J=7.5 Hz, 3H).

Example A-86: (S)-6-(4-((1-(5-Ethylpyrimidin-2-yl)pyrrolidin-3-yl)methoxy)-3-fluorophenyl)-2H-benzo[d][1,3]oxathiole 3,3-dioxide

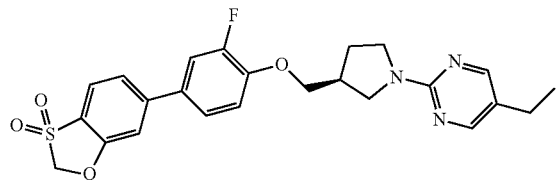 [SMILES: CCc1cnc(N2CC[C@H](COc3ccc(-c4ccc5c(c4)OCS5(=O)=O)cc3F)C2)nc1]

To a solution of 3,3-dioxido-2H-benzo[d][1,3]oxathiol-6-yl trifluoromethanesulfonate (150 mg, 0.47 mmol) and (S)-5-ethyl-2-(3-((2-fluoro-4-(4,4,5,5-tetramethyl-1,3,2-dioxaborolan-2-yl)phenoxy)methyl)pyrrolidin-1-yl}pyrimidine (201 mg, 0.47 mmol) in dioxane (5 mL) was added slowly a solution of potassium carbonate (195 mg, 1.41 mmol) in water (5 mL). After stirring under argon for 10 minutes, (bisdiphenylphosphino) ferrocene dichloropalladium (II) Pd(dppf)Cl₂ (24 mg, 0.03 mmol) was added and the reaction mixture was stirred at ambient temperature overnight. Water (30 mL) was then added and a precipitate was formed, filtered off and air-dried. The precipitate was purified by column chromatography on silica gel eluting with hexanes:ethyl acetate mixture (1:1) to give the title product (95 mg, 43%) as a white powder. $^1$H-NMR (400 MHz, DMSO-d$_6$) δ 8.22 (s, 2H), 7.88 (d, J=8.1 Hz, 1H), 7.73 (d, J=14.0 Hz, 1H), 7.64-7.54 (m, 3H), 7.33 (t, J=8.8 Hz, 1H), 5.43 (s, 2H), 4.21-4.09 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example A-87: (S)-2-(3-((4-Bromo-2-fluorophenoxy)methyl)pyrrolidin-1-yl)-5-chloropyrimidine

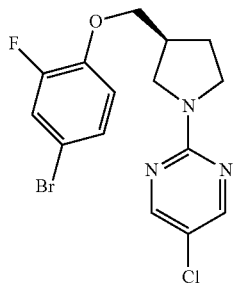 [SMILES: Fc1cc(Br)ccc1OC[C@H]1CCN(c2ncc(Cl)cn2)C1]

To a solution of (S)-3-((4-bromo-2-fluorophenoxy)methyl)pyrrolidine hydrochloride (4.09 g, 13.2 mmol) in dimethylformamide (15 mL) was added 2,5-dichloropyrimidine (1.0 g, 14.5 mmol) and triethylamine (4.0 g, 39.6 mmol). The reaction mixture was stirred and heated in "CEM" microwave system (150° C., 3 hours). Upon completion, the mixture was evaporated to dryness under reduced pressure, water (50 mL) was added to the residue and the mixture was extracted with ethyl acetate (3×50 mL). The combined extracts were washed with 5% aqueous solution citric acid, aqueous solution of sodium bicarbonate, brine, dried over Na$_2$SO$_4$, filtered and the filtrate was evaporated. The product was purified by column chromatography on silica gel eluting with hexanes:ethyl acetate (1:1) mixture. The product was obtained as a colorless oil (4.5 g, 88.2%). and used in the next step without further purification.

Example A-88: (S)-5-Chloro-2-(3-((2-fluoro-4-(4,4,5,5-tetramethyl-1,3,2-dioxaborolan-2-yl)phenoxy)methyl)pyrrolidin-1-yl)pyrimidine

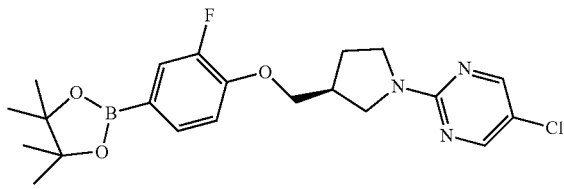 [SMILES: CC1(C)OB(c2ccc(OC[C@H]3CCN(c4ncc(Cl)cn4)C3)c(F)c2)OC1(C)C]

To a solution containing (S)-2-(3-((4-bromo-2-fluorophenoxy)methyl]pyrrolidin-1-yl}-5-chloropyrimidine (4.5 g, 11.6 mmol), 4,4,4',4',5,5,5',5'-octamethyl-2,2'-bi-1,3,2-dioxaborolane (1.0 g, 4.1 mmol,) and (bisdiphenylphosphino)ferrocene dichloropalladium (II) Pd(dppf)Cl$_2$ (878 mg, 1.2 mmol) was added potassium acetate (1.3 g, 12 mmol) in dioxane (50 mL) under argon atmosphere and the resulting mixture was stirred with heating to 90° C. overnight. The reaction mixture was then poured in mixture of ethyl acetate (100 mL) and water (100 mL). The mixture was filtered through a pad of celite and the organic layer was separated, washed with water, brine, dried over Na$_2$SO$_4$, filtered and the filtrate was evaporated to dryness. The product was purified by column chromatography on silica gel eluting with hexanes:ethyl acetate (1:1) mixture. The product was obtained as a yellow solid (1.9 g, 29.8%) and was used in the next step without further purification.

Example A-89: (S)-6-(4-((1-(5-Chloropyrimidin-2-yl)pyrrolidin-3-yl)methoxy)-3-fluorophenyl)-2H-benzo[d][1,3]oxathiole 3,3-dioxide

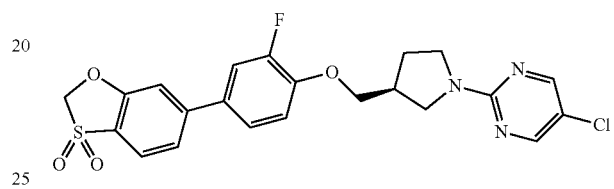

To a solution of (S)-5-chloro-2-(3-((2-fluoro-4-(4,4,5,5-tetramethyl-1,3,2-dioxaborolan-2-yl)phenoxy)methyl)pyrrolidin-1-yl)pyrimidine (300 mg, 0.7 mmol) in dioxane (15 mL) was added 3,3-dioxido-2H-benzo[d][1,3]oxathiol-6-yl trifluoromethanesulfonate (223 mg, 0.7 mmol), 2M aqueous solution of sodium carbonate (15 mL) and (bisdiphenylphosphino)ferrocene dichloropalladium (II) Pd(dppf)Cl$_2$ (73 mg, 0.1 mmol). The mixture was stirred and heated to 85° C. for 3 hours and then allowed to stir at ambient temperature overnight. To the mixture was then added water (50 mL) and was extracted with ethyl acetate (3×30 mL). The combined extracts were washed with water, brine, dried over Na2SO4, filtered and the filtrate was evaporated to dryness. The product was purified by column chromatography on silica gel eluting with hexanes:ethyl acetate mixture (1:1) to afford the title compound (232 mg, 69.63%) as a white solid. 1H NMR (300 MHz, DMSO-d6) δ 8.40 (s, 2H), 7.89 (d, J=8.1 Hz, 1H), 7.72 (d, J=12.7 Hz, 1H), 7.67-7.47 (m, 3H), 7.32 (t, J=8.8 Hz, 1H), 5.44 (s, 2H), 4.35-4.00 (m, 2H), 3.79-3.35 (m, 4H), 2.94-2.67 (m, 1H), 2.29-2.03 (m, 1H), 1.99-1.81 (m, 1H).

Example A-90: (S)-2-(3-((4-Bromo-2-fluorophenoxy)methyl)pyrrolidin-1-yl)-4-ethylpyrimidine

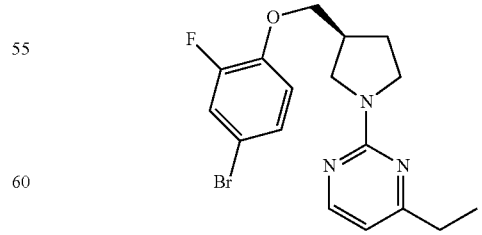

To a solution of (S)-3-((4-bromo-2-fluorophenoxy)methyl)pyrrolidine hydrochloride (2.0 g, 6.4 mmol) in dimethylacetamide (10 mL) was added 2-chloro-4-ethylpyrimidine (1.0 g, 7.0 mmol) and diisopropylethylamine (1.7 g, 12.8 mmol). The reaction mixture was stirred and heated in "CEM" microwave system (150° C., 3 hours). Upon completion, the mixture was evaporated to dryness, and to the residue was added water and then extracted with ethyl acetate (3×50 mL). The combined extracts were washed with 5% aqueous citric acid, saturated aqueous solution of sodium bicarbonate₃, brine, dried over Na₂SO₄, filtered and the filtrate was evaporated. The crude product was purified by column chromatography on silica gel eluting with hexanes:ethyl acetate mixture (1:1) to afford the title product (1.8 g, 74%) as a colorless oil. $^1$H NMR (400 MHz, CDCl$_3$) δ 8.21 (d, J=5.0 Hz, 1H), 7.26-7.10 (m, 2H), 6.85 (t, J=8.7 Hz, 1H), 6.40 (d, J=5.1 Hz, 1H), 4.04 (d, J=6.9 Hz, 2H), 3.95-3.70 (m, 2H), 3.69-3.56 (m, 1H), 3.49 (dd, J=11.3, 6.6 Hz, 1H), 2.93-2.76 (m, 1H), 2.62 (q, J=7.6 Hz, 2H), 2.33-2.15 (m, 1H), 2.04-1.87 (m, 1H), 1.27 (t, J=7.6 Hz, 3H).

Example A-91: (S)-4-Ethyl-2-(3-((2-fluoro-4-(4,4,5,5-tetramethyl-1,3,2-dioxaborolan-2-yl)phenoxy)methyl)pyrrolidin-1-yl)pyrimidine

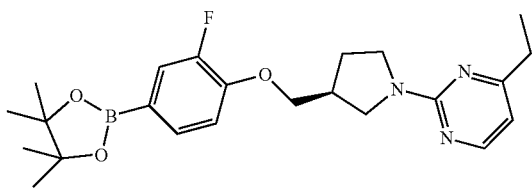 [SMILES: CCc1ccnc(N2CC[C@H](COc3ccc(B4OC(C)(C)C(C)(C)O4)cc3F)C2)n1]

To a solution of: (S)-2-(3-((4-bromo-2-fluorophenoxy)methyl)pyrrolidin-1-yl)-4-ethylpyrimidine (1.8 g, 4.7 mmol), 4,4,4',4,5,5,5',5'-octamethyl-2,2'-bi-1,3,2-dioxaborolane (1.0 g, 4.1 mmol), (1.42 g, 5.6 mmol) and (bisdiphenylphosphino)ferrocene dichloropalladium (II) Pd(dppf)Cl₂ (220 mg, 0.3 mmol) in 1,4-dioxane (60 mL) was added potassium acetate (1.9 g, 18.8 mmol) and the resulting mixture was stirred and heated to 90° C. overnight. Upon cooling, the reaction mixture was poured into a mixture of ethyl acetate (100 mL) and water (100 mL), then filtered through a pad of celite and the organic layer was separated, washed with water, brine, dried over Na₂SO₄, filtered and the filtrate was evaporated to dryness. The product was purified by column chromatography on silica gel eluting with hexanes:ethyl acetate mixture (1:1) to obtain the title product (1.9 g, 94%). as a yellow solid. $^1$H NMR (400 MHz, CDCl$_3$) δ 8.20 (d, J=5.1 Hz, 1H), 7.56-7.45 (m, 2H), 6.95 (t, J=8.2 Hz, 1H), 6.38 (d, J=5.1 Hz, 1H), 4.08 (d, J=6.9 Hz, 2H), 3.89 (dd, J=11.3, 7.4 Hz, 1H), 3.82-3.72 (m, 1H), 3.68-3.57 (m, 1H), 3.49 (dd, J=11.4, 6.7 Hz, 1H), 2.94-2.80 (m, 1H), 2.61 (q, J=7.6 Hz, 2H), 2.32-2.20 (m, 1H), 2.00-1.89 (m, 1H), 1.34 (s, 12H), 1.25 (t, J=7.6 Hz, 3H).

Example A-92: (S)-6-(4-((1-(4-Ethylpyrimidin-2-yl)pyrrolidin-3-yl)methoxy)-3-fluorophenyl)-2H-benzo[d][1,3]oxathiole 3,3-dioxide

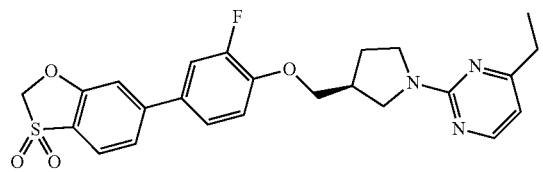 [SMILES: CCc1ccnc(N2CC[C@H](COc3ccc(-c4ccc5c(c4)OCS5(=O)=O)cc3F)C2)n1]

To a solution of (S)-4-ethyl-2-(3-((2-fluoro-4-(4,4,5,5-tetramethyl-1,3,2-dioxaborolan-2-yl)phenoxy)methyl)pyrrolidin-1-yl)pyrimidine (295 mg, 0.69 mmol) in dioxane (13 mL) was added sequentially 3,3-dioxido-2H-benzo[d][1,3]oxathiol-6-yl trifluoromethanesulfonate (220 mg, 0.69 mmol), 2M aqueous solution of sodium carbonate (1.1 mL) and (bisdiphenylphosphino)ferrocene dichloropalladium (II) Pd(dppf)Cl₂ (25 mg, 0.03 mmol). The mixture was stirred and heated to 85° C. for 2 hours. Upon cooling, water (50 mL) was added and the solution was extracted with ethyl acetate (3×30 mL). The combined extracts were washed with water, brine, dried over Na₂SO₄, filtered and the filtrate was evaporated to dryness. The product was purified by column chromatography on silica gel eluting with hexanes:ethyl acetate mixture (1:1). The product was washed with methanol (20 mL) and air-dried to afford the title compound (85 mg, 26%) as a white solid. $^1$H NMR (400 MHz, DMSO-d$_6$) δ 8.20 (d, J=4.7 Hz, 1H), 7.89 (d, J=7.9 Hz, 1H), 7.82-7.47 (m, 4H), 7.34 (t, J=7.8 Hz, 1H), 6.49 (d, J=4.4 Hz, 1H), 5.44 (s, 2H), 4.32-4.07 (m, 2H), 3.84-3.37 (m, 4H), 2.87-2.69 (m, 1H), 2.61 (q, J=7.6 Hz, 2H), 2.23-2.06 (m, 1H), 1.97-1.77 (m, 1H), 1.17 (t, J=7.5 Hz, 3H).

Example B-1: tert-Butyl 2,2,2-trichloroacetaimidate

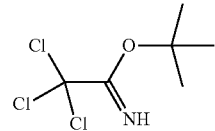

To a cold solution of trichloroacetonitrile (100 g, 0.69 mol), in diethyl ether (69 mL) was added dropwise a solution of potassium t-butoxide (69 mL, 1M in t-butanol) in diethyl ether (69 mL) maintained at 0° C., over a period of 30 minutes. The mixture was then allowed to warm to room temperature over one hour, and was then stirred for an additional hour with heating at reflux. The mixture was cooled to room temperature and evaporated under reduced pressure to yield an oil. The oil was dissolved in hexanes (140 mL) and filtered to remove potassium salts. The filtrate was evaporated under reduced pressure and the residual oil was purified by vacuum distillation. The fraction distilling at 2.4 mm Hg and 40° C. was collected to furnish the title compound (105 g, 69%). $^1$H-NMR (CDCl$_3$, 400 MHz): δ 8.21 (br, s, 1H), 1.58, (s, 9H).

Example B-2: 6-tert-Butoxy-1,3-benzoxathiol-2-one

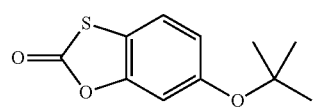

To a solution of 6-hydroxy-1,3-benzoxathiol-2-one (9.2 g, 54.7 mmol) dissolved in 100 mL of tetrahydrofuran was added at room temperature a solution of t-butyl trichloroacetaimidate (23.9 g, 109.4 mmol) in tetrahydrofuran (50 mL) and boron trifluoride etherate (0.5 g, 3.5 mmol) and the mixture was stirred at room temperature overnight. Solid sodium bicarbonate (9.24 g, 110 mmol) was then added to the solution with stirring and the solution was filtered through a silica gel column and was washed with cold tetrahydrofuran. The filtrate was evaporated in vacuo to give a yellow oil which was purified by column chromatography eluting with methylene chloride to give 6-tert-butoxy-1,3-benzoxathiol-2-one (10.4 g, 85%). $^1$H-NMR (CDCl$_3$, 400 MHz): δ 7.27 (d, J=3.8 Hz, 1H), 6.97 (d, J=2.2 Hz, 1H), 6.92 (dd, J$_1$=8.6 Hz, J$_2$=2.2 Hz, 1H), 1.39 (s, 9H).

Example B-3: 6-tert-Butoxy-1,3-benzoxathiole

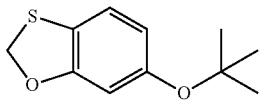

To a solution of 6-tert-butoxy-1,3-benzoxathiol-2-one (10.4 g, 46.3 mmol) in 200 mL of dibromomethane and 10 mL of water was added successively potassium carbonate (19.2 g, 139 mmol) and 18-crown-6-ether (1 g, 3.7 mmol). The reaction mixture was stirred and gently refluxed under an argon atmosphere 48 hours. After cooling, the inorganic salts were removed by filtration and the solvents were removed in vacuo. The residual oil was poured into methylene chloride (400 mL). The methylene chloride layer was washed with saturated sodium chloride solution (2×100 mL), dried over sodium sulfate, filtered and the filtrate was evaporated in vacuo. The residual oil was purified by column chromatography eluting with methylene chloride to furnish 6-tert-butoxy-1,3-benzoxathiole (8.8 g, 90%). $^1$H-NMR (CDCl$_3$, 400 MHz): δ 7.04 (d, J=8.1 Hz, 1H), 6.55 (m, 2H), 5.71 (s, 2H), 1.33 (s, 9H).

Example B-4: 1,3-Benzoxathiol-6-ol

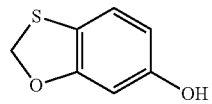

Trifluoroacetic acid (20 mL) was added to a solution of 6-tert-butoxy-1,3-benzoxathiole (1.5 g, 7.1 mmol) in methylene chloride (50 mL) and the mixture was cooled to 0° C. The mixture was stirred for 1 hour at 0° C. and then allowed to warm to room temperature. The solvents were removed under reduced pressure and the residue was dissolved in CH$_2$Cl$_2$ (30 mL) and purified by column chromatography eluting with CH$_2$Cl$_2$:CH$_2$Cl$_2$:Et$_2$O (1:1) to give 1,3-benzoxathiol-6-ol (0.45 g, 41%). $^1$H-NMR (CDCl$_3$, 400 MHz): δ 6.99 (d, J=8.1 Hz, 1H), 6.44-6.38 (m, 2H), 5.70 (s, 2H), 4.90 (br s, 1H).

Example B-5: 1,3-Benzoxathiol-6-trifluoromethanesulfonate

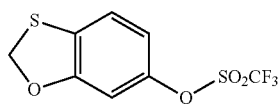

Trifluoromethanesulfonic anhydride (0.82 g, 2.9 mmol) was added dropwise to a solution of 1,3-benzoxathiol-6-ol (0.45 g, 2.9 mmol) in 10 mL of pyridine at 0° C. The mixture was stirred for 30 minutes at 0° C. and then allowed to warm to room temperature with stirring overnight. The reaction mixture was then evaporated to dryness and the residual oil was dissolved in 50 mL of methylene chloride and washed with 50 mL of 10% aqueous solution of citric acid, 50 mL of saturated sodium chloride solution and then with 100 mL of water. The organic layer separated and dried over sodium sulfate, filtered and the filtrate was evaporated in vacuo. The residue was dissolved in methylene chloride (20 mL) and was purified by column chromatography eluting with methylene chloride to give 1,3-benzoxathiol-6-yl trifluoromethanesulfonate (8) (0.81 g, 97%). $^1$H-NMR (CDCl$_3$, 400 MHz): δ 7.18 (d, J=8.4 Hz, 1H), 6.82 (dd, J$_1$=2.3 Hz, J$_2$=8.4 Hz, 1H), 6.76 (d, J=2.3 Hz, 1H), 5.81 (s, 2H).

Example B-6: tert-butyl-4-((methylsulfonyl)oxy)methyl)piperidine-1-carboxylate

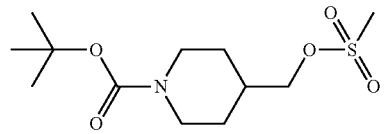 [SMILES: CC(C)(C)OC(=O)N1CCC(COS(C)(=O)=O)CC1]

To a solution of tert-butyl 4-(hydroxymethyl)piperidine-1-carboxylate (100.0 g, 0.46 mol) and triethylamine (94.0 g, 0.93 mol) in dichloromethane (1500 mL) at 0° C. was added methanesulfonyl chloride (58.5 g, 0.51 mol). The reaction mixture was stirred at ambient temperature for 4 hours and then washed sequentially with 0.1N hydrochloric acid (500 mL) and brine (300 mL). The organic layer was separated, dried over sodium sulfate, filtered and the filtrate was concentrated in vacuo to afford the title compound (120.1 g, 88%) as a white solid. $^1$H NMR (400 MHz, DMSO-d$_6$) δ 4.06 (d, J=6.3 Hz, 2H), 3.95 (m, 2H), 3.16 (s, 3H), 2.71 (br s, 2H), 1.86 (m, 1H), 1.64 (d, J=12.7 Hz, 2H), 1.39 (s, 9H), 1.09 (m, 2H).

Example B-7: Tert-Butyl-4-((4-bromo-2-fluorophenoxy)methyl)piperidine-1-carboxylate

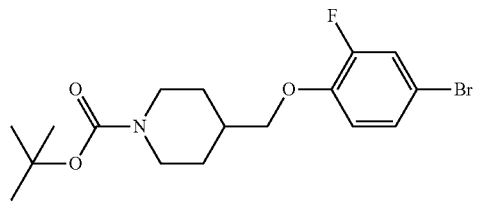 [SMILES: CC(C)(C)OC(=O)N1CCC(COc2ccc(Br)cc2F)CC1]

A suspension containing tert-butyl-4-((methylsulfonyl)oxy)methyl)piperidine-1-carboxylate (80.0 g, 0.27 mol), 4-bromo-2-fluorophenol (62.5 g, 0.33 mol) and potassium carbonate (75.4 g, 0.55 mol) in dimethylsulfoxide (800 mL) was stirred at 110° C. for 16 hours. Upon completion of reaction as evidenced by thin layer chromatography, dimethylsulfoxide was distilled off under reduced pressure. The residual oil was quenched with water (800 mL) and the resultant precipitate was filtered off and re-crystallized from isopropanol to afford tert-butyl-4-((4-bromo-2-fluoro phenoxy)methyl) pyperidine-1-carboxylate (88.0 g, 83.1%) as a white crystalline powder: $^1$H NMR (400 MHz, DMSO-$d_6$) δ 7.50 (dd, J=10.8, 2.3 Hz, 1H), 7.30 (m, 1H), 7.15 (m, 1H), 3.96 (d, J=10.7 Hz, 2H), 3.90 (d, J=6.4 Hz, 2H), 2.66-2.79 (m, 2H), 1.89-1.98 (m, 1H), 1.72 (d, J=10.9 Hz, 2H), 1.39 (s, 9H), 1.09-1.23 (m, 2H).

Example B-8: tert-Butyl-4-((2-fluoro-4-(4,4,5,5-tetramethyl-1,3,2-dioxoborolan-2-yl)phenoxy]methyl)piperidine-1-carboxylate

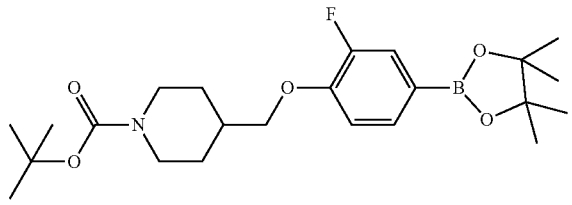 [SMILES: CC(C)(C)OC(=O)N1CCC(COc2ccc(B3OC(C)(C)C(C)(C)O3)cc2F)CC1]

To a mixture of tert-butyl-4-((4-bromo-2-fluorophenoxy)methyl)piperidine-1-carboxylate (60.0 g, 0.15 mol) and 4,4,4',4,5,5,5',5'-octamethyl-2,2'-bi-1,3,2-dioxoborolane (51.0 g, 0.2 mol) in acetonitrile (1000 mL) was added of 1,1'-(bisdiphenylphosphino)ferrocene dichloropalladium (II) (Pd(dppf)Cl$_2$ (5.63 g, 8 mmol) and potassium acetate (45.5 g, 0.46 mol) and the solution was stirred under argon at 70° C. for 16 hours. Upon completion, the reaction mixture was diluted with ethyl acetate (1000 mL) and washed with brine (1000 mL). The organic layers were combined, dried over magnesium sulfate, filtered and the filtrate was evaporated under reduced pressure. The residue after evaporation was purified by column chromatography eluting with hexanes-ethyl acetate mixture (10:1) to afford the title compound (50.0 g, 74.3%) as a white powder. $^1$H NMR (400 MHz, DMSO-$d_6$) δ 7.42 (d, J=8.1 Hz, 1H), 7.31 (m, 1H), 7.15 (m, 1H), 3.91-4.02 (m, 4H), 2.66-2.80 (m, 2H), 1.89-2.02 (m, 1H), 1.73 (d, J=11.2 Hz, 2H), 1.39 (s, 9H), 1.27 (s, 12H), 1.07-1.22 (m, 2H).

Example B-9: (1-(5-Chloropyrimidin-2-yl)piperidin-4-yl)methylmethanesulfonate

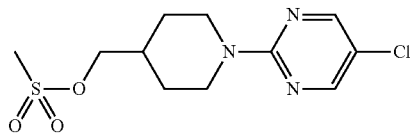

Step 1: A suspension of piperidin-4-ylmethanol (124.6 g, 1.08 mol) and 2,5-dichloropyrimidine (161.2 g, 1.08 mol) and triethylamine (438 g, 4.3 mol) in acetonitrile (1000 mL) was heated under reflux for 16 hours. Upon cooling to room temperature, a precipitate was formed which was filtered, washed with ether (300 mL) and dried to afford (1-(5-chloropyrimidin-2-yl)piperidin-4-yl)methanol (203.2 g, 82.4%) as a beige powder. $^1$H NMR (400 MHz, DMSO-$d_6$) δ 8.36 (s, 2H), 4.58 (d, J=13.3 Hz, 2H), 4.47 (t, J=5.3 Hz, 1H), 3.26 (t, J=5.7 Hz, 2H), 2.87 (td, J=12.7, 2.2 Hz, 2H), 1.67 (m, 3H), 1.05 (m, 2H).

Step 2: To a solution of (1-(5-chloropyrimidin-2-yl)piperidin-4-yl)methyl methanesulfonate (203 g, 0.89 mol) and triethylamine (180.4 g, 1.78 mol) in dichloromethane (1500 mL) at 0° C. was added methanesulfonyl chloride (112.34 g, 0.98 mol). The reaction mixture was stirred at ambient temperature for 4 hours and then washed sequentially with 0.1N hydrochloric acid solution (500 mL) and brine (300 mL). The organic layer was separated, dried over sodium sulfate, filtered and the filtrate was concentrated in vacuo to afford the title compound (120.1 g, 88%) as a white solid. $^1$H NMR (400 MHz, CDCl$_3$) δ 8.22 (s, 2H), 4.76 (d, J=13.5 Hz, 2H), 4.10 (d, J=6.6 Hz, 2H), 3.02 (s, 3H), 2.90 (td, J=12.9, 2.5 Hz, 2H), 2.06 (m, 1H), 1.84 (d, J=12.5 Hz, 2H), 1.30 (m, 2H).

Example B-10: 2-(4-((4-Bromo-2-fluorophenoxy)methyl]piperidin-1-yl}-5-chloropyrimidine

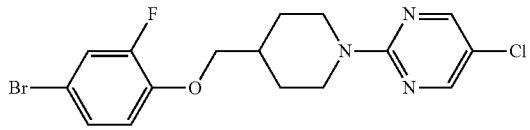 [SMILES: Fc1cc(Br)ccc1OCC1CCN(c2ncc(Cl)cn2)CC1]

A suspension of (1-(5-chloropyrimidin-2-yl)piperidin-4-yl)methyl methanesulfonate (244.3 g, 0.8 mol), 4-bromo-2-fluorophenol (206.0 g, 1.07 mol) and potassium carbonate (331.0 g, 2.4 mol) in dimethylsulfoxide (2.5 L) was stirred at 110° C. for 16 hours. Upon completion dimethylsulfoxide was distilled off under reduced pressure and a residue was treated with water (2.0 L). A solid precipitate was filtered off and re-crystallized from isopropanol (1.5 L) to afford the title product (246.1 g, 77%) as a white crystalline powder: $^1$H NMR (400 MHz, CDCl$_3$) δ 8.22 (s, 2H), 7.24 (dd, J=10.5, 2.3 Hz, 1H), 7.18 (dt, J=8.7, 1.9 Hz, 1H), 6.83 (t, J=8.8 Hz, 1H), 4.77 (d, J=13.4 Hz, 2H), 3.87 (d, J=6.5 Hz, 2H),), 2.94 (td, J=12.9, 2.5 Hz, 2H), 2.14 (m, 1H), 1.93 (d, J=12.4 Hz, 2H), 1.34 (qd, J=12.5, 4.2 Hz, 2H).

Example B-11: 9-Chloro-2-(4-((2-fluoro-4-(4,4,5,5-tetramethyl-1,3,2-dioxaborolan-2-yl)phenoxy)methyl}piperidin-1-yl)pyrimidine

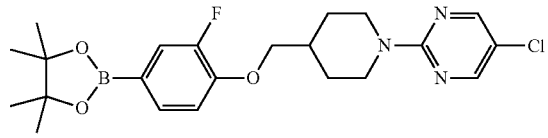 [SMILES: CC1(C)OB(c2ccc(OCC3CCN(c4ncc(Cl)cn4)CC3)c(F)c2)OC1(C)C]

A mixture of 2-(4-((4-bromo-2-fluorophenoxy)methyl)piperidin-1-yl)-5-chloropyrimidine (246.0 g, 0.6 mol), 4,4,4',4,5,5,5',5'-octamethyl-2,2'-bi-1,3,2-dioxoborolane (187.0 g, 0.746 mol), Pd(dppf)Cl$_2$ (22.5 g, 0.05 mol) and potassium acetate (241.0 g, 2.45 mol) in acetonitrile (2.5 L) was stirred under argon at 70° C. for 16 hours. Upon completion the reaction mixture was diluted with ethyl acetate (2.0 L) and washed with brine (1.0 L). The organic phase was separated, dried over magnesium sulfate, filtered and the filtrate was evaporated under reduced pressure. The residue after evaporation was subjected to column chromatography eluting with hexanes-ethyl acetate mixture 10:1 by volume to afford the title product (234.8 g, 85.4%) as a white powder. $^1$H NMR (400 MHz, DMSO-$d_6$) δ 8.38 (s, 2H), 7.42 (d, J=8.2 Hz, 1H), 7.31 (d, J=11.7, 1.85 Hz, 1H), 1.27 (s, 12H), 7.15 (t, J=8.2 Hz, 1H), 4.61 (d, J=13.5 Hz, 2H), 3.96 (d, J=6.5 Hz, 2H), 2.94 (t, J=14 Hz, 2H), 2.06 (m, 1H), 1.82 (d, J=13.5 Hz, 2H).

Example B-12: 2-(4-((4-Benzo[d][1,3]oxathiol-6-yl)-2-fluorophenoxy]methyl)piperidin-1-yl)-5-chloropyrimidine

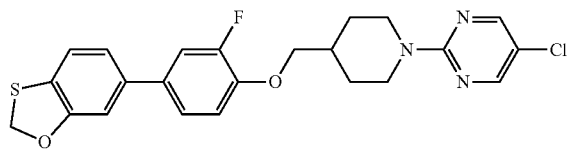

To a solution of 5-chloro-2-(4-((2-fluoro-4-(4,4,5,5-tetramethyl-1,3,2-dioxaborolan-2-yl)phenoxy)methyl}piperidin-1-yl)pyrimidine (0.5 g, 1.1 mmol) in dioxane (30 mL) was added 1,3-benzoxathiol-6-yl trifluoromethanesulfonate (0.32 g, 1.1 mmol) and cesium carbonate (1 g, 3 mmol). The reaction mixture was purged with argon and 1,1' (bisdiphenylphosphino)ferrocenepalladium (II) dichloride (Pd(dppf)Cl$_2$ (0.1 g, 0.1 mmol) was added and the resultant solution was stirred at room temperature for 1 hour and then heated at 60° C. for 12 hours. After cooling, the solvents were evaporated in vacuo and the residual oil was purified by column chromatography eluting with CH$_2$Cl$_2$:CH$_2$Cl$_2$:Et$_2$O (1:1) to give the title compound (0.08 g, 16%). $^1$H-NMR (400 MHz, DMSO-d$_6$): δ 8.40 (s, 2H), 7.52 (d, J=12.1 Hz, 1H), 7.40 (d, J=7.3 Hz, 1H), 7.32 (d, J=7.3 Hz, 1H), 7.18 (m, 3H), 5.80 (s, 2H), 4.64 (d, J=12.0 Hz, 2H), 3.97 (d, J=5.1 Hz, 2H), 2.96 (t, J=12.2 Hz, 2H), 2.11 (m, 1H), 1.85 (d, J=11.4 Hz, 2H), 1.25 (m, 2H).

Example B-13: 6-tert-Butoxy-1,3-benzoxathiole 3-oxide

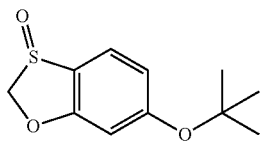

m-Chloroperbenzoic acid (70%, 5.25 g, 21.3 mmol) was added to a solution of 6-tert-butoxy-1,3-benzoxathiole (4.48 g, 21.3 mmol)) dissolved in 100 mL of CH$_2$Cl$_2$ and cooled to 0° C. The reaction mass was stirred 2 hours at 0° C. and filtered to remove a precipitate. The filtrate was washed with sodium carbonate solution (2×100 mL), dried over sodium sulfate and filtered. The solvent was evaporated in vacuo and the residual oil was purified by column chromatography eluting with CH$_2$Cl$_2$:CH$_2$Cl$_2$:Et$_2$O (1:1) to furnish 6-tert-butoxy-1,3-benzoxathiole 3-oxide (4 g, 83%). $^1$H-NMR (400 MHz, CDCl$_3$): δ 7.74 (d, J=8.2 Hz, 1H), 6.79 (m, 2H), 5.48 (d, J=11.0 Hz, 1H), 5.04 (d, J=11.0 Hz, 1H), 1.44 (s, 9H).

Example B-14: 1,3-Benzoxathiol-6-ol 3-oxide

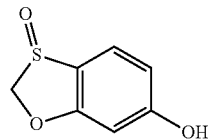 [SMILES: O=S1COc2cc(O)ccc21]

To a solution of 6-tert-butoxy-1,3-benzoxathiole 3-oxide (4 g, 17.6 mmol) dissolved in methylene chloride (50 mL) was added trifluoroacetic acid (20 mL) and the resultant solution was stirred for 1 hour at room temperature followed by evaporation of solvents in vacuo. The residual oil was poured into ether and the precipitate formed was filtered off and dried to yield 1,3-benzoxathiol-6-ol 3-oxide (1.9 g, 63%). $^1$H-NMR (400 MHz, DMSO-d$_6$): δ 10.51 (s, 1H), 7.80 (d, J=8.3 Hz, 1H), 6.62 (m, 2H), 5.52 (d, J=11.0 Hz, 1H), 5.15 (d, J=1.0 1 Hz, 1H).

Example B-15: 3-Oxido-1,3-benzoxathiol-6-yl trifluoromethanesulfonate

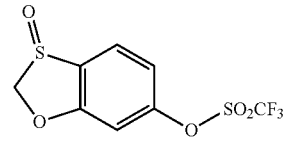

Trifluoromethanesulfonic anhydride (3.15 g, 1.1 mmol) was added dropwise to a solution of 1.9 g (11.1 mmole) of 1,3-benzoxathiol-6-ol 3-oxide (1.9 g, 11.1 mmol) in 20 mL of pyridine at 0° C. The mixture was stirred for 30 minutes at that temperature and overnight at room temperature. The reaction mixture was then evaporated to dryness and the residual oil was dissolved in 100 mL of methylene chloride and washed consecutively with 100 mL of 10% aqueous solution of citric acid, 100 mL of saturated sodium chloride solution and then with 100 mL of water. The organic layer was dried over sodium sulfate, filtered and the filtrate was evaporated in vacuo. The residual oil was dissolved in methylene chloride (20 mL) and was purified by column chromatography eluting with CH$_2$Cl$_2$ to give 3-oxido-1,3-benzoxathiol-6-yl trifluoromethanesulfonate (1.79 g, 53%). $^1$H-NMR (400 MHz, CDCl$_3$): δ 7.99 (d, J=8.6 Hz, 1H), 7.18 (d, J=2.1 Hz, 1H), 7.13 (dd, J$_1$=2.1 Hz, J$_2$=8.6 Hz, 1H), 5.61 (d, J=11.1 Hz, 1H), 5.14 (d, J=11.1 Hz, 1H).

Example B-16: 6-(4-((1-(5-Chloropyrimidin-2-yl)piperidin-4-yl)methoxy)-3-fluorophenyl)-2H-benzo[d][1,3]oxathiole 3-oxide

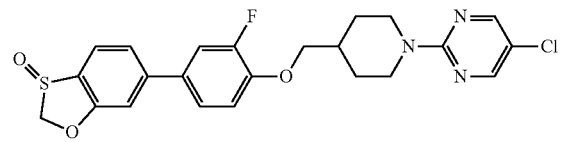 [SMILES: O=S1COc2cc(-c3ccc(OCC4CCN(c5ncc(Cl)cn5)CC4)c(F)c3)ccc21]

To a solution of 5-chloro-2-(4-((2-fluoro-4-(4,4,5,5-tetramethyl-1,3,2-dioxaborolan-2-yl)phenoxy)

methyl}piperidin-1-yl)pyrimidine (0.63 g, 1.4 mmol) in dioxane (30 mL) was added 3-oxido-1,3-benzoxathiol-6-yl trifluoromethanesulfonate (0.43 g, 1.4 mmol) and cesium carbonate (1 g, 3 mmol) and stirred at room temperature. The reaction mixture was purged with argon and 1,1' (bis-diphenylphosphino)ferrocenepalladium(II) dichloride (Pd (dppf)Cl$_2$ (0.1 g, 0.1 mmol) was added and the resultant solution was stirred at room temperature for 1 hour and then heated at 60° C. for 2 hours. After cooling, the solvents were evaporated in vacuo and the residual oil was purified by column chromatography eluting with CH$_2$Cl$_2$:Et$_2$O (1:1) to furnish the title compound (0.35 g, 52%). $^1$H-NMR (400 MHz, CDCl$_3$): δ 8.23 (s, 2H), 7.92 (d, J=8.4 Hz, 1H), 7.38-7.30 (m, 4H), 7.04 (t, J=8.3 Hz, 1H), 5.55 (d, J=11.0 Hz, 1H), 5.06 (d, J=11.0 Hz, 1H), 4.78 (d, J=13.0 Hz, 2H), 3.96 (d, J=6.0 Hz, 2H), 2.96 (t, J=12.5 Hz, 2H), 2.20 (m, 1H), 1.99 (d, J=12.3 Hz, 2H), 1.38 (m, 2H).

Example B-17: tert-Butyl 4-((2-fluoro-4-(3-oxido-1, 3-benzoxathiol-6-yl)phenoxy)methyl) piperidine-1-carboxylate

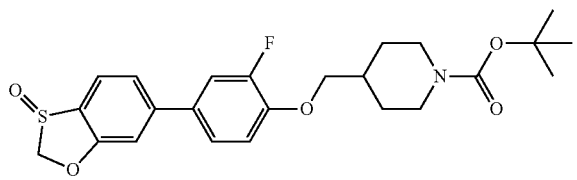 [SMILES: CC(C)(C)OC(=O)N1CCC(COc2ccc(-c3ccc4c(c3)OCS4=O)cc2F)CC1]

A solution of tert-butyl-4-((2-fluoro-4-(4,4,5,5-tetramethyl-1,3,2-dioxoborolan-2-yl)phenoxy]methyl)piperidine-1-carboxylate (0.6 g, 1.4 mmol), 3-oxido-1,3-benzoxathiol-6-yl trifluoromethanesulfonate (0.43 g, 1.4 mmol) and cesium carbonate (1 g, 3 mmol) in dioxane (30 mL) was purged with argon and 1,1' (bisdiphenylphosphino)ferrocene dichloropalladium (II) (Pd(dppf)Cl$_2$ (0.1 g, 0.1 mmol). The resulting solution was stirred at ambient temperature for 1 hour and then heated at 60° C. for 2 hours. After cooling, the volatiles were evaporated in vacuo and the residual oil was subjected to column chromatography on silica gel, eluting with dichloromethane-ether mixture 1:1 to afford the title compound (0.51 g, 80%) as a white solid. $^1$H-NMR (400 MHz, CDCl$_3$): δ 7.92 (d, J=8.4 Hz, 1H), 7.38-7.29 (m, 4H), 7.04 (t, J=8.6 Hz, 1H), 5.54 (d, J=11.1 Hz, 1H), 5.06 (d, J=11.1 Hz, 1H), 4.19 (bs, 2H), 3.94 (d, J=6.5 Hz, 2H), 2.78 (t, J=12.8 Hz, 2H), 2.10-2.00 (m, 1H), 1.87 (d, J=12.8 Hz, 2H), 1.48 (s, 9H), 1.36-1.25 (m, 2H).

Example B-18: 6-(3-Fluoro-4-(piperidin-4-yl) methoxy)phenyl)-2H-benzo[d][1,3]oxathiole 3-oxide

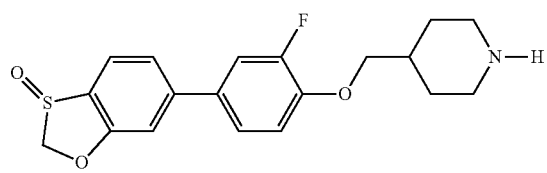 [SMILES: O=S1COc2cc(-c3ccc(OCC4CCNCC4)c(F)c3)ccc21]

To a solution of tert-butyl 4-((2-fluoro-4-(3-oxido-1,3-benzoxathiol-6-yl)phenoxy)methyl) piperidine-1-carboxylate (0.51 g, 1.1 mmol) in methylene chloride (10 mL) was added trifluoroacetic acid (5 mL) and the resulting mixture was stirred at 40° C. for 4 hours. Upon completion the volatiles were distilled off in vacuo and a residue after evaporation was with sonicated with ether. A formed precipitate was filtered off to afford upon drying the title compound (0.47 g, 90%) as a white solid. The material was used in the next step without further purification.

Example B-19: 6-(4-((1-(5-Ethylpyrimidin-2-yl) methoxy)-3-fluorophenyl)-2H-benzo[d][1,3]oxathiole-3-oxide

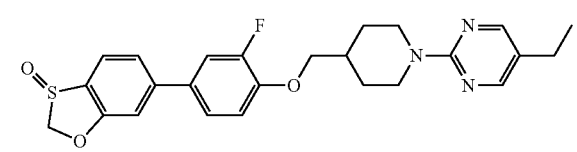 [SMILES: CCc1cnc(N2CCC(COc3ccc(-c4ccc5c(c4)OCS5=O)cc3F)CC2)nc1]

A solution of 6-(3-fluoro-4-(piperidin-4-yl)methoxy)phenyl)-2H-benzo[d][1,3]oxathiole 3-oxide. (0.27 g, 0.57 mmol)), 2-chloro-5-ethylpyrimidine (0.086 g, 0.6 mmol) and triethylamine (0.23 g, 2.3 mmol) in acetonitrile (50 mL) was stirred at reflux for 6 hours. Upon completion, the reaction mixture was allowed to come to ambient temperature and a formed precipitate was filtered off and filter cake was washed consequently with water and with hexane to allow a crude product. The crude product was subjected to column chromatography eluting with dichloromethane to obtain the title product (0.2 g, 75%). $^1$H NMR (400 MHz, DMSO-d$_6$) δ 8.23 (s, 2H), 8.08 (d, J=7.9 Hz, 1H), 7.69 (d, J=12.8 Hz, 1H), 7.62 (s, 1H), 7.59-7.49 (m, 2H), 7.28 (t, J=8.9 Hz, 1H), 5.64 (d, J=11.0 Hz, 1H), 5.22 (d, J=11.0 Hz, 1H), 4.67 (d, J=12.7 Hz 2H), 4.01 (d, J=6.1 Hz, 2H), 2.89 (t, J=12.5 Hz, 2H), 2.46-2.39 (m, 2H), 2.15-2.05 (bs, 1H), 1.84 (d, J=11.9 Hz, 2H), 1.31-1.19 (m, 2H), 1.13 (t, J=7.3 Hz, 3H).

Example B-20: 2-Oxobenzo[d][1,3]oxathiol-5-yl-trifluoromethanesulfonate

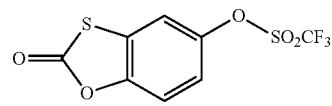

To a solution of 5-hydroxy-1,3-benzoxathiol-2-one (5.1 g, 30.0 mmol) dissolved in 50 mL of pyridine was added trifluoromethanesulfonic anhydride (10.3 g, 36.0 mmol) at 0° C. and the reaction mixture was stirred for 40 minutes at that temperature and then stirred at room temperature overnight. The solvent was evaporated in vacuo and the residue was treated with ethyl acetate (70 mL) to give a suspension which was washed with 10% citric acid (70 mL) followed by brine (50 mL) and water (50 mL). The organic layer collected, dried over magnesium sulfate, filtered and evaporated in vacuo to give an oil which was washed with ether (50 mL) and purified by column chromatography eluting with methylene chloride to give 5-tert-butoxy-1,3-benzoxathiol-2-one (10.4 g, 85%). H-NMR (400 MHz, CDCl$_3$): δ, 7.41 (d, J=2.6 Hz, 1H), 7.39 (d, J=8.9 Hz, 1H), 7.28 (m, 1H).

Example B-21: Benzo[d][1,3]oxathiol-5-yl-trifluoromethanesulfonate

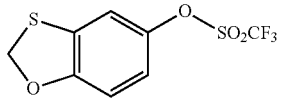

To a solution of 2-oxobenzo[d][1,3]oxathiol-5-yl-trifluoromethanesulfonate (1.4 g, 4.7 mmol) in 25 mL of dibromomethane and 2 mL of water was added successively potassium carbonate (2.6 g, 20 mmol) and 18-crown-6-ether (0.2 g, 0.8 mmol). The reaction mixture was stirred and gently refluxed under an argon atmosphere 48 hours. After cooling, the inorganic salts were removed by filtration and the solvents were removed in vacuo. The residual oil was poured into methylene chloride (150 mL). The methylene chloride layer was washed with saturated sodium chloride solution (2×100 mL), dried over sodium sulfate, filtered and the filtrate was evaporated in vacuo. The residual oil was treated with ether (50 mL) and cooled in a dry ice bath for 30 minutes. A precipitate was formed which was filtered, washed with ether (20 mL) and collected to furnish the title compound (0.8 g, 60%). $^{19}$F NMR (377 MHz, benzene-$d_6$) δ 72.64 (s, 1F).

Example B-22: 3-Oxido-benzo[d][1,3]oxathiol-5-yl-trifluoromethanesulfonate

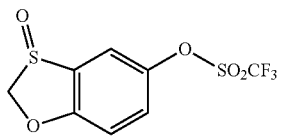

m-Chloroperbenzoic acid (70%, 0.48 g, 2.8 mmol) was added to a solution of benzo[d][1,3]oxathiol-5-yl trifluoromethanesulfonate (0.8 g, 2.8 mmol)) in dichloromethane (30 mL) at 0° C. The reaction mixture was stirred for 2 hours at that temperature and then was filtered to remove a precipitate. The filtrate was washed with saturated solution sodium carbonate (2×20 mL), dried over sodium sulfate and filtered. The filtrate was evaporated in vacuo and the residual oil was purified by column chromatography on silica gel eluting with dichloromethane-ether mixture (1:1) to afford the title product (0.6 g, 70%). $^{19}$F NMR (377 MHz, benzene-$d_6$) δ 72.49 (s, 1F).

Example B-23: 1-(4-((2-Fluoro-4-(3-oxido-2H-benzo[d][1,3]oxathiol-6-yl)phenoxy)methyl)-piperidin-1-yl)-3-methylbutane-1-one

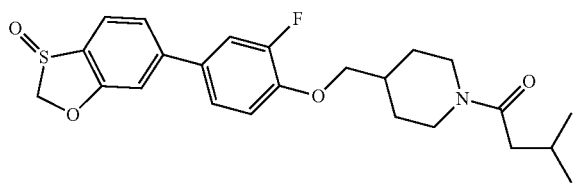 [SMILES: CC(C)CC(=O)N1CCC(COc2ccc(-c3ccc4c(c3)OCS4=O)cc2F)CC1]

To a suspension of 6-(3-fluoro-4-(piperidin-4-ylmethoxy)phenyl-2H-benzo[d][1,3]oxathiole-3-oxide hydrochloride (0.5 g, 1.4 mmol) and 3-methylbutanoic acid (0.15 g, 1.5 mmol) in acetonitrile (15 mL) was added triethylamine (0.43 g, 4.2 mmol) and N-[(1H-1,2,3-benzotriazol-1-yloxy)(dimethylamino)methylene]-N-methylmethanaminium hexafluorophosphate (0.68 g, 1.8 mmol). The resulting solution was stirred at 40° C. for 24 hours. Upon cooling, a precipitate was formed which was filtered off and dried to afford the title compound (0.4 g, 64%). $^1$H NMR (400 MHz, DMSO-$d_6$) δ 8.08 (d, J=8.2 Hz, 1H), 7.69 (dd, J=12.8, 2.1 Hz, 1H), 7.63 (d, J=1.2 Hz, 1H), 7.57 (d, J=9.5 Hz, 1H), 7.51 (dd, J=8.1, 1.3 Hz, 1H), 7.28 (t, J=8.9 Hz, 1H), 5.64 (d, J=11.4 Hz, 1H), 5.23 (d, J=11.4 Hz, 1H), 4.43 (d, J=13.7 Hz, 1H), 3.99 (d, J=6.1 Hz, 2H), 3.92 (d, J=14.1 Hz, 1H), 3.03 (t, J=13.6 Hz, 1H), 2.52 (m, 2H), 2.19 (d, J=7.0 Hz, 2H), 1.91-2.11 (m, 2H), 1.80 (t, J=16.7 Hz, 2H), 1.06-1.27 (m, 2H), 0.90 (d, J=6.6 Hz, 6H).

Example B-24: 6-(3-Fluoro-4-((1-(5-methoxypyrimidin-2-yl)piperidin-4-yl)methoxy) phenyl)-2H-benzo[d][1,3]oxathiole 3-oxide

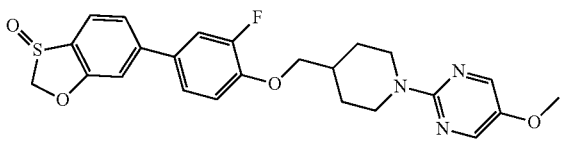 [SMILES: COc1cnc(N2CCC(COc3ccc(-c4ccc5c(c4)OCS5=O)cc3F)CC2)nc1]

A suspension of 6-(3-fluoro-4-(piperidin-4-ylmethoxy)phenyl-2H-benzo[d][1,3]oxathiole-3-oxide hydrochloride (0.20 g, 0.65 mmol), 2-chloro-5-methoxypyrimidine (0.13 g, 0.90 mmol) and cesium carbonate (0.25 g, 0.75 mmol) in dimethylacetamide (10 mL) was heated in CEM microwave system at 130° C. for 3 hours. The reaction mixture was cooled to ambient temperature and extracted with a mixture of ethyl acetate (100 mL) and water (100 mL). The layers were separated and the aqueous phase was extracted with ethyl acetate (2×30 mL). The combined organic layers were dried over sodium sulfate, filtered, and the filtrate was concentrated under reduced pressure. The oily residue was washed with methanol (20 mL) to form a solid material was filtered off and air-dried. This material was subjected to column chromatography on silica gel eluting with ethyl acetate-hexanes mixture (1:1) to afford the title compound as a white solid (76 mg, 27%). $^1$H NMR (400 MHz, DMSO-$d_6$) δ 8.19 (s, 2H), 8.07 (d, J=7.8 Hz, 1H), 7.69 (m, 1H), 7.63 (s, 1H), 7.49-7.59 (m, 2H), 7.28 (t, J=8.6 Hz, 1H), 5.63 (d, J=11.4 Hz, 1H), 5.24 (d, J=11.4 Hz, 1H), 4.56 (d, J=13.2 Hz, 2H), 4.01 (d, J=6.4 Hz, 2H), 3.76 (s, 3H), 2.88 (t, J=11.6 Hz, 2H), 2.08 (m, 1H), 1.82 (d, J=13.3 Hz, 2H), 1.18-1.32 (m, 2H).

Example B-25: 6-(4-((1-(4-Ethylpyrimidin-2-yl)piperidin-4-yl)methoxy)-3-(fluorophenyl)-2H-benzo[d][1,3]oxathiole 3-oxide

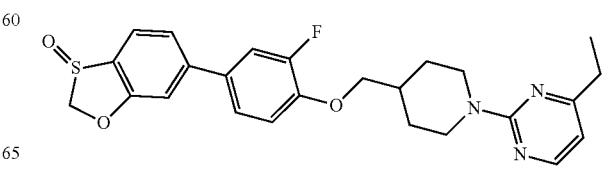

To a suspension of 6-(3-fluoro-4-(piperidin-4-ylmethoxy) phenyl-2H-benzo[d][1,3]oxathiole-3-oxide hydrochloride (0.25 g, 0.70 mmol), and 2-chloro-4-ethylpyrimidine (0.12 g, 0.83 mmol) in acetonitrile (10 mL) was added triethylamine (0.13 g, 1.04 mmol) and the mixture was heated under reflux overnight. The solvent was then removed under reduced pressure and the residue was triturated with water (20 mL). A solid precipitate was filtered off, washed with methanol (10 mL) and air-dried to afford the title compound (0.21 g, 65%) as a light yellow powder. $^1$H-NMR (400 MHz, DMSO-$d_6$): δ 8.21 (d, J=4.9 Hz, 1H), 8.07 (d, J=8.2 Hz, 1H), 7.70 (d, J=12.7 Hz, 1H), 7.63 (s, 1H), 7.60-7.48 (m, 2H), 7.28 (t, J=8.8 Hz, 1H), 6.48 (d, J=4.9 Hz, 1H), 5.64 (d, J=11.5 Hz, 1H), 5.22 (d, J=11.5 Hz, 1H), 4.75 (d, J=12.8 Hz, 2H), 4.01 (d, J=6.5 Hz, 2H), 2.89 (t, J=12.8 Hz, 2H), 2.54 (q, J=7.6 Hz, 2H), 2.18-2.02 (m, 1H), 1.85 (d, J=12.8 Hz, 2H), 1.31-1.17 (m, 5H).

Example B-26: 2-(4-((4-Benzo[d][1,3]oxathiol-6-yl)-2-fluorophenoxy)methyl)piperidin-1-yl)-4-ethylpyrimidine

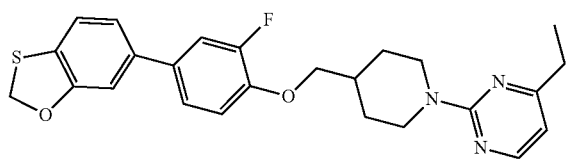 [SMILES: CCc1ccnc(N2CCC(COc3ccc(-c4ccc5c(c4)OCS5)cc3F)CC2)n1]

To a solution of 6-(4-((1-(4-ethylpyrimidin-2-yl)piperidin-4-yl)methoxy)-3-(fluorophenyl)-2H-benzo[d][1,3]oxathiole 3-oxide (90 mg, 0.19 mmol) in tetrahydrofuran (10 mL) under argon was added a solution of borane dimethylsulfide complex solution in tetrahydrofuran (2M, 0.3 mL, 0.57 mmol) and the mixture was stirred at reflux for 3 hours. After the reaction was complete, the solution was cooled to room temperature and the solution was carefully quenched with methanol (1-2 mL) dropwise, and the resulting mixture was stirred at ambient temperature for 2 hours. The solvents were then removed in vacuo and the residue was subjected to column chromatography on silica gel eluting with chloroform-methanol mixture (40:1) to afford the title compound (58 mg, 67%) of as a white powder. $^1$H-NMR (DMSO-$d_6$, 400 MHz): δ 8.21 (d, J=4.9 Hz, 1H), 7.52 (d, J=12.7 Hz, 1H), 7.41 (d, J=8.6 Hz, 1H), 7.33 (d, J=7.7 Hz, 1H), 7.25-7.16 (m, 2H), 6.48 (d, J=4.9 Hz, 1H), 5.80 (s, 1H), 4.74 (d, J=12.8 Hz, 2H), 3.97 (d, J=6.5 Hz, 2H), 2.88 (t, J=12.8 Hz, 2H), 2.54 (q, J=7.6 Hz, 2H), 2.15-2.01 (m, 1H), 1.84 (d, J=12.8 Hz, 2H), 1.31-1.12 (m, 5H).

Example B-27: 6-(4-((1-(5-Ethoxypyrimidin-2-yl)piperidin-4-yl)methoxy)-3-fluorophenyl)-2H-benzo[d][1,3]oxathiole 3-oxide

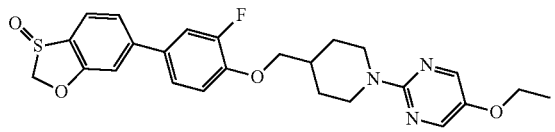 [SMILES: CCOc1cnc(N2CCC(COc3ccc(-c4ccc5c(c4)OCS5=O)cc3F)CC2)nc1]

A suspension of 6-(3-fluoro-4-(piperidin-4-ylmethoxy) phenyl-2H-benzo[d][1,3]oxathiole 3-oxide hydrochloride (0.21 g, 0.60 mmol), 2-chloro-5-ethoxypyrimidine (0.14 g, 0.90 mmol) and cesium carbonate (0.25 g, 0.75 mmol) in dimethylacetamide (10 mL) was heated in CEM microwave system at 130° C. for 3 hours. The reaction mixture was cooled to ambient temperature and extracted with a mixture of ethyl acetate (100 mL) and water (100 mL). The layers were separated and the aqueous phase was extracted with ethyl acetate (2×30 mL). The combined organic layers were dried over sodium sulfate, filtered, and the filtrate was concentrated under reduced pressure. The oily residue was washed with methanol (20 mL) to form a solid material was filtered off and air-dried. This material was subjected to column chromatography on silica gel eluting with ethyl acetate-hexanes mixture (1:1) to afford the title compound as a white solid (71 mg, 25%). $^1$H NMR (400 MHz, DMSO-$d_6$) δ 8.17 (s, 2H), 8.07 (d, J=8.0 Hz, 1H), 7.73-7.48 (m, 4H), 7.28 (t, J=9.0 Hz, 1H), 5.64 (d, J=11.5 Hz, 1H), 5.22 (d, J=11.5 Hz, 1H), 4.58 (d, J=13.7 Hz, 2H), 4.07-3.96 (m, 4H), 2.87 (t, J=11.6 Hz, 2H), 2.14-2.02 (m, 1H), 1.82 (d, J=13.3 Hz, 2H), 1.34-1.19 (m, 5H).

Example B-28: 6-(3-Fluoro-4-((1-(5-isopropylpyrimidin-2-yl)piperidin-4-yl)methoxy)phenyl)-2H-benzo[d][1,3]oxathiole 3-oxide

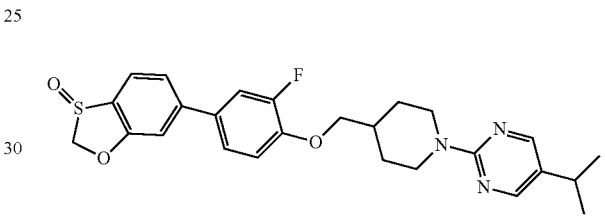

A suspension of 6-(3-fluoro-4-(piperidin-4-ylmethoxy) phenyl-2H-benzo[d][1,3]oxathiole 3-oxide hydrochloride (0.20 g, 0.55 mmol), 2-chloro-5-isopropylpyrimidine (0.09 g, 0.57 mmol) and triethylamine (0.23 g, 2.3 mmol) in dimethylformamide (10 mL) was heated at 50° C. for 3 hours. The reaction mixture was cooled to ambient temperature and diluted with water (10 mL) to form a precipitate which was filtered off and washed with cold water and hexanes. This material was subjected to column chromatography on silica gel eluting with dichloromethane to afford the title compound as a white solid 0.21 g, 81%). $^1$H NMR (400 MHz, DMSO-$d_6$) δ 8.27 (s, 2H), 8.07 (d, J=8.2 Hz, 1H), 7.70 (d, J=12.2 Hz, 1H), 7.63 (s, 1H), 7.55 (d, J=8.2 Hz, 1H), 7.51 (d, J=8.2 Hz, 1H), 7.27 (t, J=8.6 Hz, 1H), 5.64 (d, J=11.9 Hz, 1H), 5.22 (d, J=11.9 Hz, 1H), 4.67 (d, J=12.8 Hz, 2H), 4.02 (d, J=5.7 Hz, 2H), 2.89 (t, J=12.5 Hz, 2H), 2.80-2.72 (m, 1H), 2.15-2.05 (bs, 1H), 1.84 (d, J=12.3 Hz, 2H), 1.31-1.20 (m, 2H), 1.18 (d, J=6.8 Hz, 6H).

Example B-29: 6-(3-Fluoro-4-((1-(5-(trifluoromethyl)pyridin-2-yl)piperidin-4-yl)methoxy) phenyl)-2H-benzo[d][1,3]oxathiole 3-oxide

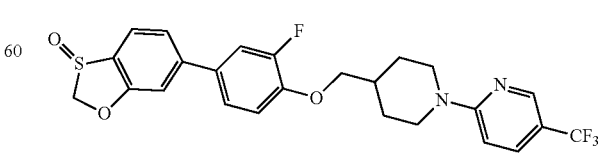

A suspension of 6-(3-fluoro-4-(piperidin-4-ylmethoxy) phenyl-2H-benzo[d][1,3]oxathiole-3-oxide hydrochloride (0.20 g, 0.55 mmol), 2-chloro-5-(trifluoromethyl)pyridine (0.11 g, 0.60 mmol) and triethylamine (0.20 g, 2.0 mmol) in dimethylformamide (10 mL) was heated at 50° C. for 3 hours. The reaction mixture was cooled to ambient temperature and diluted with water (10 mL) to form a precipitate which was filtered off and washed with cold water and hexanes. This material was subjected to column chromatography on silica gel eluting with dichloromethane to afford the title compound as a white solid 0.20 g, 71%). %). $^1$H NMR (400 MHz, DMSO-d$_6$) δ 8.41 (s, 1H), 7.92 (d, J=8.4 Hz, 1H), 7.63 (d, J=8.8 Hz, 1H), 7.40-7.30 (m, 4H), 7.05 (t, J=8.6 Hz, 1H), 6.69 (d, J=9.2 Hz, 1H), 5.55 (d, J=11.1 Hz, 1H), 5.07 (d, J=11.1 Hz, 1H), 4.51 (d, J=13.3 Hz, 2H), 3.97 (d, J=6.5 Hz, 2H), 3.01 (t, J=12.8 Hz, 2H), 2.27-2.17 (bs, 1H), 2.02 (d, J=12.7 Hz, 2H), 1.49-1.37 (m, 2H).

Example B-30: Resolution of 6-hydroxy-2H-benzo[d][1,3]oxathiole 3-oxide; (S)-6-hydroxy-2H-benzo[d][1,3]oxathiole 3-oxide and (R)-6-hydroxy-2H-benzo[d][1,3]oxathiole 3-oxide

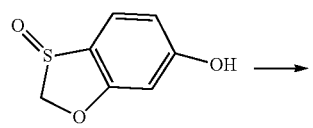

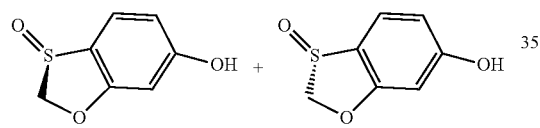

Preparative chiral resolution was carried out employing the following conditions: Shimadzu system SIL-10Ap; pump LC-20Ap x2; SPD-M20A UV detector; CBM-20A control unit; FRC-10A fraction collector; LC solution software; Preparative column: Phenomenex Lux 5u Cellulose-4 AXIA F 250×30.00; eluent: isocratic 20 mL/min hexane\isopropyl alcohol (IPA)\formic acid (HCOOH) 850/150/4 temperature 23° C.; column load 50 mg of sample (in 8 mL IPA+200 uL (HCOOH); detector set: UV 262 nm. 2 g load of 6-hydroxy-2H-benzo[d][1,3]oxathiole 3-oxide First fraction was collected from 49-56 minutes 930 mg (yield 93%; ee 99.8%) Second fraction was collected from 58-69 minutes 850 mg (yield 85%; ee 97.2%) Analytical control was carried out at analytical chromatography complex: Pump: Shimadzu LC-20; Control unit: CBM-10; autosampler: SIL-10AD; thermostat: LCT 5100; detector: Jasco model CD-2095 circular dichroism chiral detector/UV detector; column: Phenomenex Cellulose-4 4.5×50 mm 3 uM; precolumn: Phenomenex Cellulose-4 4.5×3 mm 3 uM; Software: LC Solution; eluent: isocratic 1 ml\min Hexane\IPA\HCOOH 850\150\4 23° C. with detection on UV and CD at 262 nm First enantiomer: retention time=4.92 minutes (CD negative)

Second enantiomer: retention time=5.85 minutes (CD positive)

Example B-31: (S)-3-Oxido-2H-benzo[d][1,3]oxathiol-6-yl trifluoromethanesulfonate

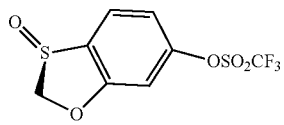

The enantiomer with a retention time of 4.92 minutes (0.25 g, 1.4 mmol) was dissolved in pyridine (20 mL) and a solution of trifluoromethanesulfonic anhydride (0.45 g, 1.6 mmol) at 0° C. was added and the mixture was stirred for 30 minutes at that temperature and then at ambient temperature overnight. Upon completion the volatiles were evaporated and a residue after evaporation was dissolved in dichloromethane (10 mL). The organic solution was consequently washed with 10% aqueous solution citric acid (10 mL), saturated sodium chloride solution (10 mL) and water (10 mL). The organic layer was dried over sodium sulfate, filtered and the filtrate was evaporated in vacuo. The residue was subjected to column chromatography on silica gel eluting with dichloromethane to afford the title compound (0.12 g, 27%) as a white solid. %). $^1$H NMR (400 MHz, DMSO-d$_6$) δ 7.99 (d, J=8.6 Hz, 1H), 7.18 (d, J=2.1 Hz, 1H), 7.13 (dd, J$_1$=2.1 Hz, J$_2$=8.6 Hz, 1H), 5.61 (d, J=11.1 Hz, 1H), 5.14 (d, J=11.1 Hz, 1H Example B-32: (S)-6-(4-((1-(5-chloropyrimidin-2-yl)piperidin-4-yl)methoxy)-3-fluorophenyl)-2H-benzo[d][1,3]oxathiole 3-oxide

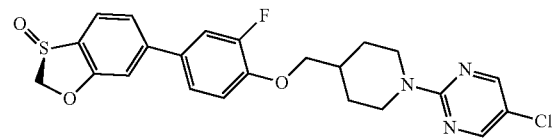 [SMILES: O=[S@@]1COc2cc(-c3ccc(OCC4CCN(c5ncc(Cl)cn5)CC4)c(F)c3)ccc21]

A solution of 5-chloro-2-(4-((2-fluoro-4-(4,4,5,5-tetramethyl-1,3,2-dioxaborolan-2-yl)phenoxy)methyl}piperidin-1-yl)pyrimidine (0.18 g, 0.4 mmol) in dioxane (30 mL) was treated with (S)-6-((trifluoromethyl)sulfonyl)-2H-benzo[d][1,3]oxathiole 3-oxide (0.12 g, 0.4 mmol) and cesium carbonate (0.3 g, 1 mmol) under argon. The reaction mixture was purged with argon and 1,1' (bisdiphenylphosphino)ferrocene dichloropalladium (II) Pd(dppf)Cl$_2$ (0.03 g, 0.03 mmol) was slowly added followed by stirring at ambient temperature for 1 hour and then at 60° C. for an additional 2 hours. Upon completion, the volatiles were evaporated in vacuo and the residue was subjected to column chromatography on silica gel eluting with dichloromethane-ether mixture (1:1) to afford the title compound (6 mg, 3%). (400 MHz, DMSO-d$_6$) δ 8.23 (s, 2H), 7.92 (d, J=8.4 Hz, 1H), 7.38-7.30 (m, 4H), 7.04 (t, J=8.3 Hz, 1H), 5.55 (d, J=11.0 Hz, 1H), 5.06 (d, J=11.0 Hz, 1H), 4.78 (d, J=13.0 Hz, 2H), 3.96 (d, J=6.0 Hz, 2H), 2.96 (t, J=12.5 Hz, 2H), 2.20 (m, 1H), 1.99 (d, J=12.3 Hz, 2H), 1.38 (m, 2H).

Example B-33: (R)-3-Oxido-2H-benzo[d][1,3]oxathiol-6-yl Trifluoromethanesulfonate

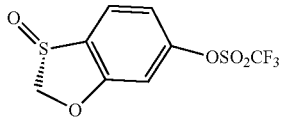

The enantiomer with a retention time of 5.85 minutes (0.25 g, 1.4 mmol) was dissolved in pyridine (20 mL) and a solution of trifluoromethanesulfonic anhydride (0.45 g, 1.6 mmol) at 0° C. was added and the mixture was stirred for 30 minutes at that temperature and then at ambient temperature overnight. Upon completion the volatiles were evaporated and a residue after evaporation was dissolved in dichloromethane (10 mL). The organic solution was consequently washed with 10% aqueous solution citric acid (10 mL), saturated sodium chloride solution (10 mL) and water (10 mL). The organic layer was dried over sodium sulfate, filtered and the filtrate was evaporated in vacuo. The residue was subjected to column chromatography on silica gel eluting with dichloromethane to afford the title compound (0.23 g, 54%) as a white solid. %). $^1$H NMR (400 MHz, DMSO-$d_6$) δ 7.99 (d, J=8.6 Hz, 1H), 7.18 (d, J=2.1 Hz, 1H), 7.13 (dd, $J_1$=2.1 Hz, $J_2$=8.6 Hz, 1H), 5.61 (d, J=11.1 Hz, 1H), 5.14 (d, J=11.1 Hz, 1H).

Example B-34: (R)-6-(4-((1-(5-chloropyrimidin-2-yl)piperidin-4-yl)methoxy)-3-fluoro phenyl)-2H-benzo[d][1,3]oxathiole-3-oxide

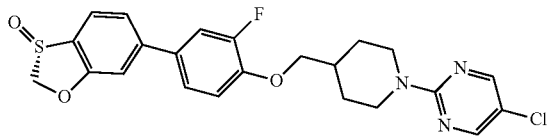 [SMILES: O=[S@]1COc2cc(-c3ccc(OCC4CCN(c5ncc(Cl)cn5)CC4)c(F)c3)ccc21]

A solution of 5-chloro-2-(4-((2-fluoro-4-(4,4,5,5-tetramethyl-1,3,2-dioxaborolan-2-yl)phenoxy)methyl}piperidin-1-yl)pyrimidine (0.34 g, 0.76 mmol) in dioxane (30 mL) was treated with (R)-6-((trifluoromethyl)sulfonyl)-2H-benzo[d][1,3]oxathiole 3-oxide (0.23 g, 0.76 mmol) and cesium carbonate (0.6 g, 2 mmol) under argon. The reaction mixture was purged with argon and 1,1' (bisdiphenylphosphino)ferrocene dichloropalladium (II) Pd(dppf)Cl$_2$ (0.06 g, 0.06 mmol) was slowly added followed by stirring at ambient temperature for 1 hour and then at 60° C. for an additional 2 hours. Upon completion, the volatiles were evaporated in vacuo and the residue was subjected to column chromatography on silica gel eluting with dichloromethane-ether mixture (1:1) to afford the title compound (6 mg, 3%). (400 MHz, DMSO-$d_6$) δ 8.23 (s, 2H), 7.92 (d, J=8.4 Hz, 1H), 7.38-7.30 (m, 4H), 7.04 (t, J=8.3 Hz, 1H), 5.55 (d, J=11.0 Hz, 1H), 5.06 (d, J=11.0 Hz, 1H), 4.78 (d, J=13.0 Hz, 2H), 3.96 (d, J=6.0 Hz, 2H), 2.96 (t, J=12.5 Hz, 2H), 2.20 (m, 1H), 1.99 (d, J=12.3 Hz, 2H), 1.38 (m, 2H).

Example B-35: 6-(4-((1-(4-Ethylpyrimidin-2-yl)piperidin-4-yl)methoxy)-3-fluorophenyl)-2H-benzo[d][1,3]oxathiole 3-oxide

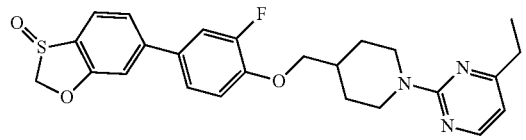 [SMILES: CCc1ccnc(N2CCC(COc3ccc(-c4ccc5c(c4)OCS5=O)cc3F)CC2)n1]

A suspension of 6-(3-fluoro-4-(piperidin-4-ylmethoxy)phenyl-2H-benzo[d][1,3]oxathiole-3-oxide hydrochloride (0.25 g, 0.69 mmol), 2-chloro-4-ethylpyrimidine (0.12 g, 0.83 mmol) and triethylamine (0.13 g, 1.04 mmol) in acetonitrile (10 mL) was heated under reflux overnight. The reaction mixture was cooled to ambient temperature and evaporated in vacuo to form an oil which was triturated with water (20 mL) to form a precipitate which was filtered off and washed with cold methanol and dried to afford the title compound as a light yellow powder (0.21 g, 65%). $^1$H NMR (400 MHz, DMSO-$d_6$) δ 8.21 (d, J=4.9 Hz, 1H), 8.07 (d, J=8.2 Hz, 1H), 7.70 (d, J=12.7 Hz, 1H), 7.63 (s, 1H), 7.60-7.48 (m, 2H), 7.28 (t, J=8.8 Hz, 1H), 6.48 (d, J=4.9 Hz, 1H), 5.64 (d, J=11.5 Hz, 1H), 5.22 (d, J=11.5 Hz, 1H), 4.75 (d, J=12.8 Hz, 2H), 4.01 (d, J=6.5 Hz, 2H), 2.89 (t, J=12.8 Hz, 2H), 2.54 (q, J=7.6 Hz, 2H), 2.18-2.02 (m, 1H), 1.85 (d, J=12.8 Hz, 2H), 1.31-1.17 (m, 5H).

Example B-36: 4-((4-(Benzo[d][1,3]oxathiol-6-yl)-2-fluorophenoxy)methyl)piperidine

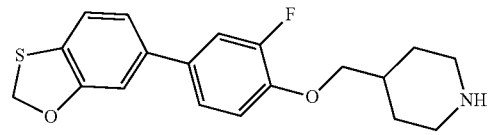 [SMILES: Fc1cc(-c2ccc3c(c2)OCS3)ccc1OCC1CCNCC1]

To a solution of 6-(3-fluoro-4-(piperidin-4-ylmethoxy)phenyl-2H-benzo[d][1,3]oxathiole-3-oxide (200 mg, 0.56 mmol) in tetrahydrofuran (20 mL) under argon atmosphere was added slowly a solution of borane-dimethylsulfide (BH$_3$*SMe$_2$) in tetrahydrofuran (1.4 mL, 2.9 mmol) and the mixture was stirred at reflux for 3 hours. The mixture was then cooled to ambient temperature and methanol (2 mL) was added dropwise, and the resulting solution was stirred at ambient temperature for 2 hours. The solvents were removed under reduced pressure and the residue was triturated with saturated aqueous solution of sodium bicarbonate. The formed precipitate was filtered off, washed with water and air-dried to give the title compound (110 mg, 57%) as a grey powder. [M+1]$^+$ 344.

Example B-37: 2-(4-((4-(Benzo[d][1,3]oxathiol-6-yl)-2-fluorophenoxy)methyl)piperidin-1-yl)-5-ethylpyrimidine

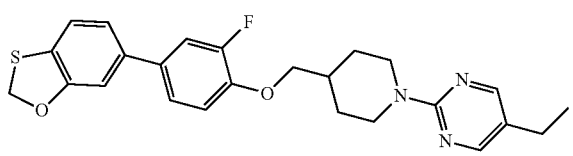 [SMILES: CCc1cnc(N2CCC(COc3ccc(-c4ccc5c(c4)OCS5)cc3F)CC2)nc1]

A solution of 4-((4-((benzo[d][1,3]oxathiol-6-yl)-2-fluorophenoxy)methyl)piperidine (0.15 g, 0.43 mmol)), 2-chloro-5-ethylpyrimidine (0.08 g, 0.6 mmol) and triethylamine (0.3 g, 3 mmol) in acetonitrile (30 mL) was stirred at reflux for 6 hours. Upon completion, the reaction mixture was allowed to come to ambient temperature and a precipitate was formed, filtered off and washed sequentially with water and with hexanes. The crude product was purified by column chromatography eluting with dichloromethane to obtain the title product (65 mg, 34%) as a white solid. $^1$H NMR (400 MHz, DMSO-$d_6$) δ 8.23 (s, 2H), 7.52 (d, J=13.1 Hz, 1H), 7.41 (d, J=8.2 Hz, 1H), 7.33 (d, J=8.2 Hz, 1H), 7.24-7.13 (m, 3H), 5.80 (s, 2H), 4.66 (d, J=12.8 Hz, 2H), 3.96 (d, J=6.5 Hz, 2H), 2.88 (t, J=12.5 Hz, 2H), 2.42 (q, J=7.6 Hz, 2H), 2.15-2.03 (bs, 1H), 1.84 (d, J=12.5 Hz, 2H), 1.29-1.17 (m, 2H), 1.12 (t, J=7.6 Hz, 3H).

Example B-38: 2-(4-((4-(Benzo[d][1,3]oxathiol-6-yl)-2-fluorophenoxy)methyl)piperidin-1-yl)-5-isopropylpyrimidine

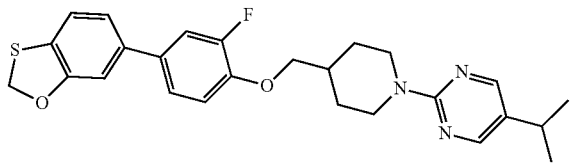 [SMILES: CC(C)c1cnc(N2CCC(COc3ccc(-c4ccc5c(c4)OCS5)cc3F)CC2)nc1]

A solution of 4-((4-((benzo[d][1,3]oxathiol-6-yl)-2-fluorophenoxy)methyl)piperidine (0.15 g, 0.43 mmol)), 2-chloro-5-(1-methylethyl)pyrimidine (80 mg, 0.5 mmol) and triethylamine (0.3 g, 3 mmol) in acetonitrile (30 mL) was stirred at reflux for 6 hours. Upon completion, the reaction mixture was allowed to cool to ambient temperature and a precipitate was formed, filtered off and washed sequentially with water and with hexanes. The crude product was purified by column chromatography eluting with dichloromethane to obtain the title product (57 mg, 27%) as a white solid. $^1$H NMR (400 MHz, DMSO-$d_6$) δ 8.27 (s, 2H), 7.52 (d, J=13.2 Hz, 1H), 7.40 (d, J=8.1 Hz, 1H), 7.33 (d, J=7.8 Hz, 1H), 7.24-7.16 (m, 3H), 5.80 (s, 2H), 4.67 (d, J=13.0 Hz, 2H), 3.97 (d, J=6.4 Hz, 2H), 2.89 (t, J=12.0 Hz, 2H), 2.80-2.71 (m, 1H), 2.15-2.05 (bs, 1H), 1.84 (d, J=11.7 Hz, 2H), 1.30-1.13 (m, 8H).

Example B-39: 2-(4-((4-(Benzo[d][1,3]oxathiol-6-yl)-2-fluorophenoxy)methyl)piperidin-1-yl)-5-methoxypyrimidine

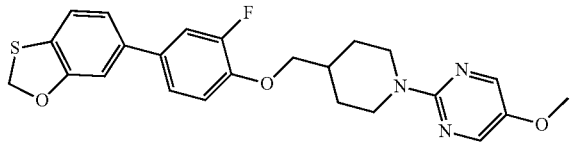 [SMILES: COc1cnc(N2CCC(COc3ccc(-c4ccc5c(c4)OCS5)cc3F)CC2)nc1]

A suspension of 4-((4-((benzo[d][1,3]oxathiol-6-yl)-2-fluorophenoxy)methyl)piperidine (155 mg, 0.45 mmol)), 2-chloro-5-methoxypyrimidine (78 mg, 0.54 mmol) and diisopropylethylamine (87 mg, 0.68 mmol) in acetonitrile (10 mL) was stirred at reflux overnight. Upon cooling, the reaction mixture was allowed to cool to ambient temperature and the solvent was removed in vacuo and the crude product was purified by column chromatography eluting with hexanes:ethyl acetate (4:1) to obtain the title product (63 mg, 31%) as a white powder. $^1$H NMR (400 MHz, DMSO-$d_6$) δ 8.19 (s, 2H), 7.52 (d, J=13.1 Hz, 1H), 7.41 (d, J=8.2 Hz, 1H), 7.33 (d, J=8.2 Hz, 1H), 7.24-7.16 (m, 3H), 5.80 (s, 2H), 4.58 (d, J=12.8 Hz, 2H), 3.96 (d, J=6.5 Hz, 2H), 3.76 (s, 3H), 2.87 (t, J=12.5 Hz, 2H), 2.15-2.03 (bs, 1H), 1.83 (d, J=12.5 Hz, 2H), 1.29-1.17 (m, 2H).

Example B-40: 1-(4-((4-(Benzo[d][1,3]oxathiol-6-yl)-2-fluorophenoxy)methyl)piperidin-1-yl)-3-methylbutan-1-one

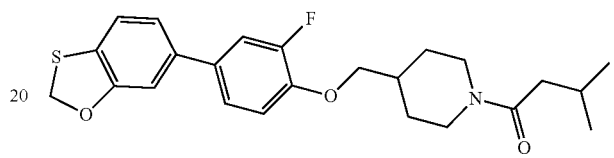

To a solution of 4-((4-((benzo[d][1,3]oxathiol-6-yl)-2-fluorophenoxy)methyl)piperidine (150 mg, 0.43 mmol) and triethylamine (300 mg, 3 mmol) in acetonitrile (30 mL) at ambient temperature was added 3-methylbutanoyl chloride (48 mg, 4 mmol) and the resulting solution was stirred for 6 hours. A precipitate was formed, filtered off and washed sequentially with water and with hexanes. The crude product was purified by column chromatography eluting with dichloromethane to obtain the title compound as a white powder (50 mg, 38%). $^1$H-NMR (400 MHz, DMSO-$d_6$) δ 7.46-7.14 (m, 3H), 7.14-6.85 (m, 3H), 5.75 (s, 2H), 5.01-4.43 (m, 1H), 4.20-3.71 (m, 3H), 3.24-2.98 (m, 1H), 2.78-2.46 (m, 1H), 2.31-2.21 (m, 2H), 2.20-2.06 (m, 2H), 2.05-1.94 (m, 1H), 1.94-1.80 (m, 1H), 1.30 (s, 2H), 1.15-0.78 (m, 6H); [M+1]$^+$ 435.5.

Example B-41: Tert-Butyl-(R)-4-((2-fluoro-4-(3-oxido-2H-benzo[d][1,3]oxathiol-6-yl)phenoxy)methyl) Piperidine-1-carboxylate

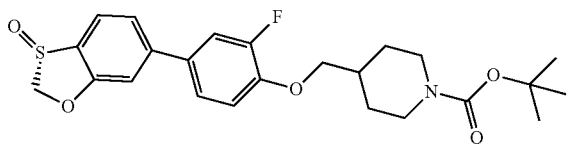 [SMILES: CC(C)(C)OC(=O)N1CCC(COc2ccc(-c3ccc4c(c3)OC[S@@]4=O)cc2F)CC1]

To a solution of tert-butyl-4-((2-fluoro-4-(4,4,5,5-tetramethyl-1,3,2-dioxoborolan-2-yl) phenoxy)methyl)piperidine-1-carboxylate (1.05 g, 2.4 mmol) in dioxane (20 mL) was added (R)-3-oxido-2H-benzo[d][1,3]oxathiol-6-yl trifluoromethanesulfonate (0.73 g, 2.4 mmol) and cesium carbonate (1.0 g, 3 mmol) and the reaction mixture was stirred at ambient temperature for 10 minutes. Then, it was purged with argon and 1,1' (bisdiphenylphosphino)ferrocene dichloropalladium (II) Pd(dppf)Cl$_2$ (0.1 g, 0.1 mmol) was added at room temperature and the resultant solution was stirred for 1 hour and then heated at 60° C. for 2 hours. After cooling, the solvents were evaporated in vacuo and the residual oil was purified by column chromatography on silica gel eluting with dichloromethane:ether mixture (1:1) to yield the title product (0.92 g, 82%) as a white solid.

¹H-NMR (400 MHz, CDCl₃): δ 7.92 (d, J=8.4 Hz, 1H), 7.38-7.29 (m, 4H), 7.04 (t, J=8.6 Hz, 1H), 5.54 (d, J=11.1 Hz, 1H), 5.06 (d, J=11.1 Hz, 1H), 4.19 (b s, 2H), 3.94 (d, J=6.5 Hz, 2H), 2.78 (t, J=12.8 Hz, 2H), 2.10-2.00 (m, 1H), 1.87 (d, J=12.8 Hz, 2H), 1.48 (s, 9H), 1.36-1.25 (m, 2H).

Example B-42: (R)-6-(3-Fluoro-4-(piperidin-4-ylmethoxy)phenyl)-2H-benzo[d][1,3]oxathiole 3-oxide

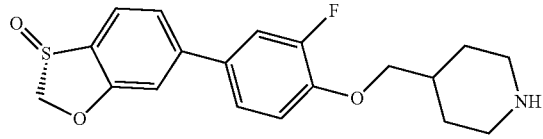 [SMILES: O=[S@]1COc2cc(-c3ccc(OCC4CCNCC4)c(F)c3)ccc21]

To a solution of tert-butyl-(R)-4-((2-fluoro-4-(3-oxido-2H-benzo[d][1.3]oxathiol-6-yl)phenoxy)methyl) piperidine-1-carboxylate (910 mg, 1.97 mmol) in methylene chloride (30 mL) was added trifluoroacetic acid (3.0 mL), and the reaction mixture was stirred at ambient temperature for 10 minutes. The solvents were removed under reduced pressure and the residue was re-dissolved in acetonitrile (2 mL) and triturated with saturated aqueous sodium bicarbonate (30 mL). A precipitate was formed, filtered off and air-dried to afford the title product (665 mg, 92%) as a white solid. LCMS [M+1]⁺ 362.1

Example B-43: Tert-Butyl-(S)-4-((2-fluoro-4-(3-oxido-2H-benzo[d][1,3]oxathiol-6-yl)phenoxy) methyl) Piperidine-1-carboxylate

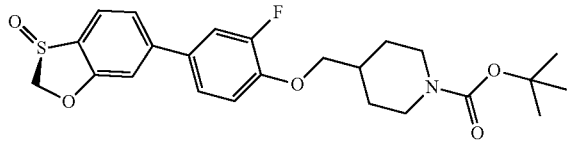 [SMILES: CC(C)(C)OC(=O)N1CCC(COc2ccc(-c3ccc4c(c3)OC[S@]4=O)cc2F)CC1]

To a solution of tert-butyl-4-((2-fluoro-4-(4,4,5,5-tetramethyl-1,3,2-dioxoborolan-2-yl) phenoxy]methyl)piperidine-1-carboxylate (1.05 g, 2.4 mmol) in dioxane (20 mL) was added (S)-3-oxido-2H-benzo[d][1,3]oxathiol-6-yl trifluoromethanesulfonate (0.73 g, 2.4 mmol) and cesium carbonate (1.0 g, 3 mmol) and the reaction mixture was stirred at ambient temperature for 10 minutes. Then, it was purged with argon and 1,1' (bisdiphenylphosphino)ferrocene dichloropalladium (II) Pd(dppf)Cl₂ (0.1 g, 0.1 mmol) was added at room temperature and the resultant solution was stirred for 1 hour and then heated at 60° C. for 2 hours. After cooling, the solvents were evaporated in vacuo and the residual oil was purified by column chromatography on silica gel eluting with dichloromethane:ether mixture (1:1) to yield the title product (0.92 g, 82%) as a white solid. ¹H-NMR (400 MHz, CDCl₃): δ 7.92 (d, J=8.4 Hz, 1H), 7.38-7.29 (m, 4H), 7.04 (t, J=8.6 Hz, 1H), 5.54 (d, J=11.1 Hz, 1H), 5.06 (d, J=11.1 Hz, 1H), 4.19 (b s, 2H), 3.94 (d, J=6.5 Hz, 2H), 2.78 (t, J=12.8 Hz, 2H), 2.10-2.00 (m, 1H), 1.87 (d, J=12.8 Hz, 2H), 1.48 (s, 9H), 1.36-1.25 (m, 2H).

Example B-44: (S)-6-(3-Fluoro-4-(piperidin-4-ylmethoxy)phenyl)-2H-benzo[d][1,3]oxathiole 3-oxide

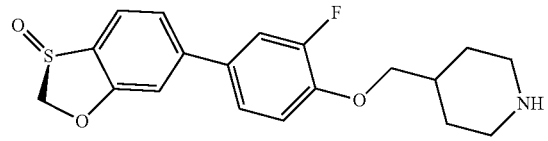 [SMILES: O=[S@@]1COc2cc(-c3ccc(OCC4CCNCC4)c(F)c3)ccc21]

To a solution of tert-butyl-(S)-4-((2-fluoro-4-(3-oxido-2H-benzo[d][1,3]oxathiol-6-yl)phenoxy]methyl} piperidine-1-carboxylate (910 mg, 1.97 mmol) in methylene chloride (30 mL) was added trifluoroacetic acid (3.0 mL), and the reaction mixture was stirred at ambient temperature for 10 minutes. The solvents were removed under reduced pressure and the residue was re-dissolved in acetonitrile (2 mL) and triturated with saturated aqueous sodium bicarbonate (30 mL). A precipitate was formed, filtered off and air-dried to afford the title compound (665 mg, 92%) as a white solid. LCMS [M+1]⁺ 362.1

Example B-45: (S)-6-(4-((1-(5-Ethylpyrimidin-2-yl) piperidin-4-yl)methoxy)-3-fluorophenyl)-2H-benzo[d][1,3]oxathiole 3-oxide

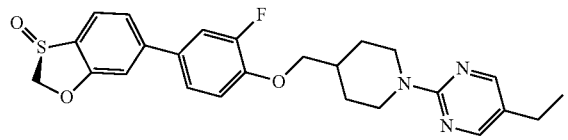 [SMILES: CCc1cnc(N2CCC(COc3ccc(-c4ccc5c(c4)OC[S@]5=O)cc3F)CC2)nc1]

A solution of (S)-4-((2-fluoro-4-piperidin-4-ylmethoxy) phenyl)-2H-benzo[d][1.3]oxathiole 3-oxide (0.27 g, 0.57 mmol)), 2-chloro-5-ethylpyrimidine (86 mg, 0.6 mmol) and triethylamine (0.23 g, 2.3 mmol) in acetonitrile (50 mL) was heated at reflux for 6 hours. Upon cooling, a precipitate was formed which was filtered off and washed sequentially with water and with hexanes and further purified by column chromatography eluting with dichloromethane to give the title product (200 mg, 75%). ¹H NMR (400 MHz, DMSO-d₆) δ 8.23 (s, 2H), 8.08 (d, J=7.9 Hz, 1H), 7.69 (d, J=12.8 Hz, 1H), 7.62 (s, 1H), 7.59-7.49 (m, 2H), 7.28 (t, J=8.9 Hz, 1H), 5.64 (d, J=11.0 Hz, 1H), 5.22 (d, J=11.0 Hz, 1H), 4.67 (d, J=12.7 Hz, 2H), 4.01 (d, J=6.1 Hz, 2H), 2.89 (t, J=12.5 Hz, 2H), 2.46-2.39 (m, 2H), 2.15-2.05 (bs, 1H), 1.84 (d, J=11.9 Hz, 2H), 1.31-1.19 (m, 2H), 1.13 (t, J=7.3 Hz, 3H).

Example B-46: (S)-6-(3-fluoro-4-((1-(5-isopropylpyrimidin-2-yl)piperidin-4-yl)methoxy)phenyl)-2H-benzo[d][1,3]oxathiole 3-oxide

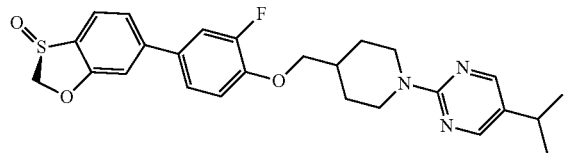 [SMILES: CC(C)c1cnc(N2CCC(COc3ccc(-c4ccc5c(c4)OC[S@]5=O)cc3F)CC2)nc1]

A solution of (S)-4-((2-fluoro-4-piperidin-4-ylmethoxy) phenyl)-2H-benzo[d][1,3]oxathiole 3-oxide (200 mg, 0.55 mmol), 2-chloro-5-isopropylpyrimidine (90 mg, 0.57 mmol) and triethylamine (0.23 g, 2.3 mmol) in dimethylformamide (10 mL) was stirred at 50° C. for 3 hours. Upon cooling, the reaction mixture was diluted with water (10 mL) a precipitate was formed which was filtered off and washed sequentially with water and with hexanes and further purified by column chromatography eluting with dichloromethane to give the title product (210 mg, 81%) as a white solid. $^1$H NMR (400 MHz, DMSO-d$_6$) δ 8.27 (s, 2H), 8.07 (d, J=8.2 Hz, 1H), 7.70 (d, J=12.2 Hz, 1H), 7.63 (s, 1H), 7.55 (d, J=8.2 Hz, 1H), 7.51 (d, J=8.2 Hz, 1H), 7.27 (t, J=8.6 Hz, 1H), 5.64 (d, J=11.9 Hz, 1H), 5.22 (d, J=11.9 Hz, 1H), 4.67 (d, J=12.8 Hz, 2H), 4.02 (d, J=5.7 Hz, 2H), 2.89 (t, J=12.5 Hz, 2H), 2.80-2.72 (m, 1H), 2.15-2.05 (bs, 1H), 1.84 (d, J=12.3 Hz, 2H), 1.31-1.20 (m, 2H), 1.18 (d, J=6.8 Hz, 6H).

Example B-47: 4-((4-Bromo-2-fluorophenoxy)methyl)piperidine Hydrochloride

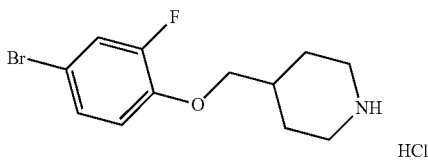 [SMILES: Fc1cc(Br)ccc1OCC1CCNCC1 ; Cl]

To a solution of tert-butyl 4-[(4-bromo-2-fluorophenoxy) methyl]piperidine-1-carboxylate (Example B-7, 6.5 g, 16.7 mmol,) in dioxane (40 mL) was added 3M solution of hydrogen chloride in dioxane (200 mL) and the mixture was stirred at ambient temperature overnight. Ether (300 mL) was then slowly added to form a precipitate which was filtered off, washed with ether and air-dried to obtain the title compound (4.7 g, 87%) as a white solid. $^1$H NMR (400 MHz, DMSO-d$_6$) δ 9.01 (br.s, 1H), 8.67 (br.s, 1H), 7.53 (dd, J=11.0, 2.3 Hz, 1H), 7.33 (d, J=8.8 Hz, 1H), 7.17 (t, J=9.0 Hz, 1H), 3.94 (d, J=6.2 Hz, 2H), 3.27 (d, J=12.8 Hz, 2H), 2.88 (q, J=12.3 Hz, 2H), 2.17-1.98 (m, 1H), 1.89 (d, J=12.5 Hz, 2H), 1.62-1.39 (m, 2H).

Example B-48: 2-(4-((4-Bromo-2-fluorophenoxy) methyl)piperidin-1-yl)-5-methoxypyrimidine

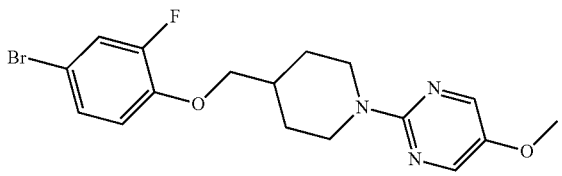 [SMILES: COc1cnc(N2CCC(COc3ccc(Br)cc3F)CC2)nc1]

To a solution of 4-((4-bromo-2-fluorophenoxy)methyl) piperidine hydrochloride (5.6 g, 17.3 mmol) in dimethylformamide (20 mL) was added 2-chloro-5-methoxypyrimidine (2.7 g, 19.0 mmol) and diisopropylethylamine (5.6 g, 43.3 mmol). The reaction mixture was stirred and heated in "CEM" microwave system (140° C., 17 hours). Upon completion, the reaction mixture was poured into water (100 mL). A precipitate was filtered, air-dried and purified by column chromatography eluting with hexanes:ethyl acetate mixture (9:1) to afford the title compound as a yellow solid (2.9 g, 42%). $^1$H NMR (400 MHz, DMSO-d$_6$) δ 8.18 (s, 2H), 7.51 (d, J=11.0 Hz, 1H), 7.31 (d, J=8.7 Hz, 1H), 7.14 (t, J=9.0 Hz, 1H), 4.56 (d, J=13.2 Hz, 2H), 3.98-3.88 (m, 2H), 3.75 (s, 3H), 2.85 (t, J=12.7 Hz, 2H), 2.15-1.92 (m, 1H), 1.80 (d, J=13.2 Hz, 2H), 1.22 (dd, J=22.1, 9.6 Hz, 2H).

Example B-49: 2-4-((2-Fluoro-4-(4,4,5,5-tetramethyl-1,3,2-dioxaborolan-2-yl) phenoxy)methyl) piperidin-1-yl)-5-methoxypyrimidine

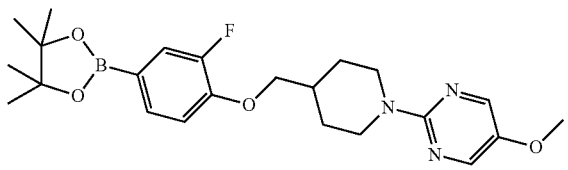

To a solution of 2-(4-((4-bromo-2-fluorophenoxy)methy]piperidin-1-yl)-5-methoxypyrimidine (2.9 g, 7.3 mmol), 4,4,4',4',5,5,5',5'-octamethyl-2,2'-bi-1,3,2-dioxaborolane (2.8 g, 11.0 mmol),) and potassium acetate (2.9 g, 29 mmol) in dioxane (15 mL) under argon atmosphere was added (bis-diphenylphosphino)ferrocene dichloropalladium (II) Pd(dppf)Cl$_2$ (0.54 g, 0.7 mmol) in dioxane (15 0 mL) was added potassium acetate (2.9 g, 29 mmol) and the reaction mixture was stirred and heated to 95° C. overnight. Upon cooling, the mixture was filtered through a pad of celite 545 and evaporated to dryness. The product was purified by column chromatography on silica gel eluting with hexanes: ethyl acetate mixture (5:1) to afford the title compound (1.9 g, 58%) as a yellow solid. $^1$H NMR (400 MHz, DMSO-d$_6$) δ 8.18 (s, 2H), 7.43 (d, J=8.0 Hz, 1H), 7.33 (d, J=11.8 Hz, 1H), 7.17 (t, J=8.2 Hz, 1H), 4.57 (d, J=13.1 Hz, 2H), 3.96 (d, J=6.3 Hz, 2H), 3.76 (s, 3H), 2.86 (t, J=12.2 Hz, 2H), 2.17-1.95 (m, 1H), 1.81 (d, J=11.9 Hz, 2H), 1.36-1.13 (m, 14H).

Example B-50: (S)-6-(3-Fluoro-4-((1-(5-methoxy-pyrimidin-2-yl)piperidin-4-yl)methoxy)phenyl)-2H-benzo[d][1,3]oxathiole 3-oxide

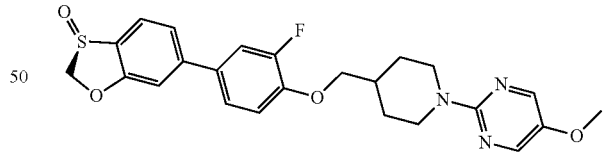

To a solution of 2-4-((2-fluoro-4-(4,4,5,5-tetramethyl-1,3,2-dioxaborolan-2-yl) phenoxy)methyl)piperidin-1-yl)-5-methoxypyrimidine (0.91 g, 2.1 mmol) in dioxane (20 mL) was added (S)-3-oxido-2H-benzo[d][1,3]oxathiol-6-yl trifluoromethanesulfonate (0.62 g, 2.1 mmol), following by the addition of a solution of potassium carbonate (0.85 g, 6.3 mmol) in water (20 mL) and 1,1' (bisdiphenylphosphino) ferrocene dichloropalladium (II) Pd(dppf)Cl$_2$ (105 mg, 0.14 mmol). The mixture was stirred and heated to 85° C. for 2 hours and upon cooling, it was evaporated to give a residue which was taken up with water (60 mL) and ethyl acetate (100 mL). The organic phase was separated, washed with brine, dried over sodium sulfate, filtered and the filtrate was evaporated to dryness. The crude product was purified by column chromatography on silica gel eluting with hexanes:ethyl acetate mixture (1:1) to obtain the title compound (0.80 g, 83%) as a white powder. ¹H NMR (400 MHz, DMSO-d$_6$) δ 8.19 (s, 2H), 8.07 (d, J=7.8 Hz, 1H), 7.69 (d, J=12.6 Hz, 1H), 7.62 (s, 1H), 7.59-7.49 (m, 2H), 7.27 (t, J=8.5 Hz, 1H), 5.64 (d, J=11.3 Hz, 1H), 5.23 (d, J=11.3 Hz, 1H), 4.58 (d, J=13.2 Hz, 2H), 4.00 (d, J=6.3 Hz, 2H), 3.77 (s, 3H), 2.87 (t, J=11.6 Hz, 2H), 2.14-2.04 (m, 1H), 1.83 (d, J=13.3 Hz, 2H), 1.30-1.20 (m, 2H).

Example B-51: (R)-6-(3-Fluoro-4-((1-(5-methoxy-pyrimidin-2-yl)piperidin-4-yl)methoxy)phenyl)-2H-benzo[d][1,3]oxathiole 3-oxide

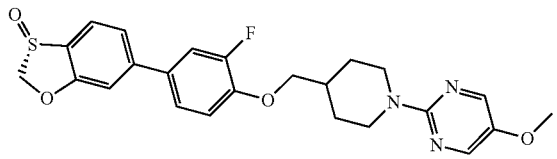 [SMILES: COc1cnc(N2CCC(COc3ccc(-c4ccc5c(c4)OC[S@@]5=O)cc3F)CC2)nc1]

A solution of (R)-4-((2-fluoro-4-piperidin-4-ylmethoxy)phenyl)-2H-benzo[d][1.3]oxathiole 3-oxide (150 mg, 0.41 mmol)), 2-chloro-5-methoxypyrimidine (72 mg, 0.49 mmol) and triethylamine (63 mg, 0.60 mmol) in acetonitrile (20 mL) was stirred at reflux for 6 hours. Upon cooling, a precipitate was formed, filtered off and washed sequentially with water and with hexanes. The crude product after washing was subjected to column chromatography eluting with dichloromethane to obtain the title compound (58 mg, 30%) as a white solid. ¹H NMR (400 MHz, DMSO-d$_6$) δ 8.19 (s, 2H), 8.07 (d, J=7.8 Hz, 1H), 7.69 (m, 1H), 7.63 (s, 1H), 7.49-7.59 (m, 2H), 7.28 (t, J=8.6 Hz, 1H), 5.63 (d, J=11.4 Hz, 1H), 5.24 (d, J=11.4 Hz, 1H), 4.56 (d, J=13.2 Hz, 2H), 4.01 (d, J=6.4 Hz, 2H), 3.76 (s, 3H), 2.88 (t, J=11.6 Hz, 2H), 2.08 (m, 1H), 1.82 (d, J=13.3 Hz, 2H), 1.18-1.32 (m, 2H).

Example B-52: (R)-6-(4-((1-(5-ethylpyrimidin-2-yl)piperidin-4-yl)methoxy)phenyl)-3-fluorophenyl)-2H-benzo[d][1,3]oxathiole 3-oxide

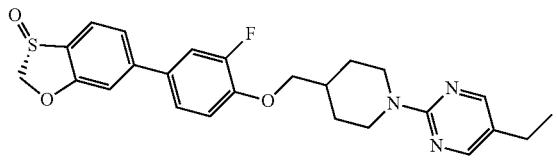 [SMILES: CCc1cnc(N2CCC(COc3ccc(-c4ccc5c(c4)OC[S@@]5=O)cc3F)CC2)nc1]

A solution of (R)-4-((2-fluoro-4-piperidin-4-ylmethoxy)phenyl)-2H-benzo[d][1.3]oxathiole 3-oxide (150 mg, 0.41 mmol)), 2-chloro-5-ethylpyrimidine (72 mg, 0.49 mmol) and triethylamine (63 mg, 0.60 mmol) in acetonitrile (20 mL) was stirred at reflux for 6 hours. Upon cooling, a precipitate was formed, filtered off and washed sequentially with water and with hexanes. The crude product after washing was subjected to column chromatography eluting with dichloromethane to obtain the title compound (78 mg, 40%) as a white solid. ¹H NMR (400 MHz, DMSO-d$_6$) δ 8.23 (s, 2H), 8.08 (d, J=7.9 Hz, 1H), 7.69 (d, J=12.8 Hz, 1H), 7.62 (s, 1H), 7.59-7.49 (m, 2H), 7.28 (t, J=8.9 Hz, 1H), 5.64 (d, J=11.0 Hz, 1H), 5.22 (d, J=11.0 Hz, 1H), 4.67 (d, J=12.7 Hz, 2H), 4.01 (d, J=6.1 Hz, 2H), 2.89 (t, J=12.5 Hz, 2H), 2.46-2.39 (m, 2H), 2.15-2.05 (b s, 1H), 1.84 (d, J=11.9 Hz, 2H), 1.31-1.19 (m, 2H), 1.13 (t, J=7.3 Hz, 3H).

Example B-53: (R)-6-(3-fluoro-4-((1-(5-isopropylpyrimidin-2-yl)piperidin-4-yl)methoxy)phenyl)-2H-benzo[d][1,3]oxathiole 3-oxide

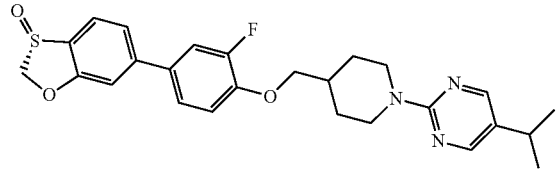 [SMILES: CC(C)c1cnc(N2CCC(COc3ccc(-c4ccc5c(c4)OC[S@@]5=O)cc3F)CC2)nc1]

A solution of (R)-4-((2-fluoro-4-piperidin-4-ylmethoxy)phenyl)-2H-benzo[d][1.3]oxathiole 3-oxide (150 mg, 0.41 mmol)), 2-chloro-5-ethylpyrimidine (72 mg, 0.49 mmol) and triethylamine (63 mg, 0.60 mmol) in acetonitrile (20 mL) was stirred at reflux for 6 hours. Upon cooling, a precipitate was formed, filtered off and washed sequentially with water and with hexanes. The crude product after washing was subjected to column chromatography eluting with dichloromethane to obtain the title compound (54 mg, 27%) as a white solid. ¹H NMR (400 MHz, DMSO-d$_6$) δ 8.27 (s, 2H), 8.07 (d, J=8.2 Hz, 1H), 7.70 (d, J=12.2 Hz, 1H), 7.63 (s, 1H), 7.55 (d, J=8.2 Hz, 1H), 7.51 (d, J=8.2 Hz, 1H), 7.27 (t, J=8.6 Hz, 1H), 5.64 (d, J=11.9 Hz, 1H), 5.22 (d, J=11.9 Hz, 1H), 4.67 (d, J=12.8 Hz, 2H), 4.02 (d, J=5.7 Hz, 2H), 2.89 (t, J=12.5 Hz, 2H), 2.80-2.72 (m, 1H), 2.15-2.05 (bs, 1H), 1.84 (d, J=12.3 Hz, 2H), 1.31-1.20 (m, 2H), 1.18 (d, J=6.8 Hz, 6H).

Example B-54: tert-Butyl 4-(((5-bromopyrimidin-2-yl)oxy)methyl)piperidine-1-carboxylate

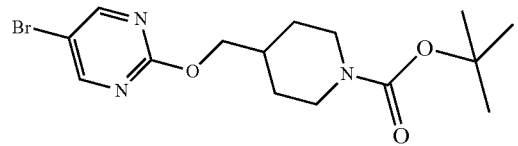 [SMILES: CC(C)(C)OC(=O)N1CCC(COc2ncc(Br)cn2)CC1]

To a mixture of tert-butyl 4-(hydroxymethyl)piperidine-1-carboxylate (18.4 g, 85 mmol) and 5-bromo-2-chloropyrimidine (15.0 g, 77 mmol) in tetrahydrofuran (200 mL) was added a suspension (60%) of sodium hydride (3.07 g, 128 mmol) in mineral oil and the resulting mixture was stirred under argon at 70° C. for 16 hours. Upon completion ethanol (15 mL) was slowly added to the reaction mixture and the reaction mixture was diluted with ethyl acetate (200 mL) and washed with brine (100 mL). The organic phase was separated, dried over magnesium sulfate, filtered and the filtrate was evaporated under reduced pressure. The residue after evaporation was subjected to column chromatography eluting with hexanes-ethyl acetate mixture 5:1 by volume to afford 15.13 g (52.4%) of the title compound as a white powder. The product was used in the next step without further purification.

Example B-55: tert-Butyl 4-(((5-(4,4,5,5-tetramethyl-1,3,2-dioxaborolan-2-yl)pyrimidin-2-yl)oxy)methyl)piperidine-1-carboxylate

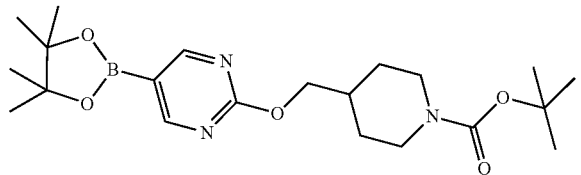 [SMILES: CC(C)(C)OC(=O)N1CCC(COc2ncc(B3OC(C)(C)C(C)(C)O3)cn2)CC1]

A mixture of tert-butyl 4-(((5-bromopyrimidin-2-yl)oxy)methyl)piperidine-1-carboxylate (11.0 g, 30 mmol), 4,4,4',4',5,5,5',5'-octamethyl-2,2'-bi-1,3,2-dioxoborolane (7.5 g, 30 mmol) and 1,1' (bisdiphenylphosphino)ferrocene dichloropalladium (II) Pd(dppf)Cl$_2$ (1.0 g, 1.3 mmol) and potassium acetate (8.7 g, 09 mmol) in acetonitrile (300 mL) was stirred under argon at 70° C. for 16 hours. Upon cooling, the reaction mixture was diluted with ethyl acetate (200 mL) and washed with brine (100 mL). The organic phase was separated, dried over magnesium sulfate, filtered and the filtrate was evaporated under reduced pressure. The residue after evaporation was subjected to column chromatography eluting with hexanes-ethyl acetate mixture 8:1 by volume to afford the title compound (4.5 g, 36.4%) as a white powder. $^1$H NMR (400 MHz, CDCl$_3$) δ 8.81 (s, 2H), 1.27 (m, 2H), 4.26 (s, J=6.7 Hz, 2H), 4.14 (m, 2H), 2.74 (t, J=12.9 Hz, 2H), 2.02 (m, 1H), 1.84 (d, J=13.2 Hz, 2H), 1.46 (s, 9H), 1.35 (s, 12H).

Example B-56: Tert-Butyl (R)-4-(((5-(3-oxido-2H-benzo[d][1,3]oxathiol-6-yl)pyrimidin-2-yl)oxy)methyl)piperidine-1-carboxylate

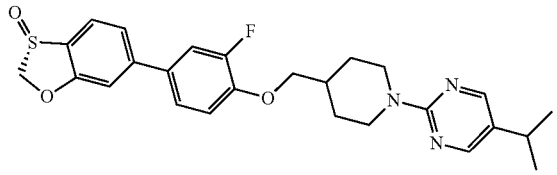 [SMILES: CC(C)c1cnc(N2CCC(COc3ccc(-c4ccc5c(c4)OC[S@@]5=O)cc3F)CC2)nc1]

A mixture tert-butyl 4-(((5-(4,4,5,5-tetramethyl-1,3,2-dioxaborolan-2-yl)pyrimidin-2-yl)oxy)methyl)piperidine-1-carboxylate (420 mg, 1 mmol), (R)-3-oxido-2H-benzo[d][1,3]oxathiol-6-yl trifluoromethanesulfonate (300 mg, 1.0 mmol), potassium carbonate (820 mg, 6.0 mmol) and 1,1' (bisdiphenylphosphino)ferrocene dichloropalladium (II) Pd(dppf)Cl$_2$ (70 mg, 0.1 mmol) in water-dioxane (1:1) mixture (30 mL) was stirred under argon at ambient temperature for 1 hour. A precipitate was formed, filtered off and purified by column chromatography on silica gel eluting with dichloromethane to afford the crude product which was further dissolved in dioxane (30 mL) and stirred with Lewatit mono plus SP-112 resin (500 mg) for 2 hours. After filtration the solvent was distilled off to afford the title product (445 mg, 99%) as a white solid. $^1$H NMR (400 MHz, DMSO-d$_6$) δ 9.01 (s, 2H), 8.16 (d, J=8.1 Hz, 1H), 7.75 (d, J=1.2 Hz, 1H), 7.59 (dd, J=8.1, 1.5 Hz, 1H), 5.67 (d, J=11.4 Hz, 1H), 5.24 (d, J=11.5 Hz, 1H), 4.24 (d, J=6.5 Hz, 2H), 3.99 (m, 2H), 2.74 (m, 2H), 1.99 (m, 1H), 1.73 (d, J=12.6 Hz, 2H), 1.40 (s, 9H), 1.11-1.24 (br m, 2H).

Example B-57: (R)-6-(2-(Piperidin-4-ylmethoxy)pyrimidin-5-yl)-2H-benzo[d][1,3]oxathiole 3-oxide

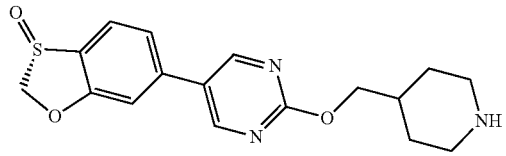 [SMILES: O=[S@]1COc2cc(-c3cnc(OCC4CCNCC4)nc3)ccc21]

To a solution of tert-butyl (R)-4-(((5-oxido-2H-benzo[d][1,3]oxathiol-6-yl]pyrimidin-2-yl}oxy)methyl)piperidine-1-carboxylate (445 mg, 1 mmol) in dichloromethane (50 mL) was added trifluoroacetic acid (25 mL). The mixture was stirred at ambient temperature for 7 minutes. Then, the reaction mixture was evaporated to dryness and to the residue was added a solution of saturated potassium carbonate. A precipitated was formed, filtered and air-dried to afford the title compound (340 mg, 99%). as a white solid: $^1$H-NMR (400 MHz, CDCl$_3$) δ 8.74 (s, 2H), 7.99 (d, J=8.1, 1H), 7.31-7.41 (m, 3H), 5.57 (d, J=10.9 Hz, 1H), 5.08 (d, J=11.0 Hz, 1H), 4.28 (d, J=6.4 Hz, 2H), 3.17 (d, J=8.4 Hz, 2H), 2.70 (m, 2H), 2.05 (m, 1H), 1.89 (d, J=13.1, 2H), 1.29-1.45 (br. m, 2H).

Example B-58: (R)-6-(2-((1-(5-Chloropyridin-2-yl)piperidin-4-yl)methoxy)pyrimidin-5-yl)-2H-benzo[d][1,3]oxathiole 3-oxide

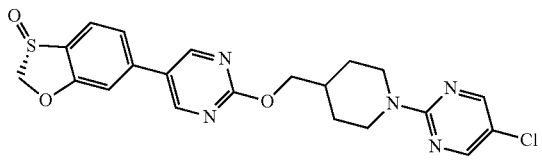 [SMILES: O=[S@]1COc2cc(-c3cnc(OCC4CCN(c5ncc(Cl)cn5)CC4)nc3)ccc21]

To a suspension of (R)-6-(2-(piperidin-4-ylmethoxy)pyrimidin-5-yl)-2H-benzo[d][1,3]oxathiole 3-oxide (346 mg, 1.0 mmol) and 2,5-dichloropyrimidine (193 mg, 1.3 mmol) in acetonitrile (20 mL) was added triethylamine (0.3 g, 3.0 mmol) and the mixture was heated under reflux overnight. The solvent was removed under reduced pressure and the residue was triturated with water. A solid precipitate was formed, filtered off, washed with ether (10 mL) and air-dried to afford the title compound (50 mg, 11%) as a white powder. $^1$H NMR (400 MHz, DMSO-d$_6$) δ 9.02 (s, 2H), 8.40 (s, 2H), 8.15 (d, J=7.9 Hz, 1H), 7.76 (s, 1H), 7.59 (d, J=7.9 Hz, 1H), 5.65 (d, J=11.2 Hz, 1H), 5.25 (d, J=11.2 Hz, 1H), 4.62 (d, J=12.5 Hz, 2H), 4.27 (d, J=56.0 Hz, 2H), 2.95 (m, 2H), 2.15 (m, 1H), 2.15 (d, J=13.6 Hz, 2H), 1.17-1.32 (br. m, 2H).

Example B-59: (S)-6-(4-((1-(5-Chloropyrimidin-2-yl)piperidin-4-yl)methoxy)-3-fluorophenyl)-2H-benzo[d][1,3]oxathiole 3-oxide

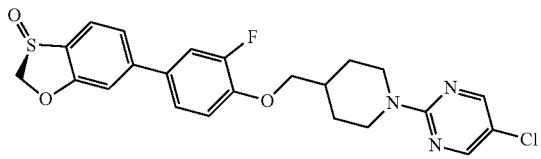 [SMILES: O=[S@@]1COc2cc(-c3ccc(OCC4CCN(c5ncc(Cl)cn5)CC4)c(F)c3)ccc21]

A solution of 5-chloro-2-(4-((2-fluoro-4-(4,4,5,5-tetramethyl-1,3,2-dioxaborolan-2-yl)phenoxy)methyl}piperidin-1-yl)pyrimidine (3.67 g, 14.9 mmol) was dissolved in a mixture of water:dioxane (150 mL, 1:1) was added (S)-3-oxido-2H-benzo[d][1,3]oxathiol-6-yl trifluoromethanesulfonate (3.75 g, 12.4 mmol) followed by sodium carbonate (3.94 g, 37.2 mmol). The reaction mixture was purged with argon and 1,1' (bisdiphenylphosphino)ferrocene dichloropalladium (II) Pd(dppf)Cl$_2$ (0.44 g, 0.6 mmol) was then slowly added and it was stirred at ambient temperature for 1 hour and then at 60° C. for 2 hours. After cooling, the solvent was evaporated in vacuo and the residue was purified by column chromatography on silica gel, eluting with a mixture of ethyl acetate:ether (1:1) to give the title product (3.8 g. 64.5%) as a white solid. $^1$H-NMR (400 MHz, DMSO-d$_6$) δ 8.40 (s, 2H), 8.08 (d, J=8.1 Hz, 1H), 7.69 (d, J=12.9 Hz, 1H), 7.6-7.52 (m, 1H), 7.26 (t, J=8.6 Hz, 1H), 5.64 (d, J=11.4 Hz, 1H), 5.23 (d, J=11.4 Hz, 1H), 4.62 (d, J=12.9 Hz, 2H), 4.01 (d, J=6.1 Hz, 2H), 2.98 (m, 2H), 2.13 (m, 1H), 1.86 (d, J=12.2 Hz, 2H), 1.27 (m, 2H).

Example B-60: Tert-Butyl(S)-4-(((5-(3-oxido-2H-benzo[d][1,3]oxathiol-6-yl)pyrimidin-2-yl)oxy)methyl)piperidine-1-carboxylate

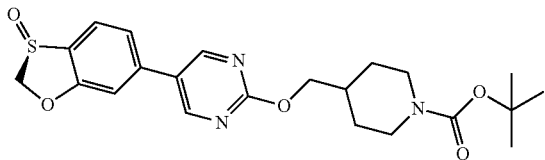 [SMILES: CC(C)(C)OC(=O)N1CCC(COc2ncc(-c3ccc4c(c3)OC[S@]4=O)cn2)CC1]

A suspension of tert-butyl 4-(((5-(4,4,5,5-tetramethyl-1,3,2-dioxaborolan-2-yl)pyrimidin-2-yl)oxy)methyl)piperidine-1-carboxylate (420 mg, 1.0 mmol), (S)-3-oxido-2H-benzo[d][1,3]oxathiol-6-yl trifluoromethanesulfonate (0.3 g, 1.0 mmol), potassium carbonate (820 mg, 6.0 mmol) and 1,1' (bisdiphenylphosphino)ferrocene dichloropalladium (II) Pd(dppf)Cl$_2$ (70 mg, 0.1 mmol) in a (30 mL) water-dioxane mixture (1:1) was stirred under argon at ambient temperature for 1 hour. A precipitate was formed, filtered off and purified by column chromatography on silica gel eluting with dichloromethane to afford crude product. This material was then dissolved in dioxane (30 mL) and stirred with Lewatit mono plus SP-112 resin (500 mg) for 2 hours. After filtration, the solvents were distilled off to afford the title compound (445 mg, 99%) as a white solid. $^1$H-NMR (400 MHz, DMSO-d$_6$) δ 9.01 (s, 2H), 8.16 (d, J=8.1 Hz, 1H), 7.75 (d, J=1.22 Hz, 1H), 7.59 (dd, J=8.1, 1.5 Hz, 1H), 5.67 (d, J=11.4 Hz, 1H), 5.24 (d, J=11.5 Hz, 1H), 4.24 (d, J=6.5 Hz, 2H), 3.99 (m, 2H), 2.74 (m, 2H), 1.99 (m, 1H), 1.73 (d, J=12.6 Hz, 2H), 1.40 (s, 9H), 1.11-1.24 (br. m, 2H).

Example B-61: (S)-6-(2-(Piperidin-4-ylmethoxy)pyrimidin-5-yl)-2H-benzo[d][1,3]oxathiole 3-oxide

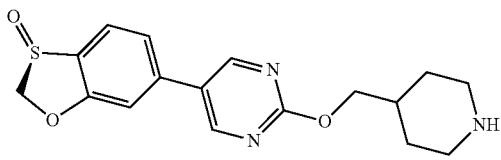 [SMILES: O=[S@@]1COc2cc(-c3cnc(OCC4CCNCC4)nc3)ccc21]

To a solution of tert-butyl (S)-4-((2-fluoro-4-(3-oxido-2H-benzo[d][1,3]oxathiol-6-yl)pyrimidin-2-yl)oxy)methyl)piperidine-1-carboxylate (0.45 g, 1.0 mmol) in dichloromethane (50 mL) was treated with trifluoroacetic acid (25 mL). The mixture was stirred at ambient temperature for 10 minutes and then it was evaporated in vacuo. The residue was poured into an aqueous solution of saturated sodium carbonate. The solid material was filtered and air-dried to afford the title compound (0.34 g, 99%) as a white solid. $^1$H-NMR (400 MHz, CDCl$_3$) δ 8.74 (s, 2H), 7.99 (d, J=8.1 Hz, 1H), 7.31-7.41 (m, 3H), 5.57 (d, J=10.9 Hz, 1H), 5.08 (d, J=11.0 Hz, 1H), 4.28 (d, J=6.4 Hz, 2H), 3.17 (d, J=8.4 Hz, 2H), 2.70 (m, 2H), 2.05 (m, 1H), 1.89 (d, J=13.1 Hz, 2H), 1.29-1.45 (br. m, 2H).

Example B-62: (S)-6-(2-((1-(5-Chloropyrimidin-2-yl)piperidin-4-yl)methoxy)pyrimidin-5-yl)-2H-benzo[d][1,3]oxathiole 3-oxide

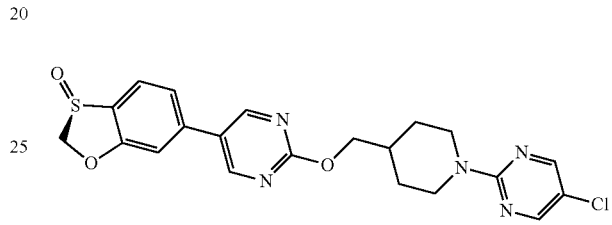

To a suspension of (S)-6-(2-piperidin-4-ylmethoxy)pyrimidin-5-yl)-2H-benzo[d][1,3]oxathiole 3-oxide (346 mg, 1.0 mmol) and 2,5-dichloropyrimidine (193 mg, 1.3 mmol) in acetonitrile (20 mL) was added triethylamine (0.3 g, 3.0 mmol) and the mixture was heated under reflux overnight. The solvent was removed under reduced pressure and the residue was triturated with water. A solid precipitate was formed, filtered off, washed with diethyl ether (10 mL) and air-dried to afford the title compound (15 mg, 3.3%) as a white powder. $^1$H-NMR (400 MHz, DMSO-d$_6$) δ 9.02 (s, 2H), 8.40 (s, 2H), 8.15 (d, J=7.9 Hz, 1H), 7.76 (s, 1H), 7.59 (d, J=7.9 Hz, 1H), 5.65 (d, J=11.2 Hz, 1H), 5.25 (d, J=11.2 Hz, 1H), 4.62 (d, J=12.5 Hz, 2H), 4.27 (d, J=6.0 Hz, 2H), 2.95 (m, 2H), 2.15 (m, 1H), 2.15 (d, J=13.6 Hz, 2H), 1.17-1.32 (br. m, 2H).

Example B-63: Tert-Butyl-(R)-3-(methylsulfonyl)oxy)methyl)pyrrolidine-1-carboxylate

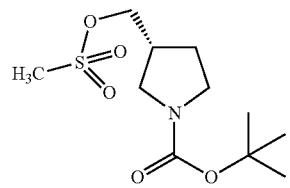 [SMILES: CC(C)(C)OC(=O)N1CC[C@@H](COS(C)(=O)=O)C1]

To a solution of tert-butyl (R)-3-(hydroxymethyl)pyrrolidine-1-carboxylate (0.4 g, 2.0 mmol) and triethylamine (0.55 mL, 4.0 mmol) in methylene chloride (15 mL) at 0° C. was dropwise added methanesulfonyl chloride (0.25 mL, 2.2 mmol). The reaction mixture was stirred at ambient temperature for 4 hours and then washed sequentially with 0.1N hydrogen chloride and brine. The organic layer was dried over Na$_2$SO$_4$ filtered, and concentrated in vacuo to yield 2.5 g (90%) of the title product as an oil. [M+1]$^+$ 280.

Example B-64: 6-(3-Fluoro-4-hydroxyphenyl)-2H-benzo[d][1,3]oxathiole 3-oxide

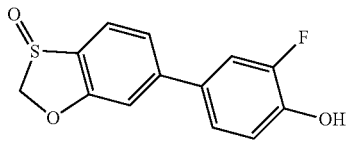 [SMILES: O=S1COc2cc(-c3ccc(O)c(F)c3)ccc21]

To a suspension of 3-oxido-2H-benzo[d][1,3]oxathiol-6-yl trifluoromethanesulfonate (3.1 g, 10.3 mmol), 2-(2-fluorophenyl)-4,4,5,5-tetramethyl-1,3,2-dioxaborolan-2-yl)phenol (2.4 g, 10.3 mmol) and 2M solution of sodium carbonate (16 mL, 30.9 mmol) in dioxane (50 mL) was added slowly 1,1′ (bisdiphenylphosphino)ferrocene dichloropalladium (II) (Pd(dppf)Cl$_2$ (375 mg, 0.52 mmol) under argon. The mixture was stirred at 50° C. overnight, cooled to ambient temperature, and then dioxane was removed under reduced pressure. The residue was acidified with 1N HCl to pH 4 to form a precipitate which was filtered off, washed with water and air-dried to give 1.5 g (55%) of title compound as a brown powder. $^1$H-NMR (400 MHz, DMSO-d$_6$):) δ 10.17 (br.s, 1H), 8.06 (d, J=8.2 Hz, 1H), 7.66-7.56 (m, 2H), 7.50-7.41 (m, 2H), 7.05 (t, J=8.7 Hz, 1H), 5.64 (d, J=11.5 Hz, 1H), 5.22 (d, J=11.5 Hz, 1H).

Example B-65: Tert-Butyl (3R)-3-((2-fluoro-4-(3-oxido-2H-benzo[d][1,3]oxathiol-6-yl)phenoxy)methyl) pyrrolidine-1-carboxylate

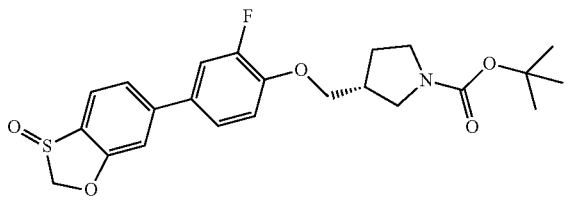 [SMILES: CC(C)(C)OC(=O)N1CC[C@@H](COc2ccc(-c3ccc4c(c3)OCS4=O)cc2F)C1]

To a stirred suspension of 6-(3-fluoro-4-hydroxyphenyl)-2-benzo[d][1,3]oxathiole 3-oxide (525 mg, 2.0 mmol) and potassium carbonate (550 mg, 4.0 mmol) in dimethylformamide (20 mL) was added tert-butyl-(R)-3-((methylsulfonyl)oxy)methyl)pyrrolidine-1-carboxylate (555 mg, 2.0 mmol) and the mixture was heated at 100° C. overnight. The reaction mixture was then cooled to ambient temperature, and the volatile compounds were removed under reduced pressure. The residue was purified by column chromatography on silica gel eluting with ethyl acetate to afford the title compound (510 mg, 57%) as a white solid. $^1$H-NMR (400 MHz, DMSO-d$_6$) δ 8.08 (d, J=8.2 Hz, 1H), 7.71 (d, J=12.6 Hz, 1H), 7.63 (s, 1H), 7.57 (d, J=8.7 Hz, 1H), 7.52 (d, J=8.2 Hz, 1H), 7.30 (t, J=8.7 Hz, 1H), 5.64 (d, J=11.5 Hz, 1H), 5.23 (d, J=11.5 Hz, 1H), 4.17-4.04 (m, 2H), 3.56-3.06 (m, 4H), 2.75-2.59 (m, 1H), 2.09-1.95 (m, 1H), 1.81-1.64 (m, 1H), 1.40 (s, 9H).

Example B-66: 6-(3-Fluoro-4(((R)-pyrrolidin-3-yl)methoxy)phenyl)-2H-benzo[d][1,3]oxathiole 3-oxide

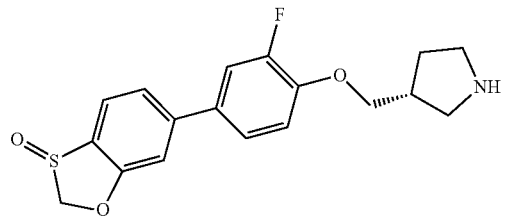 [SMILES: O=S1COc2cc(-c3ccc(OC[C@@H]4CCNC4)c(F)c3)ccc21]

Trifluoroacetic acid ((3 mL) was added to a solution of tert-butyl (3R)-3-([2-fluoro-4-(3-oxido-2H-benzo[d][1,3]oxathiol-6-yl)phenoxy)methyl) pyrrolidine-1-carboxylate (200 mg, 0.4 mmol) in dichloromethane (10 mL) and the mixture was stirred at ambient temperature for 10 minutes. The solvents were removed under reduced pressure and the residue was triturated with 10% aqueous solution of sodium bicarbonate. A precipitate was formed, filtered off and air-dried to afford the title product as a white solid (155 mg, 98%). H-NMR (400 MHz, DMSO-d$_6$) δ 8.08 (d, J=8.2 Hz, 1H), 7.71 (d, J=12.6 Hz, 1H), 7.63 (s, 1H), 7.57 (d, J=8.7 Hz, 1H), 7.52 (d, J=8.2 Hz, 1H), 7.30 (t, J=8.7 Hz, 1H), 5.64 (d, J=11.5 Hz, 1H), 5.23 (d, J=11.5 Hz, 1H), 4.13-3.94 (m, 2H), 3.37-2.66 (m, 5H), 2.05-1.77 (m, 1H), 1.72-1.35 (m, 1H)

Example B-67: 6-(4-(((R)-1-(5-Ethylpyrimidin-2-yl)pyrrolidin-3-yl)methoxy)-3-fluorophenyl)-2H-benzo[d][1,3]oxathiole 3-oxide

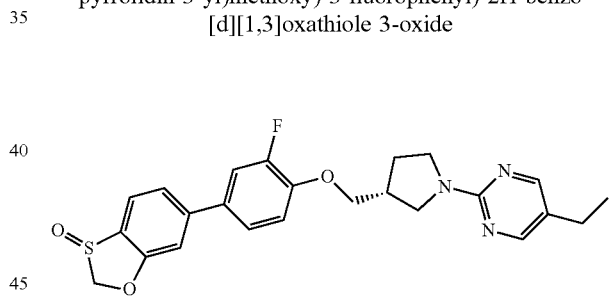

A suspension of 6-(3-fluoro-4-(((R)-pyrrolidin-3-yl)methoxy)phenyl)-2H-benzo[d][1,3]oxathiole 3-oxide (155 mg, 0.45 mmol) and 2-chloro-5-ethylpyrimidine (76 mg, 0.54 mmol) and triethylamine (87 mg, 0.67 mmol) in acetonitrile (10 mL) was heated under reflux overnight. The volatile compounds were removed under reduced pressure and the residue was triturated with water (20 mL). A solid was formed, filtered off, washed with methanol (10 mL) and air-dried to afford the title compound (138 mg, 68%) as a light yellow powder. $^1$H-NMR (400 MHz, DMSO-d$_6$) δ 8.22 (s, 2H), 8.08 (d, J=8.2 Hz, 1H), 7.71 (d, J=12.6 Hz, 1H), 7.63 (s, 1H), 7.57 (d, J=8.7 Hz, 1H), 7.52 (d, J=8.2 Hz, 1H), 7.31 (t, J=8.7 Hz, 1H), 5.64 (d, J=11.5 Hz, 1H), 5.22 (d, J=11.5 Hz, 1H), 4.21-4.09 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example B-68: (R)-3-((4-Benzo[d][1,3]oxathiol-6-yl)-2-fluorophenoxy)methyl)pyrrolidine

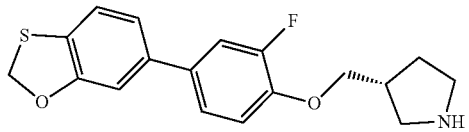 [SMILES: Fc1cc(-c2ccc3c(c2)OCS3)ccc1OC[C@@H]1CCNC1]

To a solution of 6-fluoro-4-(((R)-pyrrolidin-3-yl)methoxy)phenyl-2H-benzo[d][1,3]oxathiole 3-oxide (200 mg, 0.58 mmol) in tetrahydrofuran (20 mL) under argon atmosphere was added a solution of borane-dimethylsulfide (BH$_3$*SMe$_2$) in tetrahydrofuran (1.4 mL, 2.9 mmol) and the mixture was stirred at reflux for 3 hours. After the reaction was complete, the mixture was cooled to ambient temperature and methanol (2 mL) was added dropwise, and the resulting mixture was stirred at ambient temperature for 2 hours. The solvents were then removed under reduced pressure and the residue was triturated with saturated aqueous solution of sodium bicarbonate to form a precipitate which was filtered off, washed with water and air-dried to give the title compound (110 mg, 57%) as a grey powder. [M+1]$^+$ 332

Example B-69: (R)-2-(3-((4-benzo[d][1,3]oxathiol-6-yl)-2-fluorophenoxy)methyl) pyrrolidin-1-yl)-5-ethylpyrimidine

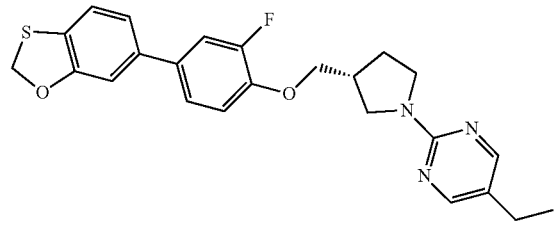 [SMILES: CCc1cnc(N2CC[C@@H](COc3ccc(-c4ccc5c(c4)OCS5)cc3F)C2)nc1]

To a suspension of (R)-3-((4-benzo[d][1.3]oxathiol-6-yl)-2-fluorophenoxy]methyl}pyrrolidine (134 mg, 0.40 mmol) and 2-chloro-5-ethylpyrimidine (69 mg, 0.48 mmol) in acetonitrile (10 mL) was added triethylamine (78 mg, 0.60 mmol) and the mixture was heated under reflux overnight. The volatile compounds were removed under reduced pressure and the residue was purified by column chromatography on silica gel eluting with chloroform:methanol mixture (40:1) to give the title compound as a white powder (62 mg, 35%). $^1$H-NMR (400 MHz, DMSO-d$_6$) δ 8.21 (s, 2H), 7.53 (d, J=12.7 Hz, 1H), 7.41 (d, J=8.6 Hz, 1H), 7.33 (d, J=7.7 Hz, 1H), 7.28-7.16 (m, 3H), 5.80 (s, 1H), 4.20-4.06 (m, 2H), 3.75-3.58 (m, 2H), 3.53-3.33 (m, 2H), 2.84-2.72 (m, 1H), 2.42 (q, J=7.5 Hz, 2H), 2.21-2.10 (m, 1H), 1.92-1.80 (m, 1H), 1.12 (t, J=7.5 Hz, 3H).

Example B-70: Tert-Butyl-(S)-3-((methylsulfonyl)oxy)methyl)pyrrolidine-1-carboxylate

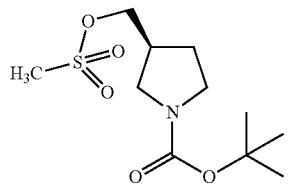 [SMILES: CC(C)(C)OC(=O)N1CC[C@H](COS(C)(=O)=O)C1]

To a solution of tert-butyl (S)-3-(hydroxymethyl)pyrrolidine-1-carboxylate (2.0 g, 9.9 mmol) and triethylamine (2.8 mL, 19.8 mmol) in methylene chloride (50.0 mL) at 0° C. was dropwise added methanesulfonyl chloride (0.85 mL, 10.9 mmol). The reaction mixture was stirred at ambient temperature for 4 hours and then washed sequentially with 0.1 N hydrogen chloride and brine. The organic layer was dried over Na$_2$SO$_4$ filtered, and concentrated in vacuo to yield 2.5 g (90%) of the title product as an oil. [M+1]$^+$ 280.

Example B-71: Tert-Butyl-(S)-3-((4-bromo-2-fluorophenoxy)methyl)pyrrolidine-1-carboxylate

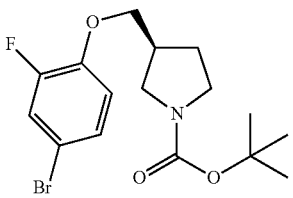 [SMILES: CC(C)(C)OC(=O)N1CC[C@H](COc2ccc(Br)cc2F)C1]

A solution of tert-butyl-(S)-3-((methylsulfonyl)oxy)methyl)pyrrolidine-1-carboxylate (2.2 g, 7.9 mmol), 4-bromo-2-fluorophenol (1.8 g, 9.5 mmol) and potassium carbonate (2.2 g, 15.8 mmol) in dimethylformamide (100 mL) was stirred at 100° C. overnight. After cooling to ambient temperature, the solvent was removed under reduced pressure. The residue was treated with acetonitrile (100 mL) and the resultant suspension was filtered through a pad of celite. The filtrate was evaporated to dryness and the residue was treated with water (50 mL). The mixture was extracted with ethyl acetate (2×50 mL), dried over sodium sulfate and filtered. The filtrate was evaporated, and purified by chromatography on a silica gel pad (3 cm) eluting with a mixture of hexanes:ethyl acetate (4:1) to give the title product (2.9 g, 98%) as alight yellow oil. $^1$H-NMR (400 MHz, DMSO-d$_6$,) δ 7.52 (d, J=8.7 Hz, 1H), 7.32 (d, J=8.7 Hz, 1H), 7.16 (t, J=8.7 Hz, 1H), 4.08-3.96 (m, 2H), 3.56-3.06 (m, 4H), 2.75-2.59 (m, 1H), 2.09-1.95 (m, 1H), 1.81-1.64 (m, 1H), 1.40 (s, 9H).

Example B-72: (S)-3-((4-Bromo-2-fluorophenoxy)methyl)pyrrolidine Hydrochloride

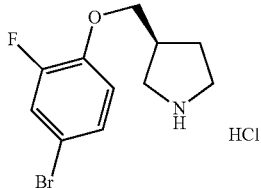 [SMILES: Fc1cc(Br)ccc1OC[C@H]1CCNC1 ; Cl]

To a stirred solution of tert-butyl-(S)-3-((4-bromo-2-fluorophenoxy)methyl)pyrrolidine-1-carboxylate (2.9 g, 7.7 mmol) in dioxane (30 mL) was added 3M solution of hydrogen chloride in dioxane (10 mL) and the mixture was stirred at 40° C. overnight. Upon completion dioxane was evaporated to the residual volume of 10 mL, and diethyl ether (150 mL) was added. A precipitate was formed, stirred for 20 minutes then, filtered off and air-dried to give the title product (1.7 g, 71%). as a white powder. $^1$H-NMR (400 MHz, DMSO-$d_6$,) δ 9.48 (br.s, 2H), 7.52 (d, J=8.7 Hz, 1H), 7.32 (d, J=8.7 Hz, 1H), 7.16 (t, J=8.7 Hz, 1H), 4.15-4.03 (m, 2H), 3.40-3.10 (m, 3H), 3.03-2.94 (m, 1H), 2.80-2.66 (m, 1H), 2.15-2.02 (m, 1H), 1.81-1.67 (m, 1H).

Example B-73: (S)-2-(3-((4-Bromo-2-fluorophenoxy)methyl]pyrrolidin-1-yl)-5-ethylpyrimidine

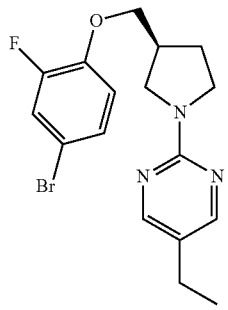 [SMILES: CCc1cnc(N2CC[C@H](COc3ccc(Br)cc3F)C2)nc1]

A mixture of (S)-3-((4-bromo-2-fluorophenoxy)methyl)pyrrolidine hydrochloride (1.70 g, 5.5 mmol), 2-chloro-5-ethylpyrimidine (0.85 g, 6.1 mmol) and diisopropylethylamine (1.77 g, 13.8 mmol) in dimethylformamide (150 mL) was stirred at 130° C. overnight. After cooling to ambient temperature, dimethylformamide was removed under reduced pressure and the residue was treated with water (200 mL). A brown precipitate was formed which was filtered and re-dissolved in methylene chloride until the solution was clear. This was then dried over sodium sulfate, and filtered through a 3 cm silica gel pad. The solution was then evaporated in vacuo and the residue was purified by column chromatography by eluting with hexanes-ethyl acetate mixture (4:1) to obtain the title product (1.3 g, 62%) as colorless crystals. $^1$H-NMR (400 MHz, DMSO-$d_6$) δ 8.21 (s, 2H), 7.52 (d, J=8.7 Hz, 1H), 7.32 (d, J=8.7 Hz, 1H), 7.19 (t, J=8.7 Hz, 1H), 4.17-4.02 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example B-74: (S)-5-Ethyl-2-(3-((2-fluoro-4-(4,4,5,5-tetramethyl-1,3,2-dioxaborolan-2-yl)phenoxy)methyl]pyrrolidin-1-yl)pyrimidine

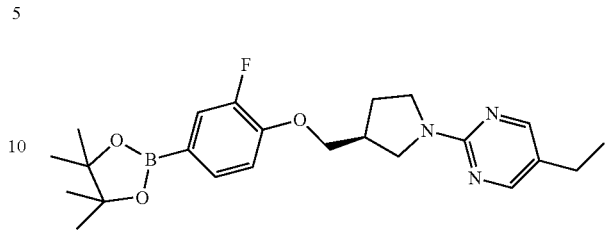

To a solution of (S)-2-(3-((4-bromo-2-fluorophenoxy)methyl)pyrrolidin-1-yl)-5-ethylpyrimidine (1.3 g, 3.4 mmol), 4,4,4',4',5,5,5',5'-octamethyl-2,2'-bi-1,3,2-dioxaborolane (1.0 g, 4.1 mmol), and potassium acetate (1.3 g, 12 mmol) in dioxane (50 mL) under argon atmosphere was added (bisdiphenylphosphino)ferrocene dichloropalladium (II) Pd(dppf)Cl$_2$ (170 mg, 0.2 mmol) and the mixture was heated to 85° C. and stirred at that temperature overnight. The mixture was cooled and filtered through a pad of celite. The celite pad was washed with hot (50° C.) dioxane (100 mL) and the washings were combined with the filtrate and evaporated to dryness. The residue was subjected to column chromatography eluting with ether to obtain the crude product as a light yellow oil. This oil was dissolved in hexanes (100 mL) and placed into freezer for three days. White crystals were formed, filtered off and dried to afford the title compound (0.83 g, 56%). $^1$H-NMR (400 MHz, DMSO-$d_6$) δ 8.21 (s, 2H), 7.43 (d, J=8.7 Hz, 1H), 7.34 (d, J=8.7 Hz, 1H), 7.21 (t, J=8.7 Hz, 1H), 4.19-4.05 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.16 (s, 12H), 1.12 (t, J=7.5 Hz, 3H).

Example B-75: (S)-6-(4-(((S)-1-(5-Ethylpyrimidin-2-yl)pyrrolidin-3-yl)methoxy)-3-flurophenyl)-2H-benzo [d][1,3]oxathiole 3-oxide

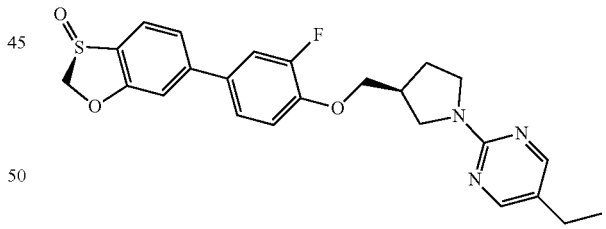

To a solution of (S)-3-oxido-2H-benzo[d][1,3]oxathiol-6-yl trifluoromethanesulfonate (112 mg, 0.37 mmol) and (S)-5-ethyl-2-(3-((2-fluoro-4-(4,4,5,5-tetramethyl-1,3,2-dioxaborolan-2-yl)phenoxy)methyl]pyrrolidin-1-yl}pyrimidine (158 mg, 0.37 mmol) in dioxane (2.5 mL) was added a solution of potassium carbonate (153 mg, 1.11 mmol) in water (2.5 mL). After stirring under argon atmosphere for 10 minutes, 1,1' (bisdiphenylphosphino)ferrocene dichloropalladium (II) Pd(dppf)Cl$_2$ (19 mg, 0.03 mmol) was added then the reaction mixture was stirred at ambient temperature Water (30 mL) was then added and a grey precipitate was formed, filtered off and air-dried. The precipitate was purified by column chromatography eluting with ethyl acetate to give the title compound as a white powder (24 mg, 15%).

H-NMR (400, MHz, DMSO-d$_6$) δ 8.22 (s, 2H), 8.08 (d, J=8.2 Hz, 1H), 7.71 (d, J=12.6 Hz, 1H), 7.63 (s, 1H), 7.57 (d, J=8.7 Hz, 1H), 7.52 (d, J=8.2 Hz, 1H), 7.31 (t, J=8.7 Hz, 1H), 5.64 (d, J=11.5 Hz, 1H), 5.22 (d, J=11.5 Hz, 1H), 4.21-4.09 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example B-76: (R)-6-(4-(((S)-1-(5-Ethylpyrimidin-2-yl)pyrrolidin-3-yl)methoxy-3-flurophenyl)-2H-benzo [d][1,3]oxathiole 3-oxide

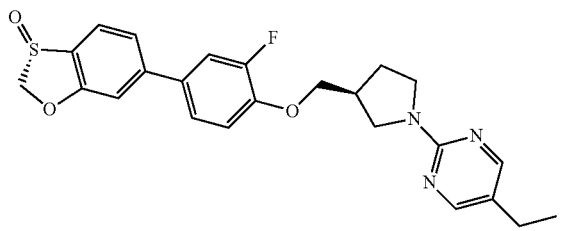 [SMILES: CCc1cnc(N2CC[C@H](COc3ccc(-c4ccc5c(c4)OC[S@@]5=O)cc3F)C2)nc1]

To a solution of (R)-3-oxido-2H-benzo[d][1,3]oxathiol-6-yl trifluoromethanesulfonate (121 mg, 0.40 mmol) and (S)-5-ethyl-2-(3-((2-fluoro-4-(4,4,5,5-tetramethyl-1,3,2-dioxaborolan-2-yl)phenoxy)methyl)pyrrolidin-1-yl)pyrimidine (171 mg, 0.40 mmol) in dioxane (3.0 mL) was added a solution of potassium carbonate (166 mg, 1.20 mmol) in water (3.0 mL). After stirring under argon atmosphere for 10 minutes, 1,1' (bisdiphenylphosphino)ferrocene dichloropalladium (II) Pd(dppf)Cl$_2$ (21 mg, 0.03 mmol) was added then the reaction mixture was stirred at ambient temperature overnight. Water (30 mL) was then added and a grey precipitate was formed, filtered off and air-dried. The precipitate was purified by column chromatography eluting with ethyl acetate to give the title compound as a white powder (24 mg, 14%). $^1$H-NMR (400 MHz, DMSO-d$_6$) δ 8.22 (s, 2H), 8.08 (d, J=8.2 Hz, 1H), 7.71 (d, J=12.6 Hz, 1H), 7.63 (s, 1H), 7.57 (d, J=8.7 Hz, 1H), 7.52 (d, J=8.2 Hz, 1H), 7.31 (t, J=8.7 Hz, 1H), 5.64 (d, J=11.5 Hz, 1H), 5.22 (d, J=11.5 Hz, 1H), 4.21-4.09 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example B-77: (S)-6-(4-(((R)-1-(5-Ethylpyrimidin-2-yl)pyrrolidin-3-yl)methoxy-3-flurophenyl)-2H-benzo [d][1,3]oxathiole 3-oxide

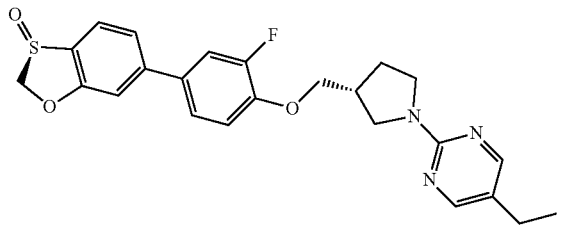 [SMILES: CCc1cnc(N2CC[C@@H](COc3ccc(-c4ccc5c(c4)OC[S@]5=O)cc3F)C2)nc1]

To a solution of (S)-3-oxido-2H-benzo[d][1,3]oxathiol-6-yl trifluoromethanesulfonate (112 mg, 0.37 mmol) and (R)-5-ethyl-2-(3-((2-fluoro-4-(4,4,5,5-tetramethyl-1,3,2-dioxaborolan-2-yl)phenoxy)methyl)pyrrolidin-1-yl)pyrimidine (158 mg, 0.37 mmol) in dioxane (2.5 mL) was added a solution of potassium carbonate (153 mg, 1.11 mmol) in water (2.5 mL). After stirring under argon atmosphere for 10 minutes, 1,1' (bisdiphenylphosphino)ferrocene dichloropalladium (II) Pd(dppf)Cl$_2$ (19 mg, 0.03 mmol) was added then the reaction mixture was stirred at ambient temperature overnight. Water (30 mL) was then added and a grey precipitate was formed, filtered off and air-dried. The precipitate was purified by column chromatography eluting with ethyl acetate to give the title compound as a white powder (25 mg, 15%). $^1$H-NMR (400, MHz, DMSO-d$_6$) δ 8.22 (s, 2H), 8.08 (d, J=8.2 Hz, 1H), 7.71 (d, J=12.6 Hz, 1H), 7.63 (s, 1H), 7.57 (d, J=8.7 Hz, 1H), 7.52 (d, J=8.2 Hz, 1H), 7.31 (t, J=8.7 Hz, 1H), 5.64 (d, J=11.5 Hz, 1H), 5.22 (d, J=11.5 Hz, 1H), 4.21-4.09 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example B-78: (R)-6-(4-(((R)-1-(5-Ethylpyrimidin-2-yl)pyrrolidin-3-yl)methoxy-3-flurophenyl)-2H-benzo [d][1,3]oxathiole 3-oxide

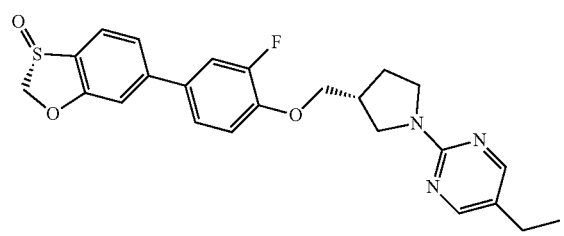 [SMILES: CCc1cnc(N2CC[C@@H](COc3ccc(-c4ccc5c(c4)OC[S@@]5=O)cc3F)C2)nc1]

To a solution of (R)-3-oxido-2H-benzo[d][1,3]oxathiol-6-yl trifluoromethanesulfonate (112 mg, 0.37 mmol) and (R)-5-ethyl-2-(3-((2-fluoro-4-(4,4,5,5-tetramethyl-1,3,2-dioxaborolan-2-yl)phenoxy)methyl]pyrrolidin-1-yl)pyrimidine (158 mg, 0.37 mmol) in dioxane (2.5 mL) was added a solution of potassium carbonate (153 mg, 1.11 mmol) in water (2.5 mL). After stirring under argon atmosphere for 10 minutes, 1,1' (bisdiphenylphosphino)ferrocene dichloropalladium (II) Pd(dppf)Cl$_2$ (19 mg, 0.03 mmol) was added then the reaction mixture was stirred at ambient temperature overnight. Water (30 mL) was then added and a grey precipitate was formed, filtered off and air-dried. The precipitate was purified by column chromatography eluting with ethyl acetate to give the title compound as a white powder (25 mg, 15%). $^1$H-NMR (400, MHz, DMSO-d$_6$) δ 8.22 (s, 2H), 8.08 (d, J=8.2 Hz, 1H), 7.71 (d, J=12.6 Hz, 1H), 7.63 (s, 1H), 7.57 (d, J=8.7 Hz, 1H), 7.52 (d, J=8.2 Hz, 1H), 7.31 (t, J=8.7 Hz, 1H), 5.64 (d, J=11.5 Hz, 1H), 5.22 (d, J=11.5 Hz, 1H), 4.21-4.09 (m, 2H), 3.77-3.58 (m, 2H), 3.53-3.35 (m, 2H), 2.87-2.73 (m, 1H), 2.41 (q, J=7.5 Hz, 2H), 2.22-2.11 (m, 1H), 1.94-1.80 (m, 1H), 1.12 (t, J=7.5 Hz, 3H).

Example B-79: (S)-2-(3-((4-Bromo-2-fluorophenoxy)methyl)pyrrolidin-1-yl)-5-chloropyrimidine

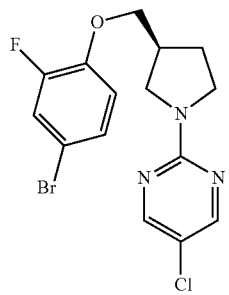 [SMILES: Fc1cc(Br)ccc1OC[C@H]1CCN(c2ncc(Cl)cn2)C1]

A solution of (S)-3-((4-bromo-2-fluorophenoxy)methyl)pyrrolidine hydrochloride (4.09 g, 13.2 mmol), 2,5-dichloropyrimidine (1.0 g, 7.1 mmol) and triethylamine (4.0 g, 39.6 mmol) in dimethylacetamide (15 mL) was stirred and heated in CEM microwave system (150° C., 3 hours). After cooling to ambient temperature, dimethylacetamide was removed under reduced pressure and the residue was treated with water and extracted with ethyl acetate (3×50 mL). The combined organic extracts were washed 5% citric acid, sodium bicarbonate solution, brine and then dried over sodium sulfate, and filtered. The solution was then evaporated in vacuo and the residue was purified by column chromatography by eluting with hexanes:ethyl acetate mixture (1:1) to afford the title product (4.5 g, 88%) as a colorless oil.

Example B-80: (S)-5-Chloro-2-(3-((2-fluoro-4-(4,4,5,5-tetramethyl-1,3,2-dioxaborolan-2-yl)phenoxy)methyl)pyrrolidin-1-yl)pyrimidine

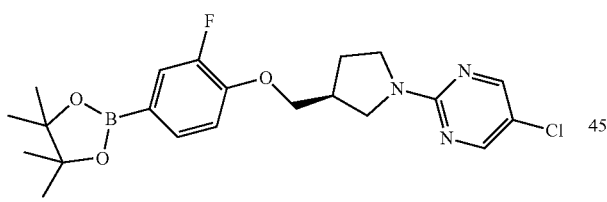

To a solution of (S)-2-(3-((4-bromo-2-fluorophenoxy)methyl)pyrrolidin-1-yl}-5-chloropyrimidine (4.50 g, 11.6 mmol), 4,4,4',4',5,5,5',5'-octamethyl-2,2'-bi-1,3,2-dioxaborolane (1.0 g, 4.1 mmol),) and potassium acetate (4.55 g, 45.2 mmol) in dioxane (120 mL) under argon atmosphere was added 1,1' (bisdiphenylphosphino)ferrocene dichloropalladium (II) Pd(dppf)Cl$_2$ (878 mg, 1.2 mmol) and the mixture was heated to 90° C. and stirred at that temperature overnight. The mixture was cooled and poured into a solution of ethyl acetate and water (100 mL:100 mL) and filtered through a celite 545 pad (1 cm). The celite pad was washed with ethyl acetate and the washings were combined with the filtrate, dried over sodium sulfate and evaporated to dryness. The residue was subjected to column chromatography eluting with hexanes:ethyl acetate to obtain the title compound as a light yellow oil. (1.9 g, 30%). $^1$H-NMR (400 MHz, DMSO-d$_6$) δ 8.21 (s, 2H), 7.43 (d, J=8.7 Hz, 1H), 7.34 (d, J=8.7 Hz, 1H), 7.21 (t, J=8.7 Hz, 1H), 4.19-4.05 (m, 2H), 3.77-3.58 (m, 2H), 3.53-3.35 (m, 2H), 2.87-2.73 (m, 1H), 2.22-2.11 (m, 1H), 1.94-1.80 (m, 1H), 1.16 (s, 12H).

Example B-81: (S)-6-(4-(((S)-1-(5-Chloropyrimidin-2-yl)pyrrolidin-3-yl)methoxy)-3-fluorophenyl)-2H-benzo[d][1,3]oxathiole 3-oxide

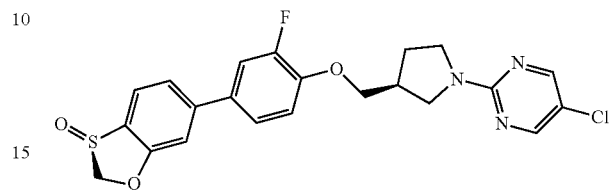

To a solution of (S)-5-chloro-2-(3-((2-fluoro-4-(4,4,5,5-tetramethyl-1,3,2-dioxaborolan-2-yl)phenoxy)methyl)pyrrolidin-1-yl)pyrimidine (300 mg, 0.7 mmol) in dioxane (15 mL) was added (S)-3-oxido-2H-benzo[d][1,3]oxathiol-6-yl trifluoromethanesulfonate (212 mg, 0.7 mmol), 2M aqueous solution of sodium carbonate (15 mL) and 1,1' (bisdiphenylphosphino)ferrocene dichloropalladium (II) Pd(dppf)Cl$_2$ (73 mg, 0.1 mmol). The mixture was stirred with heating to 85° C. for 3 hours and then at ambient temperature overnight. To the mixture was then added water (50 mL) and the organic phase was extracted with ethyl acetate (3×30 mL). The combined extracts were washed with water, brine, dried over magnesium sulfate, filtered and the filtrate was evaporated. The product was purified by column chromatography on silica gel eluting with hexanes:ethyl acetate mixture (1:1) to afford the title product (112 mg, 37.2%) as a white solid. $^1$H NMR (300 MHz, DMSO-d$_6$) δ 8.40 (s, 2H), 8.08 (d, J=8.1 Hz, 1H), 7.71 (d, J=12.8 Hz, 1H), 7.63 (s, 1H), 7.57 (d, J=8.5 Hz, 1H), 7.52 (d, J=8.1 Hz, 1H), 7.31 (t, J=8.8 Hz, 1H), 5.64 (d, J=11.4 Hz, 1H), 5.23 (d, J=11.4 Hz, 1H), 4.33-3.99 (m, 2H), 3.82-3.58 (m, 2H), 3.57-3.44 (m, 1H), 3.42-3.34 (m, 1H), 2.98-2.69 (m, 1H), 2.30-2.06 (m, 1H), 2.01-1.76 (m, 1H).

Example B-82: (S)-2-(3-((4-Bromo-2-fluorophenoxy)methyl)pyrrolidin-1-yl)-4-ethylpyrimidine

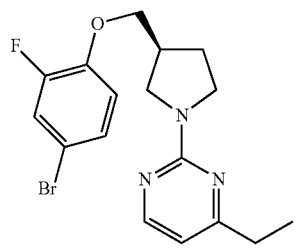 [SMILES: CCc1ccnc(N2CC[C@H](COc3ccc(Br)cc3F)C2)n1]

A solution of (S)-3-((4-bromo-2-fluorophenoxy)methyl)pyrrolidine hydrochloride (2.0 g, 6.4 mmol), 2-chloro-4-ethylpyrimidine (1.0 g, 7.0 mmol) and diisopropylethylamine (1.7 g, 12.8 mmol) in dimethylacetamide (10 mL) was stirred and heated in CEM microwave system (150° C., 3 hours). After cooling to ambient temperature, dimethylacetamide was removed under reduced pressure and the residue was treated with water and extracted with ethyl acetate (3×50 mL). The combined organic extracts were washed with 5% citric acid, sodium bicarbonate solution, brine and then dried over sodium sulfate, and filtered. The solution was then evaporated in vacuo and the residue was purified by column chromatography by eluting with hexanes:ethyl acetate mixture (1:1) to afford the title compound (1.8 g, 74%) as a colorless oil. $^1$H NMR (400 MHz, CDCl$_3$) δ 8.21 (d, J=5.0 Hz, 1H), 7.26-7.10 (m, 2H), 6.85 (t, J=8.7 Hz, 1H), 6.40 (d, J=5.1 Hz, 1H), 4.04 (d, J=6.9 Hz, 2H), 3.95-3.70 (m, 2H), 3.69-3.56 (m, 1H), 3.49 (dd, J=11.3, 6.6 Hz, 1H), 2.93-2.76 (m, 1H), 2.62 (q, J=7.6 Hz, 2H), 2.33-2.15 (m, 1H), 2.04-1.87 (m, 1H), 1.27 (t, J=7.6 Hz, 3H).

Example B-83: (S)-4-Ethyl-2-(3-((2-fluoro-4-(4,4,5,5-tetramethyl-1,3,2-dioxaborolan-2-yl)phenoxy)methyl]pyrrolidin-1-yl)pyrimidine

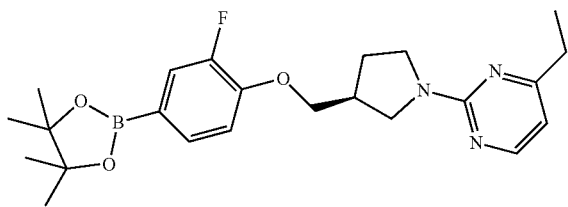 [SMILES: CCc1ccnc(N2CC[C@H](COc3ccc(B4OC(C)(C)C(C)(C)O4)cc3F)C2)n1]

To a solution of (S)-2-(3-((4-bromo-2-fluorophenoxy)methyl)pyrrolidin-1-yl}-4-ethylpyrimidine (1.8 g, 4.7 mmol), 4,4,4',4',5,5,5',5'-octamethyl-2,2'-bi-1,3,2-dioxaborolane (1.4 g, 5.6 mmol),) and potassium acetate (1.9 g, 18.8 mmol) in dioxane (120 mL) under argon atmosphere was added 1,1' (bisdiphenylphosphino)ferrocene dichloropalladium (II) Pd(dppf)Cl$_2$ (220 mg, 0.3 mmol) and the mixture was heated to 90° C. and stirred at that temperature overnight. The mixture was cooled and poured into a solution of ethyl acetate and water (100 mL:100 mL) and filtered through a celite 545 pad (1 cm). The celite pad was washed with ethyl acetate and the washings were combined with the filtrate, dried over sodium sulfate and evaporated to dryness. The residue was subjected to column chromatography eluting with hexanes:ethyl acetate (2:1) to obtain the title compound as a light yellow oil. (1.9 g, 94%). H NMR (400 MHz, CDCl$_3$) δ 8.20 (d, J=5.1 Hz, 1H), 7.56-7.45 (m, 2H), 6.95 (t, J=8.2 Hz, 1H), 6.38 (d, J=5.1 Hz, 1H), 4.08 (d, J=6.9 Hz, 2H), 3.89 (dd, J=11.3, 7.4 Hz, 1H), 3.82-3.72 (m, 1H), 3.68-3.57 (m, 1H), 3.49 (dd, J=11.4, 6.7 Hz, 1H), 2.94-2.80 (m, 1H), 2.61 (q, J=7.6 Hz, 2H), 2.32-2.20 (m, 1H), 2.00-1.89 (m, 1H), 1.34 (s, 12H), 1.25 (t, J=7.6 Hz, 3H).

Example B-84: (S)-6-(4-(((S)-1-(4-Ethylpyrimidin-2-yl)pyrrolidine-3-yl)methoxy)-3-fluorophenyl)-2H-benzo[d][1,3]oxathiole 3-oxide

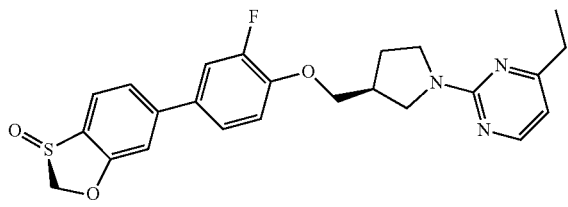 [SMILES: CCc1ccnc(N2CC[C@H](COc3ccc(-c4ccc5c(c4)OC[S@]5=O)cc3F)C2)n1]

To a solution of (S)-4-ethyl-2-(3-((2-fluoro-4-(4,4,5,5-tetramethyl-1,3,2-dioxaborolan-2-yl)phenoxy)methyl]pyrrolidin-1-yl}pyrimidine (311 mg, 0.73 mmol) in dioxane (15 mL) was added (S)-3-oxido-2H-benzo[d][1,3]oxathiol-6-yl trifluoromethanesulfonate (220 mg, 0.73 mmol), 2M aqueous solution of sodium carbonate (1.1 mL) and 1,1' (bisdiphenylphosphino)ferrocene dichloropalladium (II) Pd(dppf)Cl$_2$ (27 mg, 0.04 mmol. The mixture was stirred and heated at 40° C. overnight. Upon cooling, water was added water (50 mL) and the mixture was extracted with ethyl acetate (3×30 mL). The combined organic extracts were washed with water, brine, dried over Na$_2$SO$_4$, filtered and the filtrate was evaporated to dryness. The residue after evaporation was purified to column chromatography on silica gel eluting hexanes:ethyl acetate mixture (1:1) to afford the title compound (73 mg, 22%) as a white solid. $^1$H NMR (400 MHz, DMSO-d$_6$) δ 8.21 (d, J=4.9 Hz, 1H), 8.08 (d, J=8.1 Hz, 1H), 7.77-7.43 (m, 4H), 7.32 (t, J=8.8 Hz, 1H), 6.49 (d, J=4.9 Hz, 1H), 5.65 (d, J=11.4 Hz, 1H), 5.23 (d, J=11.4 Hz, 1H), 4.26-4.05 (m, 2H), 3.81-3.59 (m, 2H), 3.57-3.33 (m, 2H), 2.88-2.70 (m, 1H), 2.55 (q, J=7.5 Hz, 2H), 2.23-2.07 (m, 1H), 1.95-1.77 (m, 1H), 1.17 (t, J=7.5 Hz, 3H).

Example B-85: (R)-6-(4-(((S)-1-(4-Ethylpyrimidin-2-yl)pyrrolidine-3-yl)methoxy)-3-fluorophenyl)-2H-benzo[d][1,3]oxathiole 3-oxide

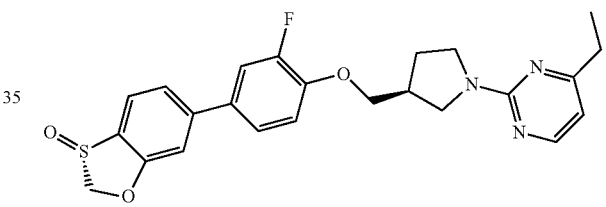

To a solution of (S)-4-ethyl-2-(3-((2-fluoro-4-(4,4,5,5-tetramethyl-1,3,2-dioxaborolan-2-yl)phenoxy)methyl]pyrrolidin-1-yl}pyrimidine (311 mg, 0.73 mmol) in dioxane (15 mL) was added (R)-3-oxido-2H-benzo[d][1,3]oxathiol-6-yl trifluoromethanesulfonate (220 mg, 0.73 mmol), 2M aqueous solution of sodium carbonate (1.1 mL) and 1,1' (bisdiphenylphosphino)ferrocene dichloropalladium (II) Pd(dppf)Cl$_2$ (27 mg, 0.04 mmol. The mixture was stirred and heated at 40° C. overnight. Upon cooling, water was added water (50 mL) and the mixture was extracted with ethyl acetate (3×30 mL). The combined organic extracts were washed with water, brine, dried over Na$_2$SO$_4$, filtered and the filtrate was evaporated to dryness. The residue after evaporation was purified to column chromatography on silica gel eluting hexanes:ethyl acetate mixture (1:1) to afford the title compound (127 mg, 38%) as a white solid. $^1$H NMR (400 MHz, DMSO-d$_6$) δ 8.21 (d, J=4.9 Hz, 1H), 8.08 (d, J=8.1 Hz, 1H), 7.77-7.43 (m, 4H), 7.32 (t, J=8.8 Hz, 1H), 6.49 (d, J=4.9 Hz, 1H), 5.65 (d, J=11.4 Hz, 1H), 5.23 (d, J=11.4 Hz, 1H), 4.26-4.05 (m, 2H), 3.81-3.59 (m, 2H), 3.57-3.33 (m, 2H), 2.88-2.70 (m, 1H), 2.55 (q, J=7.5 Hz, 2H), 2.23-2.07 (m, 1H), 1.95-1.77 (m, 1H), 1.17 (t, J=7.5 Hz, 3H).

Example B-86: (R)-6-(4-(((S)-1-(5-Chloropyrimidin-2-yl)pyrrolidine-3-yl)methoxy)-3-fluorophenyl)-2H-benzo[d][1,3]oxathiole 3-oxide

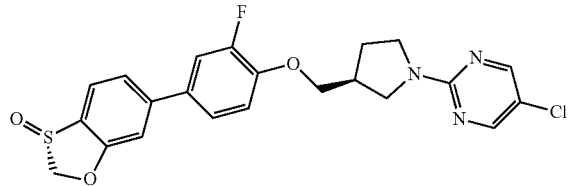 [SMILES: O=[S@]1COc2cc(-c3ccc(OC[C@H]4CCN(c5ncc(Cl)cn5)C4)c(F)c3)ccc21]

To a solution of (S)-5-chloro-2-(3-((2-fluoro-4-(4,4,5,5-tetramethyl-1,3,2-dioxaborolan-2-yl)phenoxy)methyl]pyrrolidin-1-yl}pyrimidine (300 mg, 0.7 mmol) in dioxane (15 mL) was added (R)-3-oxido-2H-benzo[d][1,3]oxathiol-6-yl trifluoromethanesulfonate (212 mg, 0.7 mmol), 2M aqueous solution of sodium carbonate (1.1 mL) and 1,1' (bisdiphenylphosphino)ferrocene dichloropalladium (II) Pd(dppf)Cl$_2$ (73 mg, 0.7 mmol). The mixture was stirred and heated at 85° C. for 3 hours. Upon cooling, water was added water (50 mL) and the mixture was extracted with ethyl acetate (3×30 mL). The combined organic extracts were washed with water, brine, dried over Na$_2$SO$_4$, filtered and the filtrate was evaporated to dryness. The residue after evaporation was purified to column chromatography on silica gel eluting hexanes:ethyl acetate mixture (1:1) to afford the title compound (100 mg, 31%) as a white solid. $^1$H NMR (300 MHz, DMSO) δ 8.40 (s, 2H), 8.08 (d, J=8.1 Hz, 1H), 7.71 (d, J=12.8 Hz, 1H), 7.63 (s, 1H), 7.57 (d, J=8.5 Hz, 1H), 7.52 (d, J=8.1 Hz, 1H), 7.31 (t, J=8.8 Hz, 1H), 5.64 (d, J=11.4 Hz, 1H), 5.23 (d, J=11.4 Hz, 1H), 4.33-3.99 (m, 2H), 3.82-3.58 (m, 2H), 3.57-3.44 (m, 1H), 3.42-3.34 (m, 1H), 2.98-2.69 (m, 1H), 2.30-2.06 (m, 1H), 2.01-1.76 (m, 1H).

Example B-87: tert-Butyl (S)-3-((4-bromophenoxy)methyl)pyrrolidine-1-carboxylate

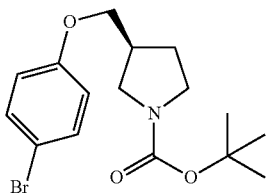 [SMILES: CC(C)(C)OC(=O)N1CC[C@H](COc2ccc(Br)cc2)C1]

A solution containing tert-butyl (S)-3-(((methylsulfonyl)oxy)methyl)pyrrolidine-1-carboxylate (2.7 g, 9.7 mmol), 4-bromophenol (2.0 g, 11.6 mmol) and potassium carbonate (4.0 g, 29.1 mmol) in dimethylformamide (100 mL) was stirred at 100° C. overnight. After cooling to ambient temperature the solvent was removed under reduced pressure and the residue was treated with acetonitrile (100 mL) and then was filtered through a pad of celite. The filtrate was evaporated to dryness then treated with water (50 mL) and extracted with ethyl acetate (2×50 mL), dried over sodium sulfate, filtered and the filtrate was evaporated. The residue was purified by column chromatography on a silica gel pad (3 cm) eluting with a mixture of hexanes:ethyl acetate (4:1) to afford the title product (3.2 g, 93%) as a light yellow liquid. $^1$H-NMR (400 MHz, DMSO-d$_6$) δ 7.44 (d, J=8.6 Hz, 2H), 6.92 (d, J=8.8 Hz, 2H), 4.01-3.86 (m, 2H), 3.50-3.34 (m, 2H), 3.29-3.15 (m, 1H), 3.11-3.01 (m, 1H), 2.68-2.54 (m, 1H), 2.08-1.88 (m, 1H), 1.79-1.59 (m, 1H), 1.39 (s, 9H).

Example B-88: (S)-3-((4-Bromophenoxy)methyl)pyrrolidine Hydrochloride

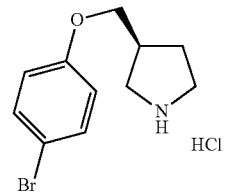 [SMILES: Brc1ccc(OC[C@H]2CCNC2)cc1 ; Cl]

To a solution of tert-butyl (S)-3-((4-bromophenoxy)methyl)pyrrolidine-1-carboxylate (3.2 g, 9.0 mmol) in dioxane (30 mL) was added 3M solution of hydrogen chloride in dioxane (10 mL) and the mixture was stirred with heating at 40° C. overnight. Dioxane was evaporated to a residual volume of about 10 mL, and the residue was triturated with diethyl ether (150 mL). A precipitate was formed and stirred for 20 minutes then filtered off and air-dried to give the title compound (2.3 g, 87%). as a white powder. $^1$H-NMR (400 MHz, DMSO-d$_6$) δ 9.29 (br.s, 2H), 7.46 (d, J=9.0 Hz, 2H), 6.93 (d, J=9.0 Hz, 2H), 4.06-3.92 (m, 2H), 3.32-3.07 (m, 3H), 3.06-2.92 (m, 1H), 2.77-2.63 (m, 1H), 2.18-1.98 (m, 1H), 1.83-1.64 (m, 1H).

Example B-89: (S)-2-(3-((4-Bromophenoxy)methyl)pyrrolidin-1-yl)-5-ethylpyrimidine

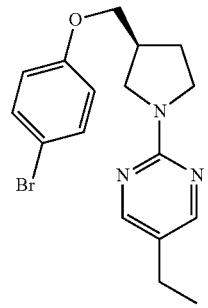 [SMILES: CCc1cnc(N2CC[C@H](COc3ccc(Br)cc3)C2)nc1]

A mixture of (S)-3-((4-bromophenoxy)methyl)pyrrolidine hydrochloride (1.15 g, 3.9 mmol), 2-chloro-5-ethylpyrimidine (0.62 g, 4.3 mmol) and diisopropylethylamine (1.27 g, 9.7 mmol) in dimethylformamide (50 mL) was stirred at 130° C. overnight. After cooling to ambient temperature, dimethylformamide was removed under reduced pressure and the residue was treated with water (200 mL). A brown precipitate was formed and then the mother liquor was decanted. The precipitate was re-dissolved in dichloromethane, dried over sodium sulfate and purified on a 3 cm silica gel pad eluted with hexanes:ethyl acetate mixture gradient (4:1 to 2:1) to afford the title product (0.73 g, 51%) as colorless powder. $^1$H-NMR (400 MHz, DMSO-d$_6$) δ 8.21 (s, 2H), 7.44 (d, J=9.0 Hz, 2H), 6.94 (d, J=9.0 Hz, 2H), 4.12-3.87 (m, 2H), 3.75-3.55 (m, 2H), 3.52-3.39 (m, 1H), 3.37-3.26 (m, 1H), 2.79-2.64 (m, 1H), 2.41 (q, J=7.5 Hz, 2H), 2.20-2.05 (m, 1H), 1.91-1.75 (m, 1H), 1.11 (t, J=7.6 Hz, 3H).

Example B-90: (S)-5-Ethyl-2-(3-((4-(4,4,5,5-tetramethyl-1,3,2-dioxaborolan-2-yl)phenoxy) methyl)pyrrolidin-1-yl)pyrimidine

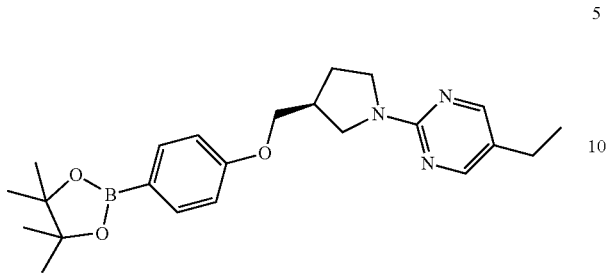

To a solution of (S)-2-(3-((4-bromophenoxy)methyl)pyrrolidin-1-yl)-5-ethylpyrimidine (900 mg, 2.5 mmol), 4,4,4',4',5,5,5',5'-octamethyl-2,2'-bi-1,3,2-dioxaborolane (950 mg, 3.8 mmol),) and potassium acetate (970 mg, 10 mmol) in dioxane (50 mL) under argon atmosphere was added 1,1' (bisdiphenylphosphino)ferrocene dichloropalladium (II) Pd(dppf)Cl$_2$ (0.18 g, 0.25 mmol) and the mixture was heated to 85° C. overnight. After cooling, it was filtered through a pad of celite, then washed with hot (50° C.) dioxane (100 mL). The filtrate was evaporated to dryness and the residue was adsorbed on a silica gel column and eluted with ether to obtain the crude product as a light yellow oil. This oil was used in the next step without purification. LCMS [M+1]$^+$ 410

Example B-91: (S)-6-(4-(((S)-1-(5-Ethylpyrimidin-2-yl)pyrrolidine-3-yl)methoxy)phenyl)-2H-benzo[d][1,3]oxathiole 3-oxide

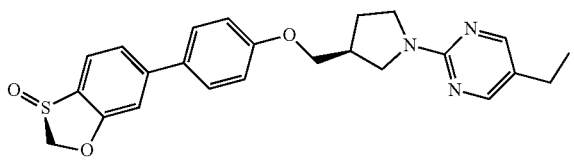 [SMILES: CCc1cnc(N2CC[C@H](COc3ccc(-c4ccc5c(c4)OC[S@]5=O)cc3)C2)nc1]

To a solution containing (S)-3-oxido-2H-benzo[d][1,3]oxathiol-6-yl trifluoromethanesulfonate (150 mg, 0.50 mmol), 2M aqueous solution of sodium carbonate (1.1 mL) and (S)-5-ethyl-2-(3-((4-(4,4,5,5-tetramethyl-1,3,2-dioxaborolan-2-yl)phenoxy)methyl)pyrrolidin-1-yl)pyrimidine (203 mg, 0.50 mmol) in dioxane (3 mL) was added 1,1' (bisdiphenylphosphino)ferrocene dichloropalladium (II) Pd(dppf)Cl$_2$ (25 mg, 0.035 mmol) under an argon atmosphere and then stirred at ambient temperature overnight. Water (30 mL) was then added and a grey precipitate was formed, filtered off and air-dried. The precipitate was purified by column chromatography eluting with ethyl acetate to give the title compound (100 mg, 46%) as a white powder. $^1$H-NMR (400 MHz, DMSO-d$_6$) δ 8.22 (s, 2H), 8.07 (d, J=8.1 Hz, 1H), 7.71 (d, J=8.2 Hz, 2H), 7.57 (s, 1H), 7.48 (d, J=8.0 Hz, 1H), 7.09 (d, J=8.2 Hz, 2H), 5.64 (d, J=11.2 Hz, 1H), 5.22 (d, J=11.2 Hz, 1H), 4.18-3.97 (m, 2H), 3.78-3.56 (m, 2H), 3.54-3.41 (m, 1H), 3.40-3.34 (m, 1H), 2.85-2.67 (m, 1H), 2.42 (q, J=7.6 Hz, 2H), 2.23-2.06 (m, 1H), 1.96-1.78 (m, 1H), 1.12 (t, J=7.6 Hz, 3H).

Example C-1: 2-oxo-1,3-benzoxathiol-6-yl trifluoromethanesulfonate

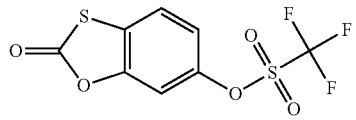 [SMILES: O=c1oc2cc(OS(=O)(=O)C(F)(F)F)ccc2s1]

Into a solution of 6-hydroxy-1,3-benzoxathiol-2-one (26.0 g, 155 mmol) in pyridine (250 mL) at 0° C. was slowly added triflic anhydride (52.3 g, 185 mmol). The reaction mixture was stirred for 40 min at 0° C. and overnight at ambient temperature. The volatiles were distilled off under reduced pressure and the residue after evaporation was treated with ethyl acetate (400 mL). The suspension was washed with 10% water solution of citric acid (300 mL) followed by brine (300 mL) and water (500 mL). The organic layer was dried over magnesium sulfate and filtered. The filtrate was evaporated under reduced pressure. A residue after evaporation was washed with ether (250 mL) and was subjected to column chromatography elution with dichloromethane to produce 2-oxo-1,3-benzoxathiol-6-yl trifluoromethanesulfonate (40.1 g, 86%) as a white powder. $^1$H-NMR (DMSO-d$_6$, 400 MHz): δ 7.97 (d, J=8.80 Hz, 1H), 7.91 (d, J=2.45 Hz, 1H), 7.51 (dd, J=8.68, 2.45 Hz, 1H).

Example C-2: 3-hydroxy-4-mercaptophenyl Trifluoromethanesulfonate

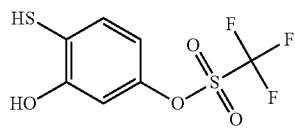 [SMILES: O=S(=O)(Oc1ccc(S)c(O)c1)C(F)(F)F]

A solution of 3-hydroxy-4-mercaptophenyl trifluoromethanesulfonate (40.1 g, 133 mmol) in oxygen free 2N aqueous sodium hydroxide (250 mL) under nitrogen atmosphere was boiled for 1 h in a stream of oxygen-free nitrogen. The solution was allowed to cool under nitrogen to ambient temperature and then was acidified with 2N aqueous sulfuric acid to pH 6.5. The solution was saturated with sodium sulphate and extracted with ether (2×450 mL). The combined extracts were concentrated under reduced pressure to afford the crude title product. The crude product was used in the next step without further purification (20.1 g, 54.7%).

Example C-3: 2,2-dimethyl-1,3-benzoxathiol-6-yl Trifluoromethanesulfonate

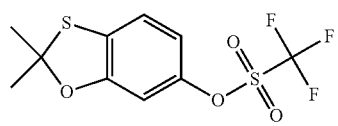 [SMILES: CC1(C)Oc2cc(OS(=O)(=O)C(F)(F)F)ccc2S1]

To a solution of 3-hydroxy-4-mercaptophenyl trifluoromethanesulfonate (2.5 g, 9.1 mmol) in benzene (100 mL) were added acetone (5.3 g, 91 mmol) and p-toluenesulfonic acid (173 mg, 0.9 mmol). The mixture was stirred at reflux with Dean-Stark adapter for 7 days with TLC control. To the mixture was added ethyl acetate (100 mL) and a saturated aqueous solution of sodium bicarbonate (50 mL). The organic layer was separated and washed with brine, dried over sodium sulfate, filtered and the filtrate was evaporated to dryness. The product was used in the next step without further purification. Brown oil (2.8 g, 100%).

Example C-4: 2,2-dimethyl-3,3-dioxido-1,3-benzoxathiol-6-yl Trifluoromethanesulfonate

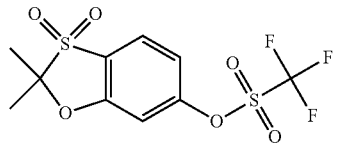 [SMILES: CC1(C)Oc2cc(OS(=O)(=O)C(F)(F)F)ccc2S1(=O)=O]

To a solution of 2,2-dimethyl-1,3-benzoxathiol-6-yl trifluoromethanesulfonate (2.8 g, 9.1 mmol) in acetic acid (40 mL) was added 30% aqueous solution hydrogen peroxide (8 mL). The mixture was stirred at −70° C. for 17 h. To the mixture was added ethyl acetate (200 mL) and the mixture was washed with water (100 mL), saturated aqueous solution sodium bicarbonate (2×100 mL), 10% aqueous solution sodium metabisulfite (2×100 mL), brine (2×100 mL), dried over sodium sulfate, filtered and the filtrate was evaporated to dryness. The residue was subjected to column chromatography eluting with hexane:ethyl acetate isocratic mixture (9:1) to produce the title product as a yellow oil (0.8 g, 25%). H-NMR (DMSO-$d_6$, 400 MHz): δ 8.15 (d, J=8.6 Hz, 1H), 7.65 (d, J=2.1 Hz, 1H), 7.42 (dd, J=8.6, 2.1 Hz, 1H), 1.72 (s, 6H).

Example C-5: 5-chloro-2-(4-{[4-(2,2-dimethyl-3,3-dioxido-1,3-benzoxathiol-6-yl)-2-fluoro phenoxy]methyl}piperidin-1-yl)pyrimidine

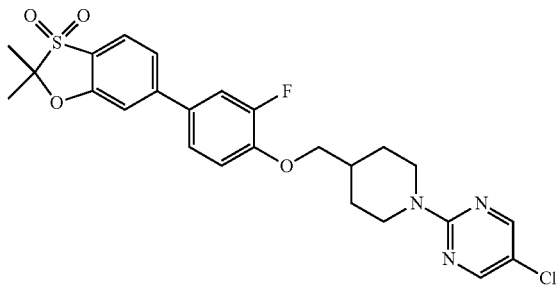 [SMILES: CC1(C)Oc2cc(-c3ccc(OCC4CCN(c5ncc(Cl)cn5)CC4)c(F)c3)ccc2S1(=O)=O]

To a solution of 5-chloro-2-(4-{[2-fluoro-4-(4,4,5,5-tetramethyl-1,3,2-dioxaborolan-2-yl)phenoxy]methyl}piperidin-1-yl)pyrimidine (129 mg, 0.29 mmol) in dioxane (5 mL) were added 2,2-dimethyl-3,3-dioxido-1,3-benzoxathiol-6-yl trifluoromethanesulfonate (100 mg, 0.29 mmol), followed by 2M aqueous solution sodium bicarbonate (5 mL) and PdCL$_2$(dppf) (15 mg). The mixture was stirred and heated to 50° C. under argon overnight. The mixture was evaporated, to the residue was added water (20 mL) and ethyl acetate (40 mL). The ethyl acetate solution was washed with brine, dried over sodium sulfate, filtered and the filtrate was evaporated to dryness. The product was subjected to column chromatography on silica gel eluting with a mixture of hexane:ethyl acetate (gradient 9:1→4:1). The product was obtained as a white solid (39 mg, 26%). $^1$H-NMR (DMSO-$d_6$, 400 MHz): δ 8.39 (s, 2H), 7.89 (d, J=8.2 Hz, 1H), 7.69 (d, J=12.0 Hz, 1H), 7.56 (d, J=8.3 Hz, 2H), 7.51 (s, 1H), 7.28 (t, J=8.8 Hz, 1H), 4.63 (d, J=12.4 Hz, 2H), 4.01 (d, J=6.3 Hz, 2H), 2.96 (t, J=12.7 Hz, 2H), 2.21-2.03 (m, 1H), 1.85 (d, J=11.3 Hz, 2H), 1.69 (s, 6H), 1.34-1.16 (m, 2H).

Example C-6: Spiro[1,3-benzoxathiole-2,1'-cyclopentan]-6-yl Trifluoromethanesulfonate

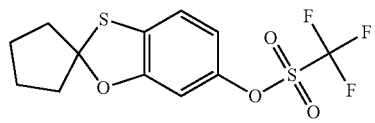 [SMILES: O=S(=O)(Oc1ccc2c(c1)OC1(CCCC1)S2)C(F)(F)F]

To a solution of 3-hydroxy-4-mercaptophenyl trifluoromethanesulfonate (2.5 g, 9.1 mmol) in toluene (100 mL) was added cyclopentanone (3.8 g, 45.5 mmol) and p-toluenesulfonic acid (173 mg, 0.9 mmol). The mixture was stirred and heated to reflux with Dean-Stark adapter under argon for 7 days with TLC control. To the mixture was added ethyl acetate (100 mL) and saturated aqueous solution sodium bicarbonate (50 mL). The organic layer was separated and washed with brine (100 mL), dried over Na$_2$SO$_4$, filtered and the filtrate was evaporated. The residue was subjected to flash chromatography on silica gel eluting with an isocratic mixture of hexane:ethyl acetate (9:1) to produce the title product as a yellow oil (2.5 g, 82%). $^1$H-NMR (DMSO-$d_6$, 400 MHz): δ 7.40 (d, J=8.5 Hz, 1H), 7.06 (d, J=2.4 Hz, 1H), 6.99 (dd, J=8.5, 2.4 Hz, 1H), 2.38-2.28 (m, 2H), 2.14-2.03 (m, 2H), 1.86-1.70 (m, 2H).

Example C-7: 3,3-dioxidospiro[1,3-benzoxathiole-2,1'-cyclopentan]-6-yl Trifluoromethane-sulfonate

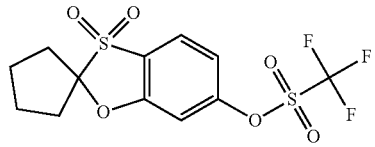 [SMILES: O=S(=O)(Oc1ccc2c(c1)OC1(CCCC1)S2(=O)=O)C(F)(F)F]

To a solution of spiro[1,3-benzoxathiole-2,1'-cyclopentan]-6-yl trifluoromethanesulfonate (2.5 g, 7.5 mmol) in acetic acid (40 mL) was added 30% aqueous solution hydrogen peroxide (8 mL). The mixture was stirred at −70° C. for 17 h. To the mixture was added ethyl acetate (200 mL) and the mixture was washed with water (100 mL), saturated aqueous solution sodium bicarbonate (2×100 mL), 10% aqueous solution sodium metabisulfite (1×100 mL), brine (1×100 mL), dried over sodium sulfate and evaporated. The residue was subjected to flash chromatography on silica gel eluting with dichloromethane to obtain the title product as a white solid (1.1 g, 39%). $^1$H-NMR (DMSO-$d_6$, 400 MHz): δ 8.18 (d, J=8.6 Hz, 1H), 7.65 (d, J=2.1 Hz, 1H), 7.44 (dd, J=8.6, 2.1 Hz, 1H), 2.48-2.39 (m, 2H), 2.08-1.99 (m, 2H), 1.97-1.79 (m, 4H).

Example C-8: 5-chloro-2-(4-{[4-(3,3-dioxidospiro [1,3-benzoxathiole-2,1'-cyclopentan]-6-yl)-2-fluoro-phenoxy]methyl}piperidin-1-yl)pyrimidine

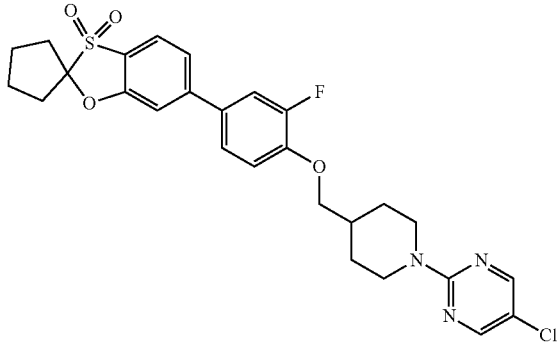 [SMILES: O=S1(=O)c2ccc(-c3ccc(OCC4CCN(c5ncc(Cl)cn5)CC4)c(F)c3)cc2OC12CCCC2]

To a solution of 5-chloro-2-(4-{[2-fluoro-4-(4,4,5,5-tetramethyl-1,3,2-dioxaborolan-2-yl)phenoxy]-methyl}piperidin-1-yl)pyrimidine (180 mg, 0.4 mmol, 1.1 eq) in dioxane (5 mL) were added 3,3-dioxidospiro[1,3-benzoxathiole-2,1'-cyclopentan]-6-yl trifluoromethanesulfonate (150 mg, 0.4 mmol), 2M aqueous solution sodium carbonate (0.42 mL) and PdCL$_2$(dppf) (10 mg, 0.01 mmol). The mixture was stirred and heated to 50° C. overnight. The mixture was rotary evaporated, to the residue were added water (20 mL) and ethyl acetate (40 mL). The organic phase was washed with brine (50 mL), dried over sodium sulfate filtered and the filtrate was evaporated to dryness. The residue was subjected to column chromatography on silica gel eluting with hexane:ethyl acetate (gradient 5:1-1:1) to produce the title product as a white solid (35 mg, 16%). $^1$H-NMR (DMSO-d$_6$, 400 MHz) δ 8.39 (s, 2H), 7.92 (d, J=8.1 Hz, 1H), 7.71 (d, J=12.7 Hz, 1H), 7.58-7.52 (m, 3H), 7.3 (t, J=8.5 Hz, 1H), 4.65 (d, J=12.6 Hz, 2H), 4.01 (d, J=6.1 Hz, 2H), 2.99 (t, J=12.2 Hz, 2H), 2.48-2.39 (m, 2H), 2.18-2.06 (m, 1H), 2.05-1.78 (m, 8H), 1.33-1.17 (m, 2H).

Example C-9: Spiro[1,3-benzoxathiole-2,1'-cyclohexan]-6-yl Trifluoromethanesulfonate

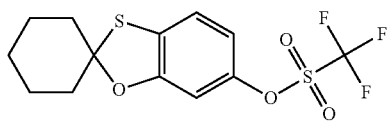 [SMILES: O=S(=O)(Oc1ccc2c(c1)OC1(CCCCC1)S2)C(F)(F)F]

To a solution of 3-hydroxy-4-sulfanylphenyl trifluoromethanesulfonate (3.0 g, 10.9 mmol) in toluene (60 mL) were added cyclohexanone (5.4 g, 54.5 mmol) and p-toluenesulfonic acid (190 mg, 1.1 mmol). The mixture was stirred and heated to reflux with Dean-Stark adapter for 3 days. To the mixture was added ethyl acetate (100 mL) and saturated aqueous solution sodium bicarbonate (50 mL). The organic layer was separated and washed with brine (50 mL), dried over sodium sulfate, filtered and the filtrate was evaporated to produce the title product as a brown oil (3.8 g, 98%). The product was used in next step without purification. LCMS [M+1]=355.4

Example C-10: 3,3-dioxidospiro[1,3-benzoxathiole-2,1'-cyclohexan]-6-yl Trifluoromethane Sulfonate

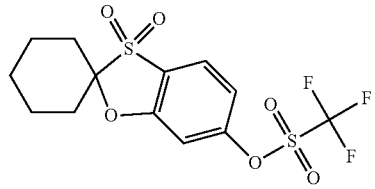 [SMILES: O=S(=O)(Oc1ccc2c(c1)OC1(CCCCC1)S2(=O)=O)C(F)(F)F]

To a solution of spiro[1,3-benzoxathiole-2,1'-cyclohexan]-6-yl trifluoromethanesulfonate (3.8 g, 10.9 mmol) in acetic acid (20 mL) was added 30% aqueous solution hydrogen peroxide (4 mL). The mixture was stirred at –70° C. for 17 h. To the mixture was added ethyl acetate (200 mL) and the mixture was washed with water (100 mL), saturated solution sodium bicarbonate (2×100 mL), brine (100 mL), dried over sodium sulfite, filtered and the filtrate was evaporated to dryness. The residue was subjected to column chromatography on silica gel eluting with dichloromethane to obtain the title product as a white solid (1.3 g, 31%). $^1$H-NMR (DMSO-d$_6$, 400 MHz) δ 8.14 (d, J=8.6 Hz, 1H), 7.65 (d, J=2.0 Hz, 1H), 7.41 (dd, J=8.6, 2.0 Hz, 1H), 2.05-1.87 (m, 4H), 1.83-1.56 (m, 5H), 1.50-1.35 (m, 1H).

Example C-11: 5-chloro-2-(4-{[4-(3,3-dioxidospiro [1,3-benzoxathiole-2,1'-cyclohexan]-6-yl)-2-fluoro-phenoxy]methyl}piperidin-1-yl)pyrimidine

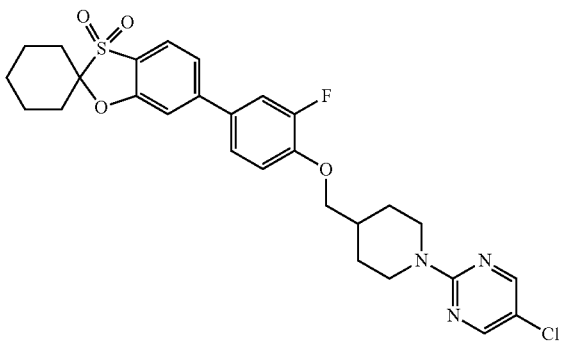 [SMILES: O=S1(=O)c2ccc(-c3ccc(OCC4CCN(c5ncc(Cl)cn5)CC4)c(F)c3)cc2OC12CCCCC2]

To a solution of 5-chloro-2-(4-{[2-fluoro-4-(4,4,5,5-tetramethyl-1,3,2-dioxaborolan-2-yl)phenoxy] methyl}piperidin-1-yl)pyrimidine (127 mg, 0.28 mmol) in dioxane (5 mL) were added 3,3-dioxidospiro[1,3-benzoxathiole-2,1'-cyclohexan]-6-yl trifluoromethanesulfonate (100 mg, 0.26 mmol), 2M aqueous solution sodium carbonate (0.4 mL) and PdCL$_2$(dppf) (10 mg, 0.01 mmol). The mixture was stirred and heated to 50° C. overnight. The mixture was rotary evaporated, to the residue was added water (20 mL) and ethyl acetate (40 mL). The organic ethyl phase was washed with brine (50 mL), dried over sodium sulfate, filtered and the filtrate was evaporated to dryness. The product was subjected to column chromatography on silica gel to obtain the title product as a white solid (40 mg, 2 7%). $^1$H-NMR (DMSO-d$_6$, 400 MHz) δ 8.39 (s, 2H), 7.87 (d, J=8.3 Hz, 1H), 7.70 (d, J=13.0 Hz, 1H), 7.61-7.48 (m, 3H), 7.27 (t, J=8.6 Hz, 1H), 4.63 (d, J=12.9 Hz, 2H), 4.00 (d, J=6.3 Hz, 2H), 2.96 (t, J=12.0 Hz, 2H), 2.20-2.05 (m, 1H), 2.03-1.58 (m, 11H), 1.51-1.36 (m, 1H), 1.32-1.16 (m, 2H).

Example C-12: Spiro[1,3-benzoxathiole-2,1'-cyclobutan]-6-yl Trifluoromethanesulfonate

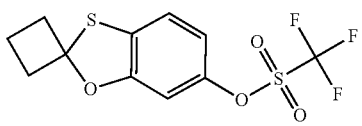 [SMILES: O=S(=O)(Oc1ccc2c(c1)OC1(CCC1)S2)C(F)(F)F]

To a solution of 3-hydroxy-4-sulfanylphenyl trifluoromethanesulfonate (3.0 g, 10.9 mmol) in toluene (60 mL) were added cyclobutanone (3.8 g, 54.5 mmol) and p-toluenesulfonic acid (190 mg, 1.1 mmol). The mixture was stirred and heated to reflux with Dean-Stark adapter for 7 days. To the mixture were added ethyl acetate (100 mL) and saturated aqueous solution sodium bicarbomate (50 mL). The organic layer was separated and washed with brine (50 mL), dried over sodium sulfate and rotary evaporated to dryness. The product was subjected to column chromatography on silica gel to afford the title product as a yellow oil (1.3 g, 36%). $^1$H-NMR (DMSO-$d_6$, 400 MHz) δ 7.41 (d, J=8.5 Hz, 1H), 7.13 (d, J=2.4 Hz, 1H), 7.01 (dd, J=8.5, 2.4 Hz, 1H), 2.84-2.69 (m, 2H), 2.62-2.52 (m, 2H), 1.99-1.86 (m, 1H), 1.85-1.71 (m, 1H).

Example C-13: 3,3-dioxidospiro[1,3-benzoxathiole-2,1'-cyclobutan]-6-yl Trifluoromethane Sulfonate

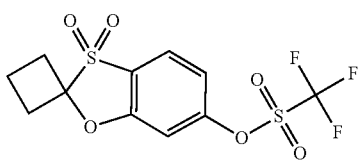 [SMILES: O=S(=O)(Oc1ccc2c(c1)OC1(CCC1)S2(=O)=O)C(F)(F)F]

To a solution of spiro[1,3-benzoxathiole-2,1'-cyclobutan]-6-yl trifluoromethanesulfonate (1.3 g, 3.9 mmol) in acetic acid (20 mL) was added 30% aqueous solution hydrogen peroxide (4 mL). The mixture was stirred at −70° C. for 17 h. To the mixture was added ethyl acetate (200 mL) and the mixture was washed with water (100 mL), saturated solution sodium bicarbomate (2×100 mL), brine (100 mL), dried over sodium sulfate, filtered and the filtrate was evaporated to dryness. The residue was subjected to flash chromatography on silica gel eluting with dichloromethane to produce the title product as a white solid (1.3 g, 91%). H-NMR (DMSO-$d_6$, 400 MHz) δ 8.19 (d, J=8.6 Hz, 1H), 7.67 (d, J=2.1 Hz, 1H), 7.43 (dd, J=8.6, 2.1 Hz, 1H), 2.90-2.76 (m, 2H), 2.73-2.59 (m, 2H), 2.13-1.96 (m, 1H), 1.84-1.67 (m, 1H).

Example C-14: 5-chloro-2-(4-{[4-(3,3-dioxidospiro [1,3-benzoxathiole-2,1'-cyclobutan]-6-yl)-2-fluorophenoxy]methyl}piperidin-1-yl)pyrimidine

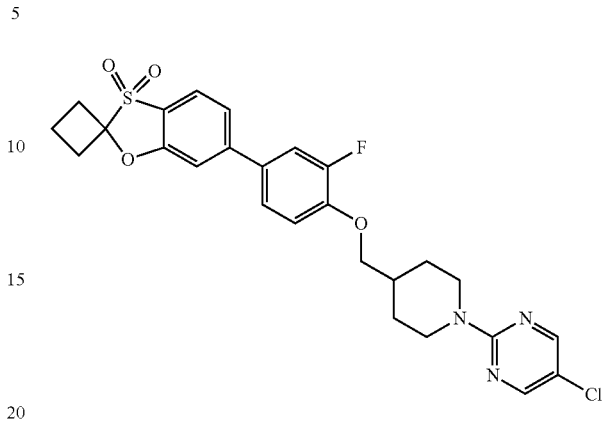

To a solution of 5-chloro-2-(4-{[2-fluoro-4-(4,4,5,5-tetramethyl-1,3,2-dioxaborolan-2-yl)phenoxy]-methyl}piperidin-1-yl)pyrimidine (137 mg, 0.31 mmol) in dioxane (5 mL) were added 3,3-dioxidospiro[1,3-benzoxathiole-2,1'-cyclobutan]-6-yl trifluoromethanesulfonate (100 mg, 0.28 mmol), 2M aqueous solution sodium bicarbonate (0.42 mL) and PdCL$_2$(dppf) (10 mg, 0.01 mmol). The mixture was stirred and heated to 50° C. overnight. The mixture was rotary evaporated, to the residue were added water (20 mL) and ethyl acetate (40 mL). The organic phase was washed with brine (50 mL), dried over sodium sulfate, filtered and the filtrate was evaporated to dryness. The residue was subjected to column chromatography on silica gel to produce the title product as a white solid (43 mg, 29%). $^1$H-NMR (DMSO-$d_6$, 400 MHz) δ 8.39 (s, 2H), 7.92 (d, J=8.1 Hz, 1H), 7.69 (d, J=12.7 Hz, 1H), 7.60-7.50 (m, 3H), 7.27 (t, J=8.5 Hz, 1H), 4.63 (d, J=12.8 Hz, 2H), 4.00 (d, J=6.2 Hz, 2H), 2.95 (t, J=12.3 Hz, 2H), 2.87-2.76 (m, 2H), 2.70-2.57 (m, 2H), 2.19-1.98 (m, 2H), 1.91-1.68 (m, 3H), 1.33-1.16 (m, 2H).

VII. Formulations

The present invention also relates to compositions or formulations which comprise the prodrug agents for producing the compounds of formula (I) once administered to a patient or subject.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known riluzole prodrug agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can be sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more riluzole prodrug according to the present invention and one or more excipients; from about 0.01 mg to about 100 mg of one or more riluzole prodrug according to the present invention and one or more excipients; and from about 0.1 mg to about 10 mg of one or more riluzole prodrug according to the present invention; and one or more excipients.

VII. Biological Testing

Biological activity of representative compounds of the disclosure is presented in Tables 2A, 2B and 2C. The potency of GPR119 receptor agonists was assessed by measuring the stimulation of GPR119-mediated cAMP production with LANCE Ultra cAMP assay (Perkin Elmer, TRF0264) in CHO cells stably expressing human GPR119 receptor (Chantest, cat. #A633). CHO-GPR119 cells were cultured in DMEM/F12 medium supplemented with 10% FBS and 1% NEAA at 37° C., 5% CO2, aliquoted and frozen in liquid nitrogen.

For assay, cells were thawed in a water bath at 37° C., washed in Hank's Balanced Salt Solution (HBSS) and resuspended in Stimulation Buffer 1 (SB1) for 30 min: 5 mM HEPES, pH 7.2-7.4, 0.1% BSA in HBSS. The cells were then recovered in SB2 buffer (1 mM IBMX in SB1) and the cell concentration was adjusted to 800,000 cells/mL. The ULight-anti-cAMP antibody (Perkin Elmer, TRF0264) was added to the cell suspension making Mix [Cell suspension/4× ULight-anti-cAMP antibodies]. The resulting cell suspension Mix was plated to 384-well assay plates (Corning, white low volume, #3674) 5 L/well. The assay plate was centrifuged 200 g, 5 sec.

Serial dilution (100×) of tested compounds were prepared in DMSO in the range of from 30 nM to 1 mM with half-log step in 384-well plates (Greiner, 781280) using Biomek 2000. 10 test concentrations in two repeats were prepared for each CRC. It was diluted 50 times in SB1 and each tested concentration was added to cells in the assay plate—5 L/well. The assay plate was incubated 30 minutes at room temperature on a shaker, 250 rpm to allow GPR119 receptor stimulation. The cAMP level was determined according to the standard kit supplier protocol (PerkinElmer, cat. #TRF0264).

The stock solution of the Eu-cAMP tracer (Perkin Elmer, TRF0264) was diluted 1:100 in cAMP Detection Buffer (Perkin Elmer, TRF0264), making 2× working concentration and added to the assay plate, 10 µL per well. Assay plate was centrifuged 180 g, 1 sec. Then the assay plate was incubated for 60' at room temperature on shaker, 250 rpm to allow cAMP detection. The TR-FRET signal was measured at Ex-340 nm/Em-615 and Ex-340 nm/Em-665 nm on the reader Tecan M1000. 0% of cAMP stimulation corresponds to the cells with DMSO only, 100% of cAMP stimulation corresponds to the cells with 10 M Forskolin. The $EC_{50}$ value defined as the concentration of the drug that gives half-maximal response, were calculated using GraphPad Prizm 5.0 software with forskolin was used as references at each test. Entries 1-17 in Table 2A and entries 1-14 in Table 2B show the biological activity of certain representative compounds using the protocol as described above. For entries 18-25 in Table 2A, entries 15-39 in Table 2B and entries 1-4 in Table 2C, the protocol was modified to use 500 cells/well, which was found to give better Signal/Noise and others statistical parameters. In this modified protocol, the natural ligand, oleoyl ethanolamide had EC50 of 592 nM at 100% maximum cAMP stimulation. Forskolin had an EC50 of 28.5 nM at 124% maximum stimulation.

TABLE 2A

Biological data for certain compounds of the disclosure

| Entry | Example | Name | $EC_{50}$ nM (% cAMP Max.relative to forscolin) |
|---|---|---|---|
| 1 | A-13 | 6-((3-fluoro-4-((1-t-butylpiperidin-4-ylmethoxy)phenyl)-2H-benzo[d][1,3]oxathiole 3,3-dioxide | 833 (75) |
| 2 | A-14 | 4-((4-3,3-dioxido-2H-benzo[d][1,3]oxathiol-6-yl)-2-fluorophenyoxy)methyl)-N,N-dimethyl-piperidine-1-carboxamide | 86.4 (77) |
| 3 | A-15 | 1-4-((4-3,3-dioxido-2H-benzo[d][1,3]oxathiol-6-yl)-2-fluorophenyoxy)methyl)-piperidin-1-yl)-2,2-dimethylpropan-1-one | 61.7 (80) |
| 4 | A-17 | (2-(4-((4-(3,3-dioxido-2H-benzo[d][1,3]oxathiol-6-yl)-2-fluorophenoxy)methyl)piperidin-1-yl)ethan-1-one | 10000 (67) |
| 5 | A-19 | ((S)-2-amino-1-(4-((4-(3,3-dioxido--2H-benzo[d][1,3]oxathiol-6-yl)-2-fluorophenoxy)methyl)piperidin-1-yl)-)-3-methylbutan-1-one | 4083 (65) |
| 6 | A-20 | 4-((4-3,3,-dioxido-2H-benzo[d][1,3]oxathiol-6-yl)-2-fluorophenyoxy)methyl)-piperidine-1-carboxamide | 10000 (70) |
| 7 | A-21 | 1-4-((4-3,3,-dioxido-2H-benzo[d][1,3]oxathiol-6-yl)-2-fluorophenyoxy)methyl)-piperidin-1-yl)-2-methylpropan-1-one | 37 (77) |
| 8 | A-23 | ethyl-2-(4-((4-(3,3-dioxido-2H-benzo[d][1,3]oxathiol-6-yl)-2-fluorophenyoxy)methyl)-piperidin-1-yl)acetic acid | 7037 (66) |
| 9 | A-24 | 6-(4-((1-(5-ethylpyrimidin-2-yl)piperidin-4-yl)methoxy-3-fluorophenyl)-2H-benzo[d][1,3]oxathiole 3,3-dioxide | 2.5 (77) |
| 10 | A-29 | 6-(2-((1-(5-chloropyrimidin-2-yl)piperidin-4-yl)methoxy)pyrimidin-5-yl)-2H-benzo[d][1,3]oxathiole 3,3-dioxide | 33.1 (80) |
| 11 | A-40 | 5-(4-((1-5-chloropyrimidin-2-yl)piperidin-4-yl)methoxy)-3-fluorophenyl)-2H-benzo[d][1,3]oxathiole 3,3-dioxide | 369 (65) |
| 12 | A-42 | 6-(4-((1-(1,3,5-triazin-2-yl)piperidin-4-yl)methoxy)-3-fluorophenyl)-2H-benzo[d][1,3]oxathiole 3,3-dioxide | 102 (75) |
| 13 | A-48 | 6-(4-((1-(5-chloropyrimidin-2-yl)azetidin-3-yl)methoxy)-3-fluorophenyl)-2H-benzo[d][1,3]oxathiole 3,3-dioxide | 67 (80) |
| 14 | A-52 | 6-(3-fluoro-4-((1-(3-isopropyl-1,2,4-oxadiazol-5-yl)azetidin-3-yl)methoxy)phenyl)-2H-benzo[d][1,3]oxathiole 3,3-dioxide | 24 (81) |
| 15 | A-58 | 6-(4-((2-(1-(5-chloropyrimidin-2-yl)piperidin-4-yl)thiazol-5-yl)methoxy)-3-fluorophenyl)-2H-benzo[d][1,3]oxathiole-3,3-dioxide | 96 (73) |

TABLE 2A-continued

Biological data for certain compounds of the disclosure

| Entry | Example | Name | EC$_{50}$ nM (% cAMP Max.relative to forscolin) |
|---|---|---|---|
| 16 | A-59 | 6-(3-fluoro-4-((1-(3-isopropyl-1,2,4-oxadiazol-5-yl)piperidin-4-yl)methoxy)phenyl)-2H-benzo[d][1,3]oxathiole 3,3-dioxide | 5.4 (77) |
| 17 | A-65 | 6-(4-(5-chloropyrimidin-2-yl)piperazin-1-yl)-3-fluorophenyl-2H-benzo[d][1,3]oxathiole 3,3-dioxide | 112.4 (84) |
| 18 | A-66 | 6-(3-fluoro-4-(1-(5-isopropylpyrimidin-2-yl)piperidin-4-yl)methoxy)phenyl-2H-benzo[d][1,3]oxathiole 3,3-dioxide | 19.1 (80) |
| 19 | A-67 | 6-(3-fluoro-4-(1-(5-methoxypyrimidin-2-yl)piperidin-4-yl)methoxy)phenyl-2H-benzo[d][1,3]oxathiole 3,3-dioxide | 21.4 (72) |
| 20 | A-71 | (R)-6-(4-((1-(5-ethylpyrimidin-2-yl)pyrrolidin-2-yl)methoxy)-3-fluorophenyl-2H-benzo[d]oxathiole 3,3-dioxide | 1690 (51) |
| 21 | A-76 | 6-(5-((1-(5-ethylpyrimidin-2-yl)piperidin-4-yl)methoxy)pyrimidin-2-yl)-2H-benzo[d][1,3]oxathiole 3,3-dioxide | 8.2 (87) |
| 22 | A-80 | (S)-6-(4-((1-(5-ethylpyrimidin-2-yl)pyrrolidin-2-yl)methoxy)-3-fluorophenyl-2H-benzo[d]oxathiole 3,3-dioxide | 1312 (25) |
| 23 | A-86 | (S)-6-(4-((1-(5-ethylpyrimidin-2-yl)pyrrolidin-3-yl)methoxy)-3-fluorophenyl)-2H-benzo[d][1,3]oxathiole 3,3-dioxide | 166 (96) |
| 24 | A-89 | (S)-6-(4-((1-(5-chloropyrimidin-2-yl)pyrrolidin-3-yl)methoxy)-3-fluorophenyl)-2H-benzo[d][1,3]oxathiole 3,3-dioxide | 46 (93) |
| 25 | A-92 | (S)-6-(4-((1-(4-ethylpyrimidin-2-yl)pyrrolidin-3-yl)methoxy)-3-fluorophenyl)-2H-benzo[d][1,3]oxathiole 3,3-dioxide | 58 (90) |

TABLE 2B

Biological data of certain compounds of the disclosure

| Entry | Example | Name | EC$_{50}$ nM; (% cAMP Max.) |
|---|---|---|---|
| 1 | B-12 | 2-(4-((4-benzo[d][1,3]oxathiol-6-yl)-2-fluorophenoxy]methyl)piperidin-1-yl)-5-chloropyrimidine | 280 |
| 2 | B-16 | 6-(4-((1-(5-chloropyrimidin-2-yl)piperidin-4-yl)methoxy)-3-fluorophenyl)-2H-benzo[d][1,3]oxathiole 3-oxide | 2.3 |
| 3 | B-19 | 6-(4-((1-(5-ethylpyrimidin-2-yl)methoxy)-3-fluorophenyl)-2H-benzo[d][1,3]oxathiole-3-oxide | 4.8 |
| 4 | B-23 | 1-(4-((2-fluoro-4-(3-oxido-2H-benzo[d][1,3]oxathiol-6-yl)phenoxy)methyl)-piperidin-1-yl)-3-methylbutane-1-one | 46.2 |
| 5 | B-24 | 6-(3-fluoro-4-((1-(5-methoxypyrimidin-2-yl)piperidin-4-yl)methoxy)phenyl)-2H-benzo[d][1,3]oxathiole 3-oxide | 2.3 |
| 6 | B-25 | 6-(4-((1-(4-ethylpyrimidin-2-yl)piperidin-4-yl)methoxy)-3-(fluorophenyl)-2H-benzo[d][1,3]oxathiole 3-oxide. | 31.8 |
| 7 | B-26 | 2-(4-((4-benzo[d][1,3]oxathiol-6-yl)-2-fluorophenoxy)methyl)piperidin-1-yl)-4-ethylpyrimidine. | >500 |
| 8 | B-27 | 6-(4-((1-(5-ethoxypyrimidin-2-yl)piperidin-4-yl)methoxy)-3-fluorophenyl)-2H-benzo[d][1,3]oxathiole 3-oxide | 4.7 |
| 9 | B-28 | 6-(3-fluoro-4-((1-(5-isopropylpyrimidin-2-yl)piperidin-4-yl)methoxy)phenyl)-2H-benzo[d][1,3]oxathiole 3-oxide. | 3.0 |
| 10 | B-29 | 6-(3-fluoro-4-((1-(5-(trifluoromethyl)pyridin-2-yl)piperidin-4-yl)methoxy)phenyl)-2H-benzo[d][1,3]oxathiole 3-oxide. | 52 |
| 11 | B-32 | (S)-6-(4-((1-(5-chloropyrimidin-2-yl)piperidin-4-yl)methoxy)-3-fluorophenyl)-2H-benzo[d][1,3]oxathiole 3-oxide | 1.2 |
| 12 | B-34 | (R)-6-(4-((1-(5-chloropyrimidin-2-yl)piperidin-4-yl)methoxy)-3-fluorophenyl)-2H-benzo[d][1,3]oxathiole 3-oxide | 0.9 |

TABLE 2B-continued

Biological data of certain compounds of the disclosure

| Entry | Example | Name | EC$_{50}$ nM; (% cAMP Max.) |
|---|---|---|---|
| 13 | B-18 | 6-(3-fluoro-4-(piperidin-4-yl)methoxy)phenyl)-2H-benzo[d][1,3]oxathiole 3-oxide | >500 |
| 14 | B-17 | tert-butyl 4-((2-fluoro-4-(3-oxido-2H-benzo[d][1,3]oxathiol-6-yl)phenoxy)methyl)piperidine-1-carboxylate | >100 |
| 15 | B-35 | 6-(4-((1-(4-ethylpyrimidin-2-yl)piperidin-4-yl)methoxy)-3-fluorophenyl)-2H-benzo[d][1,3]oxathiole 3-oxide. | 27.3 (61) |
| 16 | B-37 | 2-(4-((4-(benzo[d][1,3]oxathiol-6-yl)-2-fluorophenoxy)methyl)piperidin-1-yl)-5-ethylpyrimidine | 365 (79) |
| 17 | B-38 | 2-(4-((4-(benzo[d][1,3]oxathiol-6-yl)-2-fluorophenoxy)methyl)piperidin-1-yl)-5-isopropylpyrimidine | 10.5 (78) |
| 18 | B-39 | 2-(4-((4-(benzo[d][1,3]oxathiol-6-yl)-2-fluorophenoxy)methyl)piperidin-1-yl)-5-methoxpyrimidine | 2900 (64) |
| 19 | B-40 | 1-(4-((4-(benzo[d][1,3]oxathiol-6-yl)-2-fluorophenoxy)methyl)piperidin-1-yl)-3-methylbutan-1-one | 2000 (50) |
| 20 | B-45 | (S)-6-(4-((1-(5-ethylpyrimidin-2-yl)piperidin-4-yl)methoxy)-3-fluorophenyl)-2H-benzo[d][1,3]oxathiole 3-oxide | 2.3 (68) |
| 21 | B-46 | (S)-6-(3-fluroro-4-((1-5-isopropylpyrimidin-2-yl)piperidin-4-yl)methoxy)phenyl)-2H-benzo[d][1,3]oxathiole 3-oxide | 10.1 (82) |
| 22 | B-50 | (S)-6-(3-fluoro-4-((1-5-methoxypyrimidin-2-yl)piperidin-4-yl)methoxy)phenyl)-2H-benzo[d][1,3]oxathiole 3-oxide | 3.7 (66) |
| 23 | B-51 | (R)-6-(3-fluoro-4-((1-(5-methoxypyrimidin-2-yl)piperidin-4-yl)methoxy)phenyl)-2H-benzo[d][1,3]oxathiole 3-oxide | 40.6 (70) |
| 24 | B-52 | (R)-6-(4-((1-(5-ethylpyrimidin-2-yl)piperidin-4-yl)methoxy)phenyl)-3-fluorophenyl)-2H-benzo[d][1,3]oxathiole 3-oxide | 19.5 (73) |
| 25 | B-53 | (R)-6-(3-fluoro-4-((1-(5-isopropylpyrimidin-2-yl)piperidin-4-yl)methoxy)phenyl)-2H-benzo[d][1,3]oxathiole 3-oxide | 41 (74) |
| 26 | B-58 | (R)-6-(2-((1-(5-chloropyridin-2-yl)piperidin-4-yl)methoxy)pyrimidin-5-yl)-2H-benzo[d][1,3]oxathiole 3-oxide | 107 (66) |
| 27 | B-59 | (S)-6-(4-((1-(5-chloropyrimidin-2-yl)piperidin-4-yl)methoxy)-3-fluorophenyl)-2H-benzo[d][1,3]oxathiole 3-oxide | 1.7 (70) |
| 28 | B-62 | (S)-6-(2-((1-(5-chloropyrimidin-2-yl)piperidin-4-yl)methoxy)pyrimidin-5-yl)-2H-benzo[d][1,3]oxathiole 3-oxide | 43.5 (66) |
| 29 | B-67 | 6-(4-(((R)-1-(5-ethylpyrimidin-2-yl)pyrrolidin-3-yl)methoxy)-3-fluorophenyl)-2H-benzo[d][1,3]oxathiole 3-oxide | 54 (74) |
| 30 | B-69 | (R)-2-(3-((4-benzo[d][1,3]oxathiol-6-yl)-2-fluorophenoxy)methyl)pyrrolidin-1-yl)-5-ethylpyrimidine | >10,000 |
| 31 | B-75 | (S)-6-(4-(((S)-1-(5-ethylpyrimidin-2-yl)pyrrolidin-3-yl)methoxy)-3-flurophenyl)-2H-benzo[d][1,3]oxathiole 3-oxide | 17.7 (88) |
| 32 | B-76 | (R)-6-(4-(((S)-1-(5-ethylpyrimidin-2-yl)pyrrolidin-3-yl)methoxy-3-flurophenyl)-2H-benzo[d][1,3]oxathiole 3-oxide | 20.5 (80) |
| 33 | B-77 | (S)-6-(4-(((R)-1-(5-ethylpyrimidin-2-yl)pyrrolidin-3-yl)methoxy-3-flurophenyl)-2H-benzo[d][1,3]oxathiole 3-oxide | 32.5 (81) |
| 34 | B-78 | (R)-6-(4-(((R)-1-(5-ethylpyrimidin-2-yl)pyrrolidin-3-yl)methoxy-3-flurophenyl)-2H-benzo[d][1,3]oxathiole 3-oxide | 115 (72) |
| 35 | B-81 | (S)-6-(-4-(((S)-1-(5-chloropyrimidin-2-yl)pyrrolidin-3-yl)methoxy)-3-fluorophenyl)-2H-benzo[d][1,3]oxathiole 3-oxide | 30 (95) |
| 36 | B-84 | (S)-6-(4-(((S)-1-(4-ethylpyrimidin-2-yl)pyrrolidine-3-yl)methoxy)-3-fluorophenyl)-2H-benzo[d][1,3]oxathiole 3-oxide | 31.5 (92) |
| 37 | B-85 | (R)-6-(4-(((S)-1-(4-ethylpyrimidin-2-yl)pyrrolidine-3-yl)methoxy)-3-fluorophenyl)-2H-benzo[d][1,3]oxathiole 3-oxide | 13 (64) |
| 38 | B-86 | (R)-6-(4-(((S)-1-(5-chloropyrimidin-2-yl)pyrrolidine-3-yl)methoxy)-3-fluorophenyl)-2H-benzo[d][1,3]oxathiole 3-oxide | 4.6 (93) |

TABLE 2B-continued

Biological data of certain compounds of the disclosure

| Entry | Example | Name | EC$_{50}$ nM; (% cAMP Max.) |
|---|---|---|---|
| 39 | B-91 | (S)-6-(4-(((S)-1-(5-ethylpyrimidin-2-yl)pyrrolidine-3-yl)methoxy)phenyl)-2H-benzo[d][1,3]oxathiole 3-oxide | 10.3 (93) |

TABLE 2C

Biological data of certain compounds of formula (I) in the disclosure

| Entry | Example | Name | EC$_{50}$ nM (% cAMP Max.relative to forscolin) |
|---|---|---|---|
| 1 | C-5 | 5-chloro-2-(4-{[4-(2,2-dimethyl-3,3-dioxido-1,3-benzoxathiol-6-yl)-2-fluoro phenoxy]methyl}piperidin-1-yl)py-rimidine | 68.6 (81) |
| 2 | C-8 | 5-chloro-2-(4-{[4-(3,3-dioxidospiro[1,3-benzoxathiole-2,1'-cyclopentan]-6-yl)-2-fluorophenoxy]methyl}piperidin-1-yl)pyrimidine | 114 (66) |
| 3 | C-11 | 5-chloro-2-(4-{[4-(3,3-dioxidospiro[1,3-benzoxathiole-2,1'-cyclohexan-6-yl)-2-fluorophenoxy]methyl}piperidin-1-yl)pyrimidine | 33.0 (25) |
| 4 | C-14 | 5-chloro-2-(4-{[4-(3,3-dioxidospiro[1,3-benzoxathiole-2,1'-cyclobutan]-6-yl)-2-fluorophenoxy]methyl}piperidin-1-yl)pyrimidine | 29.8 (67) |

Certain test compounds were evaluated using the PathHunter® β-arrestin assay, which monitors the activation of GPR119 in a homogenous, non-imaging assay format using the enzyme fragment complementation (EFC) technology (DiscoverX Corporation, Fremont, Calif. U.S.A.; www.discoverx.com) with β-galactosidase as the functional reporter. These results are shown in Table 3.

TABLE 3

Biological data of certain compounds of the disclosure

| Entry | Example | Name | EC$_{50}$ nM; ( % cAMP Max.) |
|---|---|---|---|
| 1 | B-34 | (R)-6-(4-((1-(5-chloropyrimidin-2-yl)piperidin-4-yl)methoxy)-3-fluoro-phenyl)-2H-benzo[d][1,3]oxathiole 3-oxide | 35.7 (172) |
| 2 | B-46 | (S)-6-(3-fluroro-4-((1-5-isopropyl-pyrimidin-2-yl)piperidin-4-yl)methoxy)phenyl)-2H-benzo[d][1,3]oxathiole 3-oxide | 7.9 (164) |
| 3 | B-50 | (S)-6-(3-fluoro-4-((1-5-methoxy-pyrimidin-2-yl)piperidin-4-yl)methoxy)phenyl)-2H-benzo[d][1,3]oxathiole 3-oxide | 16.4 (169) |
| 4 | B-59 | (S)-6-(4-((1-(5-chloropyrimidin-2-yl)piperidin-4-yl)methoxy)-3-fluoro-phenyl)-2H-benzo[d][1,3]oxathiole 3-oxide | 6.7 (175) |
| 5 | B-75 | (S)-6-(4-(((S)-1-(5-ethylpyrimidin-2-yl)pyrrolidin-3-yl)methoxy)-3-fluro-phenyl)-2H-benzo[d][1,3]oxathiole 3-oxide | 60 (190) |
| 6 | B-84 | (S)-6-(4-(((S)-1-(4-ethylpyrimidin-2-yl)pyrrolidine-3-yl)methoxy)-3-fluoro-phenyl)-2H-benzo[d][1,3]oxathiole 3-oxide | 567 (117) |

TABLE 3-continued

Biological data of certain compounds of the disclosure

| Entry | Example | Name | EC$_{50}$ nM; ( % cAMP Max.) |
|---|---|---|---|
| 7 | B-85 | (R)-6-(4-(((S)-1-(4-ethylpyrimidin-2-yl)pyrrolidine-3-yl)methoxy-3-fluoro-phenyl)-2H-benzo[d][1,3]oxathiole 3-oxide | 657 (73) |
| 8 | B-86 | (R)-6-(4-(((S)-1-(5-chloropyrimidin-2-yl)pyrrolidine-3-yl)methoxy)-3-fluoro phenyl)-2H-benzo[d][1,3]oxathiole 3-oxide | 108 (133) |
| 9 | B-91 | (S)-6-(4-(((S)-1-(5-ethylpyrimidin-2-yl)pyrrolidine-3-yl)methoxy)phenyl)-2H-benzo[d][1,3]oxathiole 3-oxide | 222 (155) |

Certain compounds and compositions disclosed herein are therefore useful as GPR119 receptor activity modulators (e.g. as full or partial agonists), e.g. certain compounds may be for use in vitro, or alternatively certain compounds may be for use in vivo. Certain compounds and compositions disclosed herein may be useful as full or partial agonists in vitro. Certain compounds and compositions disclosed herein may be useful as full or partial agonists of GPR119 in humans or non-human animals (e.g. rodents and non-human primates). There is thus disclosed a method of modulating the activity of a GPR119 receptor (e.g. activation of the receptor) comprising contacting a GPR119 receptor in vitro, or alternatively in vivo, with a compound or composition as defined herein (e.g. a compound of any one of formula I to XXX, or any activity modulator compound shown in any one of Example C-1 to C-91).

What is claimed is:

1. A compound having formula (I):

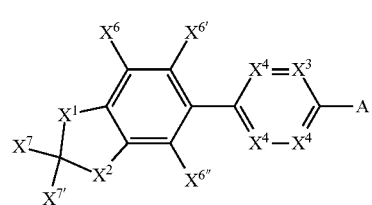

(I)

or an enantiomer, diastereomer, hydrate, solvate, or pharmaceutically acceptable salt of formula (I), or a prodrug or complex thereof, wherein:

$X^1$ is O and $X^2$ is S, SO or $SO_2$; or $X^2$ is O and $X^1$ is S, SO or $SO_2$;

$X^3$ is CH, CF and N;

each $X^4$ is independently CH and N;

A is

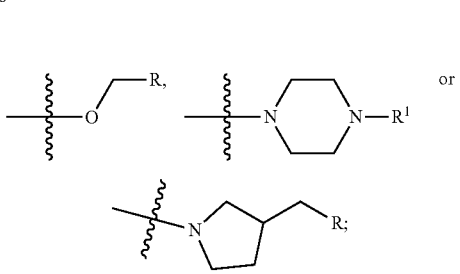

R is

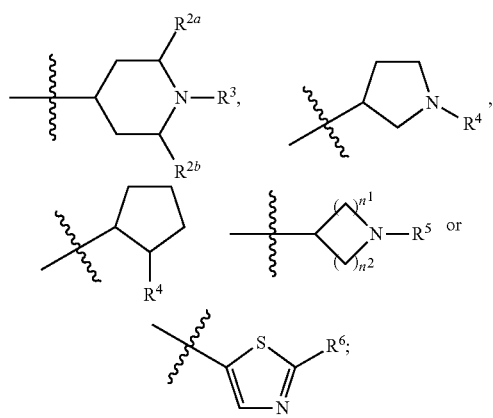

R¹ is hydrogen, C(O)O-tert-butyl or

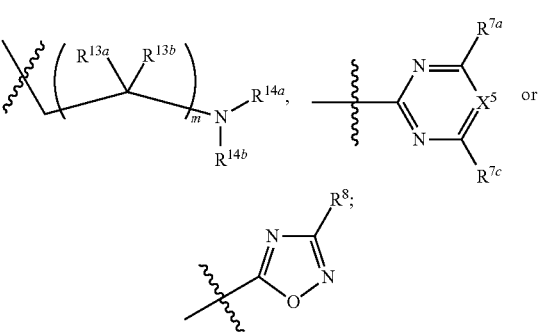

$R^{2a}$ is hydrogen or $C_{1-6}$ alkyl;
$R^{2b}$ is hydrogen or $C_{1-6}$ alkyl;
$R^3$ is hydrogen, $C_{1-6}$ alkyl, $C_{1-6}$ haloalkyl, $C(O)R^9$, $C(O)OR^{10}$, $C(O)NR^{10a}R^{10b}$, $CH_2C(O)OR^{10a}$,

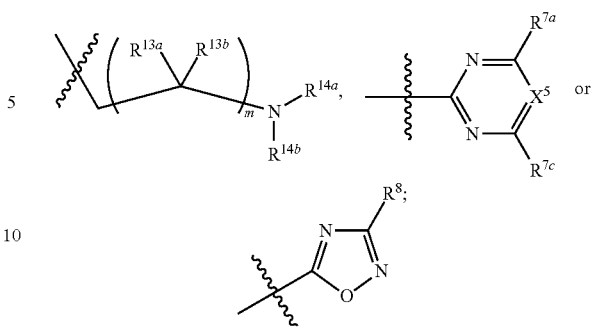

$R^4$ is hydrogen, $C_{1-6}$ alkyl, $C_{1-6}$ haloalkyl, $C(O)R^9$, $C(O)OR^{10}$, $C(O)NR^{10a}R^{10b}$, $R^5$ is hydrogen, $C_{1-6}$ alkyl, $C_{1-6}$ haloalkyl, $C(O)R^9$, $C(O)OR^{10}$, $C(O)NR^{10a}R^{10b}$,

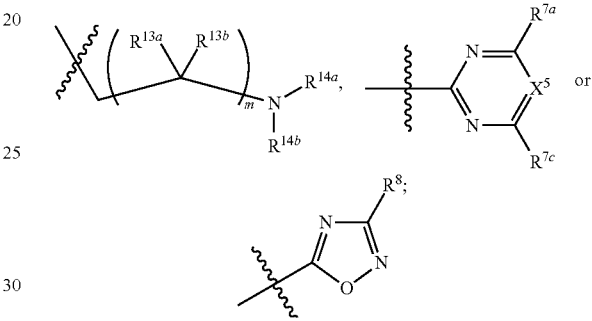

$R^6$ is

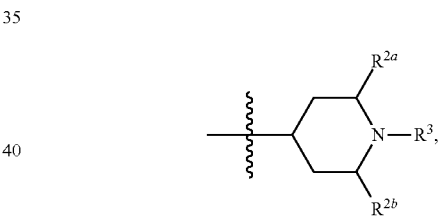

$NHR^{11}$ or $CH_2NHR^{12}$;
$R^{7a}$ is hydrogen, halogen, $C_{1-6}$ alkyl, $C_{3-7}$ branched alkyl, $C_{1-6}$ haloalkyl or $C_{1-6}$ alkoxy;
$R^{7b}$ is hydrogen, halogen, $C_{1-6}$ alkyl, $C_{3-7}$ branched alkyl, $C_{1-6}$ haloalkyl or $C_{1-6}$ alkoxy;
$R^{7c}$ is hydrogen, halogen, $C_{1-6}$ alkyl, $C_{3-7}$ branched alkyl, $C_{1-6}$ haloalkyl or $C_{1-6}$ alkoxy;
$R^8$ is hydrogen, halogen, $C_{1-6}$ alkyl, $C_{3-7}$ branched alkyl or $C_{3-7}$ cycloalkyl;
$R^9$ is $C_{1-6}$ alkyl, $C_{3-7}$ branched alkyl or

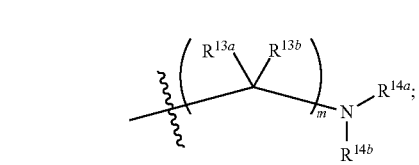

$R^{10}$ is $C_{1-6}$ alkyl or $C_{3-7}$ branched alkyl;
$R^{10a}$ is hydrogen, $C_{1-6}$ alkyl or $C_{3-7}$ branched alkyl;
$R^{10b}$ is hydrogen, $C_{1-6}$ alkyl or $C_{3-7}$ branched alkyl;

$R^{11}$ is

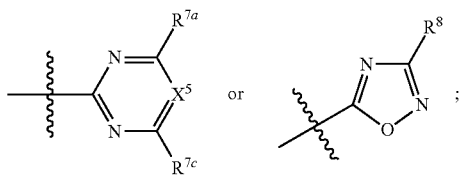

$R^{12}$ is

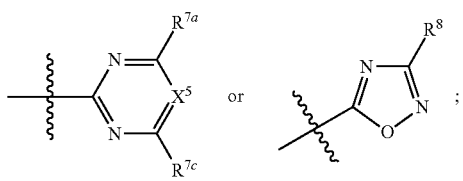

each $R^{13a}$ is independently hydrogen, $C_{1-6}$ alkyl or $C_{3-7}$ branched alkyl;
each $R^{13b}$ is independently hydrogen, $C_{1-6}$ alkyl or $C_{3-7}$ branched alkyl;
each $R^{14a}$ is independently hydrogen, $C_{1-6}$ alkyl, $C_{3-7}$ branched alkyl or C(O)O-tert-butyl;
each $R^{14b}$ is independently hydrogen, $C_{1-6}$ alkyl or $C_{3-7}$ branched alkyl;
$X^5$ is N or $CR^{7b}$;
$n^1$ is 1 or 2;
$n^2$ is 1 or 2;
and m is 1, 2, 3, 4, 5, 6 or 7;
each of $X^6$, $X^{6'}$ and $X^{6''}$ is independently H, halogen, $C_{1-3}$ alkyl, $C_{1-3}$ haloalkyl, $C_{1-3}$ alkoxy, $C_{1-3}$ hydroxyalkyl, or $C_{1-3}$ (O)$NR^{15a}R^{15b}$;
each of $X^7$ and $X^{7'}$ is independently hydrogen, halogen, $C_{1-3}$ alkyl, $C_{1-3}$ haloalkyl, $C_{1-3}$ alkoxy, $C_{1-3}$ hydroxyalkyl, $C_{1-3}$ aminoalkyl or $C_{1-3}$ (O)$NR^{15a}R^{15b}$ or both $X^7$ and $X^{7'}$ together form $C_{3-6}$ cycloalkyl or a heterocycle ring having 3-6 carbons and 0 or 1 oxygen, sulphur or nitrogen atom in the ring, wherein each carbon ring atom of the $C_{3-6}$ cycloalkyl or the heterocycle is independently substituted with hydrogen, $C_{1-3}$ alkyl, hydroxyl, halogen, amino, $C_{1-3}$ haloalkyl, $C_{1-3}$ alkoxy, $C_{1-3}$ hydroxyalkyl or $C_{1-3}$ (O)$NR^{15a}R^{15b}$;
when each of $X^6$, $X^{6'}$ and $X^{6''}$ is hydrogen, at least $X^7$ or $X^{7'}$ is not hydrogen;
when both $X^7$ and $X^{7'}$ are hydrogen, at least one of $X^6$, $X^{6'}$ and $X^{6''}$ is not hydrogen; and
each of $R^{15a}$ and $R^{15b}$ is independently hydrogen, $C_{1-3}$ alkyl or $C_3$ branched alkyl.

2. The compound of claim 1, wherein one, two or three of $X^6$, $X^{6'}$ and $X^{6''}$ are fluorine, optionally wherein $X^6$, $X^{6'}$ and $X^{6''}$ are: F, H and H, respectively; H, F and H, respectively; or H, H and F, respectively.

3. The compound of claim 1, wherein $X^6$, $X^{6'}$ and $X^{6''}$ are each H.

4. The compound of claim 1, wherein A is

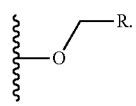

5. The compound of claim 4, wherein R is

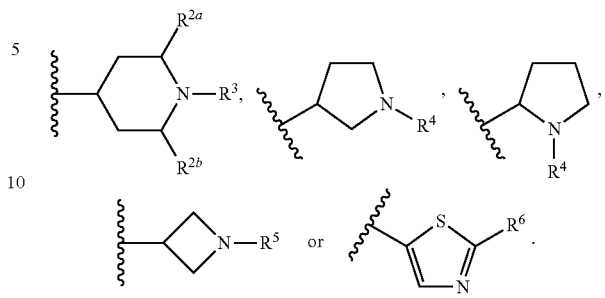

6. The compound of claim 5, wherein R is

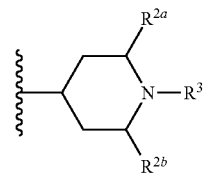

and $R^3$ is

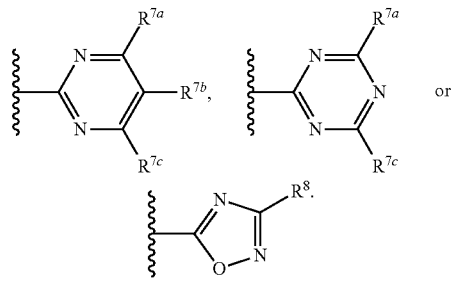

7. The compound of claim 5, wherein R is

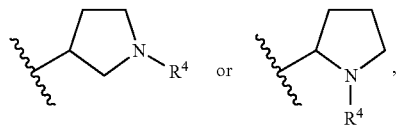

and wherein $R^4$ is

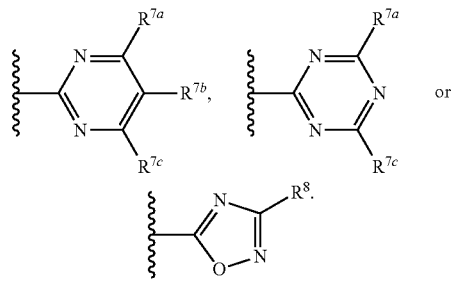

8. The compound of claim 5, wherein R is

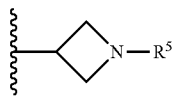

and wherein $R^5$ is

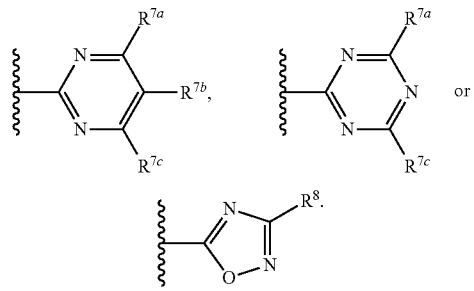

9. The compound of claim 1, wherein A is

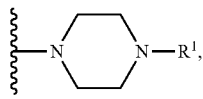

optionally wherein $R^1$ is

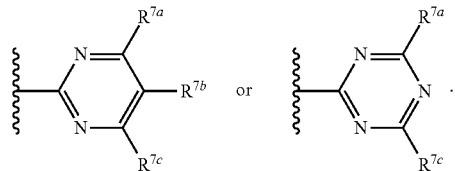

10. The compound of claim 1, wherein A is

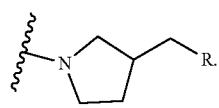

11. The compound of claim 1, wherein both of $X^7$ and $X^{7'}$ are hydrogen and at least one of $X^6$, $X^{6'}$ and $X^{6''}$ is not hydrogen.

12. The compound of claim 1, wherein both of $X^7$ and $X^{7'}$ are $CH_3$.

13. The compound of claim 1, wherein at least one of $X^7$ and $X^{7'}$ is halogen.

14. The compound of claim 1, having:

formula (II) or an enantiomer, diastereomer, hydrate, solvate, or pharmaceutically acceptable salt of formula (II), or a complex thereof

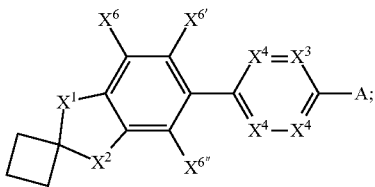

formula (III) or an enantiomer, diastereomer, hydrate, solvate, or pharmaceutically acceptable salt of formula (III), or a complex thereof

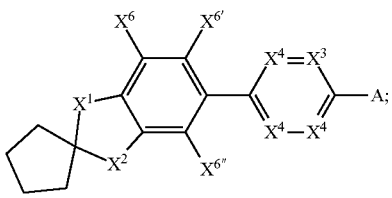

formula (IV) or an enantiomer, diastereomer, hydrate, solvate, or pharmaceutically acceptable salt of formula (IV), or a complex thereof

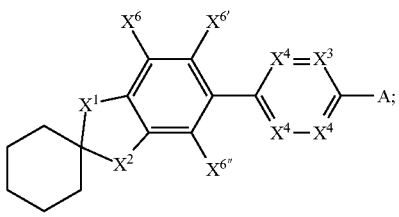

formula (V) or an enantiomer, diastereomer, hydrate, solvate, or pharmaceutically acceptable salt of formula (V), or a complex thereof

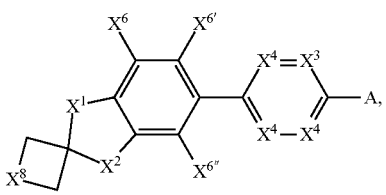

wherein $X^8$ is NH or O;

formula (VI) or an enantiomer, diastereomer, hydrate, solvate, or pharmaceutically acceptable salt of formula (VI), or a complex thereof

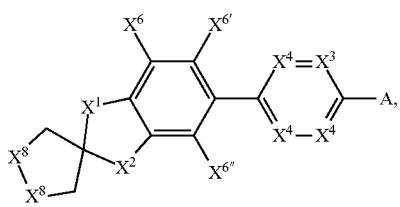

(VI)

wherein: one $X^8$ is NH or O; and one $X^8$ is CH$_2$; or formula (VII) or an enantiomer, diastereomer, hydrate, solvate, or pharmaceutically acceptable salt of formula (VII), or a complex thereof

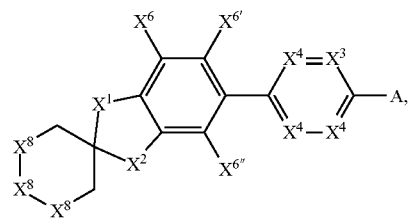

(VII)

wherein one $X^8$ is NH or O, and wherein each of two $X^8$ is CH$_2$.

15. The compound of claim 1, wherein both $X^7$ and $X^{7'}$ together form

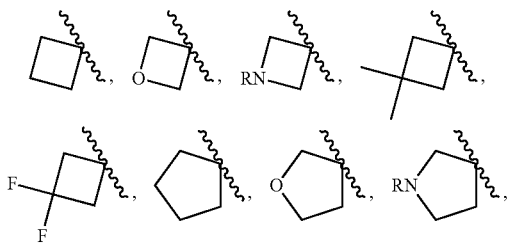

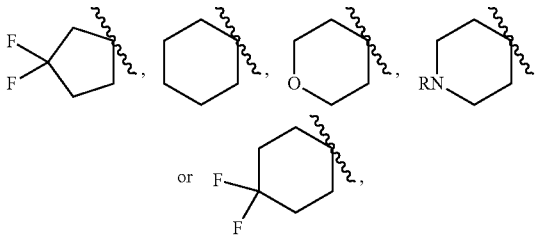

-continued wherein R is H or C$_{1-3}$ alkyl.

16. The compound of claim 1, wherein:
$X^1$ is O and $X^2$ is SO$_2$;
$X^1$ is SO$_2$ and $X^2$ is O;
$X^1$ is O and $X^2$ is SO;
$X^1$ is SO and $X^2$ is O;
$X^1$ is O and $X^2$ is S; or
$X^1$ is S and $X^2$ is O.

17. The compound of claim 1, wherein $X^3$ is selected from the group consisting of CF and N.

18. A compound, which is:
5-chloro-2-(4-{[4-(2,2-dimethyl-3,3-dioxido-1,3-benzoxathiol-6-yl)-2-fluorophenoxy]methyl}piperidin-1-yl) pyrimidine;
5-chloro-2-(4-{[4-(3,3-dioxidospiro[1,3-benzoxathiole-2,1'-cyclopentan]-6-yl)-2-fluorophenoxy] methyl}piperidin-1-yl)pyrimidine;
5-chloro-2-(4-{[4-(3,3-dioxidospiro[1,3-benzoxathiole-2,1'-cyclohexan]-6-yl)-2-fluorophenoxy] methyl}piperidin-1-yl)pyrimidine; or
5-chloro-2-(4-{[4-(3,3-dioxidospiro[1,3-benzoxathiole-2,1'-cyclobutan]-6-yl)-2-fluorophenoxy] methyl}piperidin-1-yl)pyrimidine.

19. A pharmaceutical composition comprising the compound of claim 1 and a pharmaceutically acceptable excipient and/or an anti-diabetic agent.

20. A method of treating a disease associated with GPR119 dysregulation, said method comprising administering to a subject (i): the compound of claim 1; or (ii) a pharmaceutical composition comprising the compound and a pharmaceutically acceptable excipient and/or an antidiabetic agent; optionally wherein the disease is Type 2 diabetes mellitus.

* * * * *